US011129825B2

(12) United States Patent
Jenkins

(10) Patent No.: US 11,129,825 B2
(45) Date of Patent: *Sep. 28, 2021

(54) POLYSUBUNIT OPIOID PRODRUGS RESISTANT TO OVERDOSE AND ABUSE

(71) Applicant: Elysium Therapeutics, Inc., Danville, CA (US)

(72) Inventor: Thomas E. Jenkins, Half Moon Bay, CA (US)

(73) Assignee: ELYSIUM THERAPEUTICS, INC., Akron, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/286,096

(22) Filed: Feb. 26, 2019

(65) Prior Publication Data

US 2019/0183884 A1    Jun. 20, 2019

Related U.S. Application Data

(63) Continuation of application No. 15/683,356, filed on Aug. 22, 2017, now Pat. No. 10,251,878, which is a continuation of application No. 15/284,269, filed on Oct. 3, 2016, now Pat. No. 9,808,452.

(60) Provisional application No. 62/236,048, filed on Oct. 1, 2015.

(51) Int. Cl.
| | |
|---|---|
| *A61K 31/485* | (2006.01) |
| *A61K 47/64* | (2017.01) |
| *A61K 47/55* | (2017.01) |
| *A61K 47/61* | (2017.01) |

(52) U.S. Cl.
CPC ............ *A61K 31/485* (2013.01); *A61K 47/55* (2017.08); *A61K 47/61* (2017.08); *A61K 47/64* (2017.08)

(58) Field of Classification Search
CPC .................................................. A61K 31/485
See application file for complete search history.

(56) References Cited

U.S. PATENT DOCUMENTS

| | | | |
|---|---|---|---|
| 2,996,431 A | 8/1961 | Barry | |
| 3,139,383 A | 6/1964 | Neville, Jr. | |
| 3,402,240 A | 9/1968 | Cain et al. | |
| 3,811,444 A | 5/1974 | Heller et al. | |
| 3,845,770 A | 11/1974 | Theeuwes et al. | |
| 3,916,899 A | 11/1975 | Theeuwes et al. | |
| 3,962,414 A | 6/1976 | Michaels | |
| 3,992,518 A | 11/1976 | Chien et al. | |
| 4,063,064 A | 12/1977 | Saunders et al. | |
| 4,066,747 A | 1/1978 | Capozza | |
| 4,070,347 A | 1/1978 | Schmitt | |
| 4,079,038 A | 3/1978 | Choi et al. | |
| 4,083,949 A | 4/1978 | Benedikt | |
| 4,088,864 A | 5/1978 | Theeuwes et al. | |
| 4,093,709 A | 6/1978 | Choi et al. | |
| 4,200,098 A | 4/1980 | Ayer et al. | |
| 4,285,987 A | 8/1981 | Ayer et al. | |
| 4,421,736 A | 12/1983 | Walters | |
| 4,434,153 A | 2/1984 | Urquhart et al. | |
| 4,507,466 A | 3/1985 | Tomalia et al. | |
| 4,631,337 A | 12/1986 | Tomalia et al. | |
| 4,721,613 A | 1/1988 | Urquhart et al. | |
| 4,752,470 A | 6/1988 | Mehta | |
| 4,765,539 A | 8/1988 | Noakes et al. | |
| 4,816,263 A | 3/1989 | Ayer et al. | |
| 4,820,523 A | 4/1989 | Shtohryn et al. | |
| 4,853,229 A | 8/1989 | Theeuwes | |
| 4,962,885 A | 10/1990 | Coffee | |
| 5,041,516 A | 8/1991 | Frechet et al. | |
| 5,112,598 A | 5/1992 | Biesalski | |
| 5,159,081 A | 10/1992 | Cantrell et al. | |
| 5,177,059 A | 1/1993 | Handley et al. | |
| 5,250,542 A | 10/1993 | Cantrell et al. | |
| 5,270,328 A | 12/1993 | Cantrell et al. | |
| 5,434,171 A | 7/1995 | Frank et al. | |
| 5,468,574 A | 11/1995 | Ehrenberg et al. | |
| 5,530,092 A | 6/1996 | Meijer et al. | |
| 5,556,611 A | 9/1996 | Biesalski | |
| 5,698,155 A | 12/1997 | Grosswald et al. | |
| 5,824,701 A | 10/1998 | Greenwald et al. | |
| 5,840,387 A | 11/1998 | Berlowitz-Tarrant et al. | |

(Continued)

FOREIGN PATENT DOCUMENTS

| | | |
|---|---|---|
| WO | WO-9412285 A2 | 6/1994 |
| WO | WO-9414543 A2 | 7/1994 |

(Continued)

OTHER PUBLICATIONS

Ito et al. in Cancer Science 94(1), 3-8 (2003) (Year: 2003).*
Kitayama, et al. A synthetic route to ultra-high molecular weight polystyrene ( 10 6) with narrow molecular weight distribution by emulsifier-free, emulsion organotellurium-mediated living radical polymerization (emulsion TERP). Polymer Chemistry 7.14 (2016): 2573-2580.
U.S. Appl. No. 16/572,408 Office Action dated Jun. 15, 2020.
Worthington Enzyme Manual, Trypsin Inhibitors—Worthington Enzyme Manual, available online at http://worthington-biochem.com/TI/default.html, accessed on Jun. 8, 2020. (Year: 2020).

(Continued)

*Primary Examiner* — Dennis Heyer
(74) *Attorney, Agent, or Firm* — Wilson Sonsini Goodrich & Rosati

(57) ABSTRACT

The invention provides compositions and methods for the treatment or prevention of pain. The invention provides constructs whereby hydrolysis of the construct by a specified gastrointestinal enzyme directly, or indirectly, releases an opioid when taken orally as prescribed. The gastrointestinal enzyme mediated release of opioid from constructs of the invention is designed to be attenuated in vivo via a saturation or inhibition mechanism when overdoses are ingested. The invention further provides constructs that are highly resistant to oral overdose, chemical tampering, and abuse via non-oral routes of administration.

43 Claims, 5 Drawing Sheets

(56) References Cited

U.S. PATENT DOCUMENTS

| | | | |
|---|---|---|---|
| 5,880,131 | A | 3/1999 | Greenwald et al. |
| 5,932,462 | A | 8/1999 | Harris et al. |
| 5,950,619 | A | 9/1999 | Van et al. |
| 5,954,047 | A | 9/1999 | Armer et al. |
| 5,970,974 | A | 10/1999 | Van et al. |
| 6,171,615 | B1 | 1/2001 | Roussin et al. |
| 6,375,987 | B1 | 4/2002 | Farah et al. |
| 6,379,700 | B2 | 4/2002 | Joachim et al. |
| 6,545,097 | B2 | 4/2003 | Pinchuk et al. |
| 6,664,331 | B2 | 12/2003 | Harris et al. |
| 6,716,821 | B2 | 4/2004 | Zhao et al. |
| 7,060,290 | B1 | 6/2006 | Morimoto et al. |
| 7,338,939 | B2 | 3/2008 | Mickle et al. |
| 7,375,082 | B2 | 5/2008 | Mickle et al. |
| 8,101,661 | B2 | 1/2012 | Mickle |
| 8,133,881 | B2 | 3/2012 | Mickle et al. |
| 8,163,701 | B2 | 4/2012 | Jenkins |
| 8,217,005 | B2 | 7/2012 | Jenkins et al. |
| 8,497,237 | B2 | 7/2013 | Jenkins et al. |
| 8,569,228 | B2 | 10/2013 | Jenkins et al. |
| 8,685,916 | B2 | 4/2014 | Jenkins et al. |
| 8,802,680 | B2 | 8/2014 | Jenkins et al. |
| 9,040,032 | B2 | 5/2015 | Jenkins et al. |
| 9,095,627 | B2 | 8/2015 | Jenkins et al. |
| 9,139,612 | B2 | 9/2015 | Jenkins et al. |
| 9,217,005 | B2 | 12/2015 | Touge et al. |
| 9,499,581 | B2 | 11/2016 | Jenkins et al. |
| 9,808,452 | B2 | 11/2017 | Jenkins |
| 10,335,406 | B2 | 7/2019 | Jenkins |
| 2004/0043030 | A1 | 3/2004 | Griffiths et al. |
| 2005/0037059 | A1 | 2/2005 | Miller et al. |
| 2005/0176644 | A1 | 8/2005 | Mickle et al. |
| 2009/0136980 | A1 | 5/2009 | Bebbington et al. |
| 2009/0137618 | A1 | 5/2009 | Jenkins |
| 2009/0209569 | A1 | 8/2009 | Arnelle et al. |
| 2010/0080797 | A1 | 4/2010 | Yeomans et al. |
| 2011/0262359 | A1 | 10/2011 | Jenkins et al. |
| 2011/0262360 | A1 | 10/2011 | Jenkins et al. |
| 2011/0281886 | A1* | 11/2011 | Jenkins ............... A61K 31/485 514/253.02 |
| 2012/0142718 | A1 | 6/2012 | Jenkins et al. |
| 2012/0178773 | A1 | 7/2012 | Jenkins et al. |
| 2014/0016935 | A1 | 1/2014 | Uhlhorn et al. |
| 2017/0100390 | A1 | 4/2017 | Jenkins |
| 2018/0085366 | A1 | 3/2018 | Jenkins |
| 2020/0093817 | A1 | 3/2020 | Jenkins |
| 2020/0101166 | A1 | 4/2020 | Jenkins et al. |

FOREIGN PATENT DOCUMENTS

| | | |
|---|---|---|
| WO | WO-9526234 A1 | 10/1995 |
| WO | WO-9526235 A1 | 10/1995 |
| WO | WO-9532807 A1 | 12/1995 |
| WO | WO-2004041324 A2 | 5/2004 |
| WO | WO-2004062614 A2 | 7/2004 |
| WO | WO-2004082620 A2 | 9/2004 |
| WO | WO-2006073396 A1 | 7/2006 |
| WO | WO-2007120864 A2 | 10/2007 |
| WO | WO-2007140272 A2 | 12/2007 |
| WO | WO-2008101187 A2 | 8/2008 |
| WO | WO-2009092073 A2 | 7/2009 |
| WO | WO-2010045599 A1 | 4/2010 |
| WO | WO-2011002991 A1 | 1/2011 |
| WO | WO-2011002995 A1 | 1/2011 |
| WO | WO-2011133150 A1 | 10/2011 |
| WO | WO-2012109445 A1 | 8/2012 |
| WO | WO-2012122420 A2 | 9/2012 |
| WO | WO-2017059459 A1 | 4/2017 |
| WO | WO-2018170465 A1 | 9/2018 |

OTHER PUBLICATIONS

Alderman, et al. A review of cellulose ethers in hydrophilic matrices for oral controlled-release dosage forms. Int. J. Pharm. Tech. Prod. Mfr 5.3 (1984): 1-9.

Bak, et al. Acyloxyalkoxy-based Cyclic Prodrugs of Opioid Peptides: Evaluation of the Chemical and Enzymatic Stability as well as Their Transport Properties Across Caco-2 Cell Monolayers. Pharmaceutical Research, 1999, vol. 16, pp. 24-29.

Bamba, et al. Release mechanisms in gelforming sustained release preparations. International Journal of Pharmaceutics. vol. 2, Issues 5-6, Jun. 1979, pp. 307-315.

Birk, Y. Trypsin and chymotrypsin inhibitors from soybeans. Methods Enzymol. 1976;45:700-7.

Coleman, et al. Polymer Reviews: A Practical Guide to Polymer Miscibility. 1990, 31, 1187-1231.

Definition of "ex vivo" from thefreedictionary.com, accessed Oct. 7, 2014.

During, et al. Controlled release of dopamine from a polymeric brain implant: in vivo characterization. Ann Neurol. Apr. 1989;25(4):351-6.

FDA Center for Drug Evaluation and Research, Joint Meeting of the Anesthetic and Life Support Drugs Advisory Committee and the Drug Safety and Risk Management Advisory Committee, Meeting Transcript, Jul. 23-4, 2010.

Fincher, JH. Particle size of drugs and its relationship to absorption and activity. J Pharm Sci. Nov. 1968;57(11):1825-35.

Geratz, et al. Novel Bis(benzamidine) Compounds with an Aromatic Central Link. Inhibitors of Thrombin, Pancreatic Kallkrein, I Trypsin, and Compliment. J. Medicinal Chemistry, 1976, vol. 19, pp. 634-639.

Goodson. Medical Applications of Controlled Release. vol. 2, pp. 115-138, 1984.

Gotoh, et al. The Advantages of the Ussing Chamber in Drug Absorption Studies. Journal of Biomolecular Screening 10(5), pp. 517-523, 2005.

Gunatillake, et al. Thermal polymerization of a 2-(carboxyalkyl)-2-oxazoline. Macromolecules, 1988, 21 (6), pp. 1556-1562.

Hawker, et al. One-step synthesis of hyperbranched dendritic polyesters. J. Am. Chem. Soc., 1991, 113 (12), pp. 4583-4588.

Howard, et al. Intracerebral drug delivery in rats with lesion-induced memory deficits. J Neurosurg. Jul. 1989;71(1):105-12.

International Search Report with Opinion dated Dec. 23, 2016 for PCT/US16/55231.

Ito, et al. A medium-term rat liver bioassay for rapid in vivo detection of carcinogenic potential of chemicals. Cancer Sci. Jan. 2003;94(1):3-8.

Kaneda, et al. The use of PVP as a polymeric carrier to improve the plasma half-life of drugs. Biomaterials. Jul. 2004;25(16):3259-66.

Langer, et al. Chemical and Physical Structure of Polymers as Carriers for Controlled Release of Bioactive Agents: A Review. J Macromol. Sci. Rev. Macromol. Chem. 1983, 23:61-126.

Langer, R. New methods of drug delivery. Science. Sep. 28, 1990;249(4976):1527-33.

Leong, et al. Polymeric controlled drug delivery. Advanced Drug Delivery Reviews, vol. 1, Issue 3, Sep. 1988, pp. 199-233.

Levy, et al. Inhibition of calcification of bioprosthetic heart valves by local controlled-release diphosphonate. Science. Apr. 12, 1985;228(4696):190-2.

Lin, et al. The 0.25-nm X-ray structure of the Bowman-Birk-type inhibitor from mun gean in ternary complex with porcine trypsin. Eur. J. Biochem, 1993, vol. 212, pp. 549-555.

Lu, et al. Dimensionless presentation for drug release from a coated pure drug bead: 2. Experiment. Int. J. Pharm. 1994, 112, 117-124.

Markwardt, et al. Comparative Studies on the Inhibition of Trypsin, Plasmin, and Thrombin, by Derivatives of Benzylamine and Benzylamidine. Eur. J. Biochem, 1968, vol. 6, pp. 502-506.

Notice of allowance dated Aug. 17, 2017 for U.S. Appl. No. 15/284,269.

Ozawa, et al. The reactive site of trypsin inhibitors. J Biol Chem. Sep. 10, 1966;241(17):3955-61.

Raleigh, et al. American Association for Cancer Research Anuual Meeting. 1999, 40, 397.

Roerdink, et al. Drug Carrier Systems 1989, vol. 9, chapter 3, pp. 57-109.

Rosoff. Controlled Release of Drugs. Chapter 2, pp. 53-95, 1989.

(56) References Cited

OTHER PUBLICATIONS

Saudek, et al. A preliminary trial of the programmable implantable medication system for insulin delivery. N. Engl J Med. Aug. 31, 1989;321(9):574-9.
Schanker, et al. Absorption of drugs from the rat small intestine. Journal of Pharmacology and Experimental Therapeutics 123.1 (1958): 81-88.
Sefton, MV. Implantable pumps. Crit Rev Biomed Eng. 1987;14(3):201-40.
Sekizaki et al. "The Structural Requirements for an Inverse Substrate for Enzymatic Peptide Synthesis: Position Isomers of Guanidononaphthyl Esters as the Acyl Donor Component", Chem. Pharm. Bull. 1999. vol. 47(1), pp. 104-110.
Thanou, et al. Polymer-protein and polymer-drug conjugates in cancer therapy. Curr Opin Investig Drugs. Jun. 2003;4(6):701-9.
Tomalia, et al. Discovery of dendrimers and dendritic polymers: A brief historical perspective. Journal of Polymer Science Part A: Polymer Chemistry. vol. 40, Issue 16, pp. 2719-2728, Aug. 15, 2002.
Umezawa, H. Structures and activities of protease inhibitors of microbial origin. Methods Enzymol. 1976;45:678-95.
U.S. Appl. No. 15/795,126 Notice of Allowance dated Jan. 17, 2019.
U.S. Appl. No. 15/795,126 Office Action dated Jun. 22, 2018.
Van Gelder, et al. Drug Metabolism and Disposition 30 (8) p. 924-930, 2002.
Verma, et al. Osmotically controlled oral drug delivery. Drug Dev Ind Pharm. Jul. 2000;26(7):695-708.
Veronese, et al. Bioconjugation in pharmaceutical chemistry. Farmaco. Aug. 30, 1999;54(8):497-516.
Verschoyle, et al. British J. Cancer, 1999, 80, Suppl. 2, 96. Poster Presentations.
Aoyama, et al. Synthesis and structure-activity study of protease inhibitors. IV. Amidinonaphthols and related acyl derivatives. Chem Pharm Bull (Tokyo). Apr. 1985;33(4):1458-71.
EP16852850.3 The Extended European Search report dated Mar. 21, 2019.
PCT/US2018/022986 International Search Report dated May 31, 2018.
Sekizaki, et al. Synthesis and tryptic hydrolysis of p-guanidinophenyl esters derived from amino acids and peptides. Chem Pharm Bull (Tokyo). Aug. 1996;44(8):1577-9.
Sekizaki, et al. Trypsin-catalyzed peptide synthesis and various p-guanidinophenyl esters as acyl donors. Chem Pharm Bull (Tokyo). Aug. 1996;44(8):1585-7.
Thormann, et al. Protease-catalyzed hydrolysis of substrate mimetics (inverse substrates): A new approach reveals a new mechanism. Biochemistry. May 11, 1999;38(19):6056-62.
U.S. Appl. No. 15/683,356 Notice of Allowance dated Feb. 8, 2019.
U.S. Appl. No. 15/683,356 Notice of Allowance dated Jan. 3, 2019.
U.S. Appl. No. 15/683,356 Notice of Allowance dated Jan. 9, 2019.
U.S. Appl. No. 15/683,356 Notice of Allowance dated Nov. 26, 2018.
U.S. Appl. No. 15/683,356 Office Action dated Aug. 16, 2018.
U.S. Appl. No. 16/386,671 Office Action dated Sep. 4, 2020.
EP18766937.9 The Extended European Search Report dated Dec. 14, 2020.
U.S. Appl. No. 16/386,671 Notice of Allowance dated Mar. 4, 2021.
U.S. Appl. No. 16/572,408 Notice of Allowance dated Jan. 19, 2021.

* cited by examiner

POLYSUBUNIT OPIOID PRODRUGS
RESISTANT TO OVERDOSE AND ABUSE

CROSS-REFERENCE

This application is a continuation of U.S. patent application Ser. No. 15/683,356, filed Aug. 22, 2017, now U.S. Pat. No. 10,251,878, which is a continuation of U.S. patent application Ser. No. 15/284,269, filed Oct. 3, 2016, now U.S. Pat. No. 9,808,452, which claims priority to U.S. Provisional Patent Application Ser. No. 62/236,048, filed Oct. 1, 2015, the entirety of which are incorporated herein by reference and to which applications we claim priority under 35 U.S.C. § 120.

STATEMENT AS TO FEDERALLY SPONSORED RESEARCH

This invention was made with the support of the United States government under SBIR Grant number 1R44DA037900 by the National Institute on Drug Abuse (NIDA), one of the National Institutes of Health (NIH) in the U.S. Department of Health and Human Services.

TECHNICAL FIELD

The present invention relates to compounds, methods and formulations for the prevention and/or treatment of pain. More particularly, the invention relates to pharmaceutical agents that interact with analgesic receptors, methods of preparing these agents, and their use for analgesia, pain, and other conditions, while protecting against overdose and abuse.

BACKGROUND

Pharmacologically, opioid agonists represent an important class of agents for the management of pain. The high abuse liability of opioid agonists often limits their use in the treatment of patients, and results in the under-treatment of pain, and severe social and financial costs. The U.S. Food and Drug Administration has recently described prescription opioid analgesics as being at the center of a major public health crisis of addiction, misuse, abuse, overdose, and death (FDA/Center for Drug Evaluation and Research, Joint Meeting of the Anesthetic and Life Support Drugs Advisory Committee and the Drug Safety and Risk Management Advisory Committee, Meeting Transcript, Jul. 23-4, 2010).

The class of drugs exhibiting opium or morphine-like properties are referred to as opioid agonists, or opioids, and they interact with opioid receptors in the brain, the peripheral nervous system and other tissues. The three major opioid receptor subtypes are mu, delta, and kappa. Each of these receptors has a unique anatomical distribution in the central nervous system, the peripheral nervous system and the gastrointestinal tract. Most of the clinically used opioids exert their desired therapeutic action (i.e. analgesia) at the mu receptor subtype.

Opioids include morphine, codeine, oxycodone, hydrocodone, hydromorphone, and the like. Examples of marketed opioid products in the United States include OxyContin®, Vicodin®, and Percocet®. Opioids have diverse effects, including analgesia, euphoria, drowsiness, changes in mood and alterations of the endocrine and autonomic nervous systems. Opioid analgesics comprise the major class of drugs used in the management of moderate to severe pain. As a class, opioids are among the most prescribed drugs in the US. Data provided by IMS Health, Inc. shows that about 9 billion hydrocodone containing pills are prescribed annually. However, several concerns exist regarding the nonmedical use and abuse of opioids. There exists a need for pharmaceutical products which provide the therapeutic benefits of opioids to a subject but that is not susceptible to abuse.

SUMMARY OF THE INVENTION

Provided herein are unimolecular polysubunit compositions comprising at least one GI enzyme-labile opioid releasing subunit capable of releasing an opioid agonist upon the action of a GI enzyme, wherein the at least one GI enzyme-labile opioid releasing subunit is covalently linked to at least one non-opioid releasing GI enzyme subunit capable of being cleaved by said GI enzyme. In some embodiments, the at least one GI enzyme-labile opioid releasing subunit and the at least one non-opioid releasing GI enzyme subunit are covalently linked via a scaffold moiety. For example, the scaffold moiety comprises a peptide, polypeptide, or polysaccharide.

Also provided herein are unimolecular compositions comprising at least one GI enzyme-labile opioid releasing subunit capable of releasing an opioid agonist upon the action of a GI enzyme, wherein the at least one GI enzyme-labile opioid releasing subunit is covalently linked to at least one GI enzyme inhibitor moiety. In some embodiments, the at least one GI enzyme-labile opioid releasing subunit and the at least one GI enzyme inhibitor moiety are covalently linked via a scaffold moiety. For example, the scaffold moiety can comprises a peptide, polypeptide, or polysaccharide.

Also provided herein is a pharmaceutical composition, the composition comprising: an opioid prodrug; a gastrointestinal enzyme inhibitor; and a scaffold, wherein the opioid prodrug and the inhibitor are covalently attached to the scaffold. In some embodiments, the at least one non-opioid releasing GI enzyme subunit is an inverse-substrate. In some embodiments, the at least one non-opioid releasing GI enzyme subunit is a GI enzyme inhibitor.

In some embodiments, the GI enzyme is trypsin or chymotrypsin.

In some embodiments, the GI enzyme-labile opioid releasing subunits release an opioid agonist. For example, the opioid agonist encompasses full-, partial-, mixed-, inverse- or biased-agonists, and the like. They can include, without limitation, morphine, heroin, hydromorphone, oxymorphone, buprenorphine, levorphanol, butorphanol, codeine, dihydrocodeine, hydrocodone, oxycodone, meperidine, methadone, nalbulphine, opium, pentazocine, propoxyphene, as well as less widely employed compounds such as alfentanil, allylprodine, alphaprodine, anileridine, benzylmorphine, bezitramide, clonitazene, cyclazocine, desomorphine, dextromoramide, dezocine, diampromide, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydroxypethidine, isomethadone, ketobemidone, levallorphan, levophenacylmorphan, lofentanil, meptazinol, metazocine, metopon, myrophine, narceine, nicomorphine, norpipanone, papvretum, phenadoxone, phenomorphan, phenazocine, phenoperidine, piminodine, propiram, sufentanil, tapentadol, tramadol, tilidine, PZM021 and analogs thereof, TRY130 and analogs thereof, BU08028 and analogs thereof, as well as salts, prodrugs and mixtures thereof.

In some embodiments, the non-opioid releasing GI enzyme subunit is more susceptible to cleavage by the digestive enzyme than the GI enzyme-labile opioid releasing subunit and is capable of saturating or inhibiting the GI enzyme. In some embodiments, the GI enzyme inhibitor subunit is capable of inhibiting the GI enzyme. In some embodiments, the non-opioid releasing GI enzyme subunit is susceptible to cleavage by the GI enzyme and is capable of saturating the GI enzyme. In some embodiments, the non-opioid releasing GI enzyme subunit is capable of reducing the expected systemic exposures of delivered opioid agonist when doses greater than the prescribed dose are orally co-ingested. In some embodiments, the appended GI enzyme inhibitor is capable of inhibiting the digestive enzyme. In some embodiments, the GI enzyme inhibitor is capable of reducing the expected systemic exposures of delivered opioid agonist when doses greater than the prescribed dose are orally co-ingested.

In some embodiments, compounds of the invention have the formula:

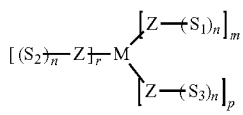

wherein:

each $S_1$ is independently a non-opioid releasing GI enzyme subunit or GI enzyme inhibitor;

each $S_2$ is independently an opioid agonist releasing GI enzyme subunit;

each $S_3$ is an opioid antagonist releasing moiety;

M is a covalent scaffold;

each Z is independently a linking moiety;

each r, m, n, is independently an integer ranging from 1 to 10, 1 to 100, 1 to 1,000, 1 to 100,000, 1 to 1,000,000, or 1 to 1,000,000,000;

p is an integer ranging from 0 to 10, 0 to 100, 0 to 1,000, 0 to 100,000, 0 to 1,000,000, or 0 to 1,000,000,000

In some embodiments, compounds of the invention have the formula:

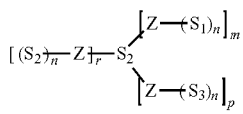

wherein:

each $S_1$ is independently a non-opioid releasing GI enzyme subunit or GI enzyme inhibitor;

each $S_2$ is independently an opioid agonist releasing GI enzyme subunit;

each $S_3$ is an opioid antagonist releasing moiety;

each Z is independently a linking moiety;

each n is independently an integer ranging from 1 to 10;

m is an integer ranging from 1 to 10; and p and r are independently integers ranging from 0 to 10.

In some embodiments, the $S_1$—Z— subunit is selected from the group consisting of:

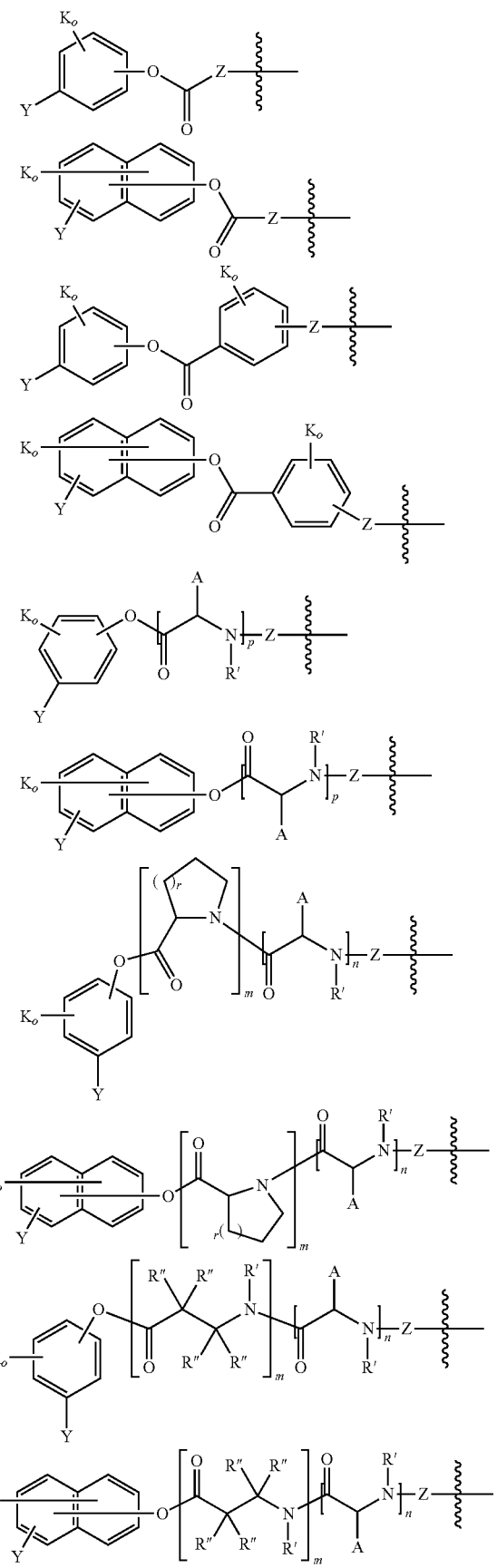

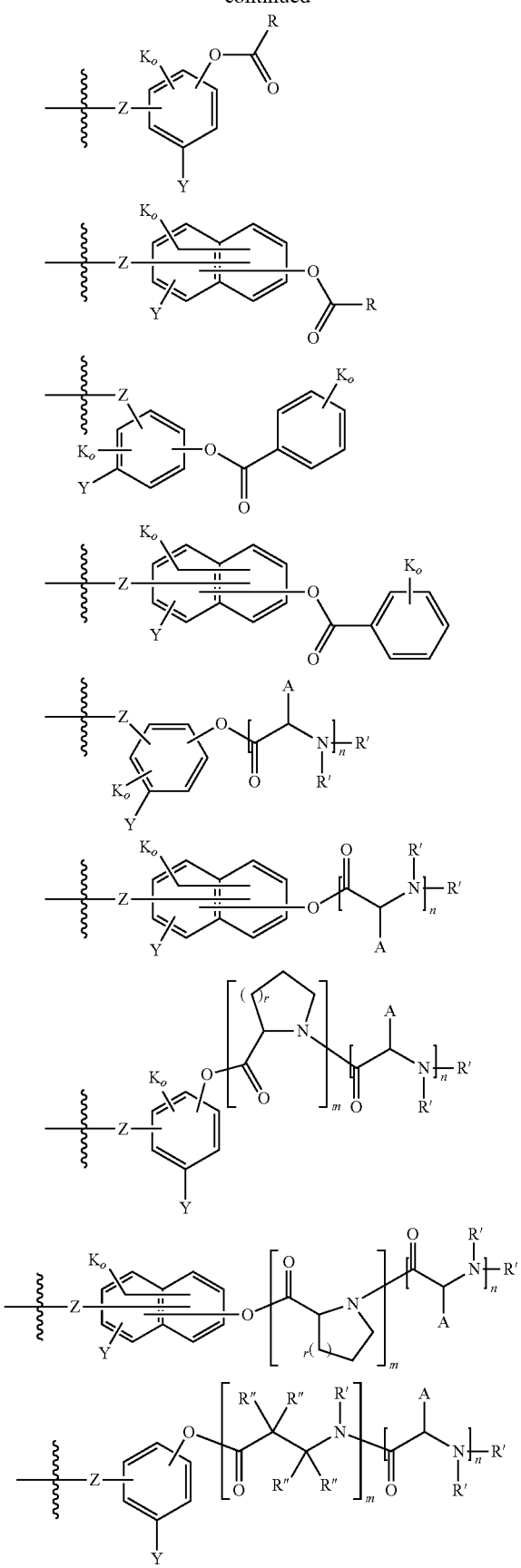

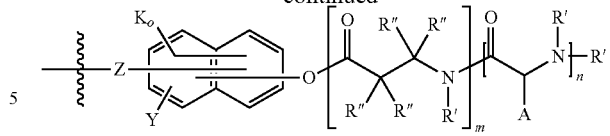

Wherein:

Y is an amidine, guanidine, benzylamine, alkyl substituted amidine, alkyl substituted guanidine, alkyl substituted benzylamine, benzylamidine, benzylguanidine, alkyl substituted benzylamidine, or alkyl substituted benzylguanidine;

Z is a linking moiety;

each $K_o$ is independently hydrogen or methyl;

A is an amino acid side chain;

r is an integer from 0-10;

m is an integer from 1-10;

o is an integer from 0-6 p is an integer from 1-10;

n is an integer from 0-10;

each R is alkyl, alkylene, alkynyl, or aryl, or substituted alkyl, substituted alkylene, substituted alkynyl, substituted aryl group;

each R' is independently alkyl, aryl, substituted alkyl, substituted aryl, acyl, substituted acyl group, or polyethylene glycol containing acyl, aryl, or alkyl group; and each R" is independently a hydrogen, methyl, alkyl, or aryl group.

In some embodiments, at least one of Z and Ko comprises an electron donating or electron withdrawing group. For instance, the electron donating group is alkyl, substituted alkyl, —OH, —OR, —NH$_2$, —NR$_2$, —SH, —SR, or —NHC(O)R. Alternatively, the electron withdrawing group is: —C(O)OH, —C(O)OR, —C(O)NH$_2$, —C(O)NR$_2$, —NO$_2$, —NR$_3^+$, —C(O)CF$_3$, halogen, —CF$_3$, cyano, —SO$_3$H, —SO$_3$R, —CHO, —COR, —C(NH)NH$_2$, or —NHC(=NH)NH$_2$.

In some embodiments, m is 1-10 and r and p are 0.

In some embodiments the $S_2$ subunit can be a reversible or non-reversible (i.e. covalent bond forming) trypsin inhibitor.

In some embodiments, the $S_2$ subunit has the structure:

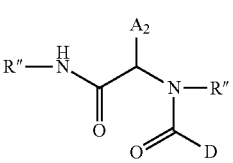

wherein:

D is an opioid agonist, for example wherein D is a morphone, a codone, or morphine;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid mimic, or a linking moiety (Z); and $A_2$ is an amino acid side chain or an amino acid side-chain mimic that is capable of being recognized by a GI enzyme.

In some embodiments, the $S_2$ subunit has the structure:

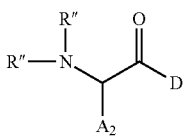

wherein:
D is an opioid agonist, for example wherein D is a morphone, a codone, or morphine;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid mimic, or a linking moiety (Z); and
$A_2$ is an amino acid side chain or an amino acid side-chain mimic that is capable of being recognized by a GI enzyme.

In some embodiments, the $S_2$ subunit has the structure:

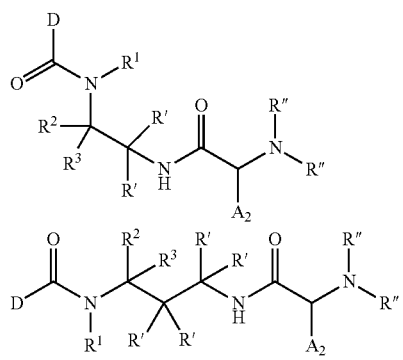

Wherein:
D is an opioid agonist, for example wherein D is a morphone, a codone, or morphine;
$R^1$, $R^2$ and $R^3$ can be R', or
$R^2$ and $R^3$ can be joined to form an optionally substituted spirocyclic ring;
$R^2$ or $R^3$ can be joined with $R^1$ to form an optionally substituted heterocyclic ring;
$R^2$ or $R^3$ can be joined with R' to form an optionally substituted ring, or
R' can be joined with a geminal R' so as to from an optionally substituted spirocyclic ring;
each R' is independently hydrogen, alkyl, aryl, substituted alkyl, substituted aryl, heteroalkyl, substituted heteroalkyl, a polyethylene glycol, or polyethylene glycol containing moiety, or a linking moiety —Z; or —Z—$(S_2)_n$, or —Z—$(S_x)_n$
wherein:
Z is as defined herein;
each x is independently 1 or 3 (thereby designating each $S_x$ as a $S_1$ or $S_3$ subunit);
n is an integer ranging from 1-10;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$ wherein:
Z is a linker moiety as previously defined;
each x is independently 1 or 3 (thereby designating each $S_x$ as a $S_1$ or $S_3$ subunit);
n is an integer ranging from 1-10; and
each $A_2$ is independently an amino acid side chain or an amino acid side-chain mimic that is capable of being recognized by a digestive enzyme.

In some embodiments, $A_2$ is:

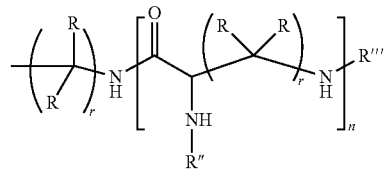

wherein:
R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$
wherein:
Z is a linker moiety as previously defined;
each x is independently 1 or 3 (thereby designating each $S_x$ as a $S_1$ or $S_3$ subunit);
n is an integer ranging from 1-10;
r is each or independently an integer from 1 to 6;
n is an integer from 0 to 10;
R''' is hydrogen, methyl, or
—C(=NR)—NR$_2$ wherein R is each or independently hydrogen or methyl; or

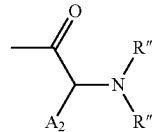

wherein $A_2$ is a natural or unnatural amino acid side chain, or an amino acid side-chain mimic that is capable of being recognized by a digestive enzyme that directs the regiospecific hydrolysis of the $S_2$ subunit prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof; R" is as defined above.

In some embodiments, the $S_2$ subunit has the structure:

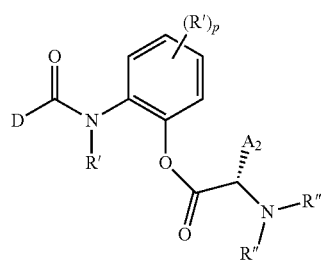

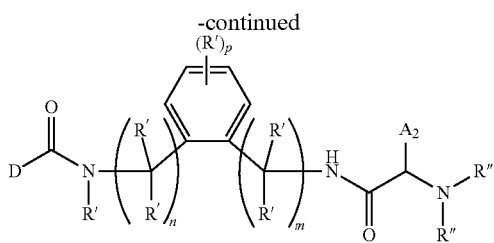

Wherein:

D is an opioid agonist, for example wherein D is a morphone, a codone, or morphine;

each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a linking moiety Z as previously defined;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid side chain, an amino acid side-chain mimic, or a linking moiety Z as defined herein; and each $A_2$ is independently an amino acid side chain or an amino acid side-chain mimic that is capable of being recognized by a digestive enzyme;

In some embodiments, $A_2$ is:

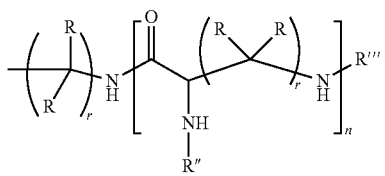

Wherein R is each or independently hydrogen or methyl; R" is as defined above; r is each or independently an integer from 1 to 6; n is an integer from 0 to 10; R''' is hydrogen, methyl, —C(=NR)—$NR_2$ wherein R is each or independently hydrogen or methyl; or

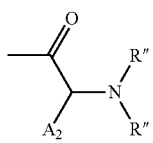

wherein $A_2$ is a natural or unnatural amino acid side chain, or an amino acid side-chain mimic that is capable of being recognized by a digestive enzyme that directs the regiospecific hydrolysis of the $S_2$ subunit prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof; R" is as defined above; and m is an integer from 0 to 10 n is an integer from 0 to 10 p is an integer from 0 to 4.

In some embodiments, the $S_3$—Z— subunit is selected from the group consisting of:

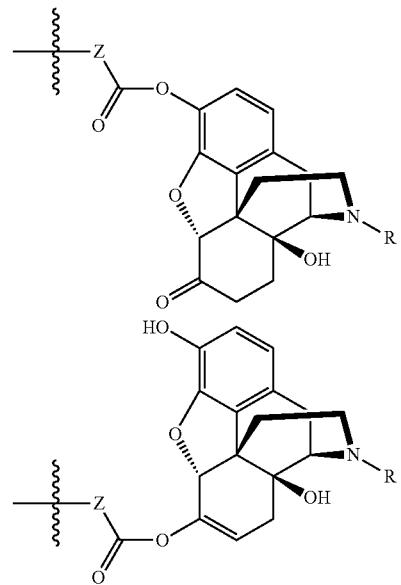

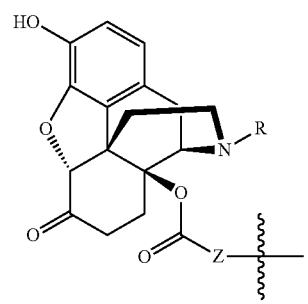

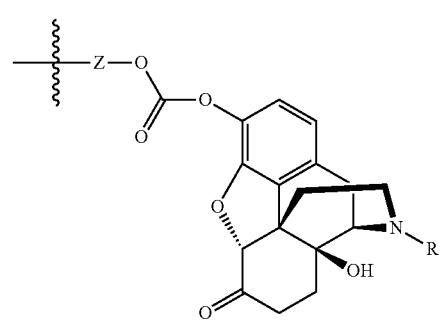

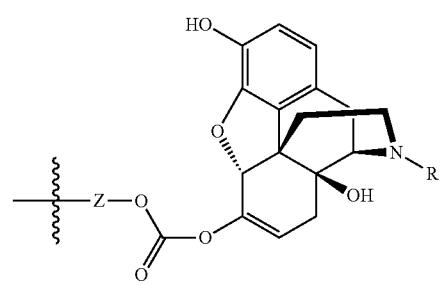

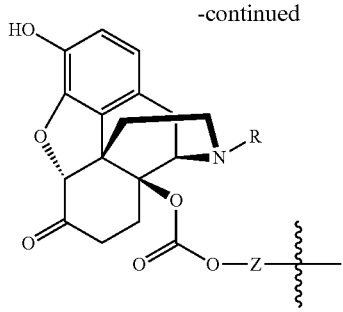

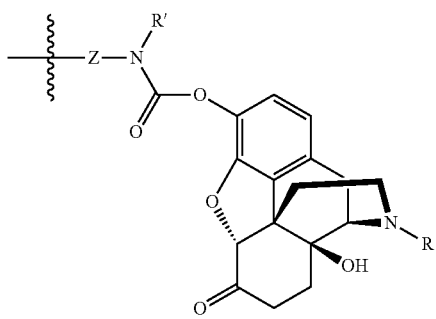

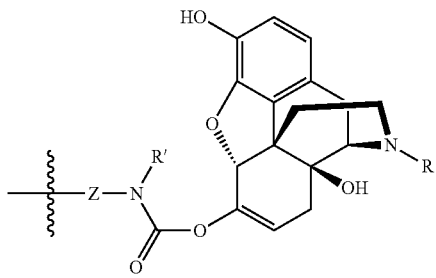

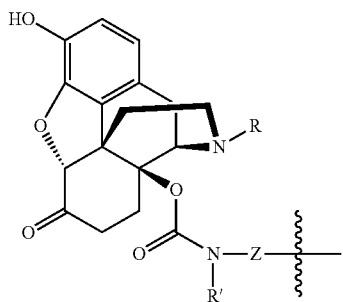

Wherein:
R is cyclopropylmethyl or allyl; R' is hydrogen, methyl, alkyl, aryl, substituted alkyl, or substituted aryl, acyl or substituted acyl; and Z is a linker as defined herein.

In some embodiments, the opioid antagonist is naltrexone or naloxone.

In some embodiments, the $S_2$ subunit has a structure selected from the group consisting of:

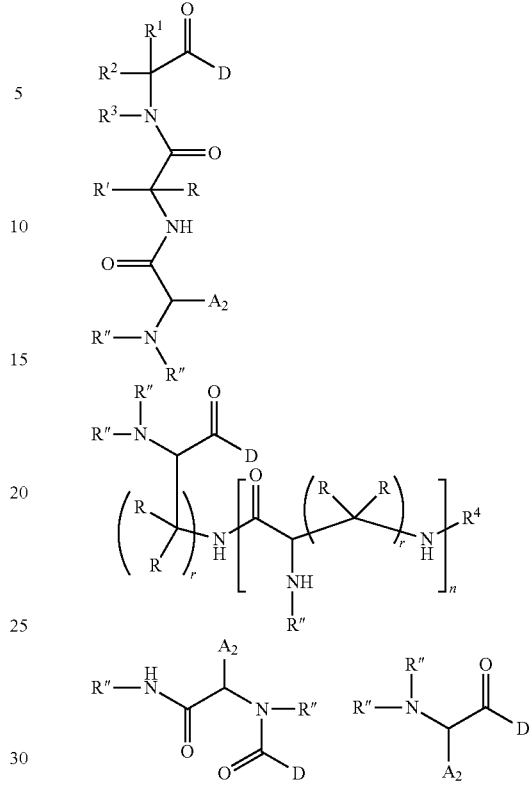

wherein:

D is an opioid agonist, for example wherein D is a morphone, a codone, or morphine;

each $R^1$ and $R^2$ is independently R or R'; or wherein $R^1$ and $R^2$ can be joined to form an optionally substituted spirocyclic ring;

$R^3$ is R"; or wherein $R^3$ is joined with $R^1$ or $R^2$ to form an optionally substituted heterocyclic ring;

each R is independently hydrogen, methyl, or alkyl, for example lower alkyl;

each R' is independently hydrogen, alkyl, aryl, substituted alkyl, substituted aryl, heteroalkyl, substituted heteroalkyl, a natural or unnatural amino acid side chain, an amino acid side-chain mimic, or —Z—$(S_2)_n$, or —Z—$(S_x)_n$ wherein:

Z is a linking moiety;

each x is independently 1 or 3 (thereby designating each $S_x$ as a $S_1$ or $S_3$ subunit);

n is an integer ranging from 1-10;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$;

wherein:

Z is a linking moiety;

each x is independently 1 or 3 (thereby designating each $S_x$ as a $S_1$ or $S_3$ subunit);

n is an integer ranging from 1-10;

$R^4$ is hydrogen, methyl, —C(=NR)—$NR_2$ (where each R is independently hydrogen or methyl), or a group of formula:

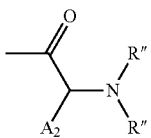

each $A_2$ independently an amino acid side chain or an amino acid side-chain mimic that is capable of being recognized by a digestive enzyme;

n is an integer ranging from 1 to 10; and r is an integer ranging from 1 to 6.

In some embodiments, the $S_2$ subunit has a structure selected from the group consisting of:

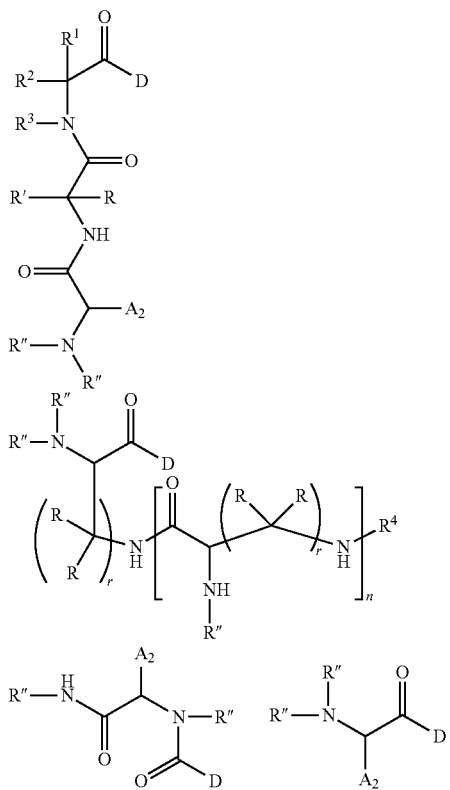

wherein:

D is an opioid agonist, for example wherein D is a morphone, a codone, or morphine;

each $R^1$ and $R^2$ is independently R or R'; or wherein $R^1$ and $R^2$ can be joined to form an optionally substituted spirocyclic ring;

$R^3$ is R"; or wherein $R^3$ is joined with $R^1$ or $R^2$ to form an optionally substituted heterocyclic ring;

each R is independently hydrogen, methyl, or alkyl, for example lower alkyl;

each R' is independently hydrogen, alkyl, aryl, substituted alkyl, substituted aryl, heteroalkyl, substituted heteroalkyl, a natural or unnatural amino acid side chain, an amino acid side-chain mimic, or —Z—$(S_2)_n$, or —Z—$(S_x)_n$ wherein:

Z is a linking moiety;

each x is independently 1 or 3 (thereby designating each $S_x$ as a $S_1$ or $S_3$ subunit);

n is an integer ranging from 1-10;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$;

wherein:

Z is a linking moiety;

each x is independently 1 or 3 (thereby designating each $S_x$ as a $S_1$ or $S_3$ subunit);

n is an integer ranging from 1-10;

$R^4$ is hydrogen, methyl, —C(=NR)—$NR_2$ (where each R is independently hydrogen or methyl), or a group of formula:

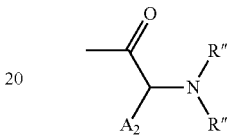

each $A_2$ independently an amino acid side chain or an amino acid side-chain mimic that is capable of being recognized by a digestive enzyme;

n is an integer ranging from 1 to 10; and r is an integer ranging from 1 to 6.

In some embodiments, Z is represented by one of the formulae:

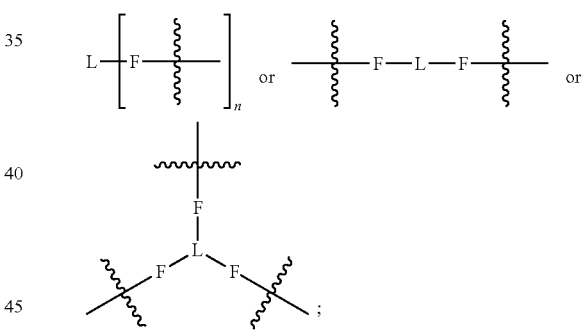

wherein:

each F is independently:

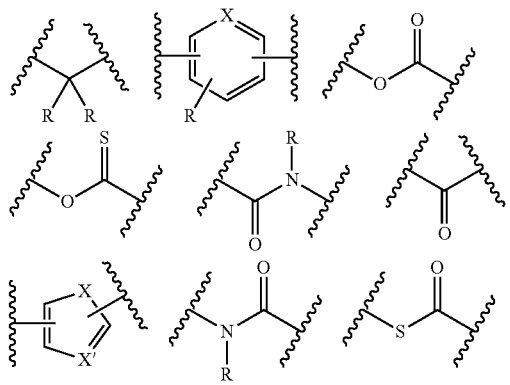

-continued

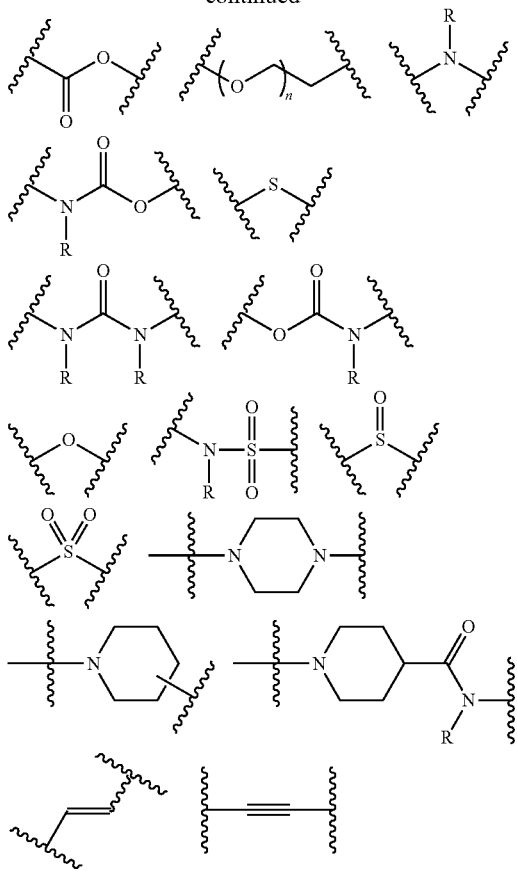

each R is independently hydrogen, methyl, lower alkyl, aryl, or arylalkyl;

X can be carbon, oxygen, or nitrogen;

L can be a covalent bond or a linear, branched, or a multivalent scaffold comprised of alkyl, aryl, substituted alkyl, substituted aryl, heteroalkyl, substituted heteroalkyl, polyalkylene glycol, peptide, polypeptide, amide, polyamide, carbamate, polycarbamate, urea, polyurea, carbonate, polycarbonate, or a combination thereof.

For example, the linking moiety F forms a substituted ester, amide, amine, carbamate, ether, alkylane, arene, or urea; and L is a covalent bond or a linear, branched, or a multivalent scaffold comprised of alkyl, aryl, substituted alkyl, substituted aryl, heteroalkyl, polyalkylene glycol, polypeptide, or polyamide.

In some embodiments, D is a morphone, codone, or morphine.

In some embodiments, the scaffold is an oligomeric or polymeric scaffold.

For example, the scaffold is a polyalkylene oxide, a polypeptide, a polysaccharide or a biopolymer. Alternatively, the scaffold is a linear, branched, brush (or comb) polymer. In some embodiments, the scaffold is polycationic.

Also provided herein is a method of treating pain in a subject in need thereof, the method comprising administrating to the subject a therapeutically-effective amount of a unimolecular polysubstrate of the invention. Further provided are pharmaceutical compositions comprising a polysubstrate.

In one aspect, the present disclosure provides a compound represented by the structure of Formula (I):

$$[R^1\text{-}L^1\!-\!]_n Q\text{-}[\text{-}L^2\text{-}R^2]_m \qquad (I)$$

or a salt thereof, wherein:

Q is independently selected from optionally substituted heteroalkyl and optionally substituted alkyl;

$L^1$ is independently at each occurrence absent or a cleavable or non-cleavable linker;

$L^2$ is independently at each occurrence absent or a cleavable or non-cleavable linker;

$R^1$ is independently selected at each occurrence from a GI enzyme substrate, a GI enzyme inhibitor, and an opioid antagonist;

$R^2$ is an opioid agonist covalently bound to a GI enzyme substrate; and m and n are independently selected at each occurrence from 1 to 1,000,000.

In some embodiments, for the compound or salt of Formula (I), Q is an optionally substituted heteroalkyl group.

In some embodiments, for the compound or salt of Formula (I), Q is an optionally substituted peptide.

In some embodiments, for the compound or salt of Formula (I), Q is an optionally substituted peptide with from 1 to 500 amino acids. In some embodiments, for the compound or salt of Formula (I), Q is an optionally substituted peptide with from 1 to 50 amino acids. In some embodiments, for the compound or salt of Formula (I), Q is an optionally substituted peptide with from 1 to 10 amino acids. In some embodiments, for the compound or salt of Formula (I), Q is an optionally substituted peptide with from 1 to 3 amino acids.

In some embodiments, a compound or salt of Formula (I) is represented by a structure of Formula (IA), (IB), or (IC):

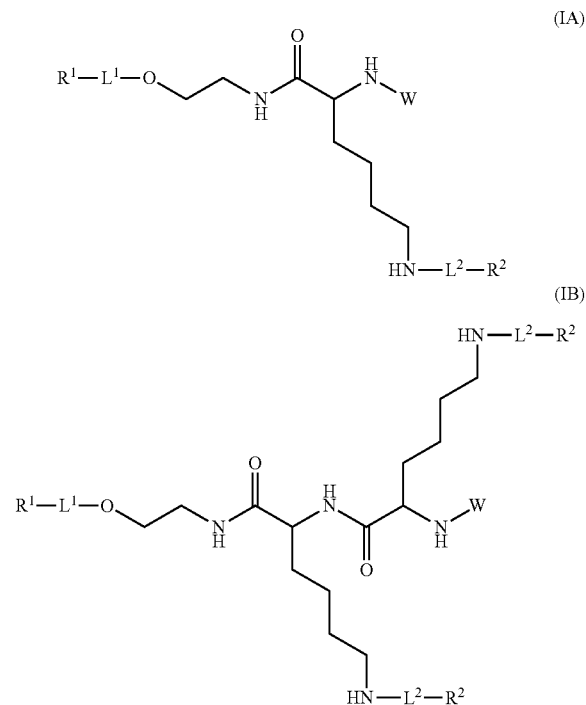

-continued

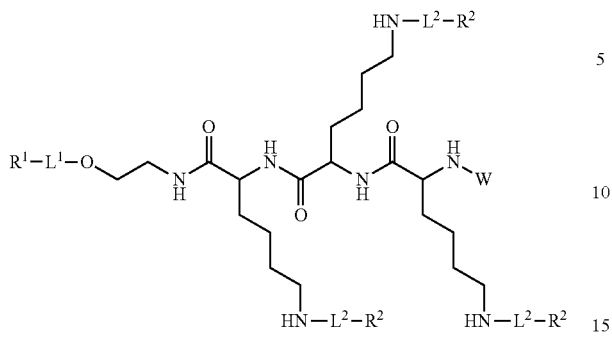

(IC)

wherein W is selected from hydrogen, optionally substituted alkyl, optionally substituted acyl, and optionally substituted alkoxycarbonyl.

In some embodiments, a compound or salt of Formula (I) is represented by a structure of Formula (ID), (IE), or (IF):

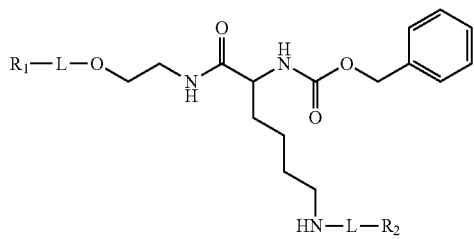

(ID)

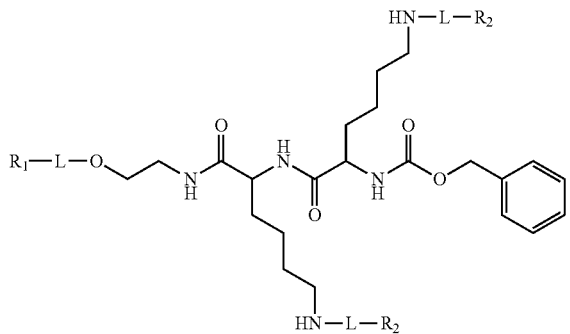

(IE)

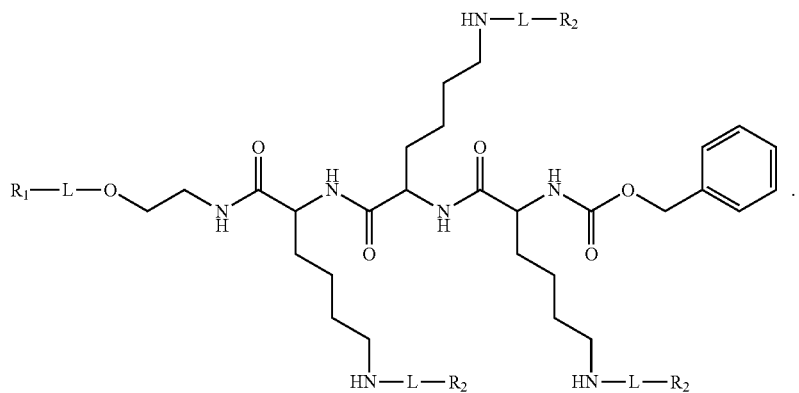

(IF)

In some embodiments, the compound or salt, wherein $R^1$ is independently selected at each occurrence from a GI enzyme inhibitor. In some embodiments, for the compound or salt of Formula (I), $R^1$ at each occurrence is a serine protease inhibitor. In some embodiments, for the compound or salt of Formula (I), Q at each occurrence is a trypsin inhibitor.

In some embodiments, for the compound or salt of Formula (I), $R^1$-$L^1$ is independently selected at each occurrence from:

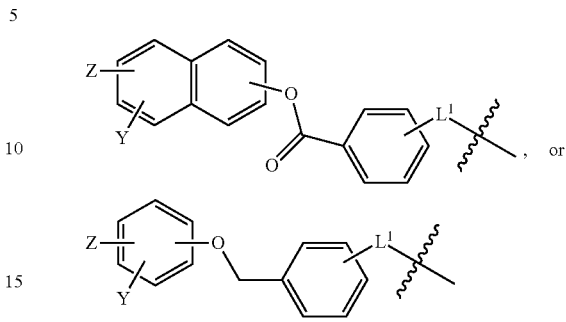

wherein:

Y is independently selected from an amidine, guanidine, benzylamine, alkyl substituted amidine, alkyl substituted guanidine, alkyl substituted benzylamine, benzylguanidine, alkyl substituted benzylamidine, or alkyl substituted benzyl; and Z is independently selected from hydrogen, cyano, nitro, halogen, alkyl and alkoxy.

In some embodiments, for the compound or salt of Formula (I), Y is amidine.

In some embodiments, for the compound or salt of Formula (I), $R^1$-$L^1$ is represented by the formula:

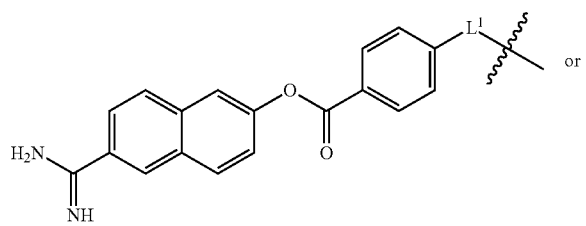

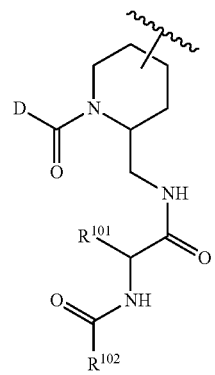

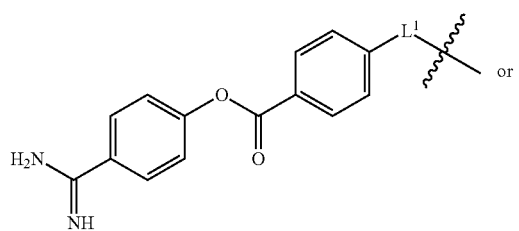

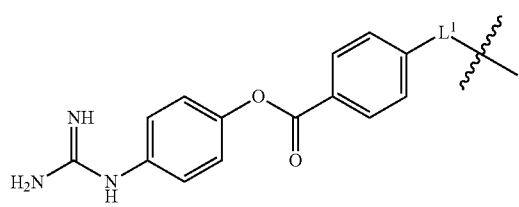

wherein:

D is an opioid agonist;

$R^{101}$ and $R^{102}$ are independently selected from optionally substituted alkyl, an amino acid side chain and an amino acid side-chain mimic.

In some embodiments, for the compound or salt of Formula (I), $R^{101}$ is selected from an amino acid side chain and $R^{102}$ is optionally substituted alkyl. In some embodiments, for the compound or salt of Formula (I), $R^{101}$ is selected from an arginine or lysine side chain and $R^{102}$ is optionally substituted methyl. In some embodiments, for the compound or salt of Formula (I), $R^{102}$ is methyl substituted with —NH-acetyl.

In some embodiments, for the compound or salt of Formula (I), D is selected from morphine, hydromorphone, hydrocodone, oxycodone, codeine, levorphanol, meperidine, methadone, oxymorphone, dihydrocodeine, tramadol, tapentadol, and buprenorphine. In some embodiments, for the compound or salt of Formula (I), D is represented by the formula:

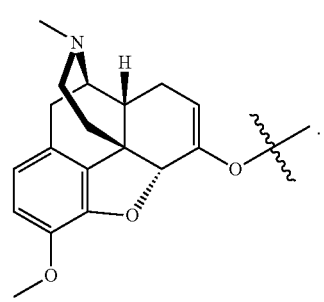

In some embodiments, for the compound or salt of Formula (I), $L^1$ at each occurrence is selected from a cleavable or non-cleavable linker including from 2 to 15 atoms.

In some embodiments, for the compound or salt of Formula (I), $L^1$ is —O—CH$_2$-CH$_2$—NH— or —O—CH$_2$-CH$_2$—O—.

In some embodiments, for the compound or salt of Formula (I), n is selected from 1 to 20. In some embodiments, for the compound or salt of Formula (I), n is selected from 1 to 10. In some embodiments, for the compound or salt of Formula (I), n is selected from 1 to 3.

In some embodiments, for the compound or salt of Formula (I), $R^2$-$L^2$ is independently selected at each occurrence from:

In some embodiments, for the compound or salt of Formula (I), m is selected from 1 to 20. In some embodiments, for the compound or salt of Formula (I), m is selected from 1 to 10. In some embodiments, for the compound or salt of Formula (I), m is 1 to 3.

In some embodiments, for the compound or salt of Formula (I), the compound is represented by the formula:

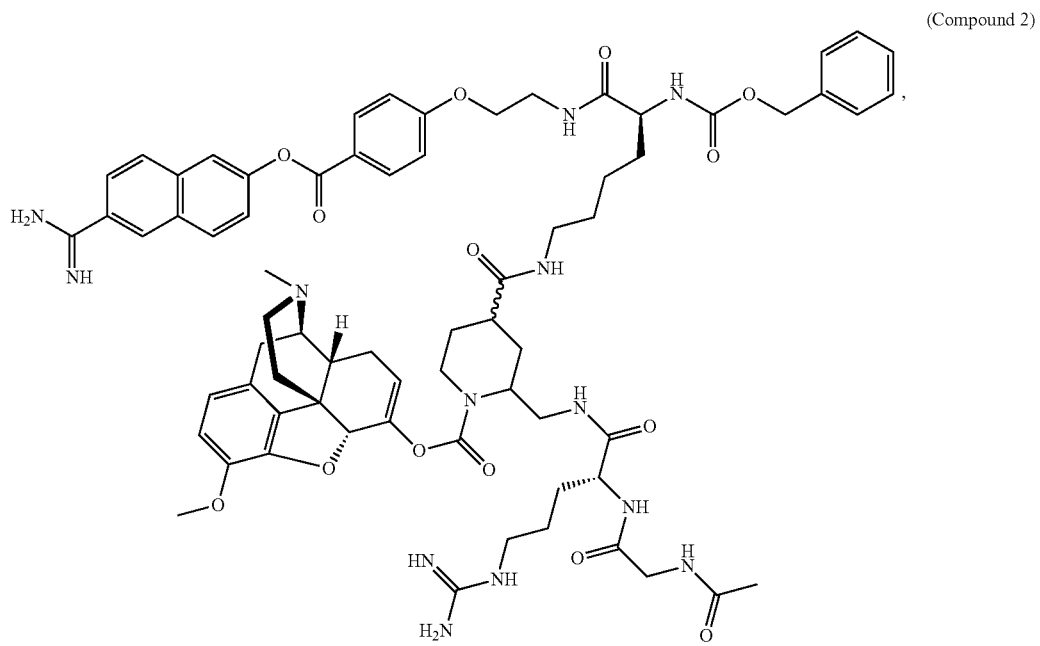

(Compound 2)

or a salt thereof.

In some embodiments, for the compound or salt of Formula (I), the compound is represented by the formula

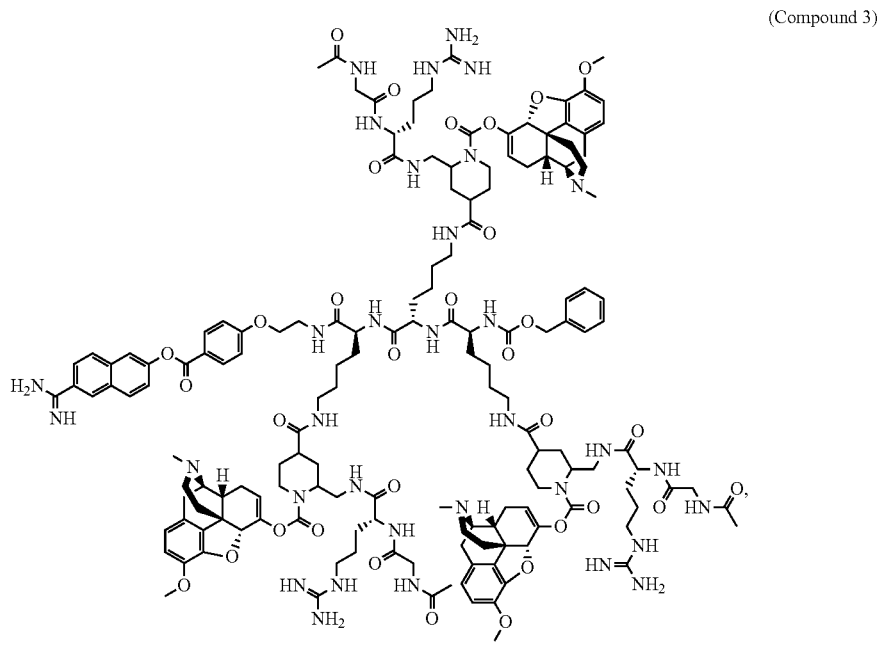

(Compound 3)

or a salt thereof.

In one aspect, the present disclosure provides a method of treating pain in a subject in need thereof, the method comprising administrating to the subject a therapeutically-effective amount of the compound or salt of Formula (I).

In one aspect, the present disclosure provides the compound or salt of Formula (I) and a pharmaceutically acceptable excipient.

In one aspect, the present disclosure provides a pharmaceutical formulation comprising:

an opioid prodrug;

a gastrointestinal enzyme inhibitor; and a scaffold, wherein the opioid prodrug and the inhibitor are covalently attached to the scaffold.

In one aspect, the present disclosure provides a pharmaceutical composition, the composition comprising:

an opioid prodrug comprising an opioid covalently bonded to a promoiety comprising a gastrointestinal enzyme-cleavable moiety; and a gastrointestinal enzyme inverse substrate wherein the opioid prodrug and the inverse substrate are covalently attached to a scaffold.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
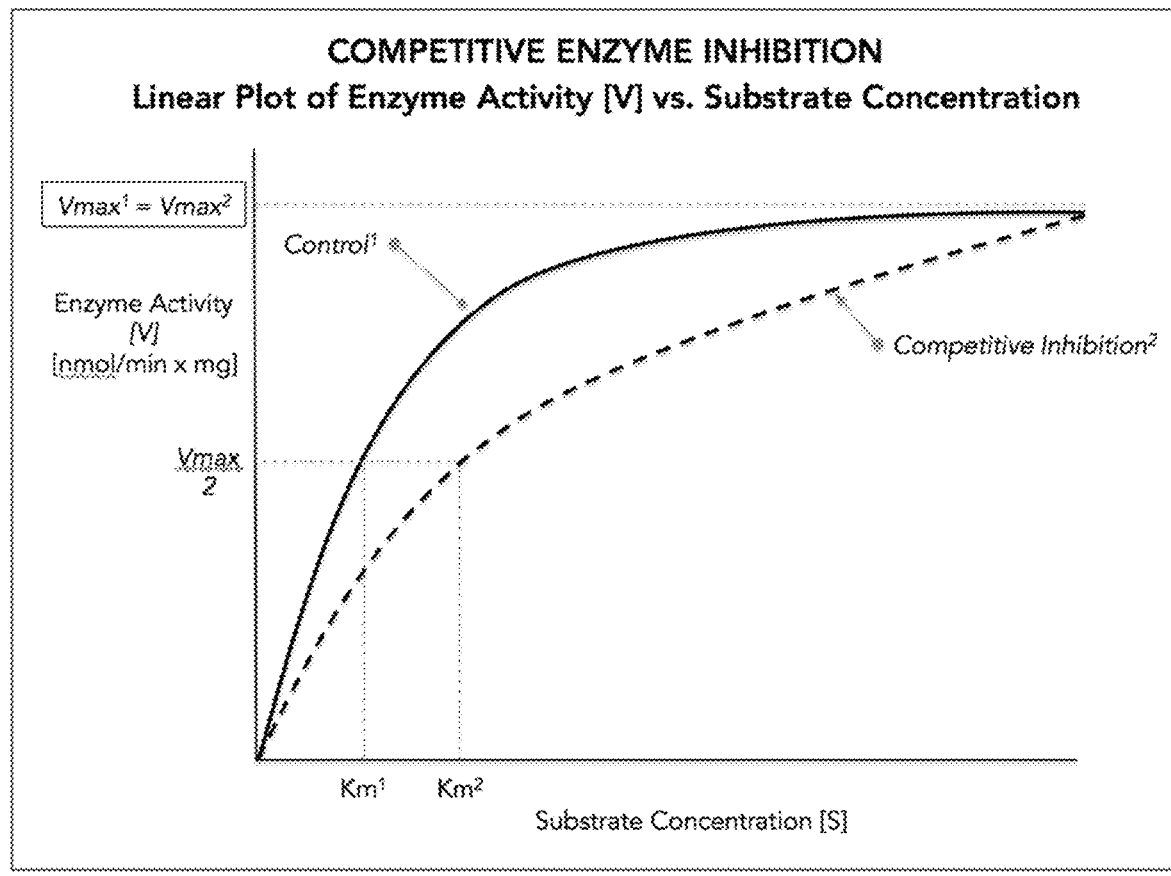
FIG. 1 illustrates the effects of competitive enzyme inhibition.

Typically, opioids pass rapidly through the blood-brain-barrier (BBB) and rapidly reach peak concentrations that produce the euphoria or "high" experienced by opioid abusers. Strategies to reduce opioid abuse have focused on formulation or alternative delivery strategies; such as orally administered delayed release tablets and transdermal patches. Abusers can easily defeat these formulations by crushing, chewing, or dissolving these formulations in commonly available household solvents, thereby enabling them to achieve the desired pharmacokinetic profile, and/or non-oral routes of administration, useful for achieving a "high". None of these technologies address the primary route of prescription opioid abuse—oral overdose. Thus, there exists a need for opioid drug products with lower abuse potential than currently available opioid products used in analgesia. In particular, there exists a need for new opioid drugs that (i) offer safe and effective pain relief to patients when taken as prescribed and (ii) prevent high plasma concentrations resulting from the co-ingestion of multiple pills, while (iii) effectively deterring non-oral abuse.

The present disclosure seeks to address these and other needs by providing a novel class of polysubstrate or polysubunit opioid analogs. The present disclosure provides unimolecular polysubstrate or polysubunit compositions comprising a GI enzyme-labile opioid releasing substrate or GI enzyme-labile opioid releasing substrates, covalently attached directly, or indirectly, via a molecular, oligomeric, or polymeric architecture, to a non-opioid releasing GI enzyme substrate or non-opioid releasing GI enzyme substrates, and an optional opioid antagonist releasing moiety or optional opioid antagonist releasing moieties. The present disclosure also provides unimolecular polysubunit compositions comprising a GI enzyme-labile opioid releasing substrate or GI enzyme-labile opioid releasing substrates, covalently attached directly, or indirectly, via a molecular, oligomeric, or polymeric architecture, to a non-opioid releasing GI enzyme inhibitor or non-opioid releasing GI enzyme inhibitors, and an optional opioid antagonist releasing moiety or optional opioid antagonist releasing moieties. These novel unimolecular polysubunit molecules are designed to (i) release effective levels of the covalently attached opioid agonist for the treatment of pain when ingested by compliant patients at the intended dose, (ii) prevent oral overdose or abuse of the composition via novel enzyme saturation or inhibition processes when multiple pills containing the composition are co-ingested by potential abusers (or accidentally by children), and may (iii) produce a safe, non-abusable mixture of opioid agonist and opioid antagonist when potential abusers tamper with pills containing the composition.

These polysubunit opioid analogs can be further designed to have a high molecular weight and/or possess a highly charged state at physiological pH ranges to prevent or minimize absorption from the GI tract, thereby (i) reducing their systemic exposures (and resulting safety risks) to the subject, and (ii) maximizing the efficiency of both the opioid delivery and overdose protection mechanisms.

In one aspect, the invention provides a pharmaceutical composition comprising a GI enzyme-labile opioid releasing substrate or GI enzyme-labile opioid releasing substrates, and a non-opioid releasing GI enzyme substrate or non-opioid releasing GI enzyme substrates, wherein the GI enzyme-labile opioid releasing substrate(s), and the non-opioid releasing GI enzyme substrate(s) are covalently attached directly to each other or to a molecular scaffold. In another aspect, the invention provides a pharmaceutical composition comprising a GI enzyme-labile opioid releasing substrate or GI enzyme-labile opioid releasing substrates, and a non-opioid releasing GI enzyme inhibitor or non-opioid releasing GI enzyme inhibitors, wherein the GI enzyme-labile opioid releasing substrate(s), and the non-opioid releasing GI enzyme inhibitor(s) are covalently attached directly to each other or to a molecular scaffold. When patients ingest the pharmaceutical compositions defined herein, endogenous GI enzymes release targeted therapeutic levels of the opioid agonist. When excessive doses of pharmaceutical compositions defined herein are ingested, the GI enzyme that releases the opioid agonist becomes saturated or inhibited so that increases in doses ingested do not lead to proportional increases in the amount of opioid agonist released. The opioid agonist can be selected from the group consisting of morphine, hydromorphone, hydrocodone, oxycodone, codeine, levorphanol, meperidine, methadone, oxymorphone, dihydrocodeine, tramadol, tapentadol, and pharmaceutically acceptable salts, prodrugs, and mixtures thereof. The opioid antagonist is selected from naltrexone and naloxone. In some embodiments, the molecular scaffold is an oligomeric scaffold. In other embodiments, the molecular scaffold is a polymeric scaffold.

Definitions

Unless otherwise stated, the following terms used in this application, including the specification and claims, have the definitions given below. Definition of standard chemistry terms may be found in reference works, including Carey and Sundberg (2004) "Advanced Organic Chemistry 4rd Ed." Vols. A and B, Springer, New York. The practice of the present invention will employ, unless otherwise indicated, conventional methods of mass spectroscopy, protein chemistry, biochemistry, synthetic organic chemistry, and pharmacology, within the skill of the art.

The term "alkyl" or "lower alkyl" means the monovalent branched or unbranched saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, butyl, isobutyl, sec-butyl, tert-butyl, pentyl, n-hexyl, octyl, dodecyl, and the like.

The term "alkylene" as used herein means the divalent linear or branched saturated hydrocarbon radical, consisting solely of carbon and hydrogen atoms, having from one to eight carbon atoms inclusive, unless otherwise indicated. Examples of alkylene radicals include, but are not limited to, methylene, ethylene, trimethylene, propylene, tetramethylene, pentamethylene, ethylethylene, and the like.

The term "alkenylene" means the divalent linear or branched unsaturated hydrocarbon radical, containing at least one double bond and having from two to eight carbon atoms inclusive, unless otherwise indicated. The alkenylene radical includes the cis or trans ((E) or (Z)) isomeric groups or mixtures thereof generated by the asymmetric carbons. Examples of alkenylene radicals include, but are not limited to ethenylene, 2-propenylene, 1-propenylene, 2-butenyl, 2-pentenylene, and the like.

The term "aryl" means the monovalent monocyclic aromatic hydrocarbon radical consisting of one or more fused rings in which at least one ring is aromatic in nature, which can optionally be substituted with hydroxy, cyano, lower alkyl, lower alkoxy, thioalkyl, halogen, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of aryl radicals include, but are not limited to, phenyl, naphthyl, biphenyl, indanyl, anthraquinolyl, and the like.

The term "agonist" means a molecule such as a compound, a drug, an enzyme activator or a hormone that enhances the activity of another molecule or the activity of the target receptor.

The term "amino acid" refers to either natural and/or unnatural or synthetic amino acids, and both the D- or L-optical isomers, the N-acyl and N-methyl derivatives thereof, and amino acid analogs, isosteres, and peptidomimetics. The natural amino acids include alanine, arginine, asparagine, cysteine, glutamic acid, glutamine, glycine, histidine, isoleucine, leucine, methionine, phenylalanine, proline, serine, threonine, tryptophan, tyrosine, valine, selenocysteine, and pyrrolysine.

Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine, and methyl sulfonium. Such analogs have modified side-chain groups, such as norleucine, homoarginine, homolysine, ε-N-methyl lysine, ε,ε-N,N-dimethyl lysine, ε,ε,ε-N,N,N-trimethyl lysine, ornithine, and the like, or modified peptide backbones, but retain the same basic chemical structure as a naturally occurring amino acid. Amino acid mimetics (or mimics) refers to chemical compounds that have a structure that is different from the general chemical structure of an amino acid, but functions in a manner similar to a naturally occurring amino acid. For example, the unnatural amino acid L-(7-hydroxycoumarin-4-yl)ethylglycine (or 7-hydroxycoumarin-ethylglycine) finds use with the invention.

The terms "enzymatically degradable" or "enzyme-labile" refer to a molecular entity that is subject to degradation by one or more enzymes under ordinary physiological conditions.

The term GI refers to "gastrointestinal." The term "gastrointestinal enzyme" or "GI enzyme" refers to an enzyme located in, derived from, or on, the gastrointestinal tract (GI tract), such as trypsin, chymotrypsin, elastase, tryptase, and the like.

The term "polysubstrate" or "polysubunit" refers to a compound of the invention designed to release an opioid agonist when administered to a subject. The release profile of the opioid agonist from a polysubstrate or polysubunit can be attenuated in vivo when overdoses are ingested via an enzyme saturation mechanism. In addition, polysubstrates or polysubunits of the invention may also release an opioid antagonist when subjected to chemical tampering by, or when administered via non-oral routes to, potential abusers.

"Gastrointestinal enzyme substrate" or "GI enzyme substrate" refers to a group comprising a site susceptible to cleavage by a GI enzyme. For example, a "trypsin-substrate" refers to a group comprising a site susceptible to cleavage by trypsin. Specifically, GI enzyme hydrolysis of a non-opioid-releasing GI enzyme substrate does not result in opioid release, and enzyme-mediated hydrolysis of an opioid-releasing GI enzyme substrate results directly, or indirectly, in opioid release.

The term "opioid-releasing gastrointestinal enzyme substrate subunit" or "opioid-releasing GI enzyme substrate subunit" refers to a group comprising an opioid and a site susceptible to cleavage by a GI enzyme. For example, an "opioid releasing trypsin-substrate" refers to a group comprising a site susceptible to cleavage by trypsin that directly, or indirectly, releases an opioid after being hydrolyzed by trypsin.

The term "non-opioid-releasing gastrointestinal enzyme substrate" or "non-opioid-releasing GI enzyme substrate" refers to a group comprising a site susceptible to cleavage by a GI enzyme. For example, a "non-opioid releasing trypsin-substrate" refers to a group comprising a site susceptible to cleavage by trypsin that does not directly, or indirectly, release an opioid after being hydrolyzed by trypsin. Also included are inverse substrates. Inverse substrates refer to any agent capable of acting as an inverse substrate for a digestive enzyme. Inverse substrates are designed to bind to, and be hydrolyzed by, enzymes in a manner that is "inverse" to "normal" substrates. With "normal" substrates, the amino acid (or amino acid mimic) recognized by the enzyme connects to the C-terminus of carbonyl containing group to be hydrolyzed (e.g. amide, ester, etc.), which is further connected to a leaving group (e.g. amine or alcohol, etc.). In contrast, inverse substrates have the amino acid, or amino acid mimic, recognized by the enzyme directly connected to the leaving group of the carbonyl group undergoing hydrolysis by the enzyme. The term also encompasses salts of gastrointestinal enzyme inverse substrates. For example, a "trypsin inverse substrate" refers to any agent capable of acting as an inverse substrate for trypsin.

The term "halogen" as used herein refers to fluorine, bromine, chlorine and/or iodine.

The term "inhibitor" refers to any agent capable of inhibiting the action of an enzyme on a substrate. For example, a trypsin inhibitor refers to any agent capable of inhibiting the action of trypsin on a substrate.

The term "modulator" means a molecule that interacts with a target. The interactions include, but are not limited to, agonist, antagonist, and the like, as defined herein.

"PEG" or "polyethylene glycol," as used herein, is meant to encompass any water-soluble poly(akylene oxide). Typically, PEG oligomers for use in the present invention contain $—(CH_2CH_2O)_n—$ or $—(CH_2CH_2O)_n—CH_2CH_2—$, but can also include polyalkylene glycols including, but not limited to polypropylene- or polybutylene glycols where the number of monomer units can be from about 2 to 1000, or about 2 to about 200.

As used herein, the terms "treat" and "treatment" are used interchangeably and are meant to indicate a postponement of development of diseases and/or a reduction in the severity of such symptoms that will or are expected to develop. The terms further include ameliorating existing symptoms, preventing additional symptoms, and ameliorating or preventing the underlying symptoms.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

In one aspect of the invention, compositions comprising a GI enzyme-labile opioid agonist releasing substrate ($S_2$ subunit) or GI enzyme-labile opioid agonist releasing substrates ($S_2$ subunits), and a non-opioid releasing GI enzyme substrate ($S_1$ subunit) or non-opioid releasing GI enzyme substrates ($S_1$ subunits), and an optional opioid antagonist releasing moiety ($S_3$ subunits), or optional opioid antagonist releasing moieties ($S_3$ subunits), are administered to a patient for the prevention and/or treatment of pain. The GI enzyme-labile opioid agonist releasing substrates ($S_2$ subunits) and the non-opioid releasing gastrointestinal (GI) enzyme substrates ($S_1$ subunits) and the optional opioid antagonist releasing moieties ($S_3$ subunits) can be covalently attached to each other via suitable linkers (Z), or assembled onto, or independently attached to, a suitably functionalized oligomer, macromolecule, or polymer via covalent linkages. In some embodiments, the release of the opioid agonist is mediated by a specific GI enzyme, whereby the opioid agonist is released concomitant with, or subsequent to, the action of a specific GI enzyme on a specific portion of the polysubstrate molecule.

In another aspect of the invention, compositions comprising a GI enzyme-labile opioid agonist releasing substrate ($S_2$ subunits) or GI enzyme-labile opioid agonist releasing substrates ($S_2$ subunits), and a non-opioid releasing GI enzyme inhibitor or non-opioid releasing GI enzyme inhibitors ($S_1$ subunits), and an optional opioid antagonist releasing moiety ($S_3$ subunits), or optional opioid antagonist releasing moieties ($S_3$ subunits), are administered to a patient for the prevention and/or treatment of pain. The GI enzyme-labile opioid agonist releasing substrates ($S_2$ subunits) and the non-opioid releasing gastrointestinal (GI) enzyme inhibitors ($S_1$ subunits) and the optional opioid antagonist releasing moieties ($S_3$ subunits) can be covalently attached to each other via suitable linkers (Z), or assembled onto, or independently attached to, a suitably functionalized oligomer, macromolecule, or polymer via covalent linkages. In some embodiments, the release of the opioid agonist is mediated by a specific GI enzyme, whereby the opioid agonist is released concomitant with, or subsequent to, the action of a specific GI enzyme on a specific portion of the polysubstrate molecule.

The opioid agonist releasing GI enzyme substrate ($S_2$) can release alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, tramadol, mixtures of any of the foregoing, salts thereof, prodrugs thereof, and derivatives, analogs, homologues, and polymorphs thereof. The opioid agonist releasing substrates and the non-opioid releasing GI enzyme substrates or inhibitors can be targeted by trypsin, and can be an alkylguanidine, alkylamidine, alkylamine, arylguanidine, arylamidine, or arylamine-based substrate, and salts thereof. The GI enzyme labile opioid releasing $S_2$ substrates and the non-opioid releasing $S_1$ GI enzyme inverse-substrates or inhibitors are preferably covalently linked to each other directly, or linked to each other indirectly via attachment to the same molecular scaffold in a suitable ratio, or co-assembled via covalent attachment to the same oligomer or polymer, such as poly-amino acid, poly-D-amino acid, poly N-methyl (D-, or L-) amino acid, a "biopolymer", or poly-alkylene glycol (e.g. PEG).

Linking moieties, or linkers "Z", are utilized for purposes of the invention for covalently conjoining one or more of the components defined herein (e.g. the $S_1$, $S_2$, $S_3$, and I subunits; and the molecular, oligomeric, or polymeric scaffolds). Based on this defined functionality, the scope of useful linkers for the present invention is intended to be broad. In an effort to define the broad scope of useful linkers, and provide non-limiting specific examples of linkers of use for the in the present invention, an array of the terminal functionalities that may be present on representative linkers, and their chemical composition are presented below. The specific choice of linker unit, or units, incorporated into particular embodiments of the invention will vary based on the molecular structures of the entities that they conjoin, with specific regard to the available atoms or functional groups present on the specific elements that they covalently conjoin. Thus, it is intended that the specific composition of linking moieties useful for the invention can vary widely with regard to composition, size (i.e. length), geometry, valency, and functional groups present on their termini.

Linking moieties can be divalent—covalently adjoining two polysubstrate components, or trivalent—adjoining several polysubstrate components, or can be multivalent—adjoining a multiplicity of polysubstrate components.

In some embodiments, linking moieties "Z" of use for the invention are described by the general formulae:

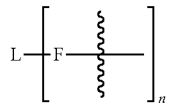

and can also be defined by

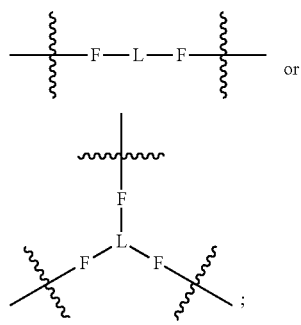

Exemplary terminal linker functionalities "F" can each or independently be as shown below:

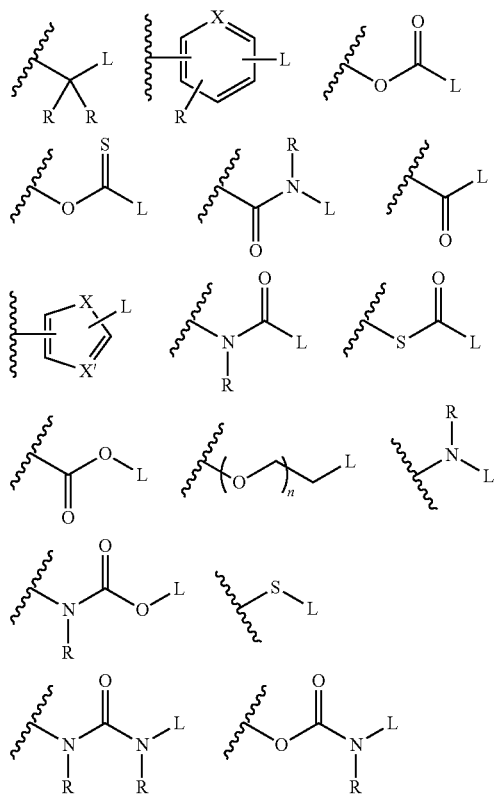

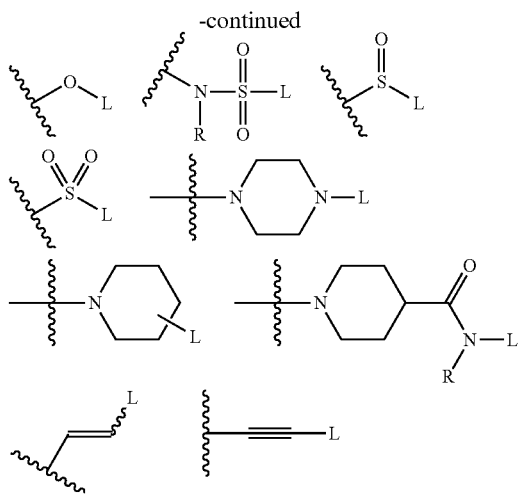

wherein:
each R is independently hydrogen, methyl, lower alkyl, aryl, or arylalkyl;
X is carbon, oxygen, or nitrogen;
L is a linear, branched, or multivalent scaffold which is alkyl, aryl, substituted alkyl, substituted aryl, heteroalkyl, substituted heteroalkyl, polyalkylene glycol, polypeptide, polyamide, polycarbamate, polyurea, or polycarbonate.

In some embodiments, L is formed of 0-100 atoms. In some embodiments, L is formed of 1-50 non-hydrogen atoms as well as additional hydrogen atoms. Such atoms may be, for example, C, N, O, P or S. In other embodiments, L may connect two or more groups comprising 1 to 50 consecutive bonds between the groups. L may have 1 to 40, 1 to 30, 1 to 20, 1 to 10, 1 to 5, 5 to 25, or 5 to 20 such consecutive bonds.

In some embodiments, compounds or compositions of the invention may have the advantages that they and their post-enzyme hydrolysis products are minimally or not absorbed by the subject, and the expected enzymatic hydrolysis of compounds of the invention can be designed to produce systemic exposures of only the opioid analgesic, and generally regarded as safe (GRAS) metabolites following oral ingestion.

Further, the compositions of the invention prevent overdose via the oral route. If multiple pharmaceutical oral dosage forms are co-ingested, such as co-ingestion of tablets or capsules containing compositions of the invention, the resulting concentration reaches a high enough level in the small intestine to effectively saturate or inhibit the digestive enzyme that mediates the release of the opioid. This saturation or inhibition of the digestive enzyme that mediates opioid release results from careful tuning of the kinetics attending the enzyme hydrolysis of, (i) the non-opioid releasing ($S_1$) substrate subunits, and (ii) the opioid releasing ($S_2$) substrate subunits that are covalently assembled. In some preferred embodiments of the invention, the digestive enzyme (e.g. trypsin) recognizes and interacts with, the non-opioid releasing substrate moieties much more rapidly than it recognizes and interacts with the opioid releasing substrate moieties. Importantly, the resulting saturation of the digestive enzyme that mediates release of the opioid agonist under overdose conditions can be extensive and sustained due to the very low absorbability of the opioid releasing polysubstrate analogs, and the fact that the covalently assembled non-opioid releasing ($S_1$) substrate subunits and the ($S_2$) opioid-releasing substrate subunits cannot separately partition away from each other. Thus, intentional ingestion of multiple pills of the invention will not enable abusers to achieve the desired pharmacokinetic profile for achieving a "high" or euphoric state. Furthermore, accidental co-ingestion of multiple pills by young children, the elderly, or the subjects will be less likely to produce toxic or lethal effects.

Without being limited by theory, the current invention provides opioid releasing compositions that can protect individuals from opioid overdoses via an enzyme saturation mechanism. Enzyme inhibition and enzyme saturation are highly distinct processes that have been described in detail, for example, in: "Enzymes: A Practical Introduction to Structure, Mechanism, and Data Analysis by Robert A. Copeland, 2000, Wiley-VCH, Inc"; incorporated herein by reference in its entirety.

Figure 2:
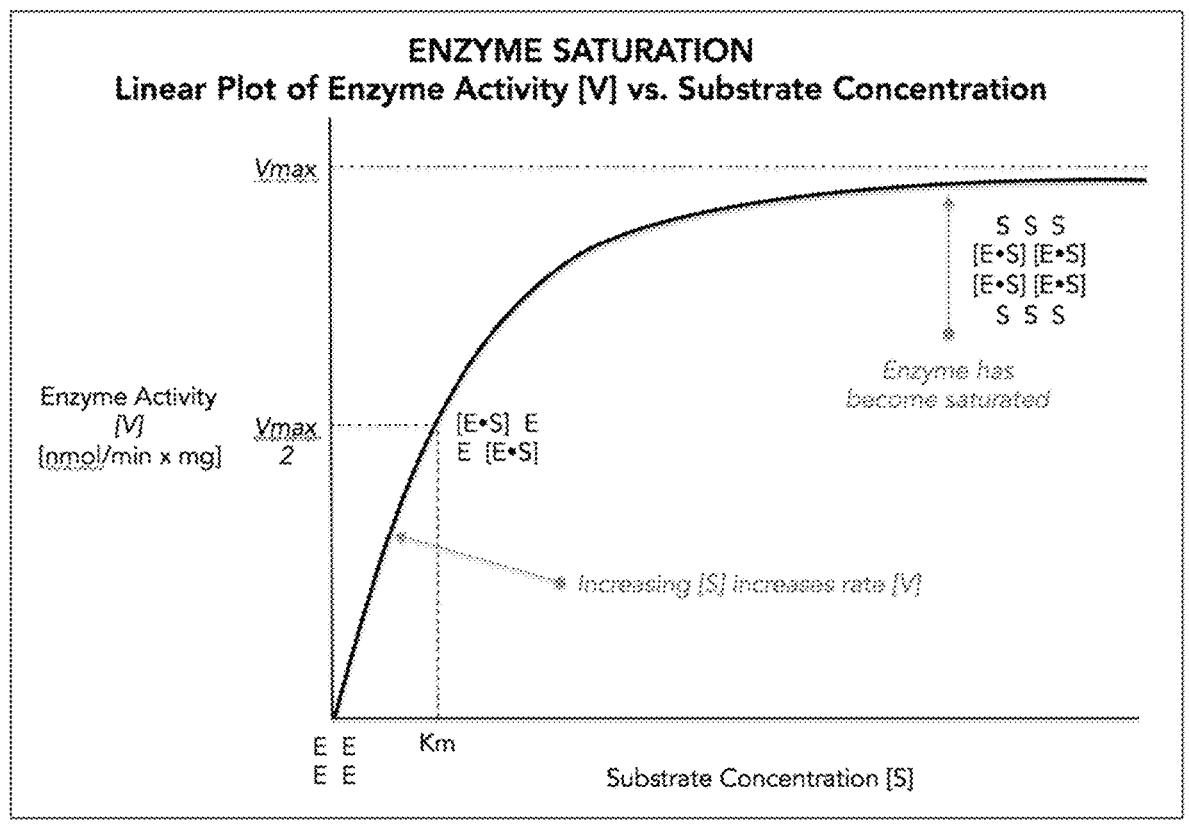
FIG. 2 illustrates the kinetics of enzyme saturation.

Mechanistic differences between enzyme inhibition and enzyme saturation are graphically illustrated in FIG. 1 and FIG. 2. The solid "control" line in FIG. 1 shows the relationship between substrate concentration and enzyme activity (i.e. the rate or "velocity" at which substrate is processed by the enzyme) for a given enzyme plus substrate system. $V_{max}$ is the maximum velocity that the enzyme can achieve and is realized at substrate concentrations whereby the enzyme becomes saturated. $K_m$ refers to the concentration of substrate where the velocity of the enzyme is equal to $V_{max}/2$, or when 50% of the enzyme active sites are occupied by substrate. The dashed line in FIG. 1 represents how enzyme activity as a function of substrate concentration is perturbed via the addition of a separate enzyme inhibitor molecule (e.g. competitive inhibitor). It is important to note that under the conditions of competitive inhibition, the value for Km is increased while the value for $V_{max}$ remains unchanged.

The process of enzyme saturation, described graphically in FIG. 2, is distinct from enzyme inhibition. As represented by the curved line in FIG. 2, the rate (i.e. velocity) at which a specific enzyme reacts with a specific substrate, increases as the substrate concentration increases through the concentration defined as $K_m$, at which point half of the enzyme active sites are occupied by substrate molecules and a rate of $V_{max}/2$ is achieved, until the substrate concentration reaches a level at which the enzyme becomes "saturated" and the maximal rate of $V_{max}$ is realized. At the point of saturation, further increases in substrate concentration do not produce further increases in the rate that the enzyme can process the substrate and excess substrate molecules begin to accumulate.

The opioid releasing polysubstrates of the present invention provide overdose protection via the mechanism of enzyme saturation. When a prescribed dose of a polysubstrate is ingested, the rate at which the targeted digestive enzyme mediates opioid agonist release from the $S_2$ subunits will be sufficient to provide the compliant patient with the intended opioid agonist exposure.

Figure 3:
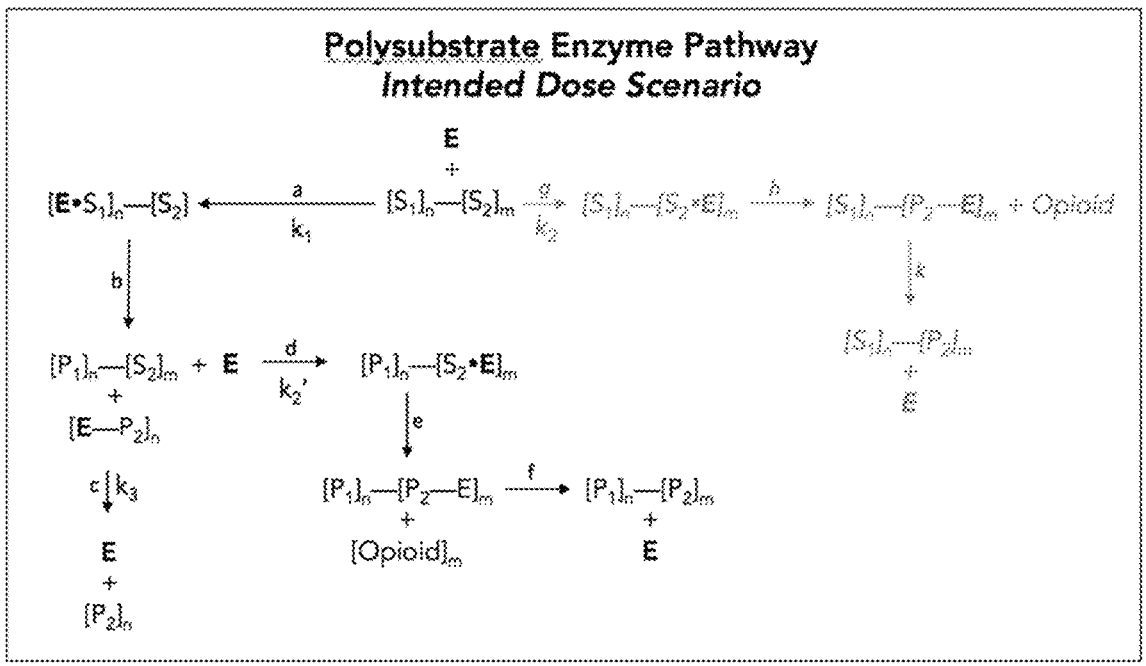
FIG. 3 illustrates a predicted enzyme pathway when an intended dose of a polysubstrate of the disclosure is ingested (black font).
Figure 4:
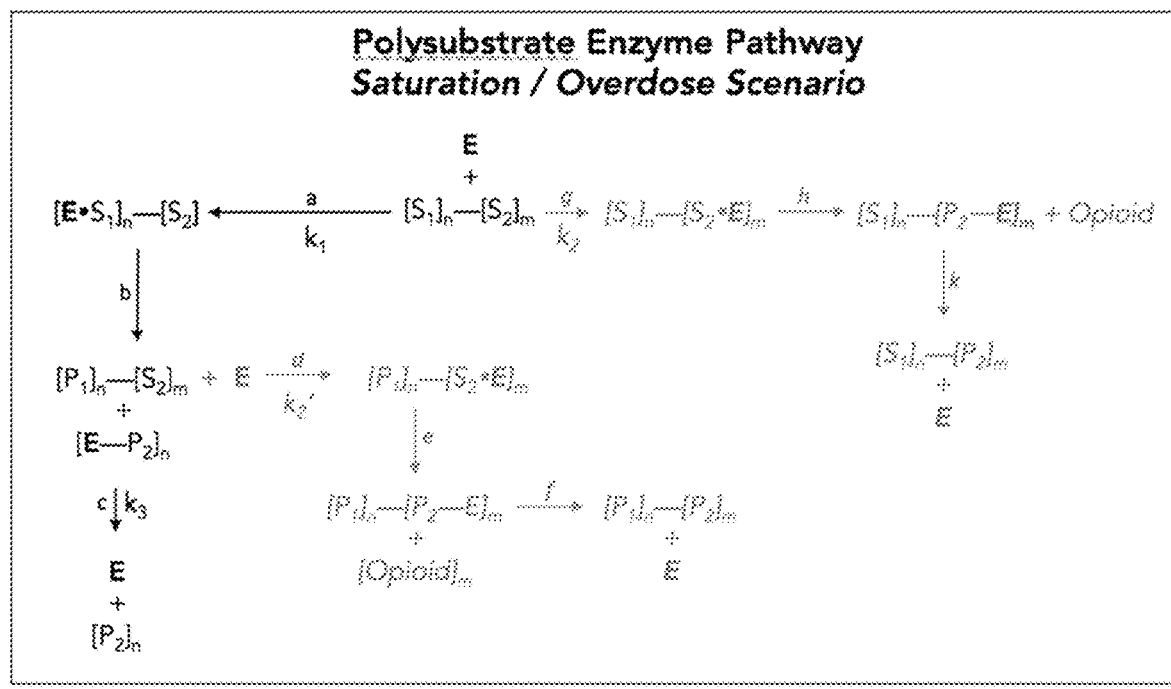
FIG. 4 illustrates saturation of the predicted enzyme pathway when excessive doses of a polysubstrate of the disclosure are ingested (black font).

The enzyme kinetics attending the digestive enzyme-mediated delivery of opioid agonist following ingestion of a single prescribed dose, and of an overdose, of polysubstrate are presented in FIG. 3 and FIG. 4. By design, recognition of the $S_1$ subunits by the targeted digestive enzyme proceeds at a significantly greater rate than recognition of the $S_2$ substrate subunit ($k_1 >> k_2$). This renders the pathway involving steps g, h, and k (shaded gray in FIGS. 3 and 4) as an unlikely, or very minor, pathway for the release of opioid agonist from the $S_2$ subunits of the polysubstrate following ingestion. By design, release of opioid agonist from the $S_2$ subunits of a polysubstrate likely proceeds via the multistep pathway described by a, b, d, and e in FIG. 3. By design, the predominant pathway for enzyme hydrolysis of polysubstrates of the invention involve the hydrolysis of the $S_1$ subunits via the pathway defined as a, b, and c. An important aspect of the design of polysubstrates, more specifically the design of the $S_1$ substrate subunits, is that step c is a slow process ($k_3$ is very small). At the intended dose of polysubstrate, the concentration of the polysubstrate in the lumen of the gastrointestinal tract is such that there is a sufficient surplus of active enzyme available after steps b and c are completed to mediate steps d and e resulting in the efficient delivery of opioid agonist from the $S_2$ subunits of the polysubstrate molecule. In contrast, when excessive doses of polysubstrate are ingested (FIG. 4), the concentration of the polysubstrate in the lumen of the gastrointestinal tract is such that there is an insufficient surplus of active enzyme available after steps b and c are completed to effectively mediate steps d and e (now shaded gray in FIG. 4). Under overdose conditions, the pathway defined by a, b, and c effectively saturates the enzyme. As a result, the delivery of opioid agonist from the $S_2$ subunits of the polysubstrate molecule is attenuated. Importantly, the critical relationships between $k_1$, $k_2$, and $k_3$ can be tuned by chemical modifications (presented herein) to the $S_1$ and $S_2$ subunits, to provide meaningful oral overdose protection. Note that the optional opioid antagonist releasing $S_3$ subunit that can be present in polysubstrates of the invention, is not a digestive enzyme substrate and has been omitted from the polysubstrates illustrated in FIGS. 3 and 4 for mechanistic clarity.

Figure 5:
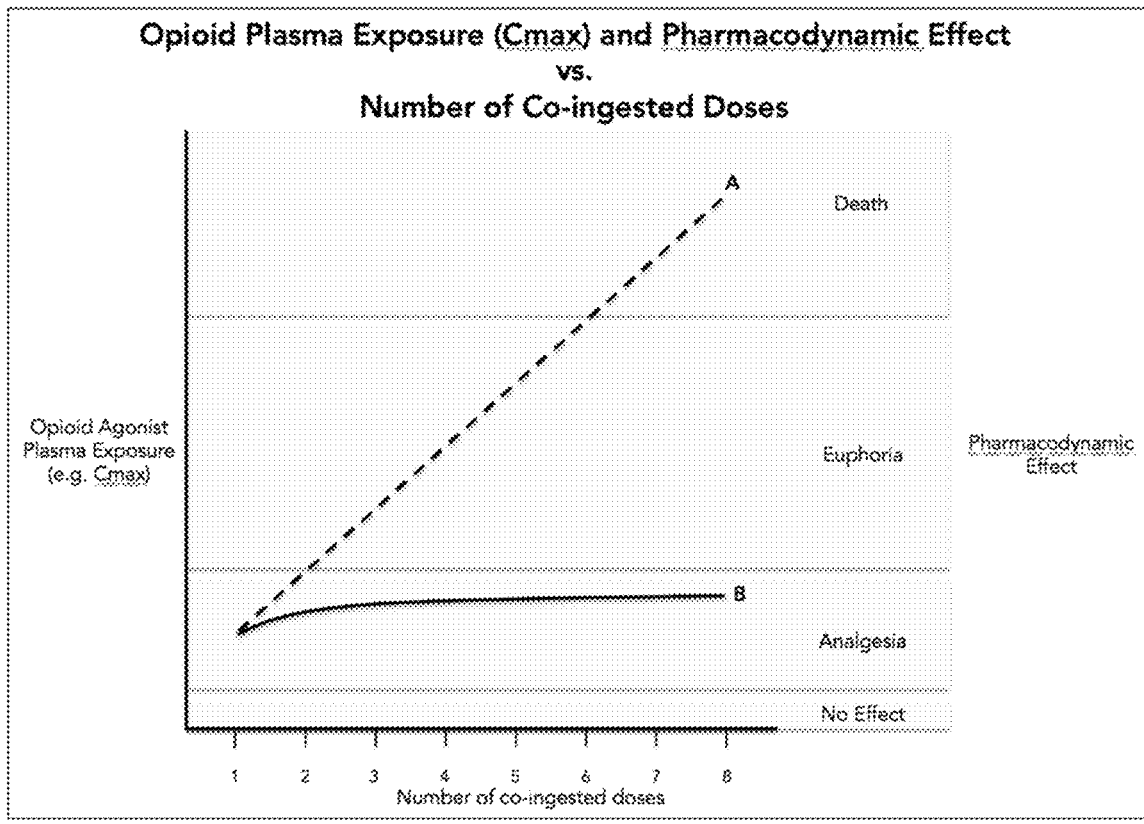
FIG. 5 is a graph illustrating an example of the predicted pharmacodynamic and pharmacokinetic parameters of (A) an opioid agonist, and (B) an opioid agonist delivered by a polysubstrate of the disclosure.

By design, the rate of opioid agonist release will not be proportional to the number of doses (aka pills) co-ingested. FIG. 5 graphically compares representative opioid agonist plasma exposures (Cmax) and pharmacodynamic effect profiles common to all current generic and emerging abuse-resistant opioid drug products (line A), to a representative polysubstrate of the invention that provides oral overdose protection (curve B).

Advantages of the subject polysubunit approaches include:

(i) The ability to readily tune the "saturation profile" (i.e. $V_{max}$ and the saturation concentration), and thereby the overdose protection profile, of polysubstrates of the invention using chemical modifications to the nature and/or number of the $S_1$ and/or $S_2$ subunits contained in the polysubstrate molecules. In addition, the ability to readily tune the "inhibition profile" (i.e. $V_{max}$), and, thereby, the overdose protection profile, of polysubunits of the invention using chemical modifications to the nature and/or number of the $S_1$ and/or $S_2$ subunits contained in the polysubunit molecules.

(ii) Compounds of the invention are unimolecular and thereby prevent partitioning of the covalently linked $S_1$ and $S_2$ substrate subunits in vivo. Consequently, the overdose protection afforded by compounds of the invention can be persistent during the time required for transport through the gastrointestinal tract where the digestive enzymes capable of effecting opioid agonist release are present.

(iii) By design, the enzymatic pathways for hydrolysis of polysubstrates and polysubunits are chemoselective, and mediated primarily by the action of the digestive enzyme they are designed to target/saturate within the gastrointestinal tract.

(iv) Compounds of the invention can be high molecular weight, and/or poly-charged molecules. In such embodiments, absorption of polysubstrates or polysubunits, or their resulting post-hydrolysis products, from the gastrointestinal tract into the systemic circulation is minimized. This serves to maximize drug delivery efficiency as effective opioid agonist delivery requires that the polysubstrate or polysubunit be exposed to digestive enzymes accessed primarily in the lumen of the gastrointestinal tract. Further, minimizing the systemic exposure of polysubstrates and polysubunits can provide important benefits from both safety and clinical development perspectives.

(v) Compounds of the invention can be designed to release opioid antagonist molecules when subjected to chemical tampering methods by potential abusers, or when exposed to enzymes found in the plasma, blood, liver, or other systemically accessible tissues.

Enzyme-Labile Opioid Agonist Releasing Polysubunit Analogs

The disclosure provides for compounds and compositions comprising subunits that interact with gastrointestinal (GI) or digestive enzymes. Such a composition can be specifically hydrolyzed by at least one of any of the GI enzymes disclosed herein. The GI enzyme can be, for example, pepsin, trypsin, chymotrypsin, colipase, elastase, aminopeptidases, dipeptidylaminopeptidase IV, tripeptidase, enteropeptidases, carboxypeptidases, dipeptidal aminopeptidases, pteroyl polyglutamate hydrolyase, gamma-glutamyl transferase, aminoaspartate aminopeptidases, amino-oligopeptidase, membrane Gly-Leu peptidase, and zinc stable Asp-Lys peptidase).

An example of a GI enzyme subunit is a protease substrate, such as a trypsin substrate, or a chymotrypsin substrate.

As used herein, the term "trypsin substrate" refers to any agent capable of being hydrolyzed by the action of trypsin, and includes salts of trypsin substrates. The ability of an agent to be a substrate for trypsin can be measured using assays well known in the art. For example, in a typical assay, one can directly measure the rate and extent of expected hydrolysis products formed in incubations containing specified concentrations of digestive enzymes and substrates using common HPLC or spectrophotometric detection methods.

There are many trypsin substrates or inhibitors known in the art, and include substrates or inhibitors that are specific to trypsin and those that are specific to other proteases such as chymotrypsin. Trypsin substrates or inhibitors include natural, synthetic, and semi-synthetic compounds. The disclosure provides for trypsin substrates or inhibitors that are proteins, peptides, and small molecules. The disclosure also provides for trypsin substrates that are hydrolyzed via "normal" or "inverse" substrate mechanisms. A trypsin substrate or inhibitor can be an arginine mimic or lysine mimic. In certain embodiments, the trypsin substrate or inhibitor is an arginine mimic or a lysine mimic, wherein the arginine mimic or lysine mimic is a synthetic compound. As used herein, an arginine mimic or lysine mimic can include moieties capable of binding to the specificity pocket of trypsin and/or interacting with the trypsin active site functionalities. The arginine or lysine mimic can comprise a cleavable moiety. In some embodiments, cleavage of the cleavable moiety will directly, or indirectly result in release of an opioid agonist from the substrate moiety. In some embodiments, cleavage of the cleavable moiety will not result in release of an opioid agonist from the substrate moiety. In some cases, when supra-therapeutic doses (overdoses) are ingested, the cleavage of $S_1$ subunits will saturate the capacity of the enzyme to cleave the cleavable moieties that directly, or indirectly, release opioid agonists resulting in overdose protection. In some cases, when supra-therapeutic doses (overdoses) are ingested, progressive enzyme inhibition by the $S_1$ subunits results in overdose protection.

Examples of trypsin substrates which are arginine mimics and/or lysine mimics include a cationic specificity pocket binding moiety designed to bind to the negatively charged specificity pocket of the enzyme and a hydrolysable functionality that is cleaved by the active site of the enzyme. Cationic specificity pocket binding moieties include, but are not limited to, alkyl-amines, alkylguanidines, alkylamidines, arylguanidines, benzamidines, benzylamines, naphthylamidines, naphthylguanidines, naphthylamines, and the like. Hydrolysable functionalities include, but are not limited to, amide, ester, carbamate, thioester, carbonate, and the like.

In one aspect of the invention, the opioid agonist releasing GI enzyme substrate $S_2$ subunit(s) and the non-opioid releasing GI enzyme substrate or enzyme inhibitor $S_1$ subunit(s) are covalently attached to a scaffold, for example a polymeric, oligomeric, or molecular scaffold. The $S_1$ or $S_2$ components can be linked directly, or indirectly, via a wide range of linkers as described herein. The particular linkage and linkage chemistry employed will depend upon the specific functional groups available on the $S_1$, $S_2$, and scaffold components. The presence of suitable functional groups within the $S_1$, $S_2$, and scaffold components, and useful chemistry for linking strategies involving these suitable functional groups can be readily determined by one skilled in the art based upon the guidance presented herein. Particular examples of unimolecular compositions comprised of linkers (Z), $S_1$ subunits, $S_2$ subunits, and/or $S_3$ subunits, and/or molecular, oligomeric or polymeric scaffolds are disclosed herein.

In another aspect of the invention, compositions of the invention are not required to be, and preferably are not, orally bioavailable. Thus, in one aspect of the invention, a composition in accordance with the invention will demonstrate low (from about 0% to about 30%) oral bioavailability. Oral bioavailability can be determined using suitable in-vivo or in-vitro assays. Thus, a polysubstrate of the invention will possess oral bioavailability of about or less than about 0%, 0.25%, 0.5%, 0.75%, 1%, 2%, 5%, 10%, 15%, 25%, or 30%, when measured in a suitable model.

In one aspect, a composition of the invention is represented by the following formula:

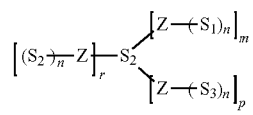

wherein:

each $S_1$ is independently a non-opioid releasing GI enzyme substrate or GI enzyme inhibitor subunit;

each $S_2$ is independently an opioid agonist releasing GI enzyme substrate;

each $S_3$ is independently an opioid antagonist releasing moiety;

each Z is independently a linking moiety;

each n is independently an integer ranging from 1 to 10;

m is an integer ranging from 1 to 10; and p and r are independently integers ranging from 0 to 10.

In another aspect, a composition of the invention is represented by the following formula:

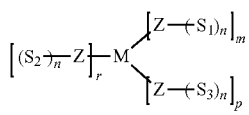

wherein:
S₁ is a non-opioid releasing GI enzyme substrate or GI enzyme inhibitor subunit;
S₂ is an opioid agonist releasing GI enzyme substrate subunit;
S₃ is an optional opioid antagonist releasing moiety;
M is a covalent scaffold;
Z is a linking moiety;
each r, m, and n is independently an integer ranging from 1 to 10, 1 to 100, 1 to 1,000, 1 to 100,000, 1 to 1,000,000, or 1 to 1,000,000,000;
p is an integer ranging from 0 to 10, 0 to 100, 0 to 1,000, 0 to 100,000, 0 to 1,000,000, or 0 to 1,000,000,000.

In some embodiments, the linking moieties Z between the covalent scaffold M and the S₁, S₂, and S₃ subunits are sufficiently stable prior to, and subsequent to, administration to a subject.

Compositions of the invention are not required to have, and preferably do not have opioid agonist activity prior to enzymatic processing of the opioid agonist releasing GI enzyme substrate subunit. Thus, in one aspect of the invention, a composition in accordance with the invention will retain from about 0% to about 30% of the specific activity of the delivered opioid agonist compound. Such activity may be determined using suitable in-vivo, or in-vitro assays, depending upon the known activity of the particular opioid parent compound. For example, a functional opioid receptor based assay, or an in vivo hot-plate or tail-flick analgesia assay can be used to assess the level of agonist activity of the polymer conjugates of the invention. Thus, compositions of the invention will possess a specific activity of about 0% or less than about 0.25%, 0.5%, 0.75%, 1% 2%, 5%, 10%, 15%, 25%, 30% or 50% relative to that of the delivered opioid agonist, when measured in a suitable model, such as those well known in the art.

In another aspect of the invention, compositions of the invention are not required to be, and preferably are not, orally bioavailable and/or do not traverse the blood-brain barrier. For example, compositions of the invention do not penetrate the central nervous system (CNS). Thus, in one aspect of the invention, a composition in accordance with the invention will retain from about 0% to about 30% of the oral bioavailability or CNS penetration of the delivered opioid agonist. Oral bioavailability and CNS penetration can be determined using suitable in-vivo assays. Thus, a composition of the invention will possess oral bioavailability or CNS penetration of about 0% or less than about 0.25%, 0.5%, 0.75%, 1% 2%, 5%, 10%, 15%, 25%, or 30% relative to that of the unmodified parent opioid, when measured in a suitable model, such as those well known in the art.

Opioid Agonists

Any opioid agonist known in the art may be used. The terms "opioid agonist" and "opioid" are used interchangeably herein to refer to any drug, whether natural and synthetic, which has morphine-like mechanism of action.

Opioid agonists useful in the present invention include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, tramadol, mixtures of any of the foregoing, salts thereof, prodrugs thereof, and derivatives, analogs, homologues, and polymorphs thereof. In certain embodiments, the amount of the opioid agonist released can be from about 0.25 nmols to about 2.5 mmols. The specified amount of opioid released by polysubstrate compositions of the invention will likely vary as a function of the potency and bioavailability of the specific opioid agonist released.

In some embodiments, a pharmaceutical composition of the present invention includes one or more opioids such as hydrocodone, hydromorphone, morphine, oxycodone, oxymorphone, and/or salts or prodrugs thereof, as the therapeutically active ingredient.

In some embodiments, a unit dose form includes an amount of opioid agonist that is about 0.003 mmols, about 0.015 mmols, about 0.03 mmols, about 0.045 mmols, about 0.075 mmols, about 1.50 mmols, about 0.225 mmols, about 0.3 mmols, about 0.375 mmols, about 0.45 mmols, about 0.525 mmols or about 0.6 mmols. More typically, the drug can be present in an amount from about 0.003 mmols to about 1.66 mmols, preferably about 0.015 mmols to 0.6 mmols. As will be understood by one of skill in the art, a dosage form preferably contains an appropriate amount of drug to provide a therapeutic effect. Dose units of the invention may also include co-formulations with additional therapeutically active drugs such as acetaminophen, ibuprofen, naltrexone, etc.

Opioid Antagonists

The term "opioid antagonist", as used herein, refers to any molecule that blocks the action of an opioid agonist at one or more opioid receptor types. Opioid antagonists include so-called "agonist-antagonist" molecules that act as an antagonist for one opioid receptor type and an agonist for another receptor type, such as, for example, naloxone, naltrexone, nalorphine or pentazocine.

When co-administered with opioid agonists, opioid antagonists are capable of blocking the effects of the opioid agonist. Antagonists such as naltrexone, naloxone or buprenorphine are often used to combat the abuse and the overdose effects of an opioid agonist. For example, naltrexone is commonly prescribed to help fight addiction to either alcohol or opioid drugs.

Suitable opioid antagonists include, but are not limited to, buprenorphine, cyclazocine, cyclorphan, naloxone, N-methylnaloxone, naltrexone, N-methylnaltrexone, nalmephene, 6-amino-6-desoxo-naloxone, levallorphan, nalbuphine, naltrendol, naltrindole, nalorphine, nor-binaltorphimine, oxilorphan, pentazocine, piperidine-N-alkylcarboxylate opioid antagonists such as those described in U.S. Pat. Nos. 5,159,081, 5,250,542, 5,270,328, and 5,434,171, and derivatives, mixtures, salts, polymorphs, or prodrugs thereof.

In one aspect of the invention, the opioid antagonist includes naltrexone, naloxone, nalmefene, cyclazacine, levallorphan and mixtures thereof. In another aspect of the invention, the opioid antagonist is naltrexone or naloxone.

In one aspect of the invention, the antagonist is naloxone. Naloxone is almost devoid of agonist effects. Subcutaneous doses of up to 12 mg of naloxone produce no discernable subjective effects, and 24 mg naloxone causes only slight drowsiness. Small doses (0.4-0.8 mg) of naloxone given intramuscularly or intravenously, in man, prevent or reverse the effects of morphine-like opioid agonists. One mg of naloxone administered intravenously has been reported to completely block the effect of 25 mg of heroin. The effects of naloxone are seen almost immediately after intravenous administration. The drug is absorbed after oral administration but has been reported to be rapidly and extensively metabolized into an inactive form via first-pass metabolism. Therefore, it has been demonstrated to have significantly lower potency when delivered orally than when parenterally administered.

Other exemplary opioid antagonists include cyclazocine and naltrexone, both of which have cyclopropylmethyl substitutions on the nitrogen, retain much of their efficacy by the oral route and their durations of action are much longer, approaching 24 hours after oral doses.

In another aspect of the invention, the antagonist is naltrexone. Naltrexone works by blocking the opioid receptors in the brain and blocking the feeling of euphoria felt when alcohol or an opioid agonist is ingested. This in turn decreases the craving for the substance, according to the National Institute of Health. Naltrexone can be delivered both orally and by intravenous injection. Naltrexone is known as a synthetic congener of oxymorphone with no opioid agonist properties, and differs in structure from oxymorphone by replacement of the methyl group located on the nitrogen atom of oxymorphone with a cyclopropylmethyl group. As a result, the physicochemical properties of naltrexone (and chemically related antagonists) are nearly identical to those inherent to structurally related opioid agonists. This renders the physical separation of naltrexone-opioid agonist mixtures essentially impossible without the employment of highly sophisticated chemical separation techniques (e.g. high-performance liquid chromatography—HPLC). The hydrochloride salt of naltrexone is soluble in water up to about 100 mg/mL. Following oral administration, naltrexone is rapidly absorbed (within 1 hour) and has an oral bioavailability ranging from 5-40%.

It is known that when co-administered with morphine, heroin or other opioid agonists, naltrexone blocks the development of physical dependence to opioid agonists, reduces "drug liking" by recreational abusers, can precipitate withdrawal symptoms in opioid dependent subjects, and can completely block the effects of the co-delivered opioid agonist. In the treatment of patients previously addicted to opioids, naltrexone has been used to prevent the euphorigenic effects of opioid agonists. Naltrexone is commercially available in oral tablet form (Revia®) for the treatment of alcohol dependence and for the blockade of exogenously administered opioids. An oral dosage of 50 mg Revia blocks the pharmacological effects of 25 mg of IV administered heroin for up to 24 hours.

When present, the molar ratio of the opioid antagonist to the opioid agonist in compositions of the invention can be from about 0.001:1 to about 10:1, preferably about 0.01:1 to about 3:1. As will be understood by one of skill in the art, compositions of the invention preferably contain an appropriate amount of opioid antagonist to provide the desired abuse-deterrent effects when released.

Non-Opioid Releasing GI Enzyme $S_1$ Subunits

Compositions of the invention comprise a covalently linked non-opioid releasing digestive enzyme substrate or inhibitor $S_1$ subunit, or multiple non-opioid releasing digestive enzyme substrate or inhibitor $S_1$ subunits. In some embodiments, the non-opioid releasing digestive enzyme substrate $S_1$ subunit is a GI enzyme inverse substrate ester. For example, the non-opioid releasing substrate is attached to a linking moiety Z via the carboxylate-containing component of the ester and can be represented by one of the following moieties shown below:

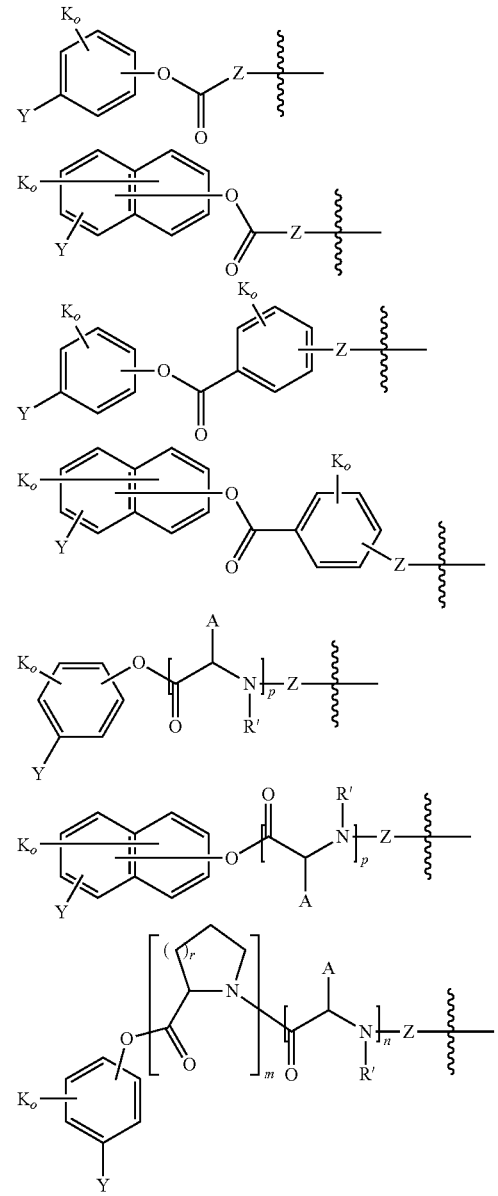

-continued

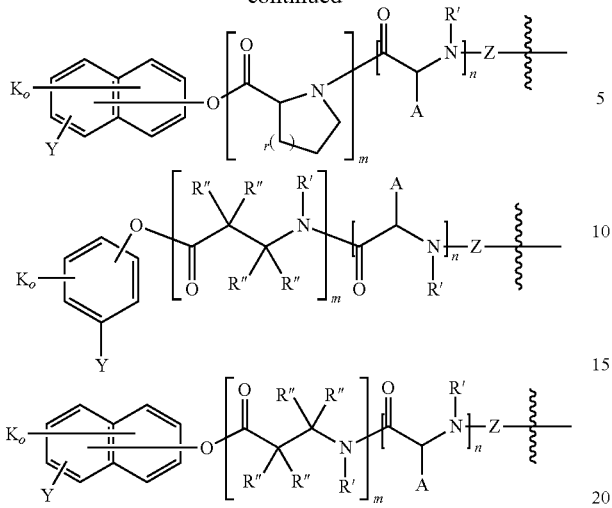

wherein:

Y is an amidine, guanidine, benzylamine, alkyl substituted amidine, alkyl substituted guanidine, alkyl substituted benzylamine, benzylamidine, benzylguanidine, alkyl substituted benzylamidine, or alkyl substituted benzylguanidine;

Z is a linking moiety;

each $K_o$ is independently hydrogen or methyl;

A is an amino acid side chain;

r is an integer from 0-10;

m is an integer from 1-10;

p is an integer from 1-10;

n is an integer from 0-10;

each R' is independently alkyl, aryl, substituted alkyl, substituted aryl, acyl, substituted acyl group, or polyethylene glycol containing acyl, aryl, or alkyl group; and each R" is independently a hydrogen, methyl, alkyl, or aryl group.

In some embodiments, at least one of Z and $K_o$ comprises an electron donating, or electron withdrawing, atom or functionality that influences the formation, or the hydrolysis, of the acyl enzyme intermediate resulting from the interaction of the $S_1$ subunit by the targeted digestive enzyme. For example, electron donating groups include alkyl, substituted alkyl, —OH, —OR, —$NH_2$, —$NR_2$, —SH, —SR, and —NHC(O)R. For example, electron withdrawing groups include —C(O)OH, —C(O)OR, —C(O)$NH_2$, —C(O)$NR_2$, —$NO_2$, —$NR_3^+$, —C(O)$CF_3$, halogen, —$CCl_3$, cyano, —$SO_3H$, —$SO_3R$, —CHO, —COR, —C(NH)$NH_2$, and —NHC(NH)$NH_2$.

In other embodiments, the $S_1$ subunit is connected to a scaffold or linking moiety via the phenol component of the ester. Examples include, but are not limited to those described below:

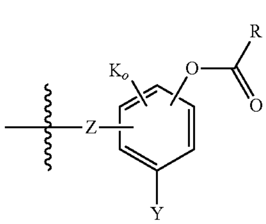

-continued 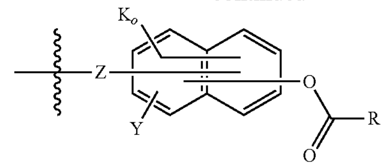 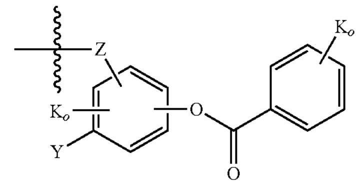 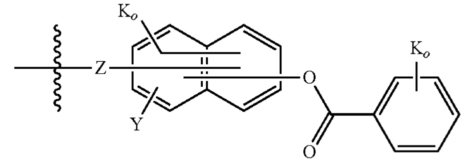 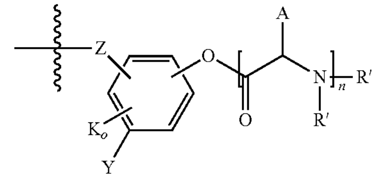 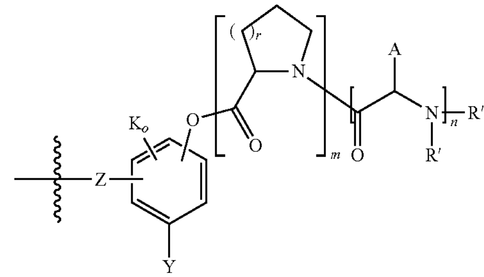 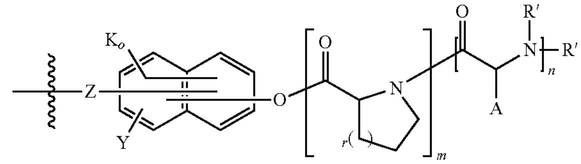 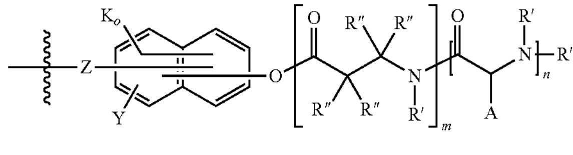 wherein:

Y is an amidine, guanidine, benzylamine, alkyl substituted amidine, alkyl substituted guanidine, alkyl substituted benzylamine, benzylamidine, benzylguanidine, alkyl substituted benzylamidine, or alkyl substituted benzylguanidine;
Z is a linking moiety;
each $K_o$ is independently hydrogen or methyl;
A is an amino acid side chain;
r is an integer from 0-10;
m is an integer from 1-10;
p is an integer from 1-10;
n is an integer from 0-10;
each R is alkyl, alkylene, alkynyl, or aryl, or substituted alkyl, substituted alkylene, substituted alkynyl, substituted aryl group;
each R' is independently alkyl, aryl, substituted alkyl, substituted aryl, acyl, substituted acyl group, or polyethylene glycol containing acyl, aryl, or alkyl group; and
each R" is independently a hydrogen, methyl, alkyl, or aryl group.

In some embodiments, at least one of Z and $K_o$ can comprises an electron donating, or electron withdrawing, atom or functionality that influences the formation, or the hydrolysis, of the acyl enzyme intermediate resulting from the interaction of the $S_1$ subunit by the targeted digestive enzyme. For example, electron donating groups include alkyl, substituted alkyl, —OH, —OR, —NH$_2$, —NR$_2$, —SH, —SR, and —NHC(O)R. For example, electron withdrawing groups include: —C(O)OH, —C(O)OR, —C(O)NH$_2$, —C(O)NR$_2$, —NO$_2$, —NR$_3^+$, —C(O)CF$_3$, halogen, —CCl$_3$, cyano, —SO$_3$H, —SO$_3$R, —CHO, —COR, —C(NH)NH$_2$, and —NHC(NH)NH$_2$.

GI enzyme hydrolysis (e.g. by trypsin) of the ester $S_1$ substrate subunits listed above results in the formation of a carboxylic acid, amino acid, or benzoic acid metabolites. In some embodiments, GI enzyme hydrolysis (e.g. by trypsin) of ester $S_1$ substrate subunits may be designed to produce an acid metabolite that is generally regarded as safe (GRAS). The hydrolysis of a representative $S_1$ substrate subunit by a GI enzyme resulting in the release of a GRAS acid metabolite is illustrated by the general mechanism below:

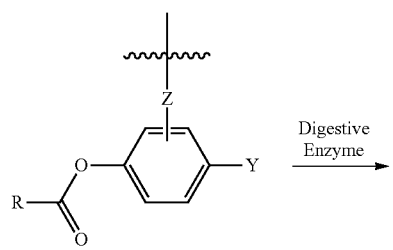

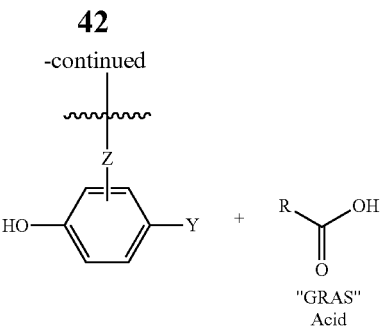

"GRAS" stands for "generally recognized as safe" and refers to a compound as defined by sections 201(s) and 409 of the Federal Food, Drug, and Cosmetic Act. Exemplary GRAS acid metabolites include, but are not limited to: benzoic acid, salicylic acid, aspirin, 3-hydroxybenzoic acid, 4-hydroxybenzoic acid, gallic acid, 2,3,4-trihydroxybenzoic acid, 2,3,6-trihydroxybenzoic acid, 2,4,5-trihydroxy benzoic acid, 6-methylsalicylic acid, o-cresotinic acid, (alkyl)-anacardic acids, o-thymotic acid, 3-O-methylgallic acid, 4-O-methylgallic acid, syringic acid, 3,4,5-trimethoxybenzoic acid, diflusinal, p-anisic acid, 2,3-dihydroxybenzoic acid, alpha-resorcylic acid, anthranilic acid, 3-aminobenzoic acid, 4,5-dimethylanthranilic acid, N-methylanthranilic acid, protocatechuic acid, gentisic acid, piperonylic acid, 3-methoxysalicylic acid, fenamic acid, toifenamic acid, mefenamic acid, flufenamic acid, vanillic acid, isovanillic acid, veratric acid, 3,5-dimethoxybenzoic acid, 2,4-diaminobenzoic acid, N-acetylanthranilic acid, 2-acetylamino-4-aminobenzoic acid, 2,4-diacetylaminobenzoic acid, 4-aminosalicylic acid, 3-hydroxyanthranilic acid, 3-methoxyanthranilic acid, nicotinic acid, isonicotinic acids, and cinnamic acids.

In one aspect of the invention, the compositions, pharmaceutical formulations, and methods disclosed herein comprise $S_1$ inverse substrate ester subunits for GI enzymes, such as trypsin, chymotrypsin, or tryptase. Thus, when trypsin is an exemplary GI enzyme, trypsin cleaves C-terminal peptide bonds of arginine and lysine, both of which are positively charged amino acids. The specificity pocket of trypsin has an aspartic acid residue (Asp-189), which has a negative charge, resulting in a negative electrostatic field in the substrate binding pocket, thereby attracting the positively charged arginine and lysine substrate side chains. The negative electrostatic field in the substrate binding pocket also helps stabilize the positive charge in the enzyme-substrate complex.

Mechanistically, the GI enzyme catalyzed hydrolysis of ester based inverse substrate $S_1$ subunits can be described using the following scheme:

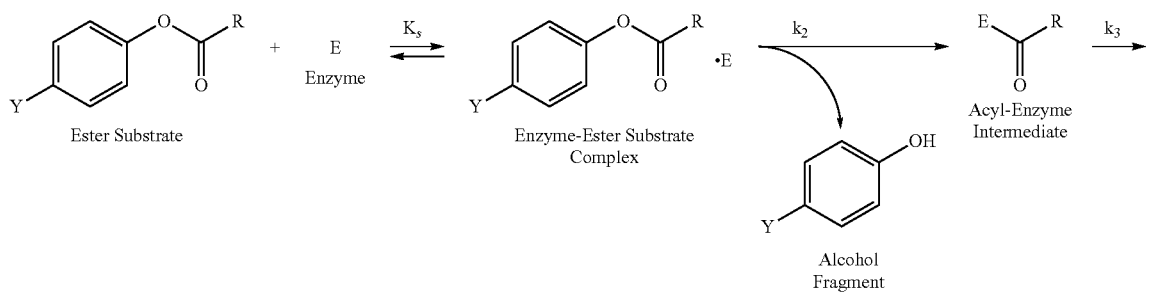

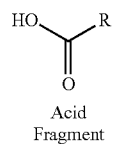

Acid Fragment

Where E is a GI enzyme. $K_s$ is the association constant of enzyme-substrate complex, $k_2$ is the rate constant of the acylation step, and $k_3$ is the rate constant of the deacylation step. In the initial step, the ester substrate and the enzyme bind to form an enzyme-substrate complex. The inverse substrate ester $S_1$ subunit is then irreversibly hydrolyzed to produce an alcohol (or phenol) fragment and an active-site acyl-enzyme intermediate. The acyl-enzyme intermediate subsequently dissociates to a free enzyme (E) and an acid fragment with a rate constant of $k_3$. The rate at which the deacylation step occurs, $k_3$, determines the lifetime of the acyl-enzyme intermediate and the proclivity of specific $S_1$ subunits to saturate trypsin.

Thus, in one aspect of the invention, the compositions, pharmaceutical formulations, and methods disclosed herein comprise a non-opioid releasing ester substrate, or non-opioid releasing ester substrates, where the ester substrate has an enzyme recognition moiety covalently linked to a carbonyl group that is capable of acylating the active site of the enzyme.

Thus, in one aspect of the invention, the products produced by the hydrolysis of $S_1$ ester-based non-opioid releasing inverse substrates are an acid and an alcohol, such as a substituted phenol, where the phenol can remain covalently attached to a polysubstrate of the invention and as a result will generally not be systemically absorbed, but rather pass through the gastrointestinal system and are excreted. Such ester containing polysubstrates of the invention can be designed to release GRAS acids and thereby have the advantage that GRAS acids have well-characterized safety profiles. In addition, these ester substrates are chemically stable in vivo and are not easily hydrolyzed by acid in the stomach, nor hydrolyzed non-specifically by digestive enzymes, of the patient.

Representative non-limiting $S_1$ subunit examples include:

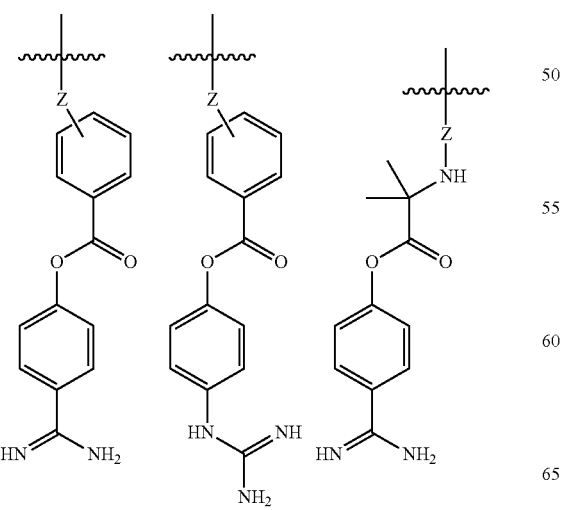

-continued

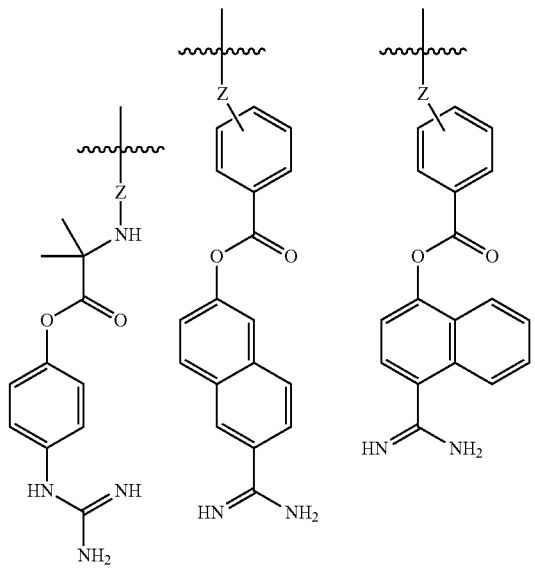

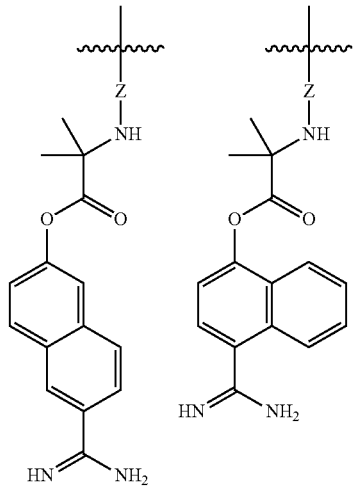

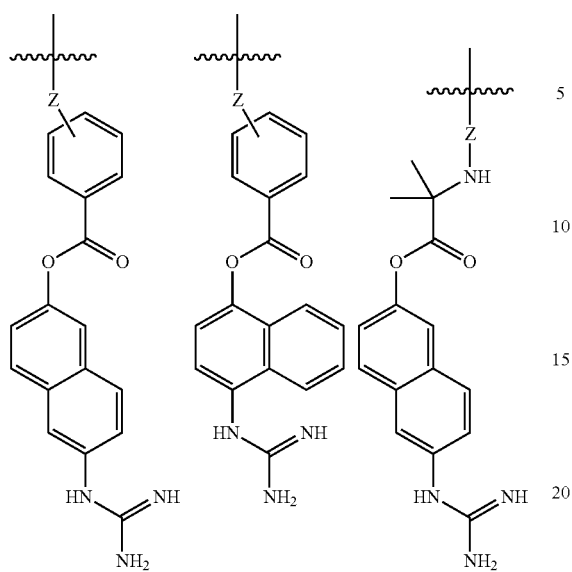
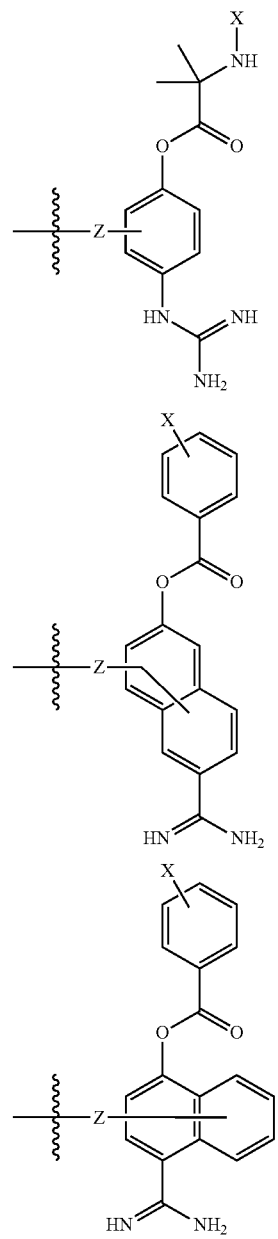
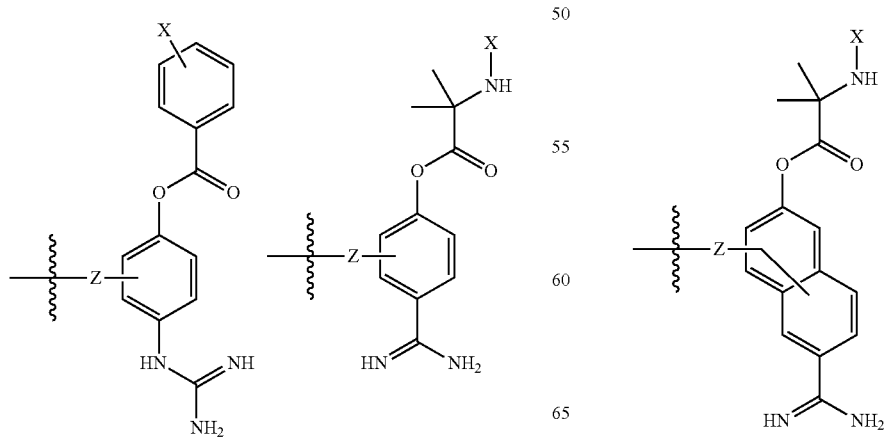

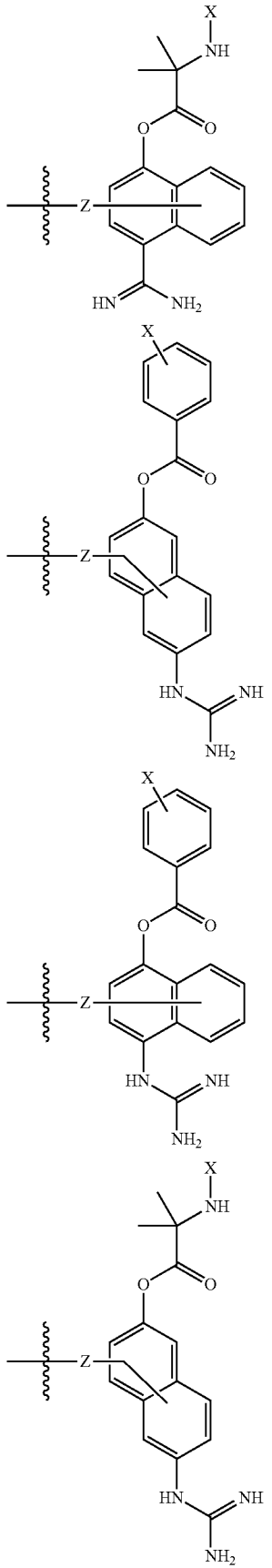

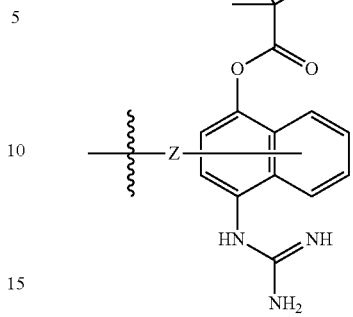

wherein Z is a linking moiety as described herein; and

X can be hydrogen, an amino acid, alkyl, heteroalkyl, aryl, substituted aryl, acyl, substituted acyl, terminally functionalized polyethylene glycol chain, or X is a substituent (or substituents) on a GRAS carboxylic acid as described above.

In some embodiments, the non-opioid releasing digestive enzyme $S_1$ subunit is a GI enzyme inhibitor. The non-opioid releasing $S_1$ GI enzyme inhibitor subunit is attached to a linking moiety Z as represented by any one of the following non-limiting examples described below.

The $S_1$ subunit can be derived from amidinophenylpyruvate (APPA) including, but not limited to:

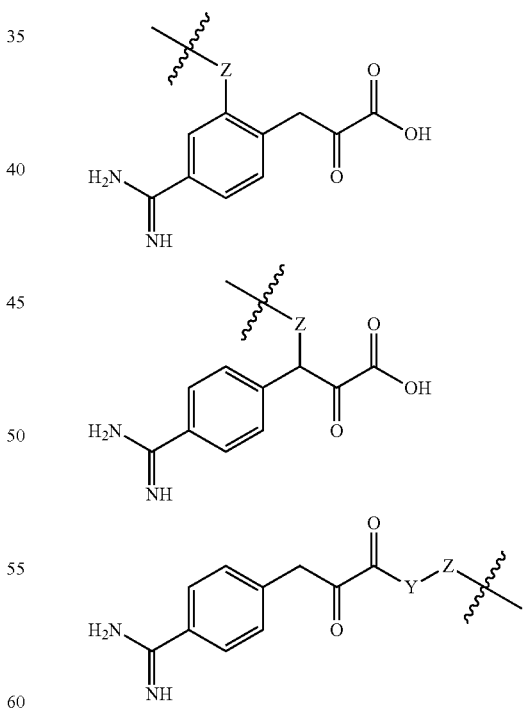

Wherein Y can be O, NH, NR or S; Z is a linker as defined above.

In another aspect of the invention, the $S_1$ subunit can be derived from an activated ketone derivative, including, but not limited to the following:

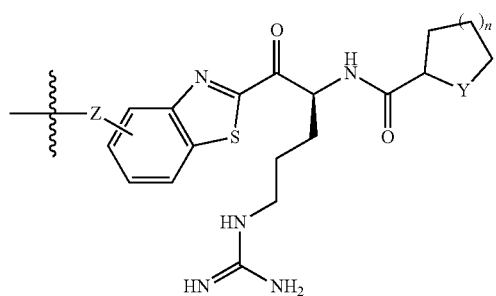
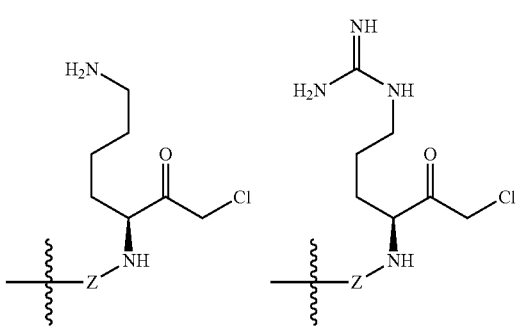
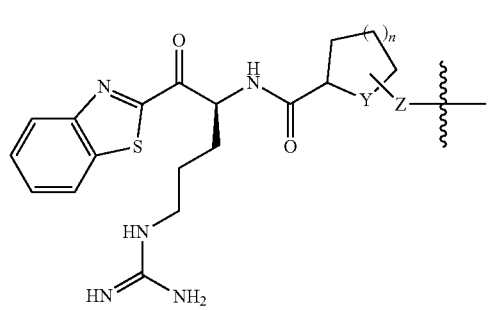
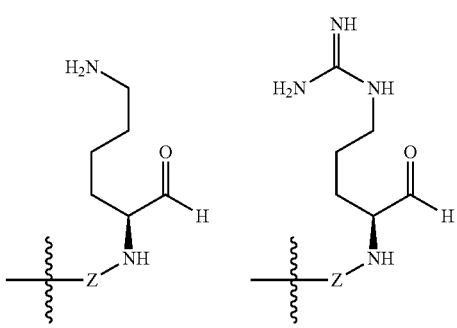
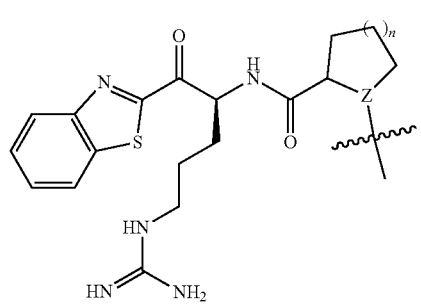
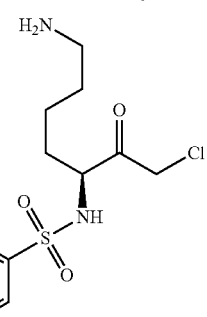
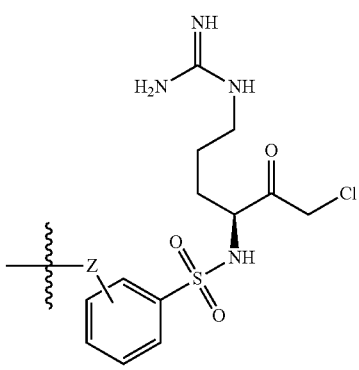
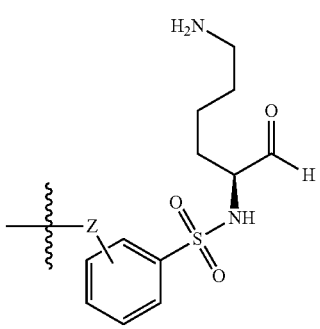

Wherein Y is N, O, N—R, or carbon, and R is methyl, ethyl, alkyl, substituted alkyl, acyl, substituted acyl, aryl, substitutes aryl, a natural or non-natural amino acid, or a polypeptide chain comprising natural or non-natural amino acids. The arginine side chain in the above structure can be substituted for a lysine side chain, or a natural or non-natural lysine or arginine side chain mimic.

In another aspect of the invention, the $S_1$ subunit can be derived from chloroketone or aldehyde analogs as shown below:

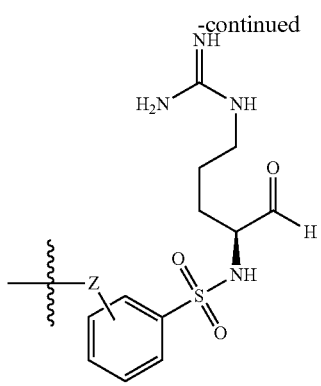

The chloroketone and aldehyde analogs illustrated above can also comprise natural or non-natural lysine-mimic or arginine-mimic side-chain variants.

In another non-limiting aspect of the invention, the $S_1$ subunit inhibitor can have cycloheteroalkyl groups, naphthylamidines, arylguanidines, arylamidines, benzylamines, 4-guanidinopiperazines, and peptide based structures, as illustrated below:

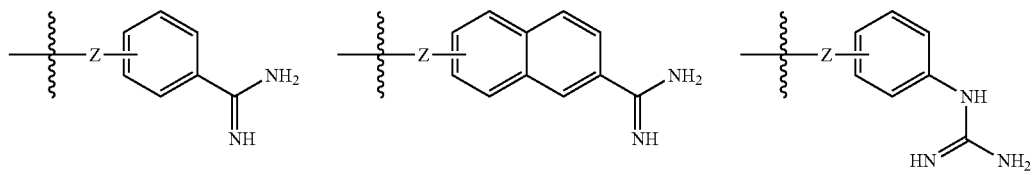

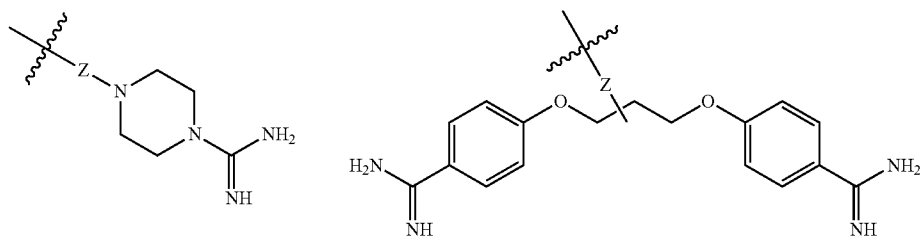

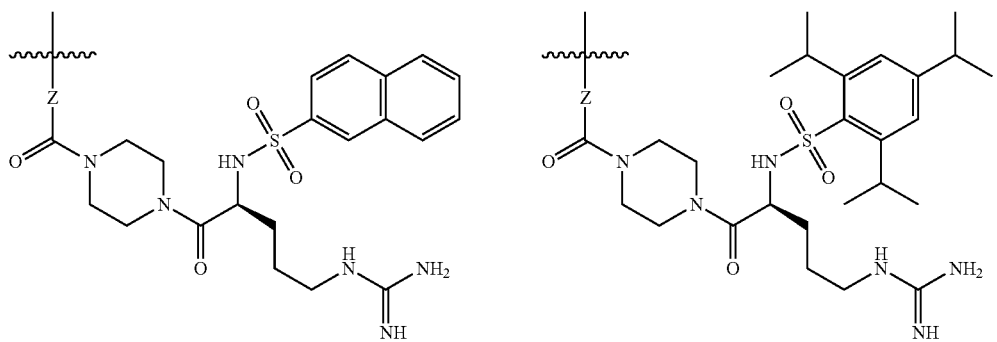

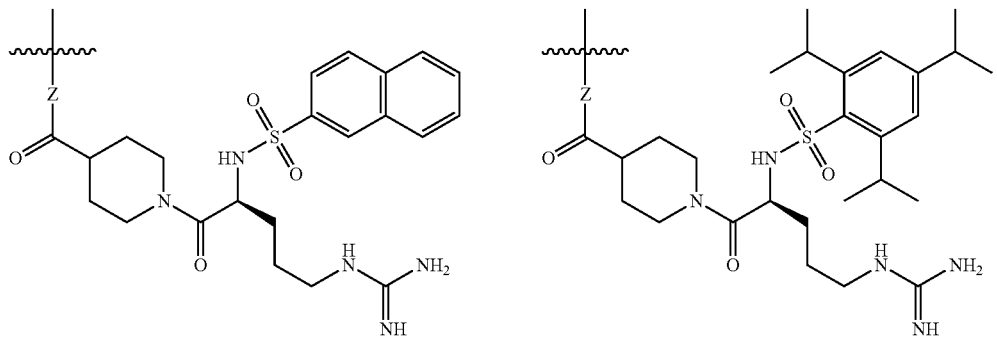

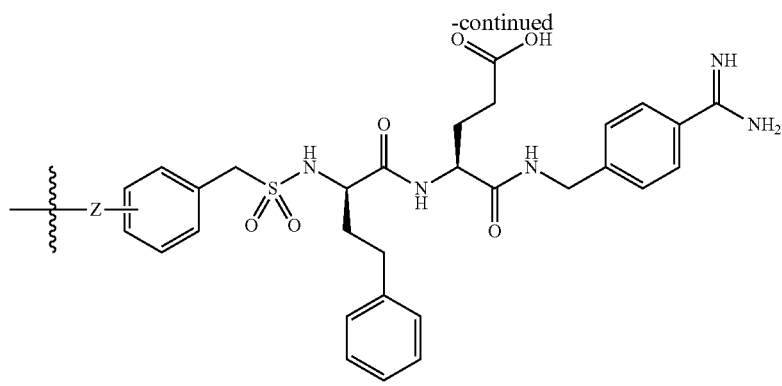

Preparation of Non-Opioid Releasing GI Enzyme S₁ Subunits

Multiple synthetic procedures useful for the preparation of $S_1$ subunits have been reported in the literature (see for example: Tanizawa, K., et al, Chem. Pharm. Bull. 1999, 47(1), 104-110, Aoyama, T., et al, Chem. Pharm. Bull. 1985, 33(4), 1458-1471, Bordusa, F., et al, Biochemistry, 1999, 38, 6056-6062, Tanizawa, K., et al, Chem. Pharm. Bull. 1996, 44, 1577-1579, 1585-1587, Lal, B., et al, Tetrahedron Lett. 1996, 37, 2483-2486, Sekizaki, H., et al, Bioorganic & Medicinal Chemistry Letters, 2003, 13, 3809-3812, Tanizawa, K., et al, Acc. Chem. Res. 1987, 20, 337-343) and commonly involve the coupling between an alcohol (or phenol) synthon and a carboxylic acid (e.g. benzoic acid) moieties that is pre-activated for coupling by first conversion to an acid chloride, or the like; or activated for coupling in situ with an appropriate coupling reagent (e.g. DCC) to form the desired ester functionality. Amidine substituted phenol synthons are commonly used in an unprotected salt form, while guanidine containing esters are often prepared via similar coupling reactions using a protected form (e.g. the bis-Cbz protected form) of the aryl guanidine synthon. Purification of the resulting esters can be accomplished using standard purification procedures involving normal or reverse phase HPLC, crystallization, trituration, etc. The chemical identity of the $S_1$ esters can be readily established by LC/MS and/or NMR analysis.

Some representative synthetic routes useful for the preparation of $S_1$ subunits are depicted below.

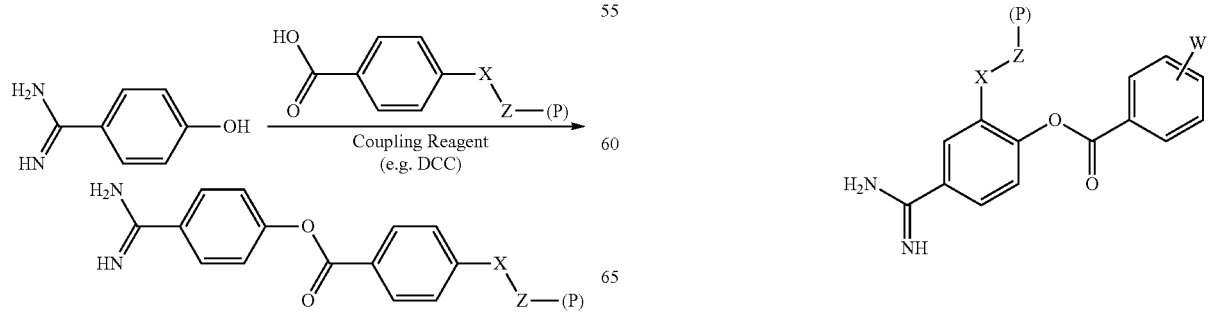

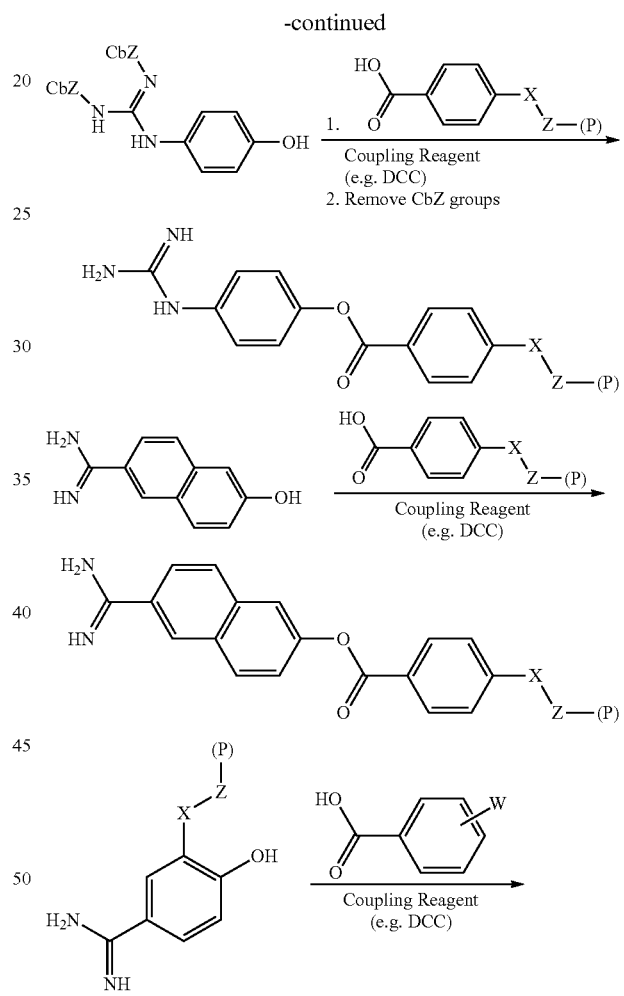

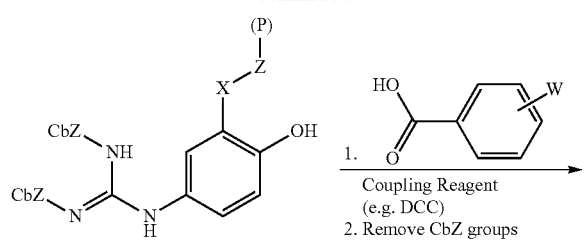
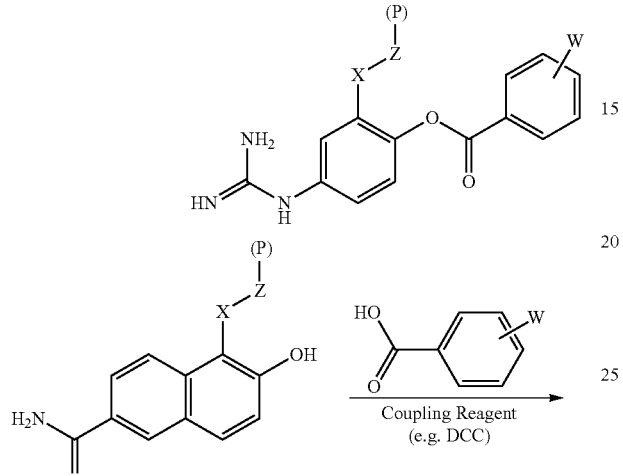
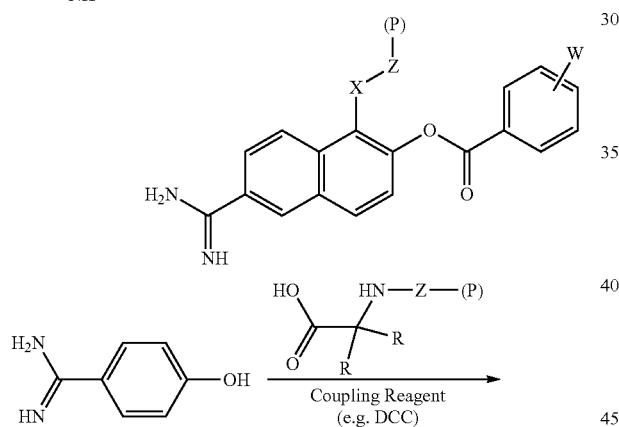
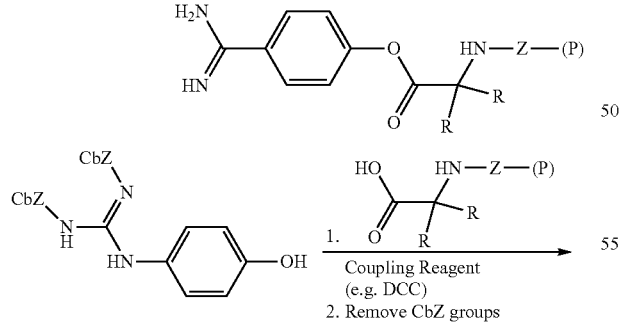
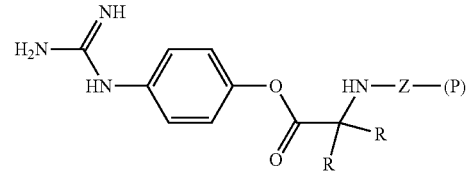
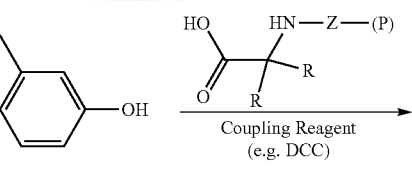
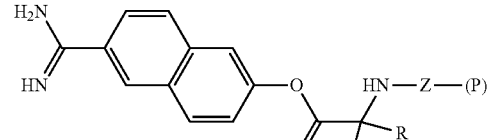
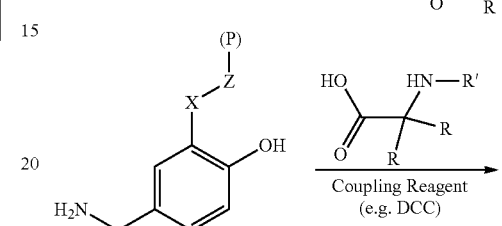
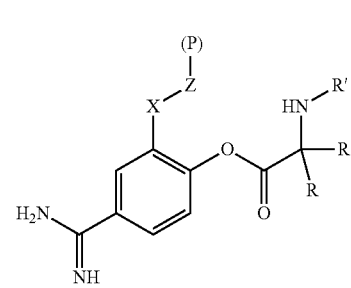
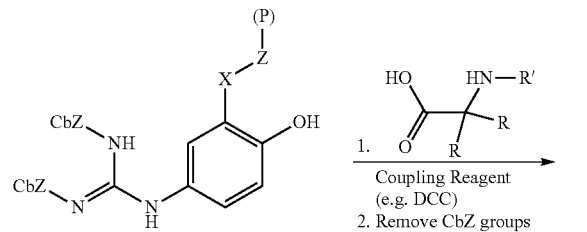
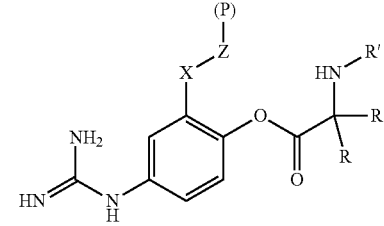
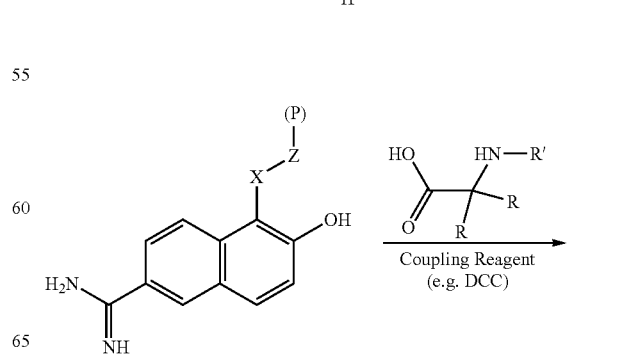

-continued

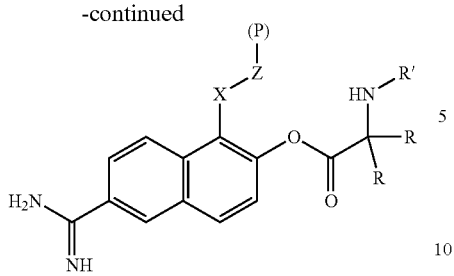

wherein:
each R' is independently alkyl, aryl, substituted alkyl, substituted aryl, acyl, substituted acyl group, or polyethylene glycol containing acyl, aryl, or alkyl group;
each R is independently a hydrogen, methyl, alkyl, or aryl group;
W is hydrogen or an atom or substituent that renders the benzoic acid metabolite of the $S_1$ subunit a GRAS compound, or W is an electron donating or withdrawing atom or functionality that influences the formation, or the hydrolysis, of the acyl enzyme intermediate resulting from the interaction of the $S_1$ subunit by the targeted digestive enzyme.
Z is a linking moiety;

X is a covalent bond or an atom such as oxygen or nitrogen, or a functional group suitable for the attachment of, or incorporated by, the linker group Z; and (P) is an optional protecting group present on the terminus of the linker Z distal to the $S_1$ subunit that may be employed to enhance the chemical efficiency of the desired ester forming coupling reaction.

Opioid Agonist Releasing GI Enzyme $S_2$ Subunits

Compositions of the invention comprise a covalently linked opioid agonist releasing digestive enzyme substrate $S_2$ subunit, or opioid agonist releasing digestive enzyme substrate $S_2$ subunits. The released opioid agonist can be morphine, a morphone or other phenol containing opioid agonist, or a codone or other ketone containing opioid agonist, such as illustrated by the formulae below. The opioid agonist releasing substrates may be linked via phenol, alcohol, or ketone (e.g. enol) functionalities as shown below.

D=

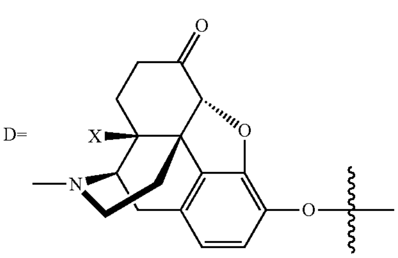

D=

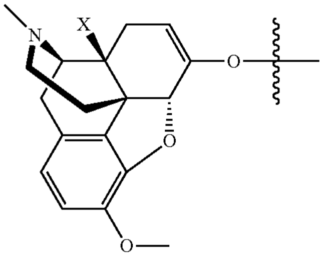

-continued

D=

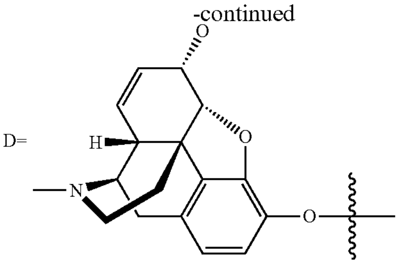

D=

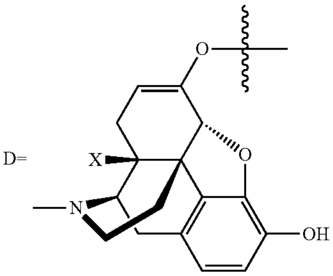

D=

Codones
(or other ketone containing opioids)
X = H, OH

D=

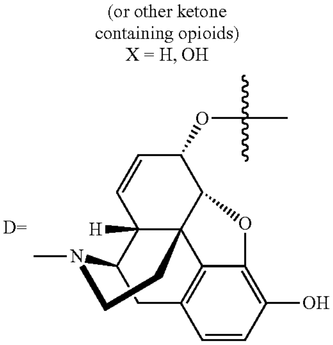

Morphine

D=

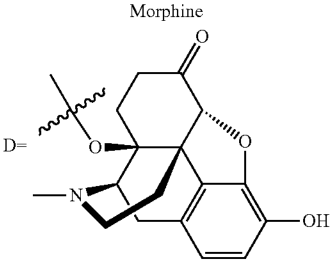

Morphones
(or other phenol containing opioids)
X = H, OH

In some embodiments, D is a phenol-linked opioid agonist. For example, D is selected from buprenorphine, dihydroetorphine, diprenorphine, etorphine, hydromorphone, levorphanol, morphine, oxymorphone, tapentadol, and the like.

In some embodiments, D is an enol-linked opioid agonist. For example, D is selected from acetylmorphone, hydrocodone, hydromorphone, oxycodone, oxymorphone, pentamorphone, ketobemidone, methadone, and the like.

According to one aspect, the invention provides pharmaceutical compositions that comprise an opioid agonist releasing digestive enzyme $S_2$ substrate. The disclosure provides novel digestive enzyme substrate moieties attached to an opioid agonist through a functional group present on the opioid agonist, where the functional group present on the opioid agonist comprises a reactive group. Any type of reactive group on an opioid agonist can provide a handle for a point of attachment to the $S_2$ substrate moiety. Examples of reactive groups on an opioid agonist include, but are not limited to, alcohol, phenol, ketone, amino, and amide. An alcohol or phenol on an opioid agonist can provide a point of attachment by reaction to form a linkage, such as a carbamate. A ketone on an opioid agonist can provide a point of attachment via reaction to form a linkage, such as an enol carbamate. An amino group on an opioid agonist can provide a point of attachment by reaction to form an amino linkage, including quaternary salts, or an amide. An amide on an opioid agonist can provide a point of attachment by reaction to form a linkage, such as an amide enol or an N-alkylated or N-acylated amide.

A $S_2$ substrate moiety can be linked via an alcoholic or phenolic opioid agonist via modification of the alcohol or phenol moiety, through the enolic oxygen atom of the ketone moiety, to an amino-containing opioid agonist through the amino moiety, to an amide-containing opioid agonist through the enolic oxygen of the amide moiety or its imine tautomer. In each case, the opioid agonist releasing digestive enzyme substrate comprises an enzyme-cleavable moiety that is susceptible to cleavage by a GI enzyme. Release of the opioid agonist is mediated by enzymatic cleavage by a digestive enzyme. Such cleavage can initiate, contribute to, or immediately effect drug release.

Examples of opioid agonist releasing digestive enzyme $S_2$ substrate moieties comprising releasable opioid agonists designated as D are shown below.

In some embodiments, the $S_2$ subunit has one of the formulas:

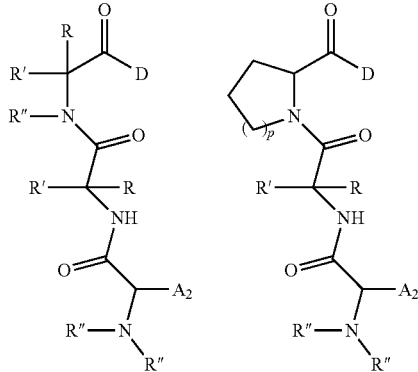

wherein:
D is an opioid agonist, for example wherein D is a morphone, a codone, or morphine;
each R is independently hydrogen, methyl, or alkyl, or a linking moiety Z;
each R' is independently hydrogen, alkyl, aryl, substituted alkyl, substituted aryl, heteroalkyl, substituted heteroalkyl, a natural or unnatural amino acid side chain, an amino acid side-chain mimic, or a linking moiety Z;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid mimic, or a linking moiety Z;
each $A_2$ is independently an amino acid side chain or an amino acid side-chain mimic that is capable of being recognized by a digestive enzyme; and
p is an integer from 0-10.

In some embodiments, the amino acid side-chain or amino acid side-chain mimic $A_2$ directs the regiospecific digestive enzyme mediated hydrolysis of the $S_2$ substrate prior to the release of the appended opioid agonist from the $S_2$ subunit. In some embodiments, the amino acid side chain can be, but is not limited to, the amino acid side chain of arginine, homoarginine, lysine, homolysine, ε-N-methyl lysine, ornithine, or structural/functional mimics thereof.

In some embodiments, the $S_2$ subunit has one of the formulas:

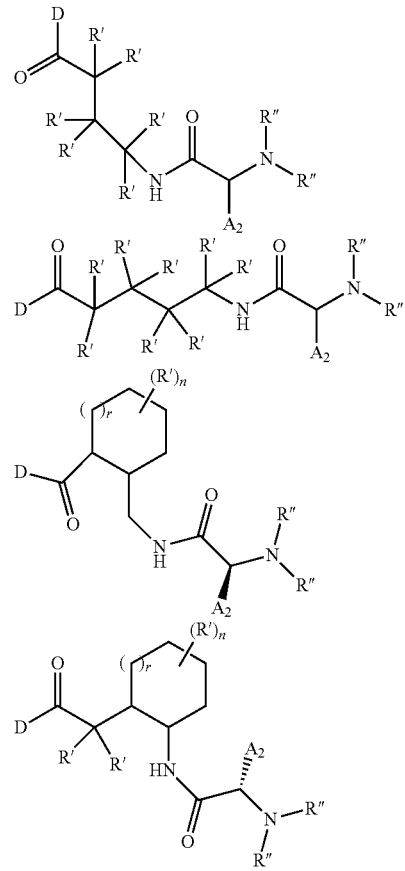

wherein:
D is an opioid agonist, for example wherein D is a morphone, a codone, or morphine;
each R' is independently hydrogen, alkyl, aryl, substituted alkyl, substituted aryl, heteroalkyl, substituted heteroalkyl, a natural or unnatural amino acid side chain, an amino acid side-chain mimic, or a linking moiety Z;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid side chain, an amino acid side-chain mimic, or a linking moiety (Z);

each $A_2$ is independently an amino acid side chain or an amino acid side-chain mimic that is capable of being recognized by a digestive enzyme; and r is an integer from 0-10;

n is an integer that can range from 0-28.

In some embodiments, the amino acid side-chain or amino acid side-chain mimic $A_2$ directs the regiospecific hydrolysis of the $S_2$ substrate prior to the release of the appended opioid agonist from the $S_2$ subunit. In some embodiments, the amino acid side chain can be, but is not limited to, the amino acid side chain of arginine, homoarginine, lysine, homolysine, ε-N-methyl lysine, ornithine, or structural/functional mimics thereof.

In some embodiments, the $S_2$ subunit has one of the formulas:

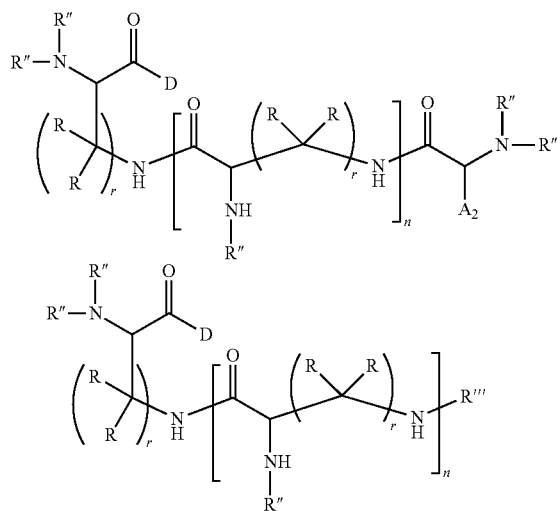

wherein D is an opioid agonist, for example wherein D is a morphone, a codone, or morphine;

each R is independently hydrogen, methyl, or alkyl;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid mimic, or a linking moiety Z;

each $A_2$ is independently an amino acid side chain or an amino acid side-chain mimic that is capable of being recognized by a digestive enzyme; and R''' is hydrogen or methyl or —C(=NR)—$NR_2$ wherein R is each or independently hydrogen or methyl;

r is an integer from 1-6; and n is an integer from 0 to 10.

In some embodiments, the amino acid side-chain or amino acid side-chain mimic $A_2$ directs the regiospecific hydrolysis of the $S_2$ substrate prior to the release of the appended opioid agonist from the $S_2$ subunit. In some embodiments, the amino acid side chain can be, but is not limited to, the amino acid side chain of arginine, homoarginine, lysine, homolysine, ε-N-methyl lysine, ornithine, or structural/functional mimics thereof.

In some embodiments, the $S_2$ subunit has the formula:

wherein:

D is an opioid agonist, for example wherein D is a morphone, a codone, or morphine;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid mimic, or a linking moiety (Z); and $A_2$ is an amino acid side chain or an amino acid side-chain mimic that is capable of being recognized by a digestive enzyme.

In some embodiments, the amino acid side-chain or amino acid side-chain mimic $A_2$ directs the regiospecific hydrolysis of the $S_2$ substrate prior to the release of the appended opioid agonist from the $S_2$ subunit. In some embodiments, the amino acid side chain can be, but is not limited to, the amino acid side chain of arginine, homoarginine, lysine, homolysine, ε-N-methyl lysine, ornithine, or structural/functional mimics thereof.

In some embodiments, the $S_2$ subunit has the formula:

wherein:

D is an opioid agonist, for example wherein D is a morphone, a codone, or morphine;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid mimic, or a linking moiety (Z); and $A_2$ is an amino acid side chain or an amino acid side-chain mimic that is capable of being recognized by a digestive enzyme.

In some embodiments, the amino acid side-chain or amino acid side-chain mimic $A_2$ directs the regiospecific hydrolysis of the $S_2$ substrate prior to the release of the appended opioid agonist from the $S_2$ subunit. In some embodiments, the amino acid side chain can be, but is not limited to, the amino acid side chain of arginine, homoarginine, lysine, homolysine, ε-N-methyl lysine, ornithine, or structural/functional mimics thereof.

As will be evident to one of skill in the art, the opioid agonist releasing digestive enzyme substrates can be covalently attached to form a polysubstrate of the invention via one or more linking moieties Z at any substitution point on the $S_2$ subunit as long as the attachment(s) do(es) not preclude either the requisite hydrolytic action of the digestive enzyme on, or the subsequent release of opioid agonist from, the $S_2$ substrate subunit.

In one aspect of the invention, the opioid agonist is an alcohol, phenol or ketone containing opioid agonist. Accordingly, an alcohol, phenol, or ketone containing opioid agonist is attached through a hydroxylic, phenolic, or enolic oxygen to a linker, which is further attached to an enzyme cleavable moiety. A single enzymatic hydrolysis of a cleavable moiety, or a cascade of enzymatic hydrolyses of cleavable moieties, may release the opioid agonist by (i) directly cleaving the bond between the enzyme cleavable moiety and the opioid agonist, or (ii) revealing a latent nucleophile, such as an amine or carboxylate, that subsequently undergoes an intramolecular cyclization-release reaction, or (iii) revealing an additional enzyme substrate, or substrates, that are further cleaved by the digestive enzyme ultimately resulting in release of the appended opioid agonist.

Mechanisms of enzyme-mediated opioid agonist release from representative $S_2$ substrate subunits are presented in the Schemes below.

General mechanism of enzyme-mediated opioid agonist release from representative 2,5-diketopiperazine forming $S_2$ subunits:

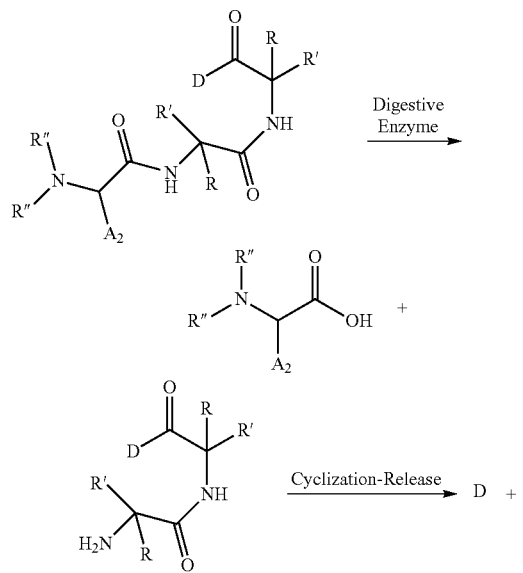

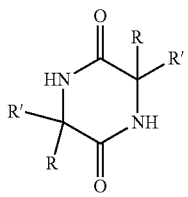

General mechanism of enzyme-mediated opioid agonist release from representative lactam forming $S_2$ subunits:

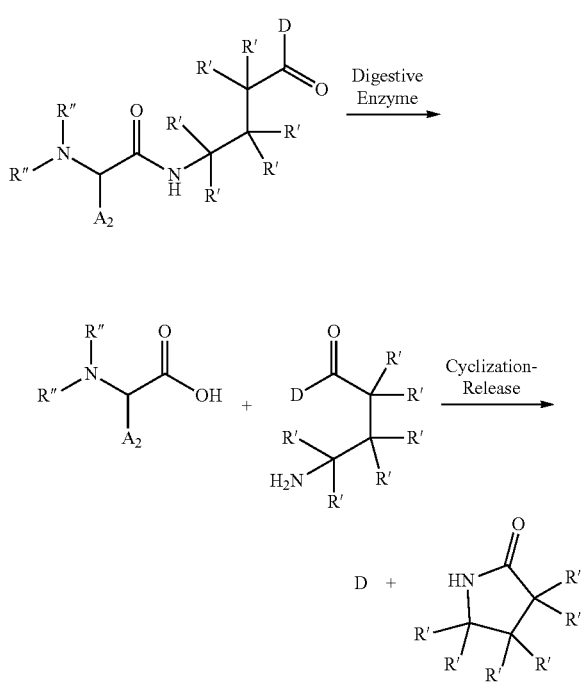

General mechanism of enzyme-mediated opioid agonist release from representative "multiple-activation" $S_2$ subunits:

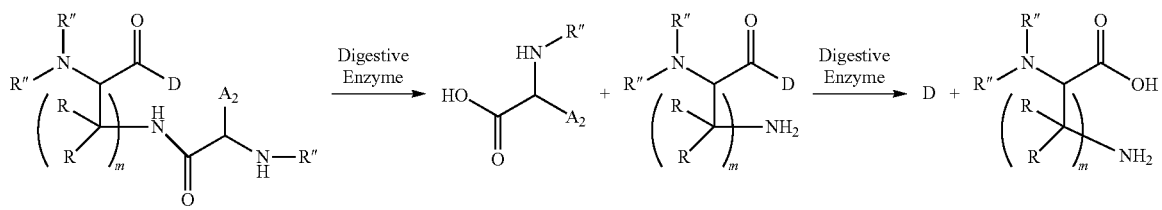

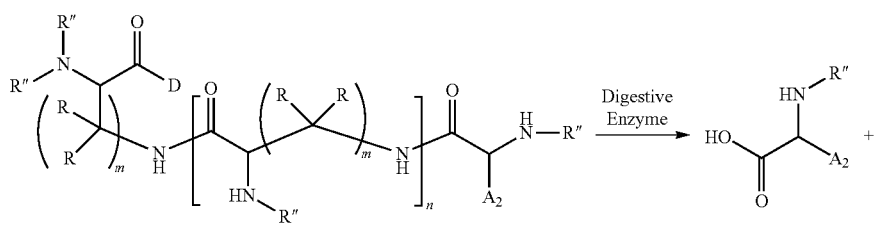

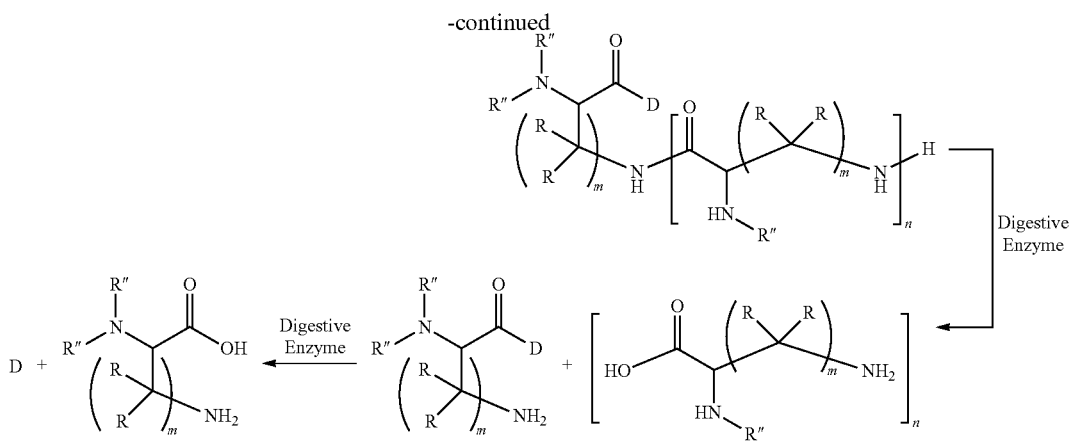
General mechanism of enzyme-mediated opioid agonist release from representative 2,4-oxazolidinedione forming $S_2$ subunits:
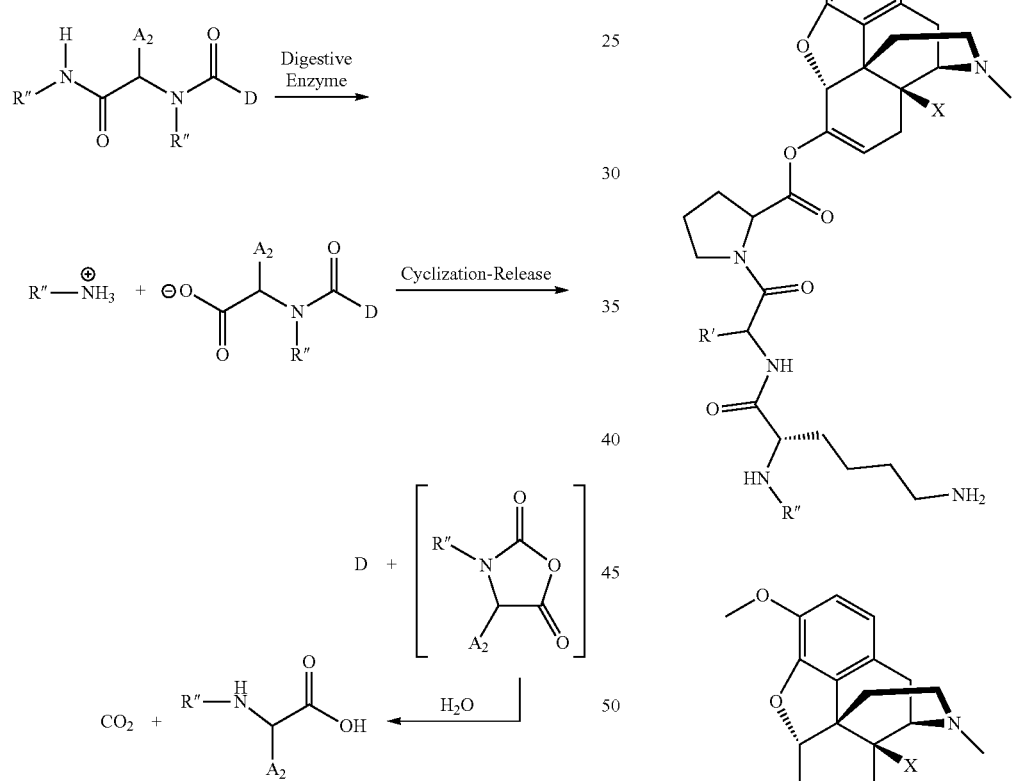
General mechanism of enzyme-mediated opioid agonist release from representative amino-acid ester $S_2$ subunits:
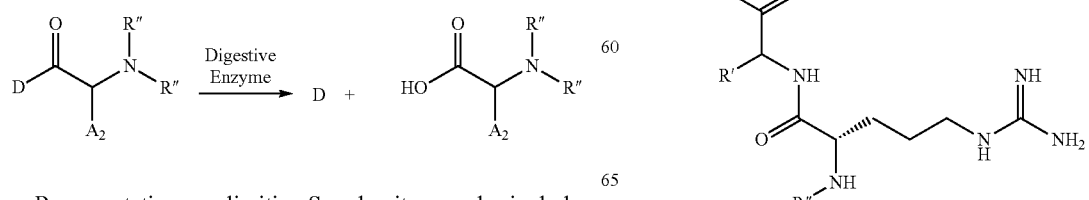
Representative non-limiting $S_2$ subunit examples include, but are not limited to:

67

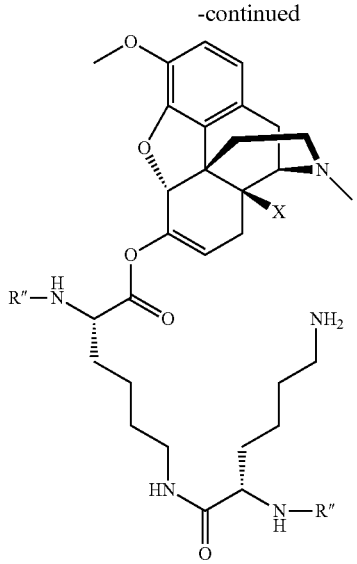

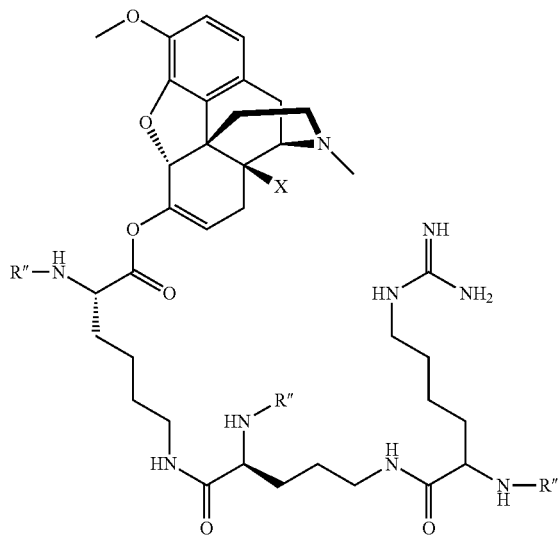

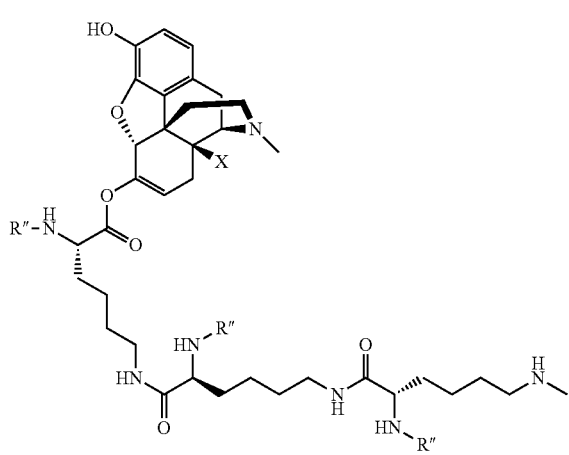

68

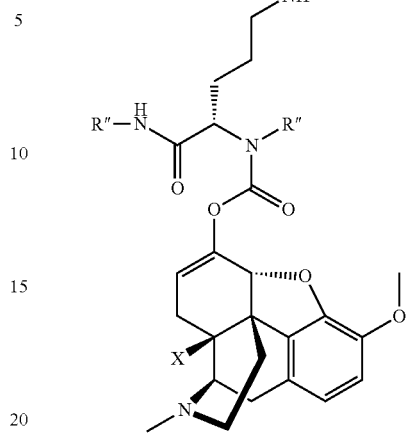

wherein R' and R" are as defined above and X is hydrogen or —OH.

Representative synthetic routes useful for the preparation of $S_2$ substrate subunits are depicted below. The syntheses utilize readily obtained peptide-derived synthons, well-established peptide-based couplings, and known protecting group strategies. Enol-ester and enol-carbamate forming opioid attachment strategies are also employed. (P) is an optional protecting group present on the terminus of the linker Z distal to the $S_2$ subunit that may be employed to enhance chemical efficiency. Purification of the resulting $S_2$ subunits can be accomplished using standard purification procedures involving normal or reverse phase chromatography, crystallization, trituration, etc. The chemical identity of the $S_2$ subunits can be established by LC/MS and/or NMR analysis.

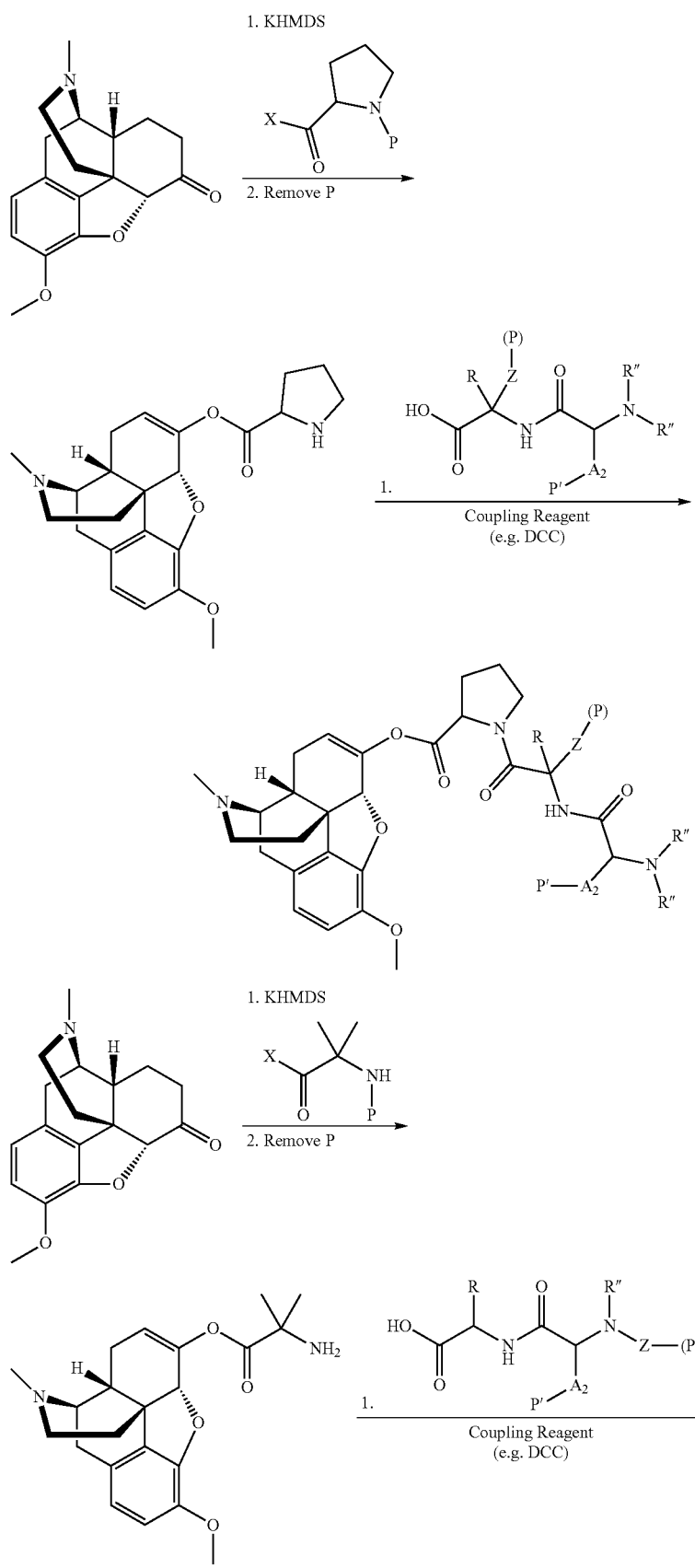

-continued
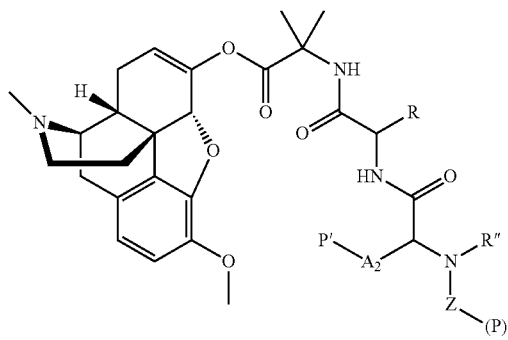
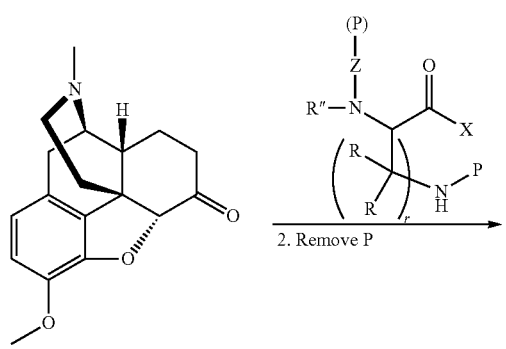
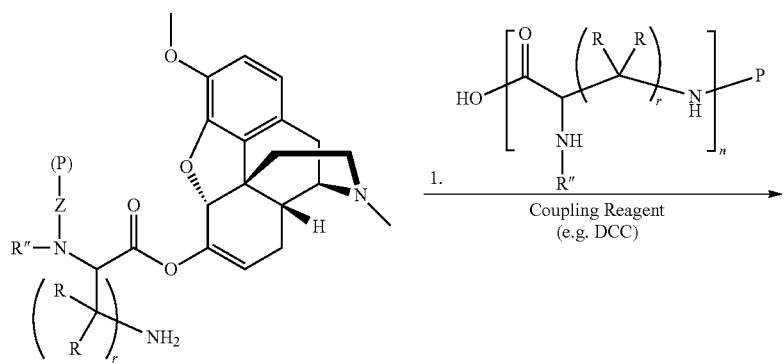

-continued
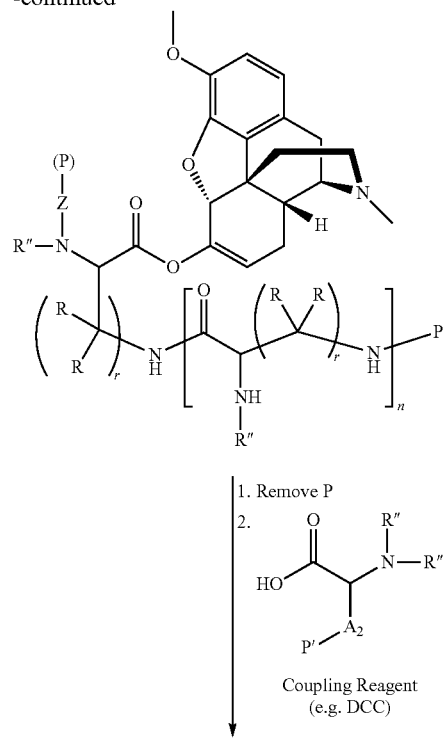
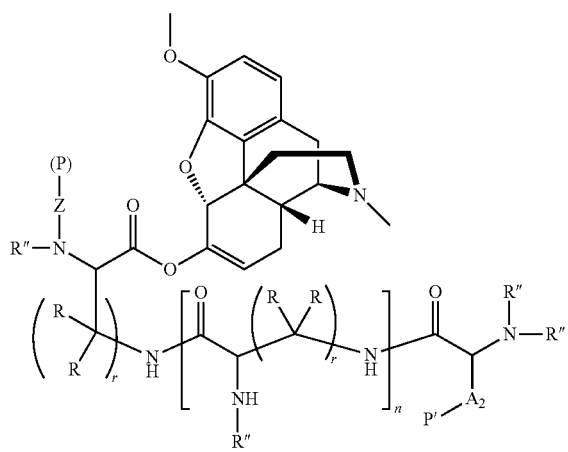
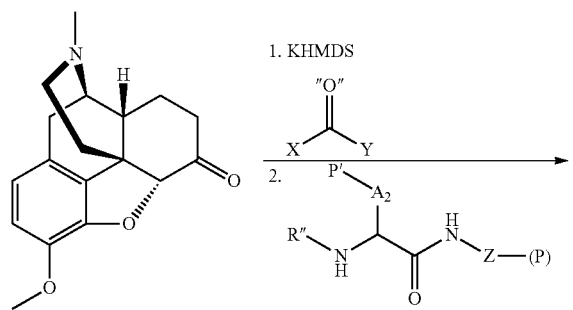

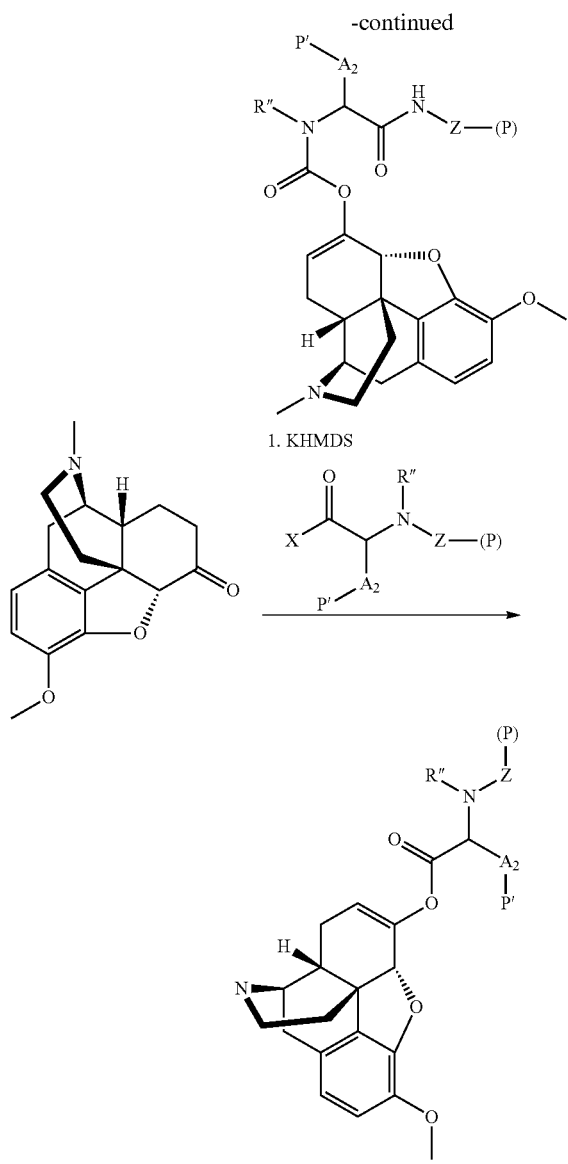

In some embodiments, the $S_2$ subunit has one of the formulas:

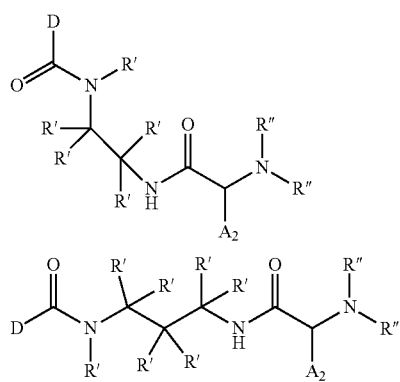

wherein:

D is an opioid agonist, for example wherein D is a morphone, a codone, or morphine;

each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a linking moiety Z;

In some embodiments, R' can also form a spirocyclic or fused aliphatic ring with a geminal or vicinal R' group;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid functional or structural mimic, or a linking moiety Z;

each $A_2$ is independently an amino acid side chain or an amino acid side-chain functional or structural mimic that is capable of being recognized by a digestive enzyme.

In some embodiments, the amino acid side-chain or amino acid side-chain functional or structural mimic $A_2$ directs the regiospecific digestive enzyme mediated hydrolysis of the $S_2$ substrate prior to the release of the appended opioid agonist from the $S_2$ subunit. In some embodiments, the amino acid side chain can be, but is not limited to, the amino acid side chain of arginine, homoarginine, lysine, homolysine, ε-N-methyl lysine, ornithine, or structural/functional mimics thereof.

In some embodiments, the $S_2$ subunit has one of the formulas:

wherein:

D is an opioid agonist, for example wherein D is a morphone, a codone, or morphine;

each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a linking moiety (Z);

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid functional or structural mimic, or a linking moiety (Z);

each $A_2$ is independently an amino acid side chain or an amino acid side-chain mimic that is capable of being recognized by a digestive enzyme;

In some embodiments, $A_2$ is:

wherein:

each R is independently hydrogen or methyl;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid functional or structural mimic, or a linking moiety (Z);

each r is independently an integer from 1 to 6;

n is an integer from 0 to 10;

R''' is hydrogen, methyl, —C(=NR)—$NR_2$ wherein R is each or independently hydrogen or methyl; or wherein $A_2$ is a natural or unnatural amino acid side chain, or an amino acid side-chain mimic that is capable of being recognized by a digestive enzyme that directs the regiospecific hydrolysis of the $S_2$ substrate prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof;

R" is as defined above; and m is an integer from 0-10 r is an integer from 0-10 q is an integer from 0-27.

In some embodiments, the amino acid side-chain or amino acid side-chain mimic $A_2$ directs the regiospecific hydrolysis of the $S_2$ substrate prior to the release of the appended opioid agonist from the $S_2$ subunit. In some embodiments, the amino acid side chain can be, but is not limited to, the amino acid side chain of arginine, homoarginine, lysine, homolysine, ε-N-methyl lysine, ornithine, or structural/functional mimics thereof.

In some embodiments, the $S_2$ subunit has the formula:

wherein:

D is an opioid agonist, for example wherein D is a morphone, a codone, or morphine;

each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a linking moiety (Z);

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid mimic, or a linking moiety (Z);

each $A_2$ is independently an amino acid side chain or an amino acid side-chain mimic that is capable of being recognized by a digestive enzyme; and In some embodiments, $A_2$ is:

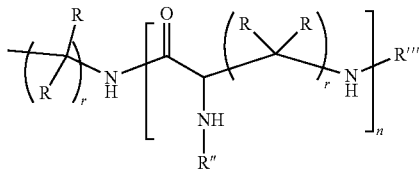

each R is independently hydrogen or methyl;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid functional or structural mimic, or a linking moiety (Z);

each r is independently an integer from 1 to 6;

n is an integer from 0 to 10;

R'" is hydrogen, methyl, —C(═NR)—$NR_2$ wherein R is each or independently hydrogen or methyl; or

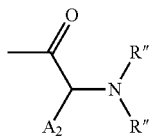

wherein $A_2$ is a natural or unnatural amino acid side chain, or an amino acid side-chain mimic that is capable of being recognized by a digestive enzyme that directs the regiospecific hydrolysis of the $S_2$ substrate prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof; R" is as defined above; and n is an integer from 0 to 10.

In some embodiments, the amino acid side chain or amino acid side-chain mimic $A_2$ directs the regiospecific hydrolysis of the $S_2$ substrate prior to the release of the appended opioid agonist from the $S_2$ subunit. In some embodiments, the amino acid side chain can be, but is not limited to, the amino acid side chain of arginine, homoarginine, lysine, homolysine, ε-N-methyl lysine, ornithine, or structural/functional mimics thereof.

In some embodiments, the $S_2$ subunit has the formula:

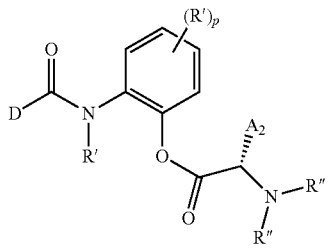

-continued

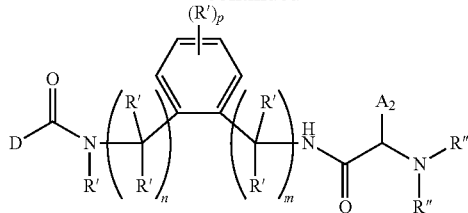

wherein

D is an opioid agonist, for example wherein D is a morphone, a codone, or morphine;

each R' is independently hydrogen, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a linking moiety Z as previously defined;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid side chain, an amino acid side-chain mimic, or a linking moiety Z as previously defined; and each $A_2$ is independently an amino acid side chain or an amino acid side-chain mimic that is capable of being recognized by a digestive enzyme;

In some embodiments, $A_2$ is:

wherein:

each R is independently hydrogen or methyl;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid, an amino acid functional or structural mimic, or a linking moiety (Z);

each r is independently an integer from 1 to 6;

n is an integer from 0 to 10;

R'" is hydrogen, methyl, —C(═NR)—$NR_2$ wherein R is each or independently hydrogen or methyl; or wherein $A_2$ is a natural or unnatural amino acid side chain, or an amino acid side-chain mimic that is capable of being recognized by a digestive enzyme that directs the regiospecific hydrolysis of the $S_2$ substrate prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof; R" is as defined above; and m is an integer from 0 to 10
n is an integer from 0 to 10
p is an integer from 0 to 4.

In some embodiments, the amino acid side chain or amino acid side-chain mimic $A_2$ directs the regiospecific hydrolysis of the $S_2$ substrate prior to the release of the appended opioid agonist from the $S_2$ subunit. In some embodiments, the amino acid side chain can be, but is not limited to, the amino acid side chain of arginine, homoarginine, lysine, homolysine, ε-N-methyl lysine, ornithine, or structural/functional mimics thereof.

As will be evident to one of skill in the art, the opioid agonist releasing digestive enzyme substrates can be covalently attached to form a polysubstrate of the invention via one or more linking moieties Z at any substitution point on the $S_2$ subunit as long as the attachment(s) do(es) not preclude either the requisite hydrolytic action of the digestive enzyme on, or the subsequent release of opioid agonist from, the $S_2$ substrate subunit.

In one aspect of the invention, the opioid agonist is an alcohol, phenol or ketone containing opioid agonist. Accordingly, an alcohol, phenol, or ketone containing opioid agonist is attached through a hydroxylic, phenolic, or enolic oxygen to a linker, which is further attached to an enzyme cleavable moiety. A single enzymatic hydrolysis of a cleavable moiety, or a cascade of enzymatic hydrolyses of cleavable moieties, may release the opioid agonist by (i) directly cleaving the bond between the enzyme cleavable moiety and the opioid agonist, or (ii) revealing a latent nucleophile, such as an amine or carboxylate, that subsequently undergoes an intramolecular cyclization-release reaction, or (iii) revealing an additional enzyme substrate, or substrates, that are further cleaved by the digestive enzyme ultimately resulting in release of the appended opioid agonist.

The mechanisms of enzyme-mediated opioid agonist release from the representative $S_2$ substrates subunits are presented below:

General mechanism of enzyme-mediated opioid agonist release from representative cyclic urea forming $S_2$ subunit example:

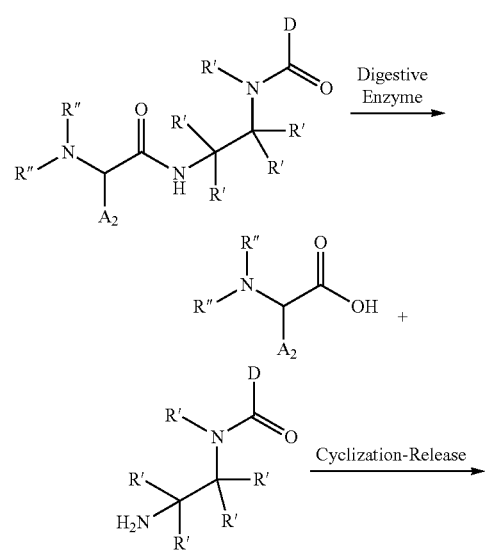

-continued

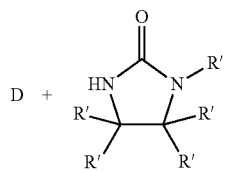

General mechanism of enzyme-mediated opioid agonist release from representative aliphatic fused-ring cyclic urea forming $S_2$ subunit example:

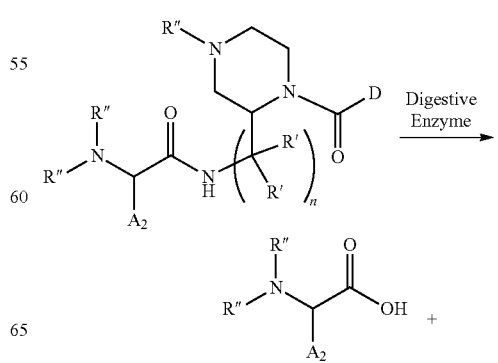

General mechanism of enzyme-mediated opioid agonist release from representative heterocyclic fused-ring cyclic urea forming $S_2$ subunit example:

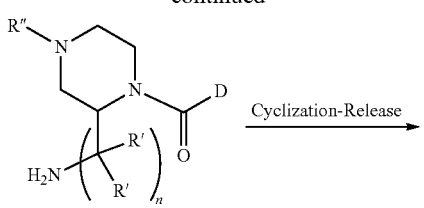
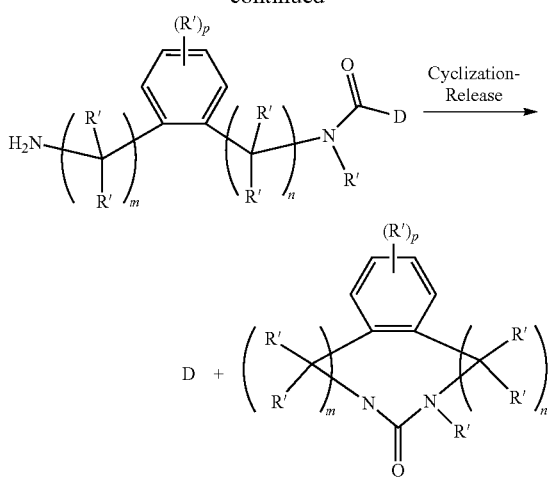
General mechanism of enzyme-mediated opioid agonist release from representative aromatic fused-ring cyclic urea forming $S_2$ subunit examples:
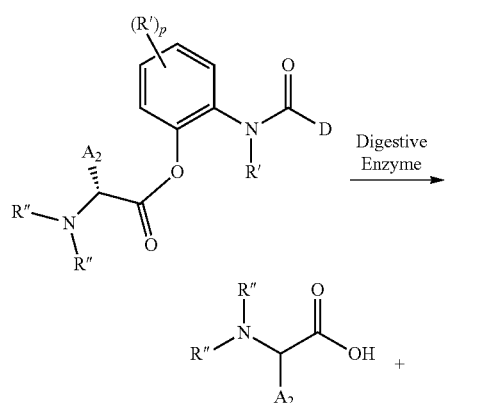
Representative non-limiting $S_2$ subunit examples include, but are not limited to:
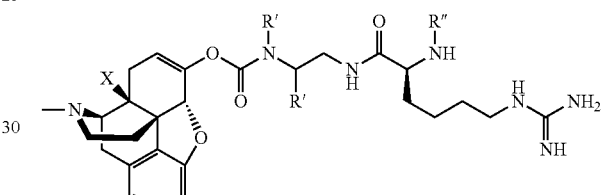
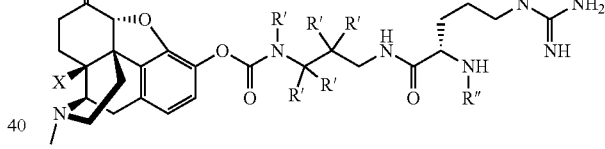
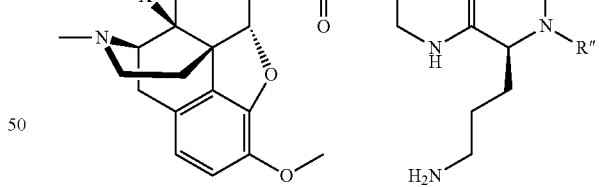
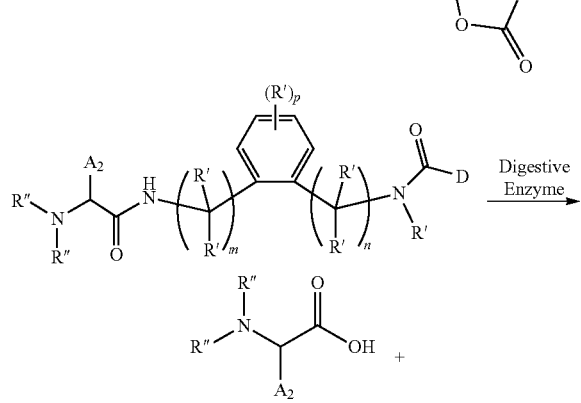
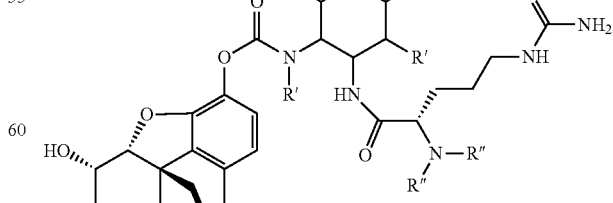

-continued

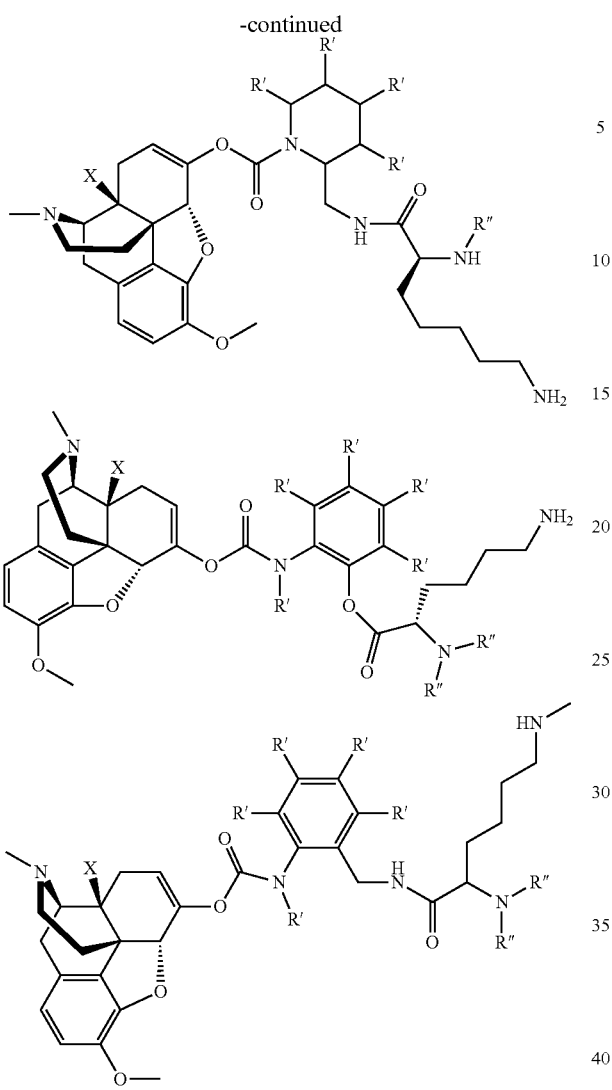

wherein:

X is hydrogen or hydroxyl;

each R' is independently hydrogen, methyl, alkyl, aryl, substituted alkyl, substituted aryl, heteroalkyl, substituted heteroalkyl, a natural or unnatural amino acid side chain, an amino acid side-chain mimic, a polyethylene glycol, or polyethylene glycol containing moiety, or a linking moiety Z;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing moiety, or a natural or unnatural amino acid side chain, an amino acid side-chain mimic, or a linking moiety Z.

Representative synthetic routes useful for the preparation of $S_2$ substrate subunits are depicted below. The syntheses utilize readily obtained peptide-derived synthons, well-established peptide-based couplings, and known protecting group strategies.

Phenol- and enol-carbamate forming opioid attachment strategies published in the art are also employed (see, for example: U.S. Pat. Nos. 8,802,681, 8,685,916, 8,217,005, and 8,163,701, 8,685,916, 8,569,228, 8,497,237 and U.S. Patent Application Nos. 2014016935). (P) is an optional protecting group present on the terminus of the linker Z distal to the $S_2$ subunit that may be employed to enhance chemical efficiency. Purification of the resulting $S_2$ subunits can be accomplished using standard purification procedures involving normal or reverse phase chromatography, crystallization, trituration, etc. The chemical identity of the $S_2$ subunits can be established by LC/MS and/or NMR analysis.

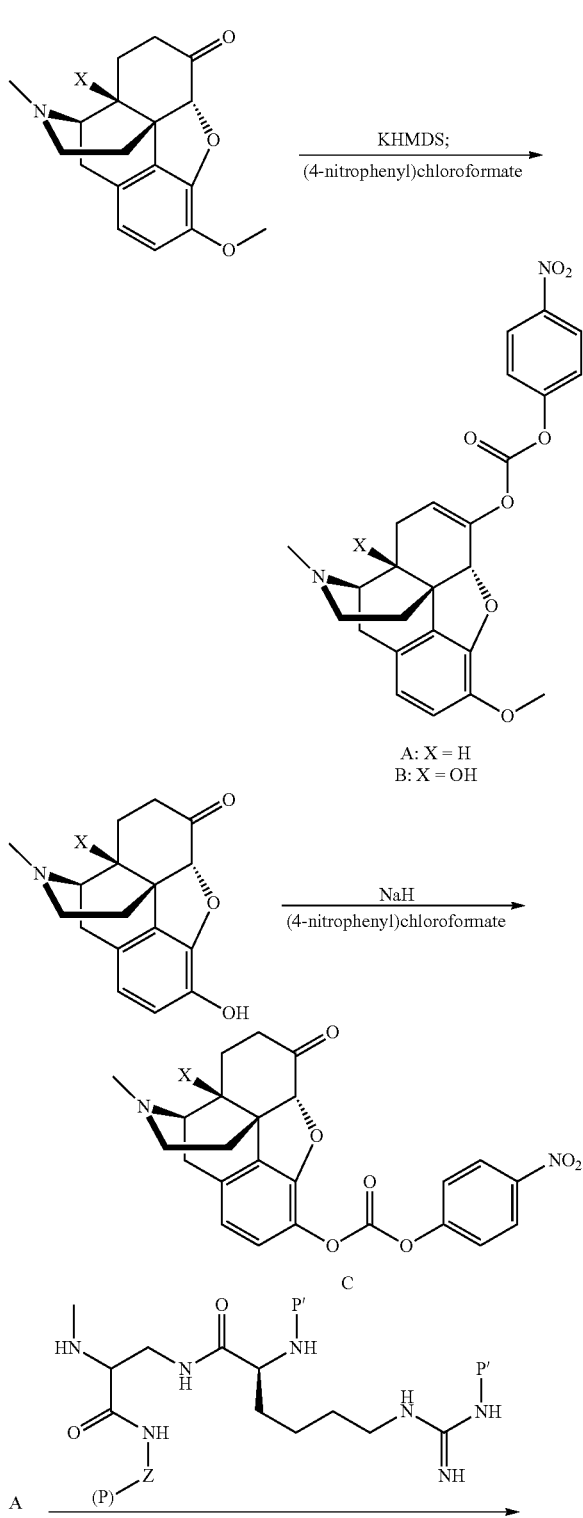

87
-continued
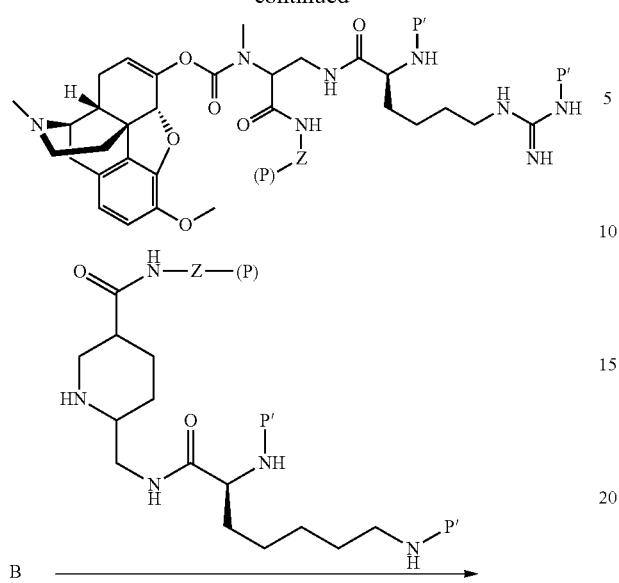
88
-continued
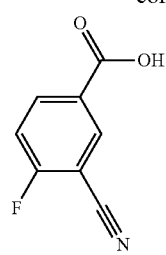
1. MeNH$_2$/(BOC)$_2$O
2. LAH/CbzCl
3. NH$_2$—Z'—(P)
4. H$_2$/Pd/C
5. Z—Lys(Z)—H
6. —Boc
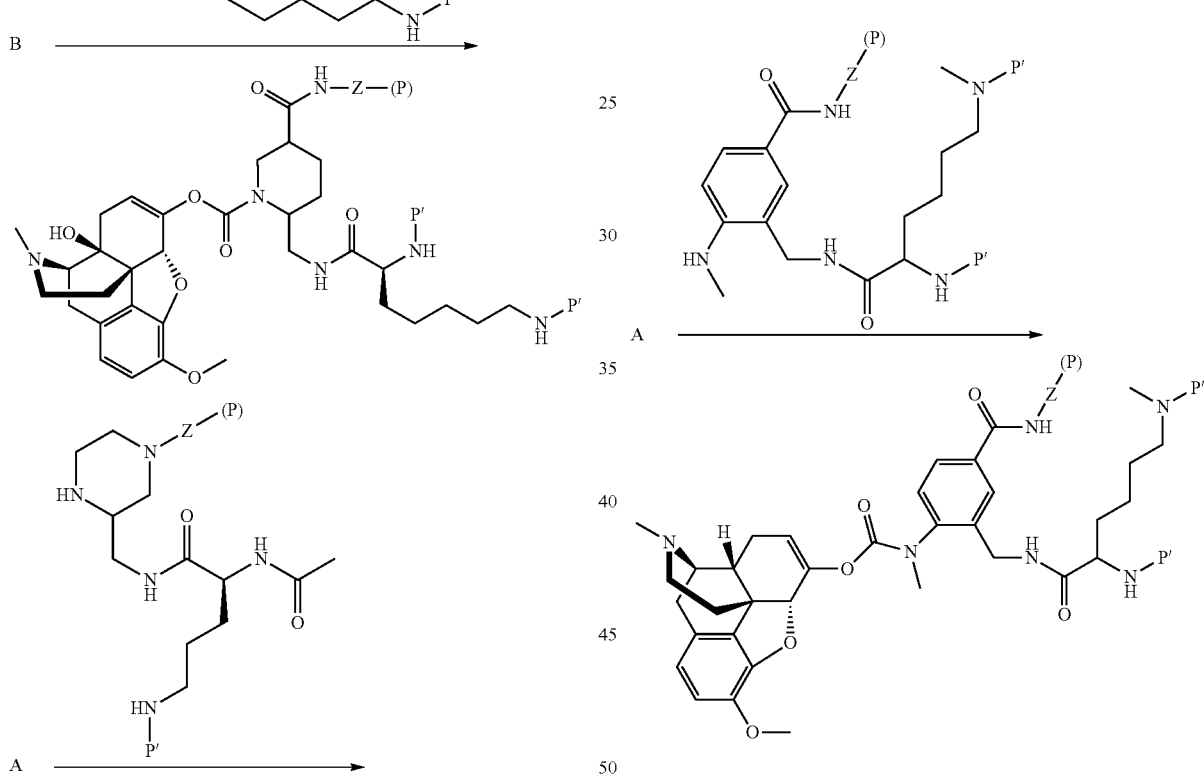
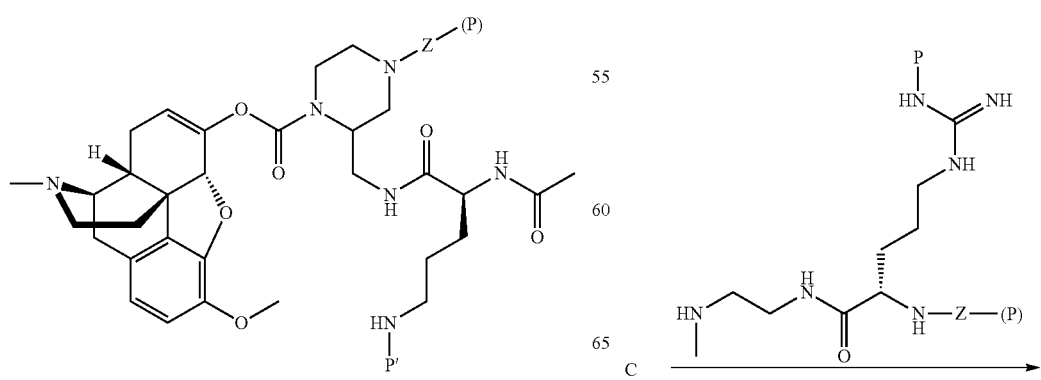

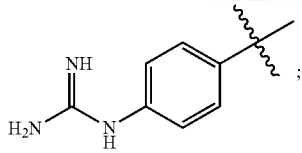

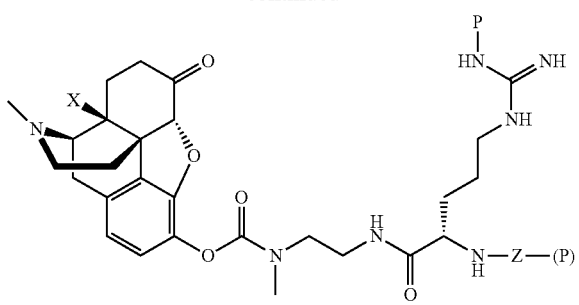

Combinations of $S_1$ and $S_2$ Subunits

In some embodiments the disclosure provides a compound comprising:
One $S_1$ Subunit Conjoined to One $S_2$ Subunit.

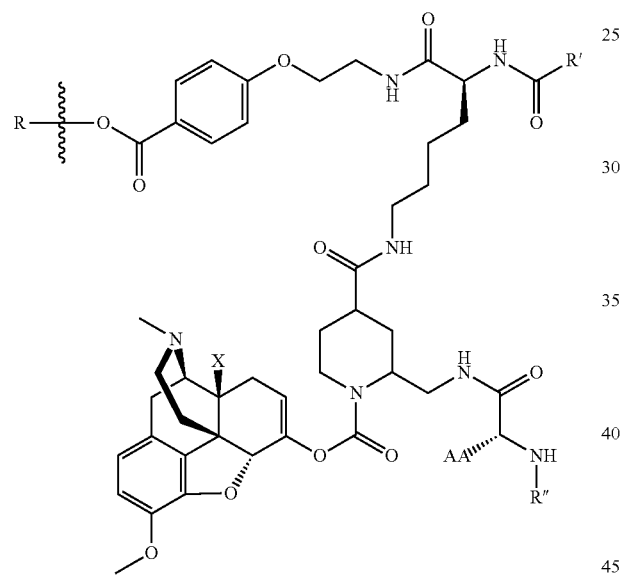

wherein:
R can be

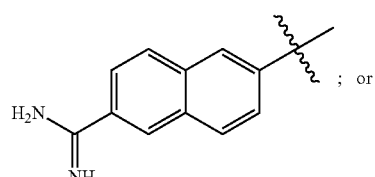; or

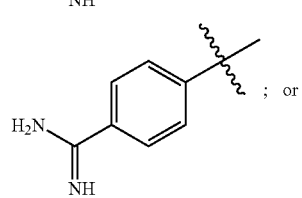; or

R' can be methyl, lower alkyl, substituted alkyl, aryl, substituted aryl, heteroalkyl, a natural or non-natural amino acid, a polypeptide chain comprising natural and/or non-natural amino acids up to 10 amino acids in length, a linear or branched polyethylene glycol chain up to 5 kDa, benzyloxy, and the like; R" can be an acetyl, substituted acyl, a natural or non-natural amino acid, or a polypeptide chain comprising natural and/or non-natural amino acids up to 10 amino acids in length; AA is a natural or non-natural amino acid side chain capable of being recognized by trypsin; X is hydrogen or OH.

In some embodiments the disclosure provides a compound comprising:
One $S_1$ subunit conjoined to two $S_2$ subunits:

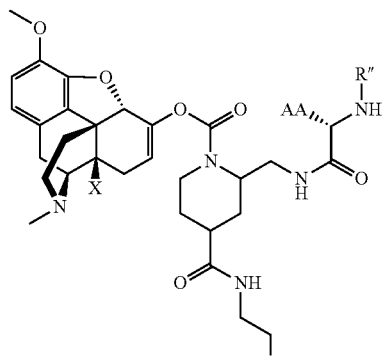

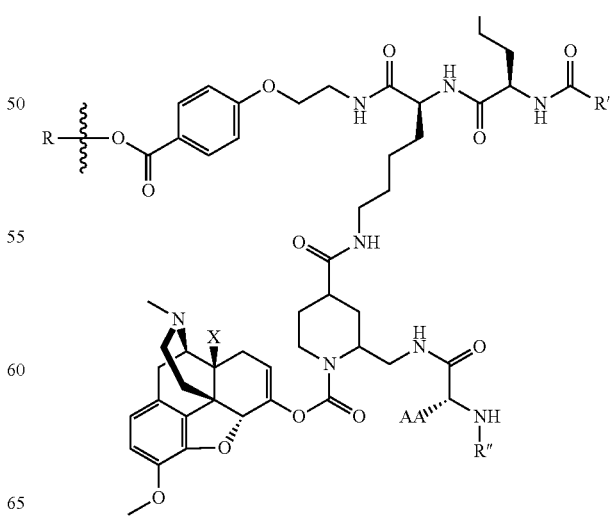

wherein:
R can be

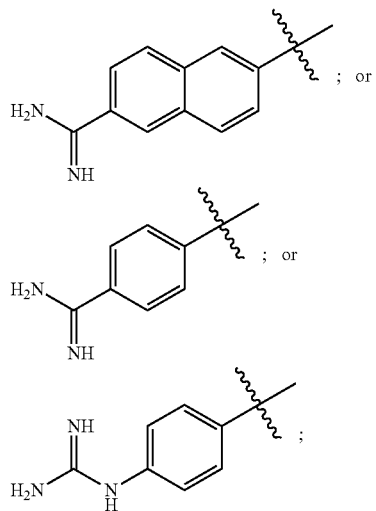

R' can be methyl, lower alkyl, substituted alkyl, aryl, substituted aryl, heteroalkyl, a natural or non-natural amino acid, a polypeptide chain comprising natural and/or non-natural amino acids up to 10 amino acids in length, a linear polyethylene glycol chain up to 5 kDa, benzyloxy, and the like; R" can be an acetyl, substituted acyl, a natural or non-natural amino acid, or a polypeptide chain comprising natural and/or non-natural amino acids up to 10 amino acids in length; AA is a natural or non-natural amino acid side chain capable of being recognized by trypsin; X is hydrogen or OH.

In some embodiments the disclosure provides a compound comprising:

One $S_1$ subunit conjoined to three $S_2$ subunits:

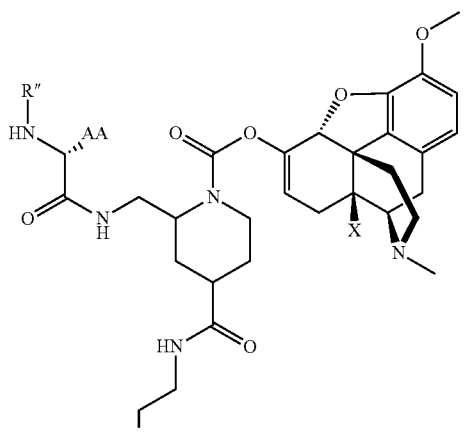

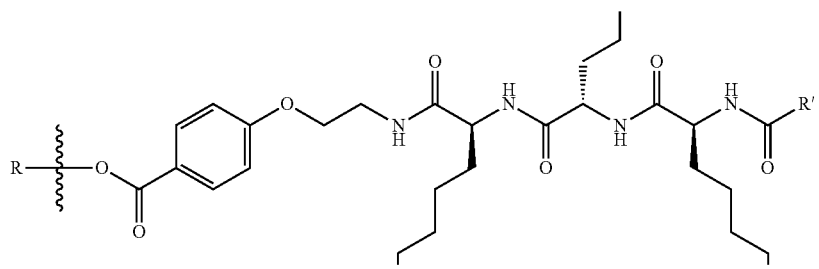

-continued

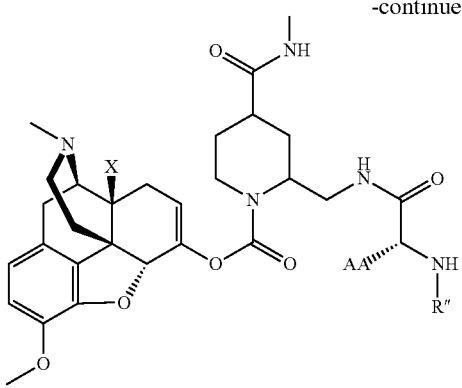

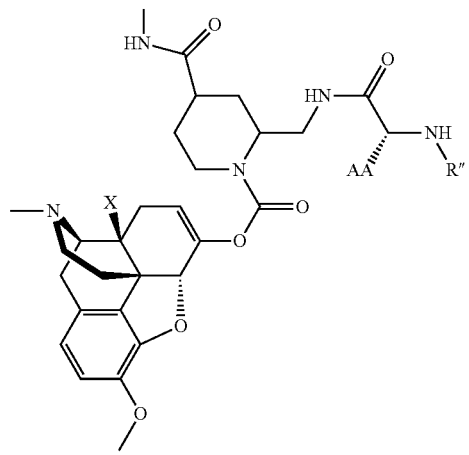

wherein:
R can be

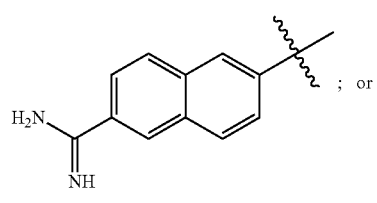; or

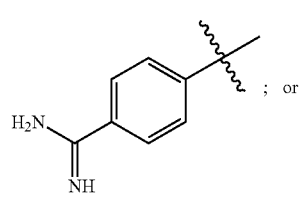; or

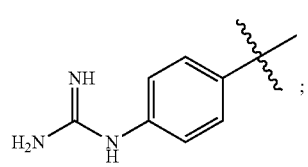;

R' can be methyl, lower alkyl, substituted alkyl, aryl, substituted aryl, heteroalkyl, a natural or non-natural amino acid, a polypeptide chain comprising natural and/or non-natural amino acids up to 10 amino acids in length, a linear polyethylene glycol chain up to 5 kDa, benzyloxy, and the like; R" can be an acetyl, substituted acyl, a natural or non-natural amino acid, or a polypeptide chain comprising natural and/or non-natural amino acids up to 10 amino acids in length; AA is a natural or non-natural amino acid side chain capable of being recognized by trypsin; X is hydrogen or OH.

In some embodiments the disclosure provides one or more of the aforementioned compounds wherein:

R can be

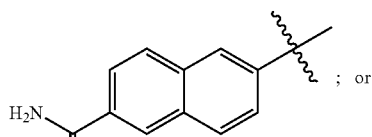; or

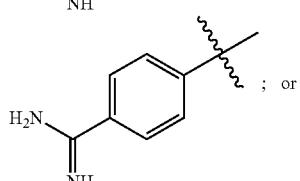; or

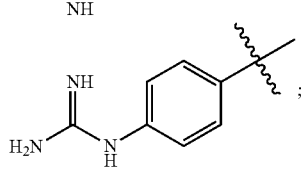;

R' can be methyl or benzyloxy; R" can be an acetyl or a substituted acyl, a natural or non-natural amino acid or a di- or tri-peptide comprising natural or non-natural amino acids; AA is a natural or non-natural amino acid side chain capable of being recognized by trypsin; X is hydrogen or OH.

In yet other embodiments the disclosure provides one or more of the aforementioned compounds wherein:

R can be

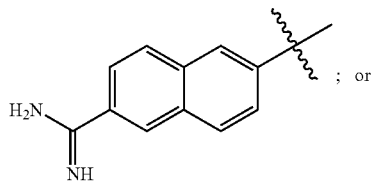; or

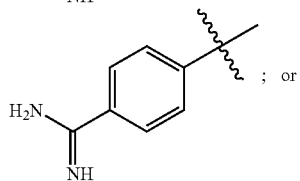; or

-continued

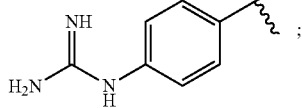

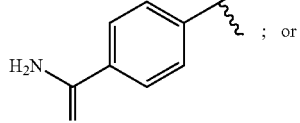; or

R' can be methyl or benzyloxy; R" can be an acetyl, a natural or non-natural amino acid or a dipeptide comprising natural or non-natural amino acids; AA is the side chain of lysine or arginine; X is hydrogen or OH.

In yet another embodiment the disclosure provides one or more of the aforementioned compounds wherein:
R can be

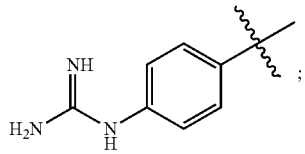;

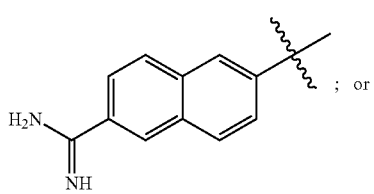; or

R' can be methyl or benzyloxy; R" can be acetyl, -Ala-NAc or -Gly-NAc; AA is the side chain of lysine or arginine; X is hydrogen or OH.

Table 3 Illustrates Various Compounds Contemplated by the Present Disclosure

TABLE 3

| Compound | R | R' | R" | AA (side chain) | X |
|---|---|---|---|---|---|
| 10 | ![structure] | Methyl | Acetyl | Lysine | Hydrogen |
| 11 | ![structure] | Methyl | Acetyl | Lysine | —OH |
| 12 | ![structure] | Methyl | Acetyl | Arginine | Hydrogen |
| 13 | ![structure] | Methyl | Acetyl | Arginine | —OH |

TABLE 3-continued

| Compound | R | R' | R" | AA (side chain) | X |
|---|---|---|---|---|---|
| 14 | 6-carbamimidoyl-naphthalen-2-yl | Methyl | -Ala-NAc | Lysine | Hydrogen |
| 15 | 6-carbamimidoyl-naphthalen-2-yl | Methyl | -Ala-NAc | Lysine | —OH |
| 16 | 6-carbamimidoyl-naphthalen-2-yl | Methyl | -Ala-NAc | Arginine | Hydrogen |
| 17 | 6-carbamimidoyl-naphthalen-2-yl | Methyl | -Ala-NAc | Arginine | —OH |
| 18 | 6-carbamimidoyl-naphthalen-2-yl | Methyl | -Gly-NAc | Lysine | Hydrogen |
| 19 | 6-carbamimidoyl-naphthalen-2-yl | Methyl | -Gly-NAc | Lysine | —OH |
| 20 | 6-carbamimidoyl-naphthalen-2-yl | Methyl | -Gly-NAc | Arginine | Hydrogen |
| 21 | 6-carbamimidoyl-naphthalen-2-yl | Methyl | -Gly-NAc | Arginine | —OH |

TABLE 3-continued
| Compound | R | R' | R" | AA (side chain) | X |
|---|---|---|---|---|---|
| 22 | 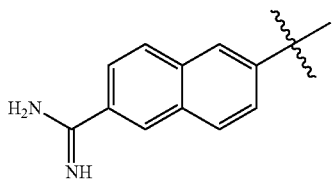 [SMILES: *c1ccc2cc(C(=N)N)ccc2c1] | Benzyloxy | Acetyl | Lysine | Hydrogen |
| 23 | 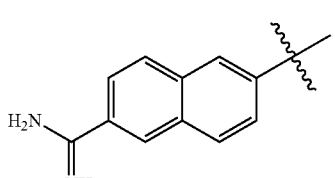 | Benzyloxy | Acetyl | Lysine | —OH |
| 24 | 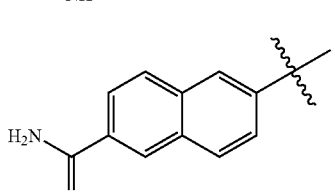 | Benzyloxy | Acetyl | Arginine | Hydrogen |
| 25 | 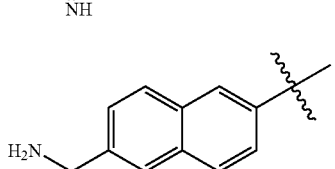 | Benzyloxy | Acetyl | Arginine | —OH |
| 26 | 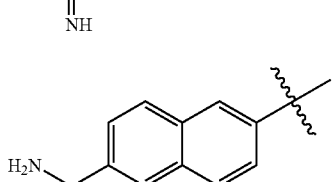 | Benzyloxy | -Ala-NAc | Lysine | Hydrogen |
| 27 | 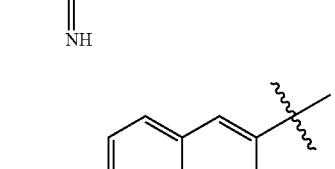 | Benzyloxy | -Ala-NAc | Lysine | —OH |
| 28 | 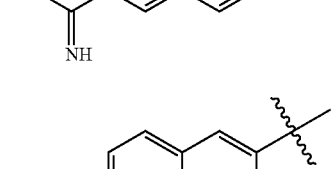 | Benzyloxy | -Ala-NAc | Arginine | Hydrogen |
| 29 | 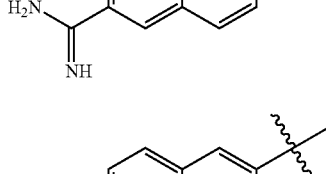 | Benzyloxy | -Ala-NAc | Arginine | —OH |

TABLE 3-continued

| Compound | R | R' | R" | AA (side chain) | X |
|---|---|---|---|---|---|
| 30 | 6-carbamimidoyl-naphth-2-yl (H$_2$N-C(=NH)-naphthalene) | Benzyloxy | -Gly-NAc | Lysine | Hydrogen |
| 31 | 6-carbamimidoyl-naphth-2-yl | Benzyloxy | -Gly-NAc | Lysine | —OH |
| 32 | 6-carbamimidoyl-naphth-2-yl | Benzyloxy | -Gly-NAc | Arginine | Hydrogen |
| 33 | 6-carbamimidoyl-naphth-2-yl | Benzyloxy | -Gly-NAc | Arginine | —OH |
| 34 | 4-carbamimidoyl-phenyl | Methyl | Acetyl | Lysine | Hydrogen |
| 35 | 4-carbamimidoyl-phenyl | Methyl | Acetyl | Lysine | —OH |
| 36 | 4-carbamimidoyl-phenyl | Methyl | Acetyl | Arginine | Hydrogen |
| 37 | 4-carbamimidoyl-phenyl | Methyl | Acetyl | Arginine | —OH |

TABLE 3-continued

| Compound | R | R' | R" | AA (side chain) | X |
|---|---|---|---|---|---|
| 38 | 4-amidinophenyl | Methyl | -Ala-NAc | Lysine | Hydrogen |
| 39 | 4-amidinophenyl | Methyl | -Ala-NAc | Lysine | —OH |
| 40 | 4-amidinophenyl | Methyl | -Ala-NAc | Arginine | Hydrogen |
| 41 | 4-amidinophenyl | Methyl | -Ala-NAc | Arginine | —OH |
| 42 | 4-amidinophenyl | Methyl | -Gly-NAc | Lysine | Hydrogen |
| 43 | 4-amidinophenyl | Methyl | -Gly-NAc | Lysine | —OH |
| 44 | 4-amidinophenyl | Methyl | -Gly-NAc | Arginine | Hydrogen |
| 45 | 4-amidinophenyl | Methyl | -Gly-NAc | Arginine | —OH |

TABLE 3-continued

| Compound | R | R' | R'' | AA (side chain) | X |
|---|---|---|---|---|---|
| 46 | 4-amidinophenyl | Benzyloxy | Acetyl | Lysine | Hydrogen |
| 47 | 4-amidinophenyl | Benzyloxy | Acetyl | Lysine | —OH |
| 48 | 4-amidinophenyl | Benzyloxy | Acetyl | Arginine | Hydrogen |
| 49 | 4-amidinophenyl | Benzyloxy | Acetyl | Arginine | —OH |
| 50 | 4-guanidinophenyl | Benzyloxy | -Ala-NAc | Lysine | Hydrogen |
| 51 | 4-guanidinophenyl | Benzyloxy | -Ala-NAc | Lysine | —OH |
| 52 | 4-guanidinophenyl | Benzyloxy | -Ala-NAc | Arginine | Hydrogen |
| 53 | 4-guanidinophenyl | Benzyloxy | -Ala-NAc | Arginine | —OH |

TABLE 3-continued

| Compound | R | R' | R'' | AA (side chain) | X |
|---|---|---|---|---|---|
| 54 | 4-guanidinophenyl | Benzyloxy | -Gly-NAc | Lysine | Hydrogen |
| 55 | 4-guanidinophenyl | Benzyloxy | -Gly-NAc | Lysine | —OH |
| 56 | 4-guanidinophenyl | Benzyloxy | -Gly-NAc | Arginine | Hydrogen |
| 57 | 4-guanidinophenyl | Benzyloxy | -Gly-NAc | Arginine | —OH |
| 58 | 4-guanidinophenyl | Methyl | Acetyl | Lysine | Hydrogen |
| 59 | 4-guanidinophenyl | Methyl | Acetyl | Lysine | —OH |
| 60 | 4-guanidinophenyl | Methyl | Acetyl | Arginine | Hydrogen |
| 61 | 4-guanidinophenyl | Methyl | Acetyl | Arginine | —OH |
| 62 | 4-guanidinophenyl | Methyl | -Ala-NAc | Lysine | Hydrogen |

TABLE 3-continued

| Compound | R | R' | R'' | AA (side chain) | X |
|---|---|---|---|---|---|
| 63 | ![guanidinophenyl] | Methyl | -Ala-NAc | Lysine | —OH |
| 64 | ![guanidinophenyl] | Methyl | -Ala-NAc | Arginine | Hydrogen |
| 65 | ![guanidinophenyl] | Methyl | -Ala-NAc | Arginine | —OH |
| 66 | ![guanidinophenyl] | Methyl | -Gly-NAc | Lysine | Hydrogen |
| 67 | ![guanidinophenyl] | Methyl | -Gly-NAc | Lysine | —OH |
| 68 | ![guanidinophenyl] | Methyl | -Gly-NAc | Arginine | Hydrogen |
| 69 | ![guanidinophenyl] | Methyl | -Gly-NAc | Arginine | —OH |
| 70 | ![guanidinophenyl] | Benzyloxy | Acetyl | Lysine | Hydrogen |
| 71 | ![guanidinophenyl] | Benzyloxy | Acetyl | Lysine | —OH |

TABLE 3-continued

| Compound | R | R' | R" | AA (side chain) | X |
|---|---|---|---|---|---|
| 72 | guanidinophenyl | Benzyloxy | Acetyl | Arginine | Hydrogen |
| 73 | guanidinophenyl | Benzyloxy | Acetyl | Arginine | —OH |
| 74 | guanidinophenyl | Benzyloxy | -Ala-NAc | Lysine | Hydrogen |
| 75 | guanidinophenyl | Benzyloxy | -Ala-NAc | Lysine | —OH |
| 76 | guanidinophenyl | Benzyloxy | -Ala-NAc | Arginine | Hydrogen |
| 77 | guanidinophenyl | Benzyloxy | -Ala-NAc | Arginine | —OH |
| 78 | guanidinophenyl | Benzyloxy | -Gly-NAc | Lysine | Hydrogen |
| 79 | guanidinophenyl | Benzyloxy | -Gly-NAc | Lysine | —OH |
| 80 | guanidinophenyl | Benzyloxy | -Gly-NAc | Arginine | Hydrogen |

TABLE 3-continued

| Compound | R | R' | R'' | AA (side chain) | X |
|---|---|---|---|---|---|
| 81 | 4-guanidinophenyl (H₂N-C(=NH)-NH-C₆H₄-) | Benzyloxy | -Gly-NAc | Arginine | —OH |
| 82 | 6-amidino-2-naphthyl | Methyl | Acetyl | Lysine | Hydrogen |
| 83 | 6-amidino-2-naphthyl | Methyl | Acetyl | Lysine | —OH |
| 84 | 6-amidino-2-naphthyl | Methyl | Acetyl | Arginine | Hydrogen |
| 85 | 6-amidino-2-naphthyl | Methyl | Acetyl | Arginine | —OH |
| 86 | 6-amidino-2-naphthyl | Methyl | -Ala-NAc | Lysine | Hydrogen |
| 87 | 6-amidino-2-naphthyl | Methyl | -Ala-NAc | Lysine | —OH |
| 88 | 6-amidino-2-naphthyl | Methyl | -Ala-NAc | Arginine | Hydrogen |

TABLE 3-continued

| Compound | R | R' | R" | AA (side chain) | X |
|---|---|---|---|---|---|
| 89 | H₂N-C(=NH)-naphthyl- | Methyl | -Ala-NAc | Arginine | —OH |
| 90 | H₂N-C(=NH)-naphthyl- | Methyl | -Gly-NAc | Lysine | Hydrogen |
| 91 | H₂N-C(=NH)-naphthyl- | Methyl | -Gly-NAc | Lysine | —OH |
| 92 | H₂N-C(=NH)-naphthyl- | Methyl | -Gly-NAc | Arginine | Hydrogen |
| 93 | H₂N-C(=NH)-naphthyl- | Methyl | -Gly-NAc | Arginine | —OH |
| 94 | H₂N-C(=NH)-naphthyl- | Benzyloxy | Acetyl | Lysine | Hydrogen |
| 95 | H₂N-C(=NH)-naphthyl- | Benzyloxy | Acetyl | Lysine | —OH |
| 96 | H₂N-C(=NH)-naphthyl- | Benzyloxy | Acetyl | Arginine | Hydrogen |

TABLE 3-continued

| Compound | R | R' | R" | AA (side chain) | X |
|---|---|---|---|---|---|
| 97 | H₂N-C(=NH)-naphthyl- | Benzyloxy | Acetyl | Arginine | —OH |
| 98 | H₂N-C(=NH)-naphthyl- | Benzyloxy | -Ala-NAc | Lysine | Hydrogen |
| 99 | H₂N-C(=NH)-naphthyl- | Benzyloxy | -Ala-NAc | Lysine | —OH |
| 100 | H₂N-C(=NH)-naphthyl- | Benzyloxy | -Ala-NAc | Arginine | Hydrogen |
| 101 | H₂N-C(=NH)-naphthyl- | Benzyloxy | -Ala-NAc | Arginine | —OH |
| 102 | H₂N-C(=NH)-naphthyl- | Benzyloxy | -Gly-NAc | Lysine | Hydrogen |
| 103 | H₂N-C(=NH)-naphthyl- | Benzyloxy | -Gly-NAc | Lysine | —OH |
| 104 | H₂N-C(=NH)-naphthyl- | Benzyloxy | -Gly-NAc | Arginine | Hydrogen |

TABLE 3-continued

| Compound | R | R' | R'' | AA (side chain) | X |
|---|---|---|---|---|---|
| 105 | (4-amidino-naphth-2-yl group with H₂N-C(=NH)- at 6-position) | Benzyloxy | -Gly-NAc | Arginine | —OH |
| 106 | (4-amidinophenyl) | Methyl | Acetyl | Lysine | Hydrogen |
| 107 | (4-amidinophenyl) | Methyl | Acetyl | Lysine | —OH |
| 108 | (4-amidinophenyl) | Methyl | Acetyl | Arginine | Hydrogen |
| 109 | (4-amidinophenyl) | Methyl | Acetyl | Arginine | —OH |
| 110 | (4-amidinophenyl) | Methyl | -Ala-NAc | Lysine | Hydrogen |
| 111 | (4-amidinophenyl) | Methyl | -Ala-NAc | Lysine | —OH |
| 112 | (4-amidinophenyl) | Methyl | -Ala-NAc | Arginine | Hydrogen |

TABLE 3-continued

| Compound | R | R' | R" | AA (side chain) | X |
|---|---|---|---|---|---|
| 113 | 4-amidinophenyl | Methyl | -Ala-NAc | Arginine | —OH |
| 114 | 4-amidinophenyl | Methyl | -Gly-NAc | Lysine | Hydrogen |
| 115 | 4-amidinophenyl | Methyl | -Gly-NAc | Lysine | —OH |
| 116 | 4-amidinophenyl | Methyl | -Gly-NAc | Arginine | Hydrogen |
| 117 | 4-amidinophenyl | Methyl | -Gly-NAc | Arginine | —OH |
| 118 | 4-amidinophenyl | Benzyloxy | Acetyl | Lysine | Hydrogen |
| 119 | 4-amidinophenyl | Benzyloxy | Acetyl | Lysine | —OH |
| 120 | 4-amidinophenyl | Benzyloxy | Acetyl | Arginine | Hydrogen |

TABLE 3-continued

| Compound | R | R' | R" | AA (side chain) | X |
|---|---|---|---|---|---|
| 121 | 4-(H₂N-C(=NH))-phenyl | Benzyloxy | Acetyl | Arginine | —OH |
| 122 | 4-(H₂N-C(=NH)-NH)-phenyl | Benzyloxy | -Ala-NAc | Lysine | Hydrogen |
| 123 | 4-(H₂N-C(=NH)-NH)-phenyl | Benzyloxy | -Ala-NAc | Lysine | —OH |
| 124 | 4-(H₂N-C(=NH)-NH)-phenyl | Benzyloxy | -Ala-NAc | Arginine | Hydrogen |
| 125 | 4-(H₂N-C(=NH)-NH)-phenyl | Benzyloxy | -Ala-NAc | Arginine | —OH |
| 126 | 4-(H₂N-C(=NH)-NH)-phenyl | Benzyloxy | -Gly-NAc | Lysine | Hydrogen |
| 127 | 4-(H₂N-C(=NH)-NH)-phenyl | Benzyloxy | -Gly-NAc | Lysine | —OH |
| 128 | 4-(H₂N-C(=NH)-NH)-phenyl | Benzyloxy | -Gly-NAc | Arginine | Hydrogen |
| 129 | 4-(H₂N-C(=NH)-NH)-phenyl | Benzyloxy | -Gly-NAc | Arginine | —OH |

TABLE 3-continued
| Compound | R | R' | R" | AA (side chain) | X |
|---|---|---|---|---|---|
| 130 | 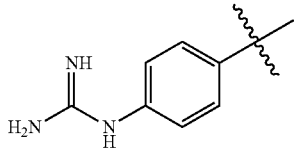 [SMILES: *c1ccc(NC(=N)N)cc1] | Methyl | Acetyl | Lysine | Hydrogen |
| 131 | 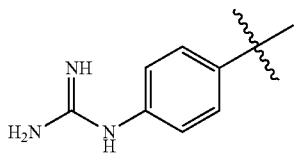 [SMILES: *c1ccc(NC(=N)N)cc1] | Methyl | Acetyl | Lysine | —OH |
| 132 | 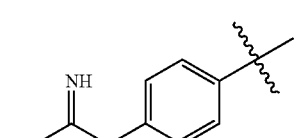 | Methyl | Acetyl | Arginine | Hydrogen |
| 133 | 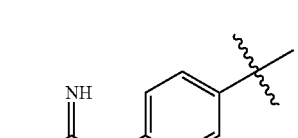 | Methyl | Acetyl | Arginine | —OH |
| 134 | 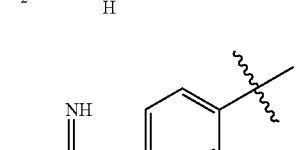 | Methyl | -Ala-NAc | Lysine | Hydrogen |
| 135 | 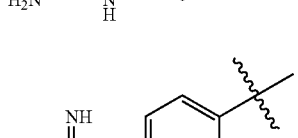 | Methyl | -Ala-NAc | Lysine | —OH |
| 136 | 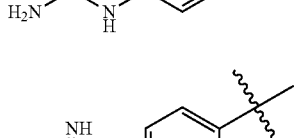 | Methyl | -Ala-NAc | Arginine | Hydrogen |
| 137 | 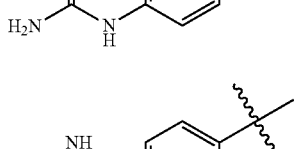 | Methyl | -Ala-NAc | Arginine | —OH |
| 138 | 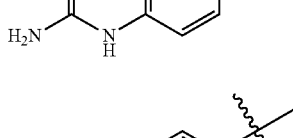 | Methyl | -Gly-NAc | Lysine | Hydrogen |

TABLE 3-continued

| Compound | R | R' | R" | AA (side chain) | X |
|---|---|---|---|---|---|
| 139 | H₂N-C(=NH)-NH-C₆H₄- | Methyl | -Gly-NAc | Lysine | —OH |
| 140 | H₂N-C(=NH)-NH-C₆H₄- | Methyl | -Gly-NAc | Arginine | Hydrogen |
| 141 | H₂N-C(=NH)-NH-C₆H₄- | Methyl | -Gly-NAc | Arginine | —OH |
| 142 | H₂N-C(=NH)-NH-C₆H₄- | Benzyloxy | Acetyl | Lysine | Hydrogen |
| 143 | H₂N-C(=NH)-NH-C₆H₄- | Benzyloxy | Acetyl | Lysine | —OH |
| 144 | H₂N-C(=NH)-NH-C₆H₄- | Benzyloxy | Acetyl | Arginine | Hydrogen |
| 145 | H₂N-C(=NH)-NH-C₆H₄- | Benzyloxy | Acetyl | Arginine | —OH |
| 146 | H₂N-C(=NH)-NH-C₆H₄- | Benzyloxy | -Ala-NAc | Lysine | Hydrogen |
| 147 | H₂N-C(=NH)-NH-C₆H₄- | Benzyloxy | -Ala-NAc | Lysine | —OH |

TABLE 3-continued

| Compound | R | R' | R" | AA (side chain) | X |
|---|---|---|---|---|---|
| 148 | guanidinophenyl | Benzyloxy | -Ala-NAc | Arginine | Hydrogen |
| 149 | guanidinophenyl | Benzyloxy | -Ala-NAc | Arginine | —OH |
| 150 | guanidinophenyl | Benzyloxy | -Gly-NAc | Lysine | Hydrogen |
| 151 | guanidinophenyl | Benzyloxy | -Gly-NAc | Lysine | —OH |
| 152 | guanidinophenyl | Benzyloxy | -Gly-NAc | Arginine | Hydrogen |
| 153 | guanidinophenyl | Benzyloxy | -Gly-NAc | Arginine | —OH |
| 154 | amidinonaphthyl | Methyl | Acetyl | Lysine | Hydrogen |
| 155 | amidinonaphthyl | Methyl | Acetyl | Lysine | —OH |
| 156 | amidinonaphthyl | Methyl | Acetyl | Arginine | Hydrogen |

TABLE 3-continued

| Compound | R | R' | R" | AA (side chain) | X |
|---|---|---|---|---|---|
| 157 | H₂N-C(=NH)-naphthyl- | Methyl | Acetyl | Arginine | —OH |
| 158 | H₂N-C(=NH)-naphthyl- | Methyl | -Ala-NAc | Lysine | Hydrogen |
| 159 | H₂N-C(=NH)-naphthyl- | Methyl | -Ala-NAc | Lysine | —OH |
| 160 | H₂N-C(=NH)-naphthyl- | Methyl | -Ala-NAc | Arginine | Hydrogen |
| 161 | H₂N-C(=NH)-naphthyl- | Methyl | -Ala-NAc | Arginine | —OH |
| 162 | H₂N-C(=NH)-naphthyl- | Methyl | -Gly-NAc | Lysine | Hydrogen |
| 163 | H₂N-C(=NH)-naphthyl- | Methyl | -Gly-NAc | Lysine | —OH |
| 164 | H₂N-C(=NH)-naphthyl- | Methyl | -Gly-NAc | Arginine | Hydrogen |

TABLE 3-continued

| Compound | R | R' | R" | AA (side chain) | X |
|---|---|---|---|---|---|
| 165 | H₂N-C(=NH)-naphthyl- | Methyl | -Gly-NAc | Arginine | —OH |
| 166 | H₂N-C(=NH)-naphthyl- | Benzyloxy | Acetyl | Lysine | Hydrogen |
| 167 | H₂N-C(=NH)-naphthyl- | Benzyloxy | Acetyl | Lysine | —OH |
| 168 | H₂N-C(=NH)-naphthyl- | Benzyloxy | Acetyl | Arginine | Hydrogen |
| 169 | H₂N-C(=NH)-naphthyl- | Benzyloxy | Acetyl | Arginine | —OH |
| 170 | H₂N-C(=NH)-naphthyl- | Benzyloxy | -Ala-NAc | Lysine | Hydrogen |
| 171 | H₂N-C(=NH)-naphthyl- | Benzyloxy | -Ala-NAc | Lysine | —OH |
| 172 | H₂N-C(=NH)-naphthyl- | Benzyloxy | -Ala-NAc | Arginine | Hydrogen |

TABLE 3-continued

| Compound | R | R' | R" | AA (side chain) | X |
|---|---|---|---|---|---|
| 173 | 6-carbamimidoyl-naphthalen-2-yl | Benzyloxy | -Ala-NAc | Arginine | —OH |
| 174 | 6-carbamimidoyl-naphthalen-2-yl | Benzyloxy | -Gly-NAc | Lysine | Hydrogen |
| 175 | 6-carbamimidoyl-naphthalen-2-yl | Benzyloxy | -Gly-NAc | Lysine | —OH |
| 176 | 6-carbamimidoyl-naphthalen-2-yl | Benzyloxy | -Gly-NAc | Arginine | Hydrogen |
| 177 | 6-carbamimidoyl-naphthalen-2-yl | Benzyloxy | -Gly-NAc | Arginine | —OH |
| 178 | 4-carbamimidoyl-phenyl | Methyl | Acetyl | Lysine | Hydrogen |
| 179 | 4-carbamimidoyl-phenyl | Methyl | Acetyl | Lysine | —OH |
| 180 | 4-carbamimidoyl-phenyl | Methyl | Acetyl | Arginine | Hydrogen |

TABLE 3-continued
| Compound | R | R' | R" | AA (side chain) | X |
|---|---|---|---|---|---|
| 181 | 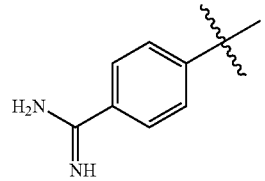 | Methyl | Acetyl | Arginine | —OH |
| 182 | 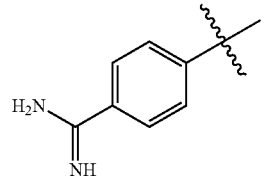 [SMILES: *c1ccc(C(=N)N)cc1] | Methyl | -Ala-NAc | Lysine | Hydrogen |
| 183 | 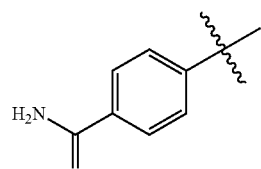 | Methyl | -Ala-NAc | Lysine | —OH |
| 184 | 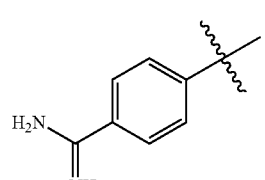 | Methyl | -Ala-NAc | Arginine | Hydrogen |
| 185 | 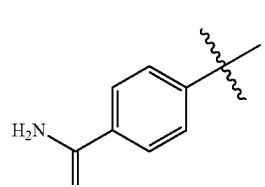 | Methyl | -Ala-NAc | Arginine | —OH |
| 186 | 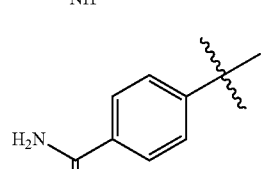 | Methyl | -Gly-NAc | Lysine | Hydrogen |
| 187 | 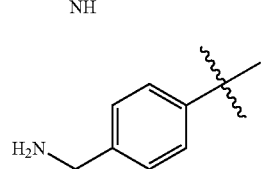 | Methyl | -Gly-NAc | Lysine | —OH |
| 188 | 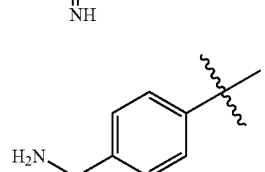 | Methyl | -Gly-NAc | Arginine | Hydrogen |

TABLE 3-continued

| Compound | R | R' | R" | AA (side chain) | X |
|---|---|---|---|---|---|
| 189 | 4-(H₂N-C(=NH))-phenyl | Methyl | -Gly-NAc | Arginine | —OH |
| 190 | 4-(H₂N-C(=NH))-phenyl | Benzyloxy | Acetyl | Lysine | Hydrogen |
| 191 | 4-(H₂N-C(=NH))-phenyl | Benzyloxy | Acetyl | Lysine | —OH |
| 192 | 4-(H₂N-C(=NH))-phenyl | Benzyloxy | Acetyl | Arginine | Hydrogen |
| 193 | 4-(H₂N-C(=NH))-phenyl | Benzyloxy | Acetyl | Arginine | —OH |
| 194 | 4-(H₂N-C(=NH)-NH)-phenyl | Benzyloxy | -Ala-NAc | Lysine | Hydrogen |
| 195 | 4-(H₂N-C(=NH)-NH)-phenyl | Benzyloxy | -Ala-NAc | Lysine | —OH |
| 196 | 4-(H₂N-C(=NH)-NH)-phenyl | Benzyloxy | -Ala-NAc | Arginine | Hydrogen |

TABLE 3-continued

| Compound | R | R' | R" | AA (side chain) | X |
|---|---|---|---|---|---|
| 197 | 4-guanidinophenyl | Benzyloxy | -Ala-NAc | Arginine | —OH |
| 198 | 4-guanidinophenyl | Benzyloxy | -Gly-NAc | Lysine | Hydrogen |
| 199 | 4-guanidinophenyl | Benzyloxy | -Gly-NAc | Lysine | —OH |
| 200 | 4-guanidinophenyl | Benzyloxy | -Gly-NAc | Arginine | Hydrogen |
| 201 | 4-guanidinophenyl | Benzyloxy | -Gly-NAc | Arginine | —OH |
| 202 | 4-guanidinophenyl | Methyl | Acetyl | Lysine | Hydrogen |
| 203 | 4-guanidinophenyl | Methyl | Acetyl | Lysine | —OH |
| 204 | 4-guanidinophenyl | Methyl | Acetyl | Arginine | Hydrogen |
| 205 | 4-guanidinophenyl | Methyl | Acetyl | Arginine | —OH |

TABLE 3-continued

| Compound | R | R' | R" | AA (side chain) | X |
|---|---|---|---|---|---|
| 206 | H₂N-C(=NH)-NH-C₆H₄- (guanidinophenyl) | Methyl | -Ala-NAc | Lysine | Hydrogen |
| 207 | H₂N-C(=NH)-NH-C₆H₄- | Methyl | -Ala-NAc | Lysine | —OH |
| 208 | H₂N-C(=NH)-NH-C₆H₄- | Methyl | -Ala-NAc | Arginine | Hydrogen |
| 209 | H₂N-C(=NH)-NH-C₆H₄- | Methyl | -Ala-NAc | Arginine | —OH |
| 210 | H₂N-C(=NH)-NH-C₆H₄- | Methyl | -Gly-NAc | Lysine | Hydrogen |
| 211 | H₂N-C(=NH)-NH-C₆H₄- | Methyl | -Gly-NAc | Lysine | —OH |
| 212 | H₂N-C(=NH)-NH-C₆H₄- | Methyl | -Gly-NAc | Arginine | Hydrogen |
| 213 | H₂N-C(=NH)-NH-C₆H₄- | Methyl | -Gly-NAc | Arginine | —OH |
| 214 | H₂N-C(=NH)-NH-C₆H₄- | Benzyloxy | Acetyl | Lysine | Hydrogen |

TABLE 3-continued
| Compound | R | R' | R" | AA (side chain) | X |
|---|---|---|---|---|---|
| 215 | 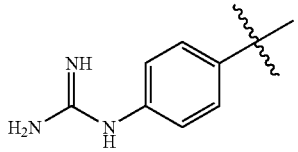 [SMILES: *c1ccc(NC(=N)N)cc1] | Benzyloxy | Acetyl | Lysine | —OH |
| 216 | 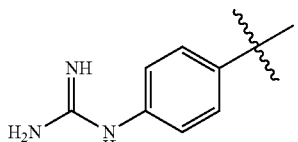 | Benzyloxy | Acetyl | Arginine | Hydrogen |
| 217 | 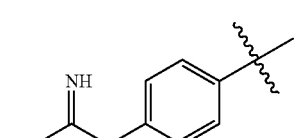 | Benzyloxy | Acetyl | Arginine | —OH |
| 218 | 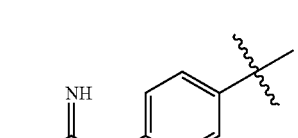 | Benzyloxy | -Ala-NAc | Lysine | Hydrogen |
| 219 | 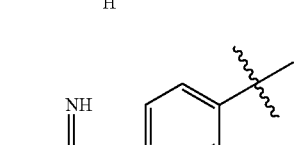 | Benzyloxy | -Ala-NAc | Lysine | —OH |
| 220 | 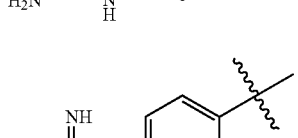 | Benzyloxy | -Ala-NAc | Arginine | Hydrogen |
| 221 | 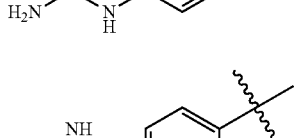 | Benzyloxy | -Ala-NAc | Arginine | —OH |
| 222 | 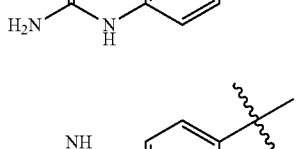 | Benzyloxy | -Gly-NAc | Lysine | Hydrogen |
| 223 | 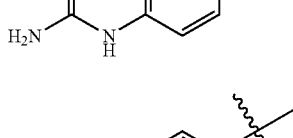 | Benzyloxy | -Gly-NAc | Lysine | —OH |

TABLE 3-continued

| Compound | R | R' | R" | AA (side chain) | X |
|---|---|---|---|---|---|
| 224 | (guanidinophenyl structure with NH, H$_2$N, NH) | Benzyloxy | -Gly-NAc | Arginine | Hydrogen |
| 225 | (guanidinophenyl structure with NH, H$_2$N, NH) | Benzyloxy | -Gly-NAc | Arginine | —OH |

Opioid Antagonist Releasing S$_3$ Subunits

Polysubstrates of the invention may optionally contain none, one, or more covalently linked opioid antagonist releasing S$_3$ subunits. The opioid antagonist releasing S$_3$ subunits preferably do not substantially release the appended opioid antagonist upon oral ingestion by a subject. By design, S$_3$ subunits preferably are not digestive enzyme substrates, but may be substrates for enzymes found in blood, plasma, liver, or other systemically accessible tissues. The opioid antagonist releasing GI enzyme substrates are designed to efficiently release the appended opioid antagonist in the systemic circulation (i.e. upon exposure to enzymes found in the plasma, liver, red blood cells, or other tissues located outside the gastrointestinal tract) and/or when subjects attempt to abuse polysubstrates of the invention via unintended non-oral routes (e.g. intravenous injection and/or snorting).

Specifically, the opioid antagonist releasing substrates are designed to release the appended opioid antagonist upon chemical tampering by potential abusers. Chemical tampering methods capable of hydrolyzing the ester functionalities contained within the S$_1$ subunits in polysubstrates of the invention aimed at destroying the S$_1$ subunits that saturate the digestive enzyme that mediate the release of the opioid agonist when oral overdoses are ingested, will also efficiently liberate the opioid antagonist from the S$_3$ subunits. As a result, both non-oral routes of abuse and tampering methods aimed at liberating the opioid agonist or defeating the oral overdose protection can be effectively thwarted by the presence of S$_3$ subunits in polysubstrates of the invention. Suitable opioid antagonists include, but are not limited to, buprenorphine, cyclazocine, cyclorphan, naloxone, naltrexone, nalmephene, 6-amino-6-desoxo-naloxone, levallorphan, nalbuphine, naltrendol, naltrindole, nalorphine, norbinaltorphimine, oxilorphan, pentazocine, piperidine-N-alkylcarboxylate opioid antagonists such as those described in U.S. Pat. Nos. 5,159,081, 5,250,542, 5,270,328, and 5,434,171, and derivatives, mixtures, salts, polymorphs, or prodrugs thereof.

The opioid antagonist-releasing substrates may be linked via an ester, or alternative chemically labile functionality, to the phenol, alcohol, or ketone (e.g. enol) functionalities found in naltrexone or naloxone as illustrated below.

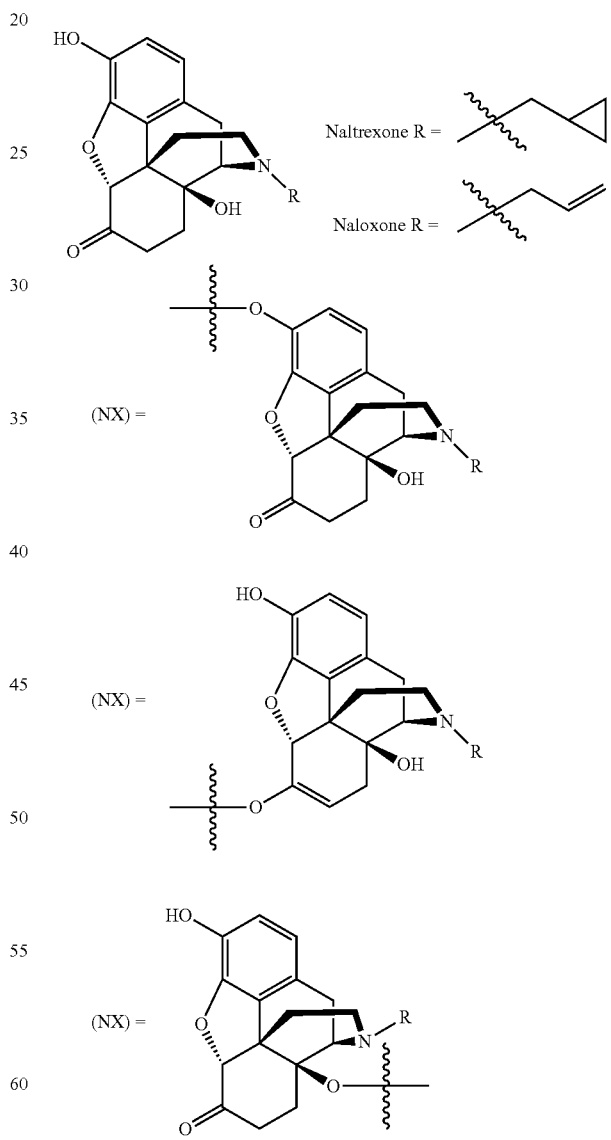

Non-limiting generic examples of opioid antagonist releasing S$_3$ subunits comprising chemically releasable opioid antagonists designated as NX and a linking moiety Z are shown below:

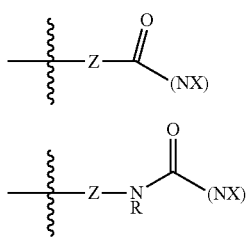
wherein:
NX is an opioid antagonist as defined above and can preferably be naltrexone or naloxone;
R is hydrogen or alkyl; and
Z is a linking moiety.
A general mechanism of chemically-mediated opioid antagonist release from generic $S_3$ subunits is shown below:
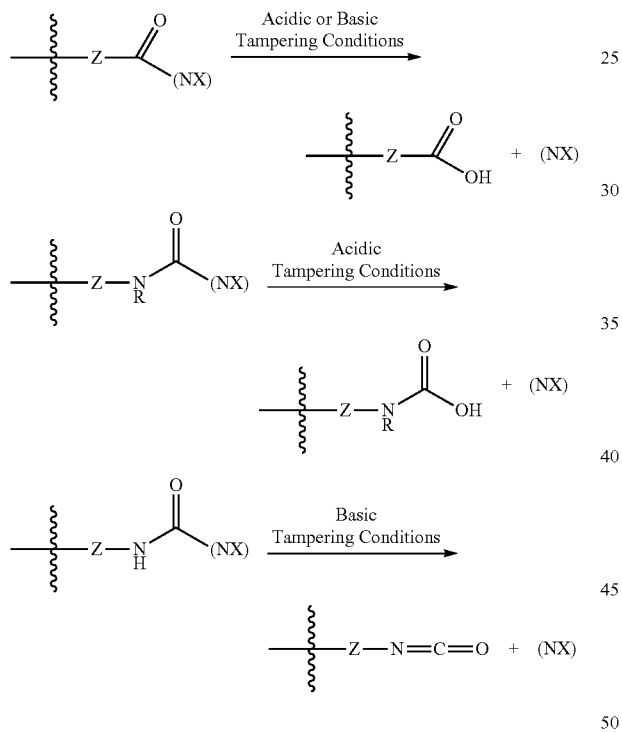
In some embodiments, the $S_3$—Z— subunit is selected from the group consisting of:
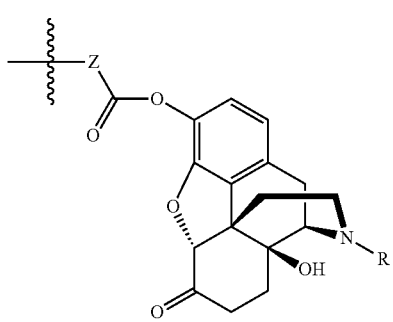
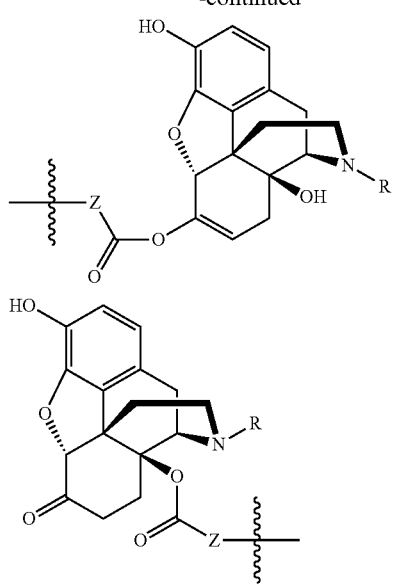
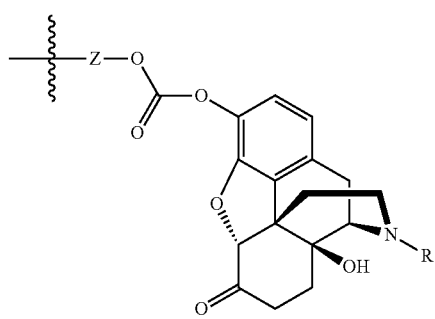
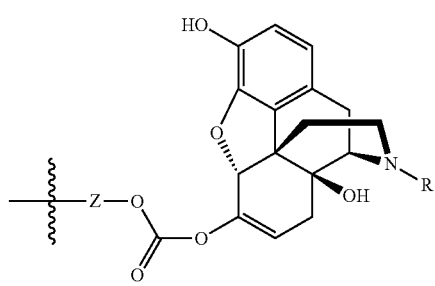
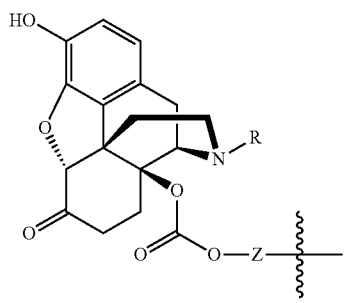

-continued

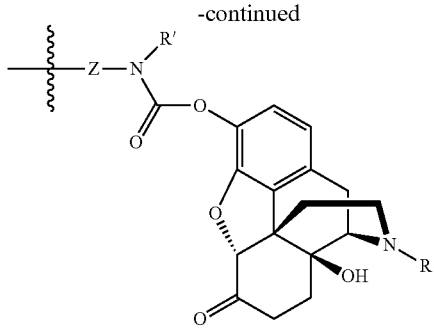

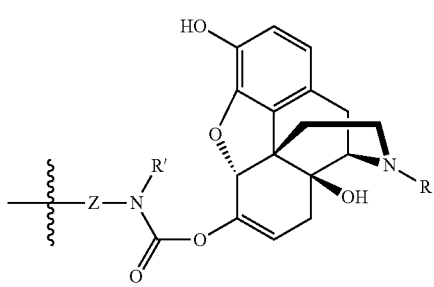

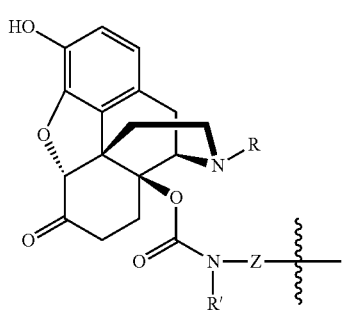

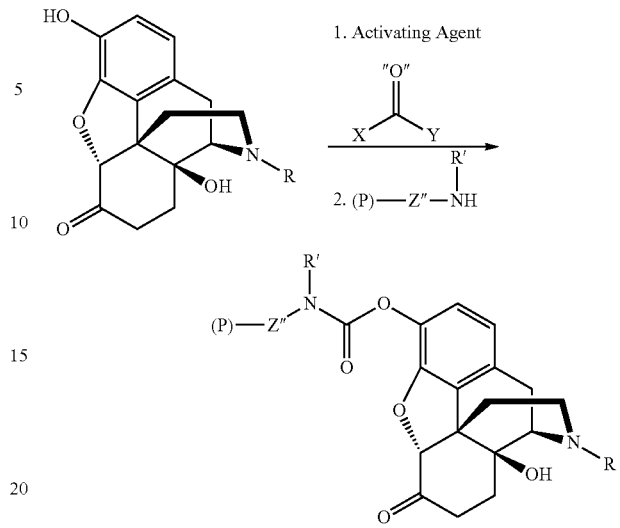

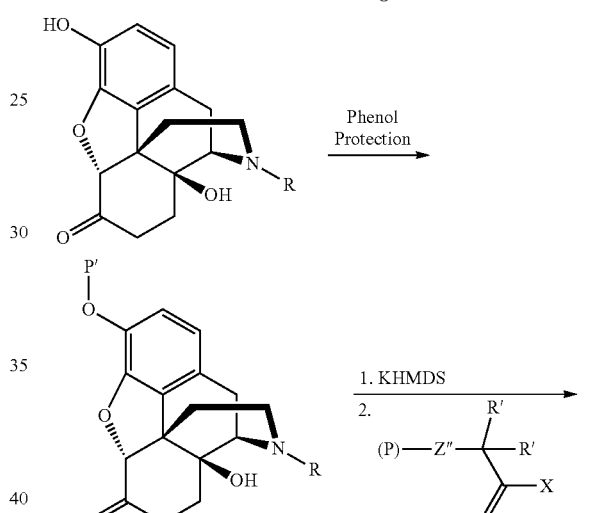

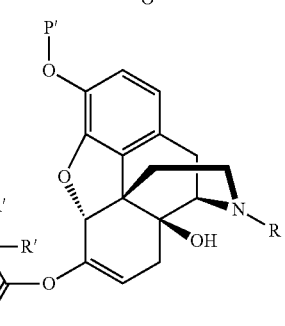

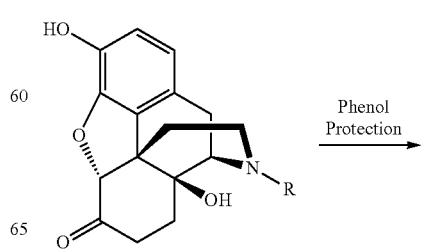

Wherein:
R is cyclopropylmethyl or allyl; R' is hydrogen, methyl, alkyl, aryl, substituted alkyl, or substituted aryl, acyl or substituted acyl; and Z is a linker as defined herein.

In some embodiments, the opioid antagonist is naltrexone or naloxone.

Representative synthetic routes useful for the preparation of $S_3$ subunits are depicted below. The syntheses utilize readily obtained synthons, well-established chemistry, and known protecting group strategies. Reported enol-carbamate forming opioid attachment strategies are also employed (see: U.S. Pat. Nos. 8,802,681, 8,685,916, 8,217,005, and 8,163,701, 8,685,916, 8,569,228, 8,497,237 and U.S. Patent Application Nos. 2014016935). P', a phenol protecting group used to enhance chemical efficiency, can be easily removed during the course of subsequent polysubstrate synthesis. (P) is an optional protecting group present on the terminus of the linker Z distal to the $S_3$ subunit that may be employed to enhance chemical efficiency. Purification of the resulting $S_3$ subunits can be accomplished using standard purification procedures involving normal or reverse phase chromatography, crystallization, trituration, etc. The chemical identity of the $S_3$ subunits can be established by LC/MS and/or NMR analysis.

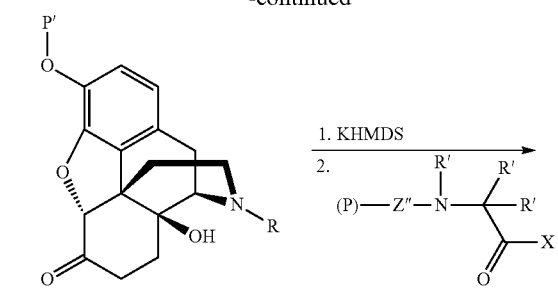
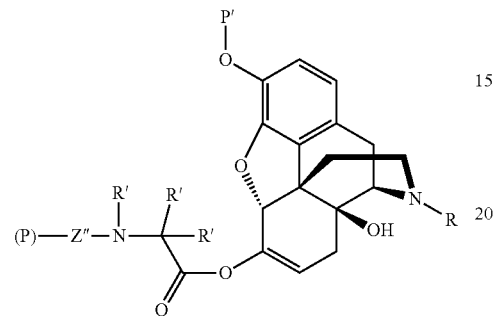
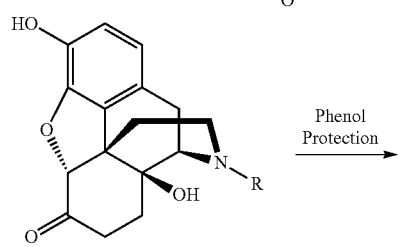
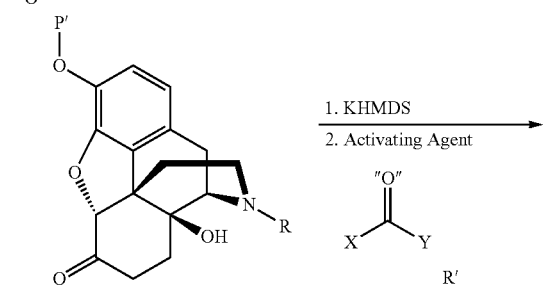
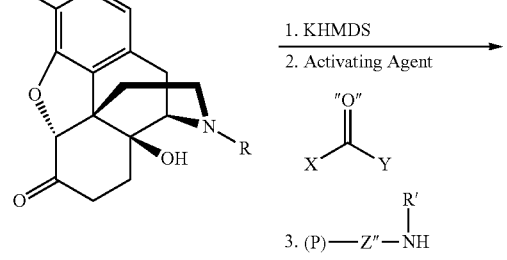
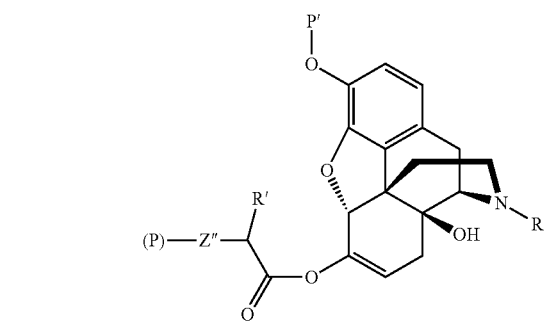
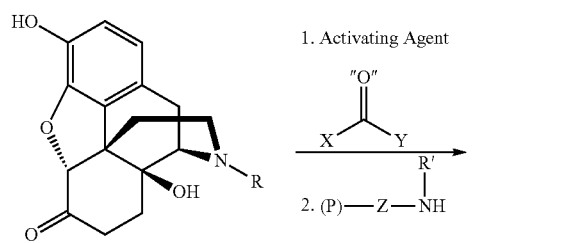
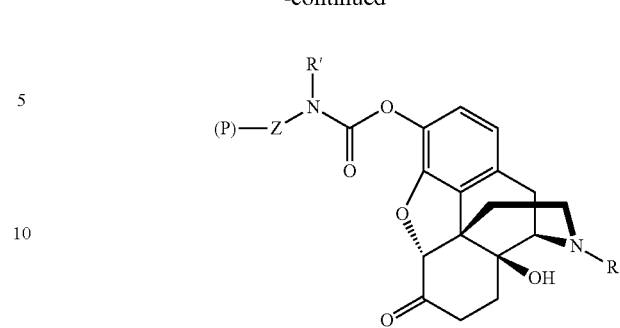
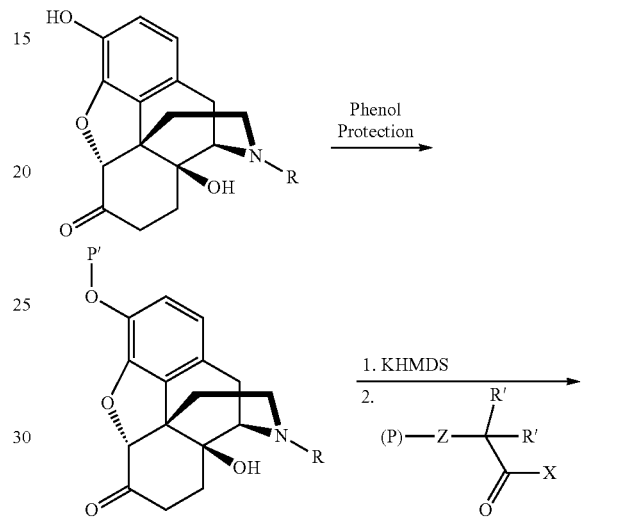
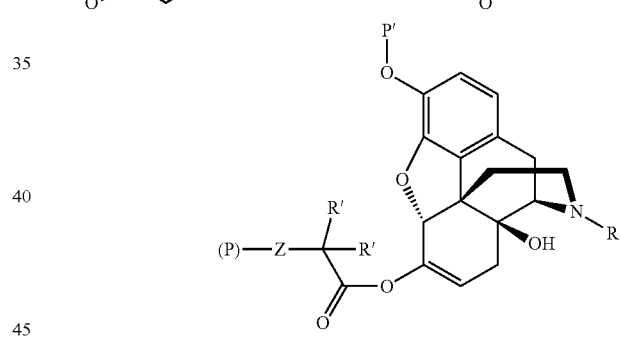
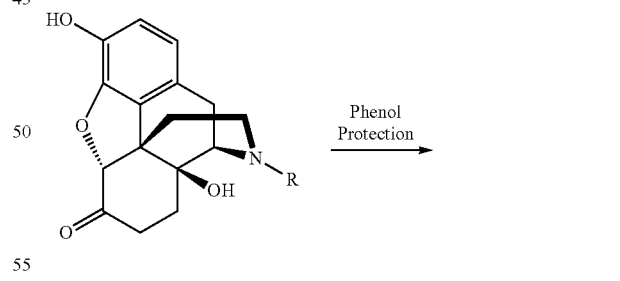
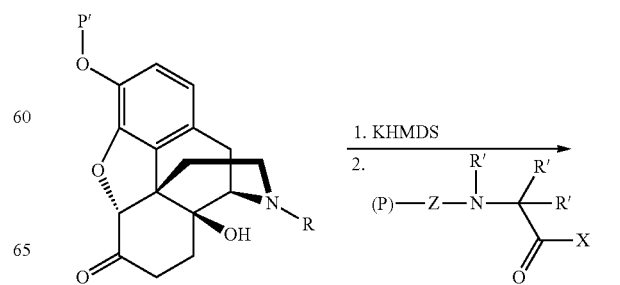

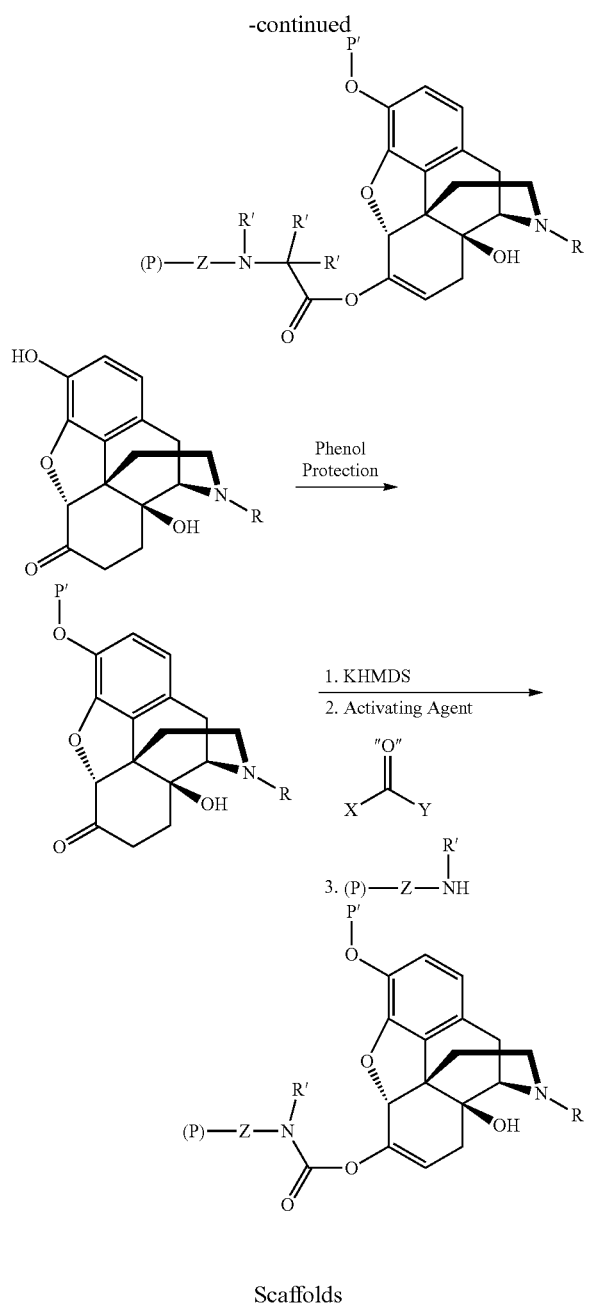

Scaffolds

In some embodiments, scaffolds (referred to interchangeably herein as "covalent scaffolds") used in the preparation of compounds of the invention are oligomeric or polymeric, such as, for example, PEG (or other polyalkylene oxide), polypeptides, polysaccharides and biopolymers. Oligomers or polymers suitable for construction of polymeric analogs of the invention include, but are not limited to, linear, dendrimeric, branched, brush (or comb) polymers. In one aspect of the invention, the polymer can be a polycationic material including natural and unnatural polyamino acids having net positive charge at neutral pH, positively charged polysaccharides, and positively charged synthetic polymers. The polymers can be prepared from monomers including, N-vinylpyrrolidone, acrylamide, N,N-dimethylacrylamide, vinyl acetate, dextran, L-glutamic acid, L-aspartic acid, L-lysine, L-threonine, L-tyrosine, D-glutamic acid, D-aspartic acid, D-lysine, D-threonine, D-tyrosine, styrene, maleic anhydride, N-(2-hydroxypropyl)methacrylamide, N-(2-hydroxyethyl)methacryalte, N-(2-hydroxyethyl)methacrylamide, ethylene glycol, ethylene oxide, propylene glycol, propylene oxide, tetrahydrofuran, butylene glycol, tetrahydropyran, ethyl vinyl ether, nonpeptide polyamines such as poly(aminostyrene), poly(aminoacrylate), poly(N-methyl aminoacrylate), poly (N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), and natural or synthetic polysaccharides such as chitosan, and copolymers of the previous, including random, alternating, block, multi-block linear copolymers, and star polymers. The polymers may be isotactic, syndiotactic, or atactic as appropriate. Methods for synthesis of biopolymers and for conjugating them to biological materials are well known in the art (see, for example, published U.S. Patent Application 20040043030; U.S. Pat. Nos. 5,177,059; 6,716,821; 5,824,701; 6,664,331; 5,880,131; Kameda, Y. et al., Biomaterials 25: 3259-3266, 2004; Thanou, M. et al, Current Opinion in Investigational Drugs 4(6): 701-709, 2003; Veronese, F. M., et al., Il Farmaco 54: 497-516, 1999).

In addition, dendritic polymers may be used for preparation of compounds of the invention. Appropriate dendrimers include, but are not limited to, polyamido amine (PAMAM) (Gunatillake et al., Macromolecules, 1988, 21, 1556; U.S. Pat. No. 4,507,466), polyethyleneimine (U.S. Pat. No. 4,631,337), polypropyleneimine (U.S. Pat. No. 5,530,092), and Frechet-type dendrimers (U.S. Pat. No. 5,041,516; Hawker et al., J. Am. Chem. Soc., 1991, 113, 4583) terminated with amines, alcohols, or carboxylic acid surface groups. A recent review on dendrimer synthesis is Tomalia et al., J. Polym. Sci., Part A: Polym. Chem., 2002, 40, 2719. The polymers can be prepared by methods known in the art, or they can be obtained from commercial sources.

In one aspect of the invention, the molecular weight of the scaffold polymer portion of a polymer conjugate of the invention is greater than about 500 Daltons (Da), and more preferably is greater than about 2,000 Da. In another aspect of the invention, the polymer has a molecular weight of about 10,000 Da to about 250,000 Da. Thus, the ranges of molecular weights for the polymer portion of the conjugate can be from about 2,000 Da to about 200,000 Da, preferably about 5,000 Da to about 50,000 Da, more preferably about 7,000 Da to about 50,000 Da, or from about 10,000 Da to about 50,000 Da. The polymer backbones having an average molecular weight of about 5,000 Da, about 7,000 Da, about 10,000, about 15,000 Da, about 17,500 Da, about 20,000 Da, about 30,000 Da, about 35,000 Da, about 40,000 Da, about 45,000 Da, and about 50,000 Da are particularly preferred.

Commercially available polymers suitable for use in the invention include, but are not limited to, mPEG-$NH_2$ ($M_w$~10 kDa, ~20 KDa), mPEG-OH ($M_w$~1 kDa, 2 KDa, ~3 KDa, ~5 KDa, ~10 KDa, ~12 KDa, ~20 KDa), 3-arm PEG-triol ($M_w$~10 kDa glycerol core, 15 kDa glycerol core, ~20 kDa glycerol core), 4-arm PEG-tetrol ($M_w$~2 kDa pentaerythritol core, ~10 kDa pentaerythritol core, ~15 kDa pentaerythritol core, ~20 kDa pentaerythritol core), 8-arm PEG-octol ($M_w$~2 kDa hexaglycerine, ~10 kDa hexaglycerine, ~15 kDa hexaglycerine, ~20 kDa hexaglycerine, ~40 kDa hexaglycerine); such as Poly(acrylic acid), $M_w$~50 kDa, Poly(1-glycerol methacrylate), Poly(acrylamide-co-acrylic acid), Poly(ethylene oxide-block-propylene oxide), Poly(L- lysine) hydrobromide, Poly(styrenesulfonic acid), Poly(vinyl alcohol), Poly(vinyl amine) hydrochloride, poly(caprolactone) diol; O,O'-bis(2-carboxyethyl)dodecaethylene glycol, Poly(allyl amine), Poly(antholesulfonic acid, sodium salt), Poly(caprolactone) triol 1,1,1-tris(hydroxymethyl)propane core, Poly(di(ethylene glycol) phthalate) diol, Poly(di(ethylene glycol)/trimethylolpropane-alt-adipic acid), polyol, PEG-bis(3-aminopropyl) terminated, PEG-bis(carboxymethyl) ether $M_w$~250 Da, PEG-bis(carboxymethyl) ether $M_w$~600 Da, PEG-block-PPG-block-PEG diol ($M_w$~1,100 Da, ~1,900 Da, ~2,000 Da, ~2,800 Da, ~2,900 Da, ~4,400 Da, ~5,800 Da, ~8,400 Da, ~14,600 Da), PEG-ran-PPG diol ($M_w$~2,500 Da, ~12,000 Da, ~970 Da, ~1,700 Da, ~3,900 Da), PEG-tetrahydrofurfuryl ether, Poly(2-hydroxyethyl methacrylate), Polyoxyethylene bis(amine) $M_w$~2,000 Da, Polyoxyethylene bis(amine) $M_w$~20,000 Da, PPG diol ($M_w$~425 Da, ~725 Da, ~1,000 Da, ~2,000 Da, ~2,700 Da, ~3,500 Da), Poly(DL-lysine) hydrobromide ($M_w$~1,000-4,000 Da, ~30,000-70,000 Da, ~500-2,000 Da, ~1,000-4,000 Da, ~4,000-15,000 Da, ~15,000-30,000 Da, ~30,000-70,000 Da), Poly(D-lysine) hydrobromide ($M_w$~1,000-4,000 Da, ~4,000-15,000 Da, ~15,000-30,000 Da, ~30,000-70,000 Da), Poly(L-tyrosine) $M_w$~10,000-40,000 Da, Poly(L-serine) $M_w$~5,000-10,000 Da, Poly(L-threonine) $M_w$~5,000-15,000 Da, PAMAM Dendrimer G(0)-$NH_2$, ethylenediamine core (surface groups: 4, 8, 16, 32, or 64), PAMAM Dendrimer G(2)-OH, ethylenediamine core (surface groups: 16, 32, 64), DAB-AM-4, polypropyleneimine tetraamine dendrimer (surface groups: 4, 8, 16, 32, 64), PAMAM-tris(hydroxymethyl)amidomethane dendrimer, Generation 2, ethylenediamine core (surface groups: 48), PAMAM-tris(hydroxymethyl)amidomethane dendrimer, Generation 3, ethylenediamine core (surface groups: 96), PAMAM-succinamic acid dendrimer, ethylenediamine core, Generation 2 (surface groups: 16), Amino-dPEG$_2$™ t-butyl ester, Amino-dPEG$_4$™ t-butyl ester, Amino-dPEG$_8$™ t-butyl ester, Amino-dPEG$_{12}$™ t-butyl ester, Amino-dPEG$_{24}$™ t-butyl ester, m-dPEG$_4$™ amine, m-dPEG$_{12}$™ amine, m-dPEG$_{24}$™ amine, Hydroxy-dPEG$_4$™ t-butyl ester, Hydroxy-dPEG$_8$™ t-butyl ester, m-dPEG$_{11}$™ alcohol, dPEG$_{12}$™ diol, Mono-N-t-boc-amido-dPEG$_3$™-amine, Mono-N-t-boc-amido-dPEG$_{11}$™-amine, Mono-N-t-CBZ-amido-dPEG$_3$™-amine, N-t-boc-amido-dPEG$_4$™ alcohol, N-t-boc-amido-dPEG$_{12}$™ alcohol, Bis-dPEG$_5$™ acid, Bis-dPEG$_7$™ acid, Bis-dPEG$_5$™ half benzyl half acid, Bis-dPEG$_9$™ half benzyl half acid, N-Fmoc-amido-dPEG$_2$™ acid, N-Fmoc-amido-dPEG$_4$™ acid, N-Fmoc-amido-dPEG$_8$™ acid, N-Fmoc-amido-dPEG$_{12}$™ acid, N-Fmoc-amido-dPEG$_{24}$™ acid, N-CBZ-amido-dPEG$_4$™-acid, N-CBZ-amido-dPEG$_8$™-acid, N-CBZ-amido-dPEG$_{12}$™-acid, N-CBZ-amido-dPEG$_{24}$™-acid, N-t-boc-amido-dPEG$_4$™-acid, and the like.

Non-limiting examples of polymers for use in the present invention include: polyesters, polyethers, poly(orthoesters), poly(vinyl alcohols), polyamides, polycarbonates, polyacrylamides, polyalkylene glycols, polyalkylene oxides, polyalkylene terephthalates, polyolefins, polyvinyl ethers, polyvinyl esters, polyvinyl halides, polyvinylpyrrolidone, polyglycolides, polysiloxanes, polylactides, polyurethanes, polyethylenes, polyanhydrides, polyhydroxyacids, polypropylfumerates, polycaprolactones, polyacetals, polyurethanes, polyphosphazenes, polyacrylates, polymethacrylates, polycyanoacrylates, polyureas, polystyrenes, polyamines, olefinic polymers derived from metatheses reactions with functionalized monomers, and block- or copolymers thereof.

Non-limiting examples of biopolymers for use in the present invention include: polyesters such as polyhyroxyalkanoates, polylactic acid and the like; proteins such as silks, collagens, gelatins, elastin, resilin, adhesives, polyamino acids, soy, zein, wheat gluten, casein, serum albumin and the like; polysaccharides such as xanthan, dextran, gellan, levan, curd ian, polygalactosamine, cellulose, pullulan, elsinan, yeast glucans, starch, agar, alginate, carrageenan, pectin, konjac, and various gums (e.g. guar), chitin, chitosan, hyaluronic acid, and the like; lipids/surfactants such as acetoglycerides, waxes, emulsions, and the like; polyphenols such as lignin, tannin, humic acid and the like; specialty polymers such as shellac, poly-gamma-glutamic acid, natural rubbers, synthetic rubbers from natural fats, and the like. Also included are chemically modified versions (to enhance solubility/functionality in the drug product formulation, resist digestion/degradation, facilitate chemical modification with antagonist synthons, etc.) of the above biopolymers.

In one aspect of the invention, the polymer is a "charged polymer" wherein the polymer can have one or more charged groups. Charged polymers can include a wide range of species, including polycations and their precursors (e.g., polybases, polysalts, etc.), polyanions and their precursors (e.g., polyacids, polysalts, etc.), polymers having multiple anionic and cationic groups (e.g., polymers having multiple acidic and basic groups such as are found in various proteins), ionomers (charged polymers in which a small but significant proportion of the constitutional units carry charges), and so forth. Typically, the number of charged groups is so large that the polymers are soluble in polar solvents (particularly water) when in ionically dissociated form (also called polyions). Some charged polymers have both anionic and cationic groups (e.g., proteins) and may have a net negative charge (e.g., because the anionic groups contribute more charge than the cationic groups—referred to herein as polyanions), a net positive charge (e.g., because the cationic groups contribute more charge than the anionic groups—referred to herein as polycations), or may have a neutral net charge (e.g., because the cationic groups and anionic groups contribute equal charge). In this regard, the net charge of a particular charged polymer may change with the pH of its surrounding environment. Charged polymers containing both cationic and anionic groups may be categorized herein as either polycations or polyanions, depending on which groups predominate.

Specific examples of suitable polycations may be selected, for instance, from the following: polyamines, including polyamidoamines, poly(amino methacrylates) including poly(dialkylaminoalkyl methacrylates) such as poly(dimethylaminoethyl methacrylate) and poly(diethylaminoethyl methacrylate), polyvinylamines, polyvinylpyridines including quaternary polyvinylpyridines such as poly(N-ethyl-4-vinylpyridine), poly(vinylbenzyltrimethylamines), polyallylamines such as poly(allylamine) hydrochloride) (PAH) and poly(diallyidialklylamines) such as poly(diallyidimethylammonium chloride), spermine, spermidine, hexadimethrene bromide(polybrene), polyimines including polyalkyleneimines such as polyethyleneimines, polypropyleneimines and ethoxylated polyethyleneimines, basic peptides and proteins, including histone polypeptides and homopolymer and copolymers containing lysine, arginine, ornithine and combinations thereof including poly-L-lysine, poly-D-lysine, poly-L,D-lysine, poly-L-arginine, poly-D-arginine, poly-D,L-arginine, poly-L-ornithine, poly-D-ornithine, and poly-L,D-ornithine, gelatin, albumin, protamine and protamine sulfate, and polycationic polysaccharides such as cationic starch and chitosan, as well as copolymers, derivatives and combinations of the preceding, among various others. The preferred polymers for use in the invention include poly(d-glutamic acid), poly(dl-glutamic acid), poly(l-aspartic acid), poly(d-aspartic acid), poly (dl-aspartic acid), poly(l-lysine), poly(d-lysine), poly(dl-lysine), and copolymers of the polyamino acids, and the polymers of the N-methyl derivatives of the amino acids. Other preferred polymers include polyethylene glycol (PEG), as well as poly(2-hydroxyethyl 1-glutamine), chitosan, carboxymethyl dextran, hyaluronic acid, human serum albumin and alginic acid.

Specific examples of suitable polyanions may be selected, for instance, from the following: polysulfonates such as polyvinylsulfonates, poly(styrenesulfonates) such as poly(sodium styrenesulfonate) (PSS), sulfonated poly(tetrafluoroethylene), sulfonated polymers such as those described in U.S. Pat. No. 5,840,387, including sulfonated styrene-ethylene/butylene-styrene triblock copolymers, sulfonated styrenic homopolymers and copolymers such as a sulfonated versions of the polystyrene-polyolefin copolymers described in U.S. Pat. No. 6,545,097 to Pinchuk et al., which polymers may be sulfonated, for example, using the processes described in U.S. Pat. Nos. 5,840,387 and 5,468,574, as well as sulfonated versions of various other homopolymers and copolymers, polysulfates such as polyvinylsulfates, sulfated and non-sulfated glycosaminoglycans as well as certain proteoglycans, for example, heparin, heparin sulfate, chondroitin sulfate, keratan sulfate, dermatan sulfate, polycarboxylates such as acrylic acid polymers and salts thereof (e.g., ammonium, potassium, sodium, etc.), for instance, those available from Atofina and Polysciences Inc., methacrylic acid polymers and salts thereof (e.g., EUDRAGIT, a methacrylic acid and ethyl acrylate copolymer), carboxymethylcellulose, carboxymethylamylose and carboxylic acid derivatives of various other polymers, polyanionic peptides and proteins such as glutamic acid polymers and copolymers, aspartic acid polymers and copolymers, polymers and copolymers of uronic acids such as mannuronic acid, galatcuronic acid and guluronic acid, and their salts, alginic acid and sodium alginate, hyaluronic acid, gelatin, and carrageenan, polyphosphates such as phosphoric acid derivatives of various polymers, polyphosphonates such as polyvinylphosphonates, polysulfates such as polyvinylsulfates, as well as copolymers, derivatives and combinations of the preceding, among various others.

Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, silks, collagen, elastin, resilin, polyamino acids, soy, wheat gluten, and casein.

Non-limiting examples of polyesters include polylactic acid, polyglycolic acid, poly(lactide-co-glycolide), poly(ε-caprolactone), polydioxanone, poly(ethylene terephthalate), poly(malic acid), poly(tartronic acid), polyphosphazenes, poly(orthoester), poly(valeric acid), poly(buteric acid), polyhydroxybutyrate, polyhydroxyvalerate, polyanhydride, and copolymers of the monomers used to synthesize any of the above-mentioned polymers, e.g., poly(lactic-co-glycolic acid) (PLGA) or the copolymer of polyhydroxy butyrate with hydroxyvaleric acid.

Non-limiting examples of polyesters include polylactic acid, polyglycolic acid, poly(lactide-co-glycolide), poly(ε-caprolactone), polydioxanone, poly(ethylene terephthalate), poly(malic acid), poly(tartronic acid), polyphosphazenes, poly(orthoester), poly(valeric acid), poly(buteric acid), polyhydroxybutyrate, polyhydroxyvalerate, polyanhydride, and copolymers of the monomers used to synthesize any of the above-mentioned polymers, e.g., poly(lactic-co-glycolic acid) (PLGA) or the copolymer of polyhydroxy butyrate with hydroxyvaleric acid.

Polyethers and poly(orthoesters) can also be used in preparing the polymer conjugate for use in the present invention. These polymers can be incorporated into multiblocks resulting in block polymers having diverse degradation rates, mechanical strengths, porosities, diffusivities, and inherent viscosities. Examples of polyethers include polyethylene glycol and polypropylene glycol. An example of a multi-block copolymer is poly(ether ester amide). Additionally, triblock copolymers of poly(orthoesters) with various poly(ethylene glycol) contents are useful for their stability in water/oil (w/o) emulsions. Other useful block copolymers include diblock copolymers of poly (lactic-co-glycolic acid) and poly(ethylene glycol) (PEG), triblock copolymers of PEG-PLGA-PEG, copolymers of PLGA and polylysine, and poly (ester ether) block copolymers.

In one aspect of the invention, the polymer is poly (ethylene glycol) (PEG) or a related poly(alkylene glycol). The term PEG includes poly(ethylene glycol) in any its forms, including linear forms (e.g., alkoxy PEG or bifunctional PEG), branched or multi-arm forms (e.g., forked PEG or PEG attached to a polyol core), pendant PEG, and the like. The general formula of PEG is —$CH_2CH_2O$—($CH_2CH_2O$)$_n$—$CH_2CH_2$— wherein n is from about 0 to about 500, typically from about 2 to about 200. Similar polymers can also be derived from polypropylene glycol and related poly(alkylene) glycols.

Multi-armed or branched PEG molecules, such as those described in U.S. Pat. No. 5,932,462 can also be used as the PEG polymer. Generally speaking, a multi-armed, branched, or star or dendrimeric polymers possess two or more polymer arms extending from a central branch point that is covalently attached, either directly or indirectly via intervening connecting atoms, to one or more active moieties such as an opioid agonist, antagonist, or digestive enzyme inverse substrate. It is understood by those skilled in the art that the term poly(ethylene glycol) or PEG represents or includes all the above forms of PEG or poly(alkylene glycols).

Preferred scaffolds selected from those listed above most useful for the construction of polysubstrates of the invention (i) are readily commercially available, (ii) comprise a sufficient number and type of chemically accessible functionalities (e.g. carboxylate, amine, thiol, alcohol, isocyanate, etc.), (iii) efficiently undergo the requisite coupling chemistry to attach the desired numbers of $S_1$, $S_2$, and optional $S_3$ subunits, and (iv) result in polysubstrate products with the desired physicochemical (e.g. solubility, stability, release of opioid antagonist upon chemical tampering in vitro, etc.) and biological (e.g. selective enzymatic release of opioid agonist in vivo, overdose protection via enzyme saturation, release of opioid antagonist in the systemic circulation, etc.) profiles.

Compounds of the Invention

In some embodiments, a compound of the invention has the Formula:

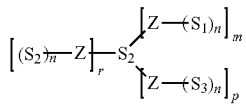

wherein:
$S_1$ is a non-opioid releasing enzyme substrate or enzyme inhibitor;
$S_2$ is an opioid agonist releasing enzyme substrate;
$S_3$ is an optional opioid antagonist-releasing moiety;
Z is a linker moiety as previously described;
n is an integer ranging from 1 to 10;
m is an integer ranging from 1 to 10; and
each p and r is independently an integer ranging from 0 to 10.

In some embodiments, a compound of the invention is represented by one of the following structures:

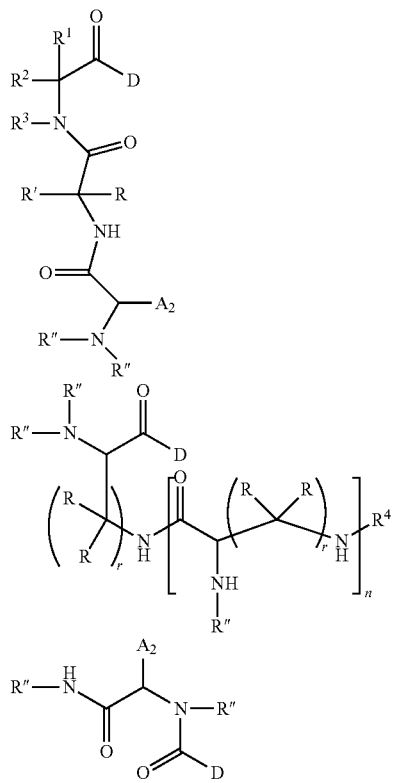

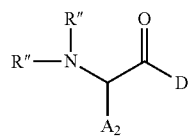
-continued wherein:
D is an opioid agonist, for example wherein D is a morphone, a codone, or morphine;
each $R^1$ and $R^2$ is independently R or R'; or wherein $R^1$ and $R^2$ can be joined to form an optionally substituted spirocyclic ring;
$R^3$ is R"; or wherein $R^3$ is joined with $R^1$ or $R^2$ to form an optionally substituted heterocyclic ring;
each R is independently hydrogen, methyl, or alkyl, for example lower alkyl;
each R' is independently hydrogen, alkyl, aryl, substituted alkyl, substituted aryl, heteroalkyl, substituted heteroalkyl, a natural or unnatural amino acid side chain, an amino acid side-chain mimic, —Z—$(S_2)_n$, or —Z—$(S_x)_n$;
wherein:
Z is a linking moiety;
each x is independently 1 or 3 (thereby designating each $S_x$ as a $S_1$ or $S_3$ subunit);
n is an integer ranging from 1-10;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, —Z—$(S_2)_n$, or —Z—$(S_x)_n$
wherein:
Z is a linking moiety;
each x is independently 1 or 3 (thereby designating each $S_x$ as a $S_1$ or $S_3$ subunit);
n is an integer ranging from 1-10;
$R^4$ is hydrogen, methyl, —C(=NR)—$NR_2$ (where each R is independently hydrogen or methyl), or a group of formula:

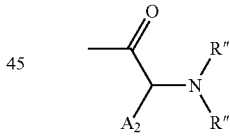

each $A_2$ independently an amino acid side chain or an amino acid side-chain mimic that is capable of being recognized by a digestive enzyme;
n is an integer ranging from 1 to 10; and
r is an integer ranging from 1 to 6.

In some embodiments, a compound of the invention is represented by one of the following structures:

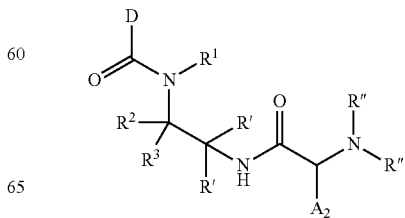

-continued

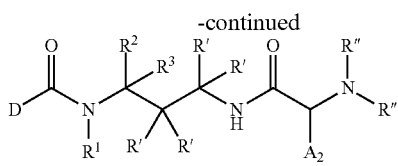

wherein:

D is an opioid agonist, for example wherein D is a morphone, a codone, or morphine;

$R^1$, $R^2$ and $R^3$ can be R', or $R^2$ and $R^3$ can be joined to form an optionally substituted spirocyclic ring;

$R^2$ or $R^3$ can be joined with $R^1$ to form an optionally substituted heterocyclic ring;

$R^2$ or $R^3$ can be joined with R' to form an optionally substituted ring, or

R' can be joined with a geminal R' so as to from an optionally substituted spirocyclic ring;

each R' is independently hydrogen, alkyl, aryl, substituted alkyl, substituted aryl, heteroalkyl, substituted heteroalkyl, a polyethylene glycol, or polyethylene glycol containing moiety, or a linking moiety Z; or —Z—$(S_2)_n$, or —Z—$(S_x)_n$
  wherein:
  Z is as previously defined;
  each x is independently 1 or 3 (thereby designating each $S_x$ as a $S_1$ or $S_3$ subunit);
  n is an integer ranging from 1-10;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$
  wherein:
  Z is a linker moiety as previously defined;
  each x is independently 1 or 3 (thereby designating each $S_x$ as a $S_1$ or $S_3$ subunit);
  n is an integer ranging from 1-10;

each $A_2$ is independently an amino acid side chain or an amino acid side-chain mimic that is capable of being recognized by a digestive enzyme.

In some embodiments $A_2$ can be:

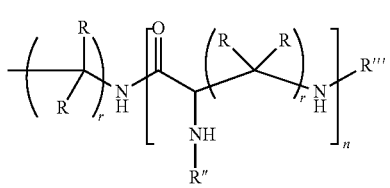

wherein:

R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$ wherein:

Z is a linker moiety as previously defined;

each x is independently 1 or 3 (thereby designating each $S_x$ as a $S_1$ or $S_3$ subunit);

n is an integer ranging from 1-10;

r is each or independently an integer from 1 to 6;

n is an integer from 0 to 10;

R''' is hydrogen, methyl, or

—C(=NR)—$NR_2$ wherein R is each or independently hydrogen or methyl; or

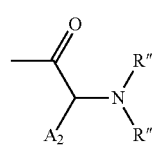

wherein $A_2$ is a natural or unnatural amino acid side chain, or an amino acid side-chain mimic that is capable of being recognized by a digestive enzyme that directs the regiospecific hydrolysis of the $S_2$ substrate prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof; R" is as defined above.

In some embodiments, $A_2$ directs the regiospecific hydrolysis of the $S_2$ substrate prior to the release of the appended opioid agonist from the $S_2$ subunit. In some embodiments, $A_2$ is the amino acid side chain of arginine, homoarginine, lysine, homolysine, ε-N-methyl lysine, ornithine, or structural/functional mimics thereof.

Each compound of the invention may contain varying numbers of $S_1$, $S_2$, or $S_3$ subunits as described throughout. In some embodiments, the molar ratio of $S_1$ to $S_2$ ranges from 1 to 2, from 1 to 4, from 1 to 8, or from 1 to 10 $S_1$ subunits from each $S_2$ subunit. However, one skilled in the art will recognize that compounds of the invention with different $S_1$ to $S_2$ and $S_3$ ratios can be readily accomplished and are included within the scope of the invention.

In some embodiments, compounds of the invention are represented by one of the following structures:

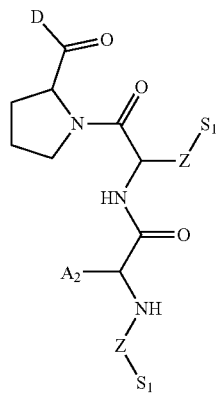

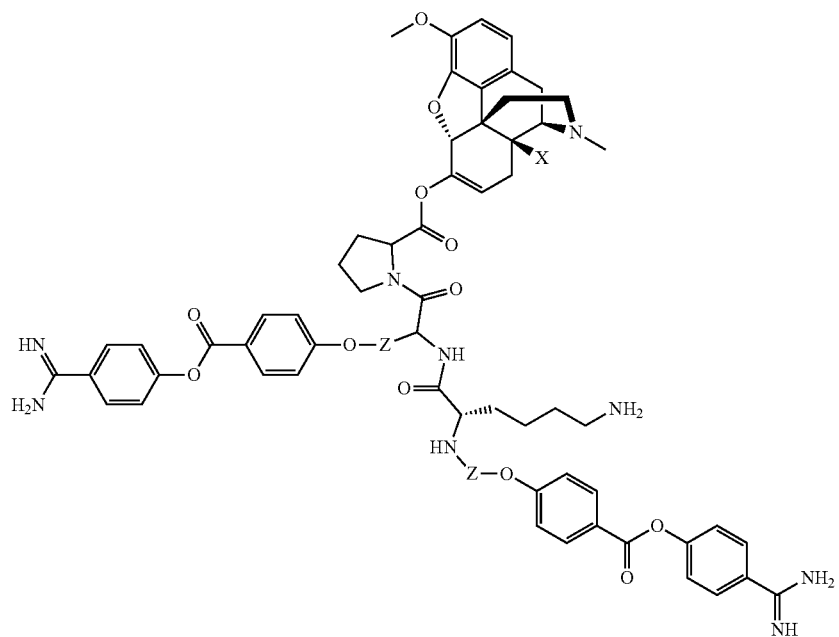

wherein:
D is an opioid agonist, for example wherein D is a morphone, a codone, or morphine;
X is OH or hydrogen;
$S_1$ is independently a non-opioid releasing GI enzyme substrate or GI enzyme inhibitor;
$A_2$ is an amino acid side chain or an amino acid side-chain mimic that is capable of being recognized by a digestive enzyme; and each Z is independently a linking moiety.

In some embodiments, compounds of the invention are represented by one of the following structures:

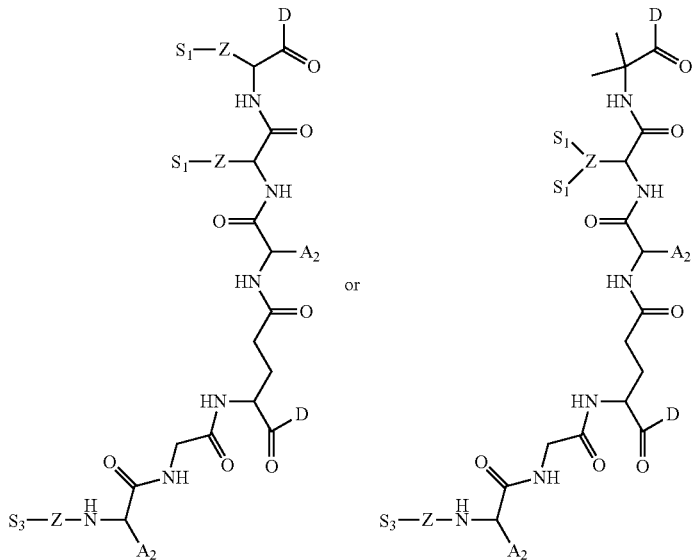

or

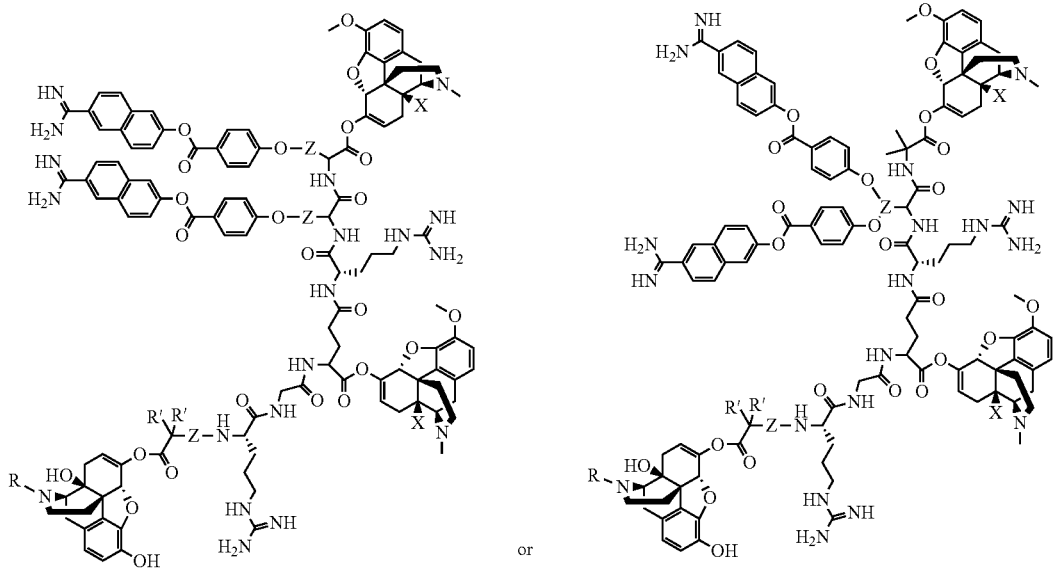

wherein:

D is an opioid agonist, for example wherein D is a morphone, a codone, or morphine;

X is OH or hydrogen;

$S_1$ is independently a non-opioid releasing GI enzyme substrate or GI enzyme inhibitor;

$A_2$ is an amino acid side chain or an amino acid side-chain mimic that is capable of being recognized by a digestive enzyme;

each Z is independently a linking moiety;

R is cyclopropylmethyl or allyl; and

R' are each or independently hydrogen or methyl.

In some embodiments, compounds of the invention are represented by one of the following structures:

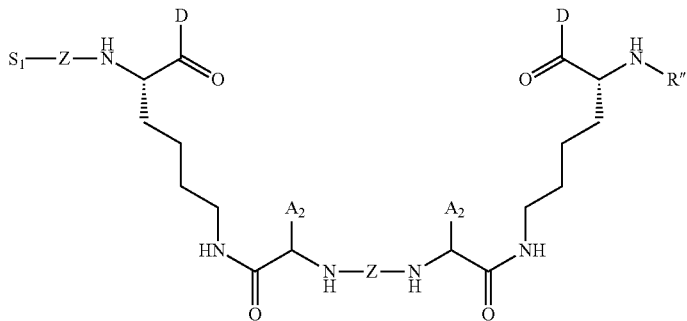

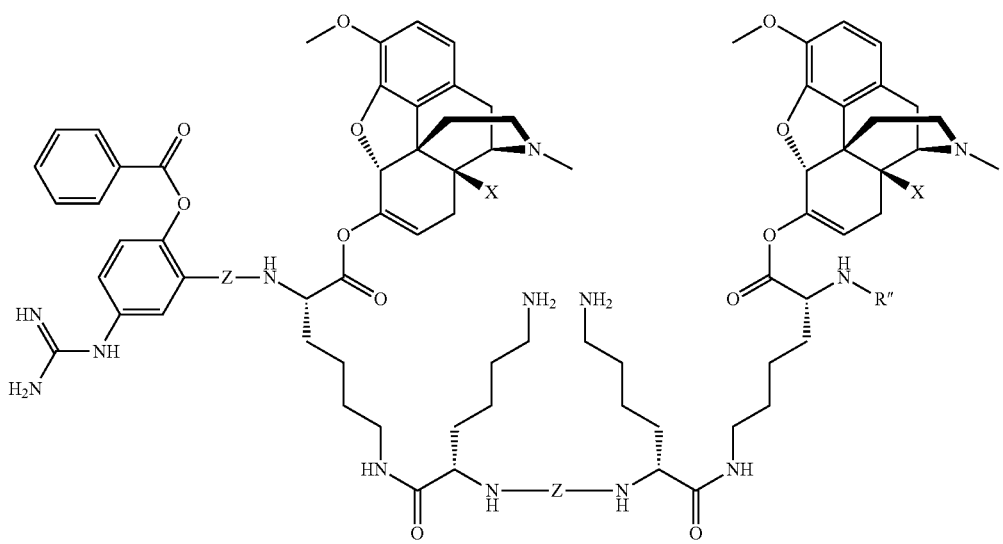

wherein:

D is an opioid agonist, for example wherein D is a morphone, a codone, or morphine;

X is OH or hydrogen;

$S_1$ is a non-opioid releasing GI enzyme substrate or GI enzyme inhibitor subunit;

$A_2$ is an amino acid side chain or an amino acid side-chain mimic that is capable of being recognized by a GI enzyme;

each Z is a linking moiety;

R" is hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or one or more amino acids or structural or functional mimics thereof.

In some embodiments, compounds of the invention are represented by one of the following structures:

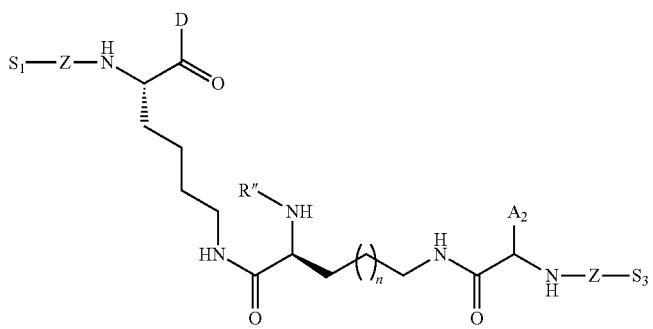

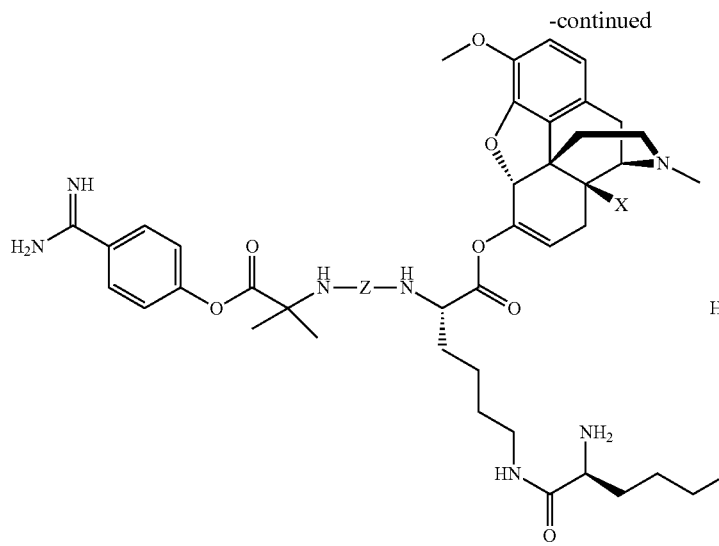

wherein:

D is an opioid agonist, for example wherein D is a morphone, a codone, or morphine;

X is OH or hydrogen;

$S_1$ is a non-opioid releasing GI enzyme substrate or GI enzyme inhibitor subunit;

$S_3$ is an opioid antagonist-releasing moiety;

$A_2$ is an amino acid side chain or an amino acid side-chain mimic that is capable of being recognized by a digestive enzyme;

R is cyclopropylmethyl or allyl;

each Z is a linking moiety;

R" is hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or one or more amino acids or structural or functional mimics thereof.

In some embodiments, compounds of the invention are represented by one of the following structures:

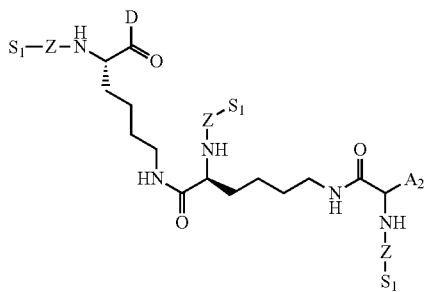

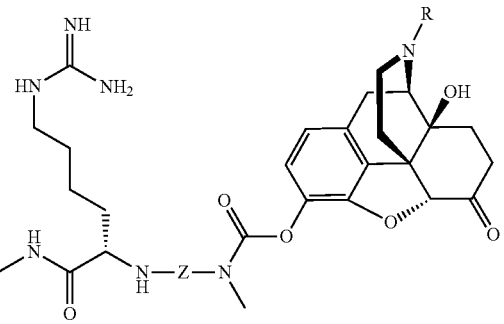

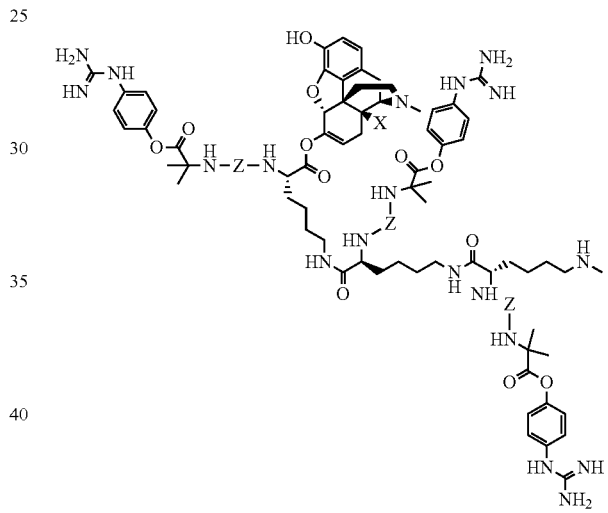

wherein:

D is an opioid agonist, for example wherein D is a morphone, a codone, or morphine;

X is OH or hydrogen;

each $S_1$ is independently a non-opioid releasing GI enzyme substrate or GI enzyme inhibitor;

$A_2$ is an amino acid side chain or an amino acid side-chain mimic that is capable of being recognized by a digestive enzyme;

each Z is a linking moiety;

In some embodiments, compounds of the invention are represented by one of the following structures:

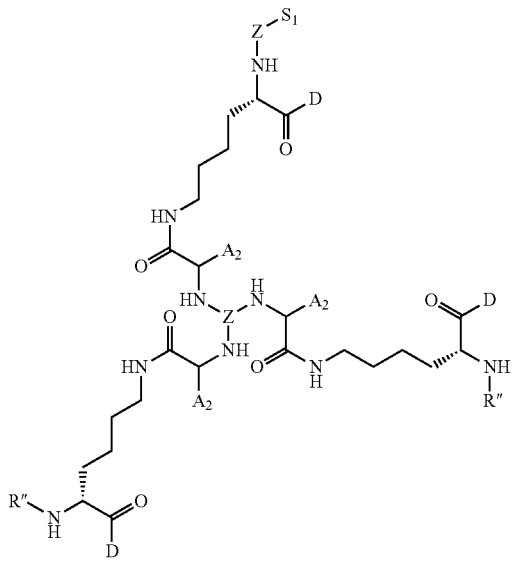

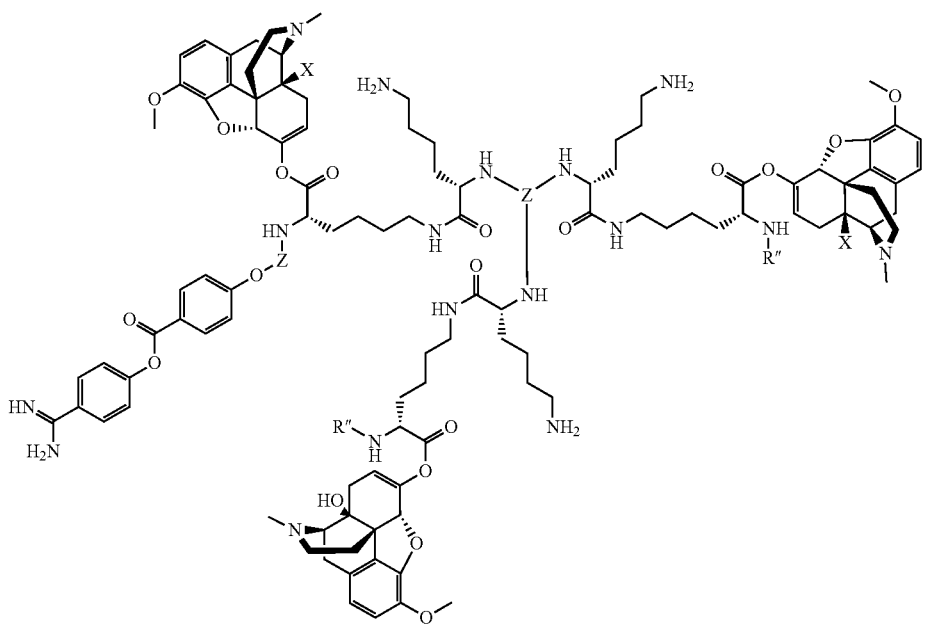

wherein:

D is an opioid agonist, for example wherein D is a morphone, a codone, or morphine;

X is OH or hydrogen;

$S_1$ is a non-opioid releasing GI enzyme substrate or GI enzyme inhibitor subunit;

$A_2$ is an amino acid side chain or an amino acid side-chain mimic that is capable of being recognized by a digestive enzyme;

R" is hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or one or more amino acids or structural or functional mimics thereof.

each Z is a linking moiety;

In some embodiments, compounds of the invention are represented by one of the following structures:

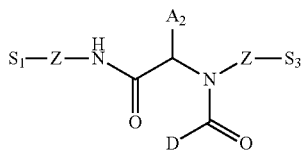

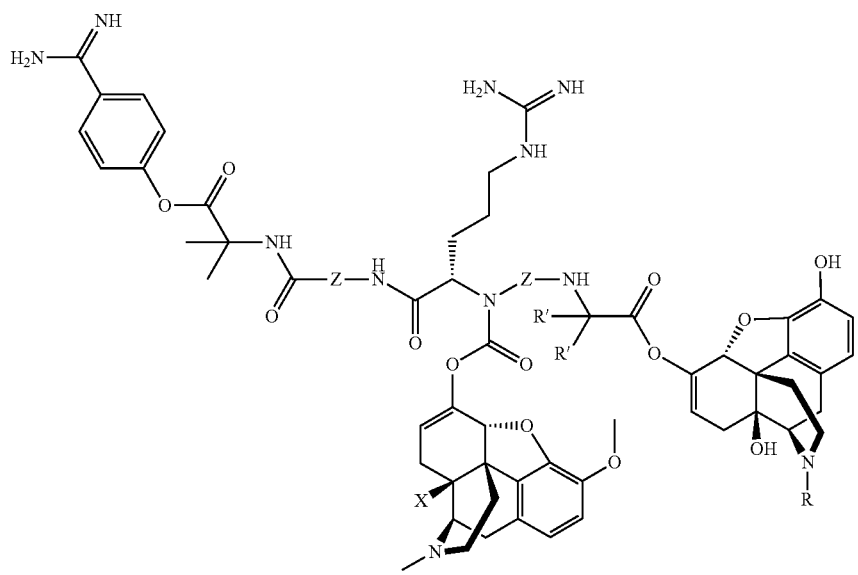

Wherein:

D is an opioid agonist, for example wherein D is a morphone, a codone, or morphine;

X is OH or hydrogen;

S₁ is a non-opioid releasing GI enzyme substrate or GI enzyme inhibitor subunit;

S₃ is an opioid antagonist-releasing moiety;

A₂ is an amino acid side chain or an amino acid side-chain mimic that is capable of being recognized by a digestive enzyme;

R is cyclopropylmethyl or allyl;

each Z is a linking moiety;

R' is each or independently hydrogen or methyl.

In some embodiments, compounds of the invention are represented by one of the following structures:

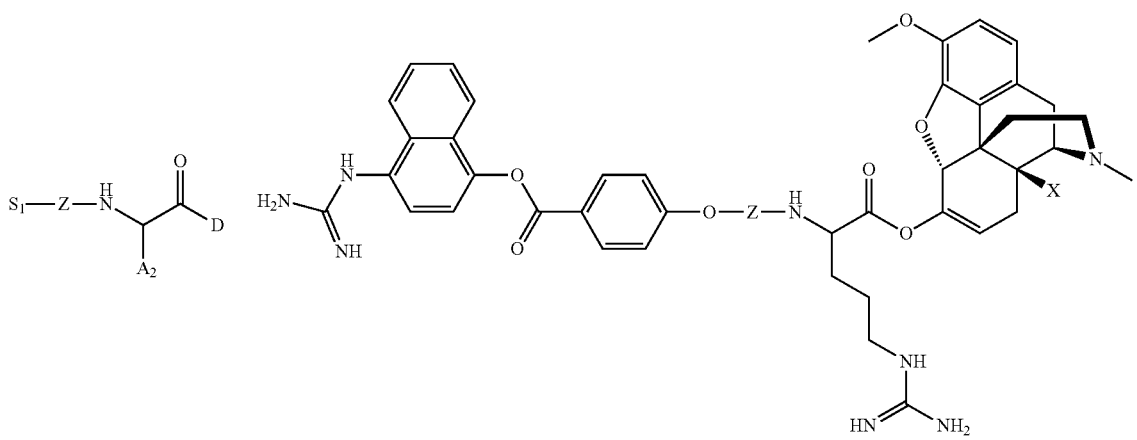

wherein:
D is an opioid agonist, for example wherein D is a morphone, a codone, or morphine;
X is OH or hydrogen;
$S_1$ is a non-opioid releasing GI enzyme substrate or GI enzyme inhibitor subunit;
$A_2$ is an amino acid side chain or an amino acid side-chain mimic that is capable of being recognized by a digestive enzyme; each Z is a linking moiety.

In some embodiments, compounds of the invention are represented by one of the following structures:

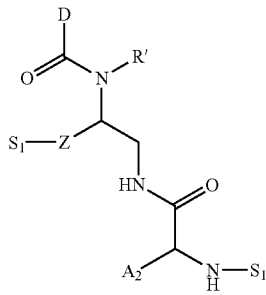

In some embodiments $A_2$ can be:

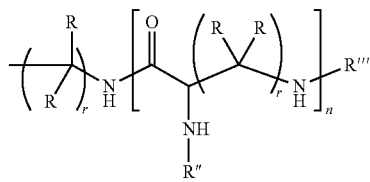

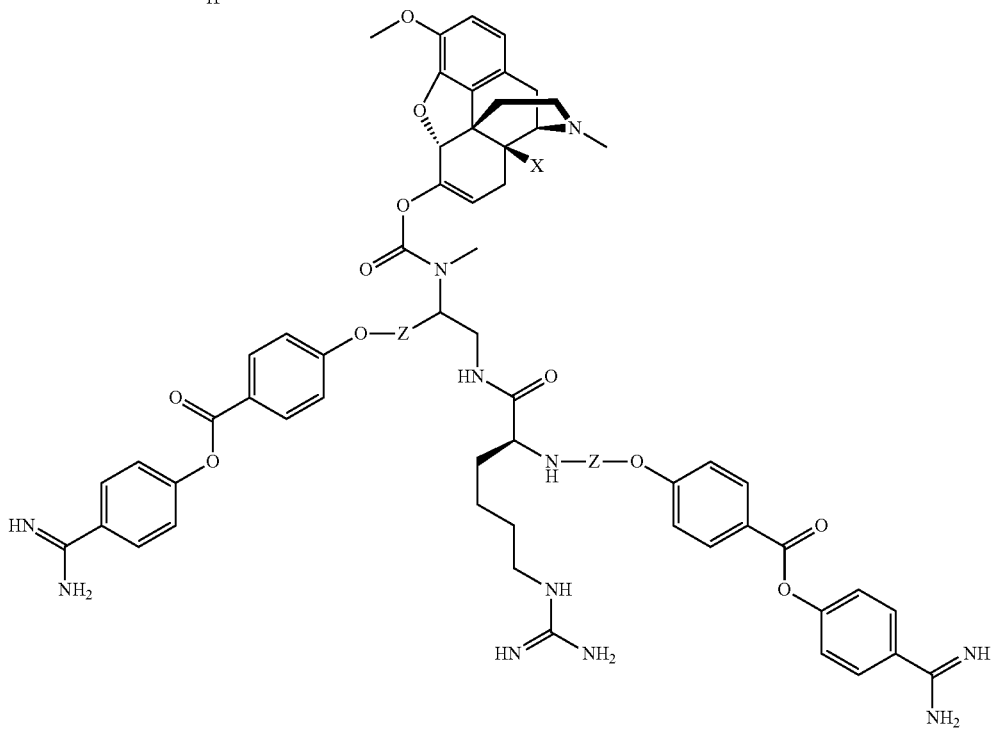

Wherein:

D is an opioid agonist, for example wherein D is a morphone, a codone, or morphine;

X is OH or hydrogen;

$S_1$ is a non-opioid releasing GI enzyme substrate or GI enzyme inhibitor subunit;

each Z is independently a linking moiety;

each $A_2$ is independently an amino acid side chain or an amino acid side-chain mimic that is capable of being recognized by a digestive enzyme.

wherein:
R is each or independently hydrogen or methyl; each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$
wherein:
Z is a linker moiety as previously defined;
each x is independently 1 or 3 (thereby designating each $S_x$ as a $S_1$ or $S_3$ subunit);
n is an integer ranging from 1-10; r is each or independently an integer from 1 to 6; n is an integer from 0 to 10; R''' is hydrogen, methyl, or —C(=NR)—NR$_2$ wherein R is each or independently hydrogen or methyl; or

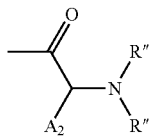

wherein:
A$_2$ is a natural or unnatural amino acid side chain, or an amino acid side-chain mimic that is capable of being recognized by a digestive enzyme that directs the regiospecific hydrolysis of the S$_2$ substrate prior to the release of the appended opioid agonist from the S$_2$ subunit and can be, but is not limited to, the amino acid side chain of arginine, homoarginine, lysine, homolysine, ε-N-methyl lysine, ornithine, or structural/functional mimics thereof; R″ is as defined above.

In some embodiments, A$_2$ directs the regiospecific hydrolysis of the S$_2$ substrate prior to the release of the appended opioid agonist from the S$_2$ subunit. In some embodiments, A$_2$ is the amino acid side chain of arginine, homoarginine, lysine, homolysine, ε-N-methyl lysine, ornithine, or structural/functional mimics thereof.

In some embodiments, compounds of the invention are represented by one of the following structures:

wherein:
D is an opioid agonist, for example wherein D is a morphone, a codone, or morphine;
X is OH or hydrogen;
S$_1$ is a non-opioid releasing GI enzyme substrate or GI enzyme inhibitor subunit;
S$_3$ is an opioid antagonist-releasing moiety;
R is cyclopropylmethyl or allyl;
each Z is independently a linking moiety;
each R' is independently hydrogen, alkyl, aryl, substituted alkyl, substituted aryl, heteroalkyl, substituted heteroalkyl, a polyethylene glycol, or polyethylene glycol containing moiety, or a linking moiety Z; or —Z—(S$_2$)$_n$, or —Z—(S$_x$)$_n$
wherein:
Z is as previously defined;
each x is independently 1 or 3 (thereby designating each S$_x$ as a S$_1$ or S$_3$ subunit);
n is an integer ranging from 1-10;
each A$_2$ is independently an amino acid side chain or an amino acid side-chain mimic that is capable of being recognized by a digestive enzyme.

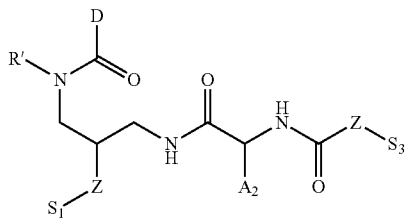

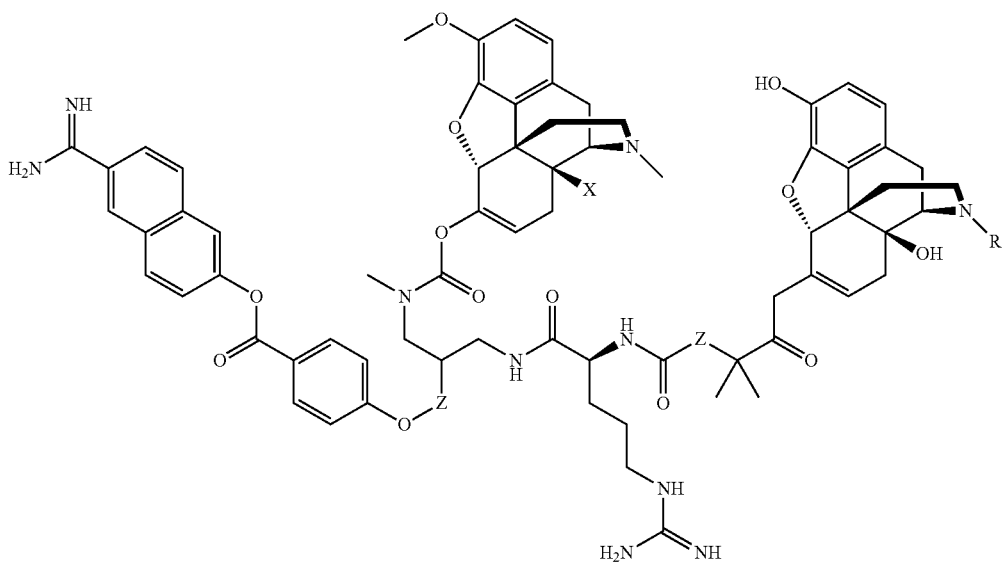

In some embodiments $A_2$ can be:

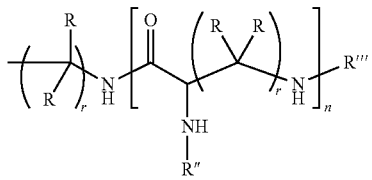

wherein:
R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$
wherein:
Z is a linker moiety as previously defined;
each x is independently 1 or 3 (thereby designating each $S_x$ as a $S_1$ or $S_3$ subunit);
n is an integer ranging from 1-10;
r is each or independently an integer from 1 to 6;
n is an integer from 0 to 10;
R'" is hydrogen, methyl, or —C(=NR)—$NR_2$ wherein R is each or independently hydrogen or methyl; or

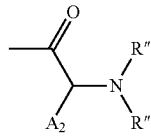

wherein $A_2$ is a natural or unnatural amino acid side chain, or an amino acid side-chain mimic that is capable of being recognized by a digestive enzyme that directs the regiospecific hydrolysis of the $S_2$ substrate prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof; R" is as defined above.

In some embodiments, $A_2$ directs the regiospecific hydrolysis of the $S_2$ substrate prior to the release of the appended opioid agonist from the $S_2$ subunit. In some embodiments, $A_2$ is the amino acid side chain of arginine, homoarginine, lysine, homolysine, ε-N-methyl lysine, ornithine, or structural/functional mimics thereof.

In some embodiments, compounds of the invention are represented by one of the following structures:

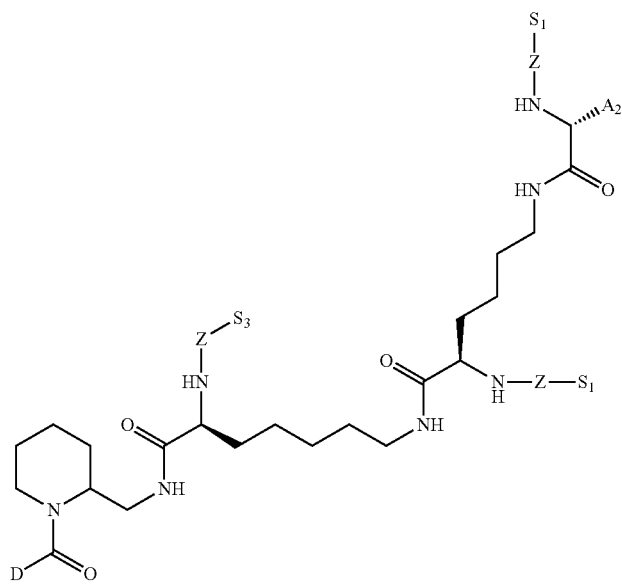

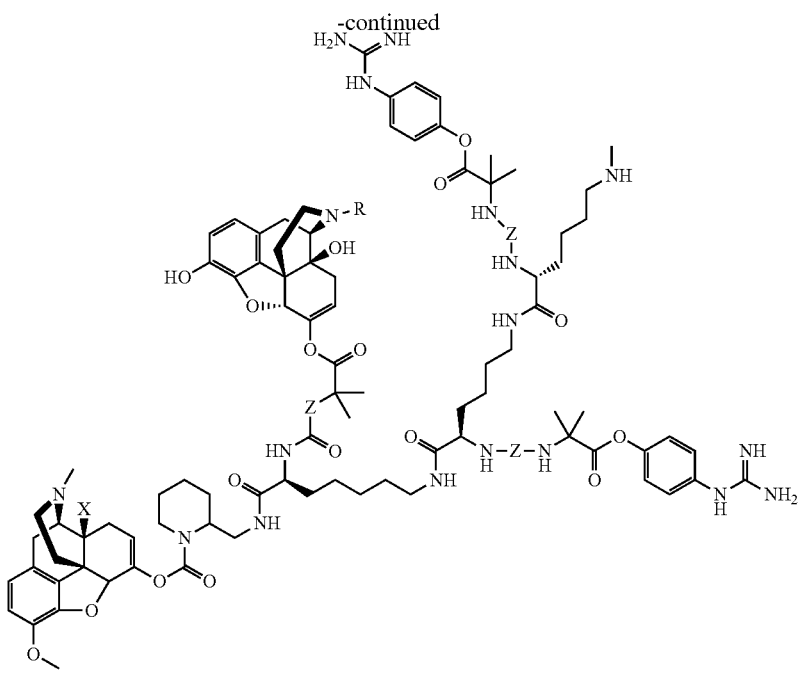

wherein:

D is an opioid agonist, for example wherein D is a morphone, a codone, or morphine;

X is OH or hydrogen;

$S_1$ is a non-opioid releasing GI enzyme substrate or GI enzyme inhibitor subunit;

$S_3$ is an opioid antagonist releasing moiety;

R is cyclopropylmethyl or allyl;

each Z is independently a linking moiety;

$A_2$ is independently an amino acid side chain or an amino acid side-chain mimic that is capable of being recognized by a digestive enzyme.

In some embodiments $A_2$ can be:

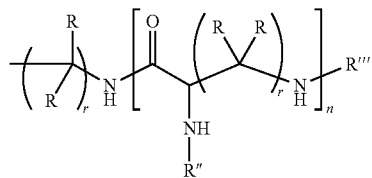

wherein:

R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$ wherein:

Z is a linker moiety as previously defined;

each x is independently 1 or 3 (thereby designating each $S_x$ as a $S_1$ or $S_3$ subunit);

n is an integer ranging from 1-10;

r is each or independently an integer from 1 to 6;

n is an integer from 0 to 10;

R''' is hydrogen, methyl, or

—C(=NR)—$NR_2$ wherein R is each or independently hydrogen or methyl; or

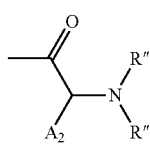

wherein $A_2$ is a natural or unnatural amino acid side chain, or an amino acid side-chain mimic that is capable of being recognized by a digestive enzyme that directs the regiospecific hydrolysis of the $S_2$ substrate prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof; R" is as defined above.

In some embodiments, $A_2$ directs the regiospecific hydrolysis of the $S_2$ substrate prior to the release of the appended opioid agonist from the $S_2$ subunit. In some embodiments, $A_2$ is the amino acid side chain of arginine, homoarginine, lysine, homolysine, ε-N-methyl lysine, ornithine, or structural/functional mimics thereof.

In some embodiments, compounds of the invention are represented by one of the following structures:

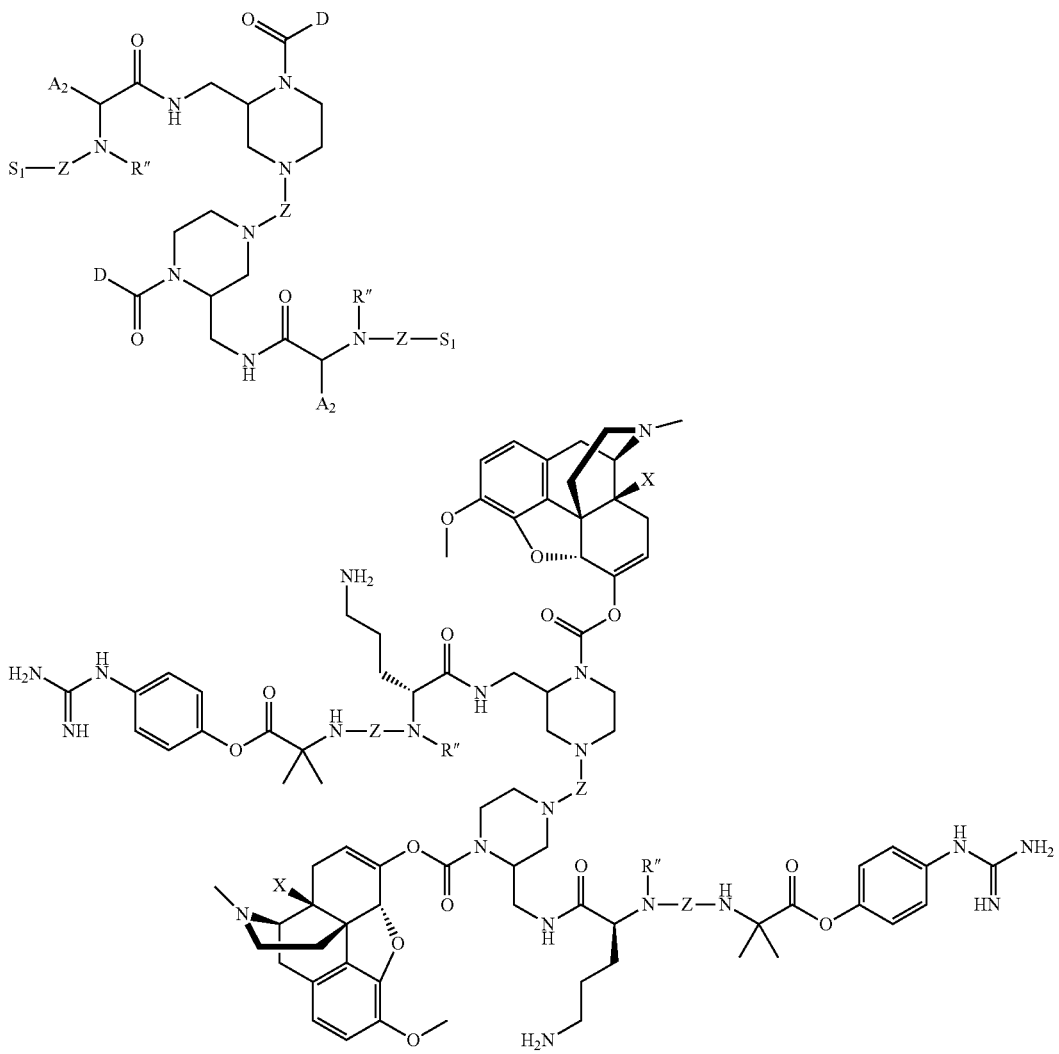

Wherein:
D is an opioid agonist, for example wherein D is a morphone, a codone, or morphine;
X is OH or hydrogen;
Each $S_1$ is a non-opioid releasing GI enzyme substrate or GI enzyme inhibitor subunit;
each Z is independently a linking moiety;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or $—Z—(S_2)_n$, or $—Z—(S_x)_n$
  wherein:
  Z is a linker moiety as previously defined;
  each x is independently 1 or 3 (thereby designating each $S_x$ as a $S_1$ or $S_3$ subunit);
  n is an integer ranging from 1-10;
each $A_2$ is independently an amino acid side chain or an amino acid side-chain mimic that is capable of being recognized by a digestive enzyme.

In some embodiments $A_2$ can be:

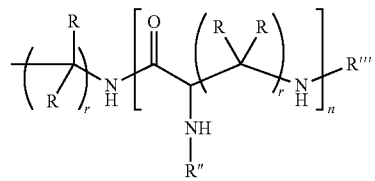

wherein:
R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or $—Z—(S_2)_n$, or $—Z—(S_x)_n$ wherein:
Z is a linker moiety as previously defined;
each x is independently 1 or 3 (thereby designating each $S_x$ as a $S_1$ or $S_3$ subunit);
n is an integer ranging from 1-10;
r is each or independently an integer from 1 to 6;
n is an integer from 0 to 10;

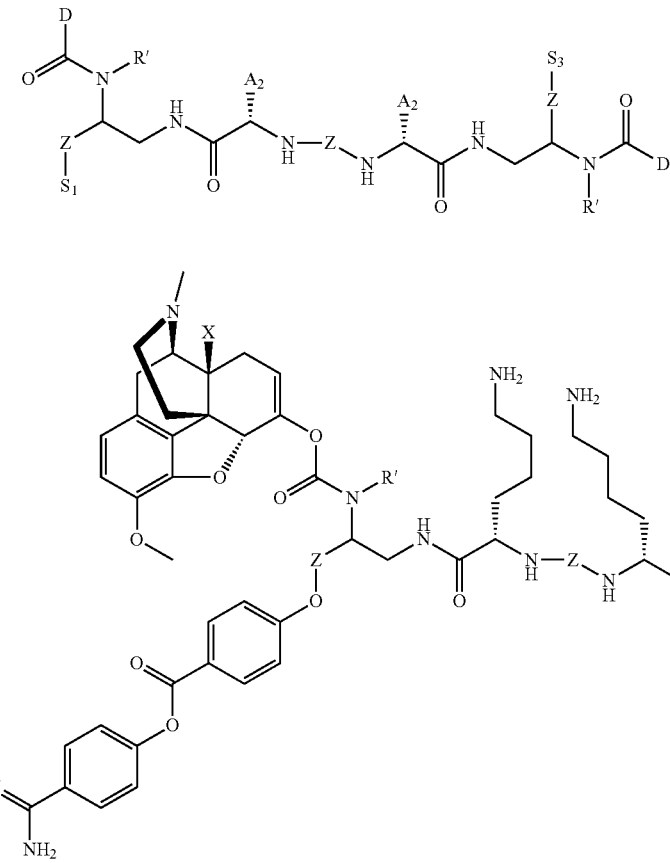

R''' is hydrogen, methyl, or
—C(=NR)—NR$_2$ wherein R is each or independently hydrogen or methyl; or

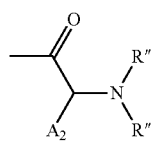

wherein A$_2$ is a natural or unnatural amino acid side chain, or an amino acid side-chain mimic that is capable of being recognized by a digestive enzyme that directs the regiospecific hydrolysis of the S$_2$ substrate prior to the release of the appended opioid agonist from the S$_2$ subunit and can be, but is not limited to, the amino acid side chain of arginine, homoarginine, lysine, homolysine, ε-N-methyl lysine, ornithine, or structural/functional mimics thereof; R'' is as defined above.

In some embodiments, A$_2$ directs the regiospecific hydrolysis of the S$_2$ substrate prior to the release of the appended opioid agonist from the S$_2$ subunit. In some embodiments, A$_2$ is the amino acid side chain of arginine, homoarginine, lysine, homolysine, ε-N-methyl lysine, ornithine, or structural/functional mimics thereof.

In some embodiments, compounds of the invention are represented by one of the following structures:

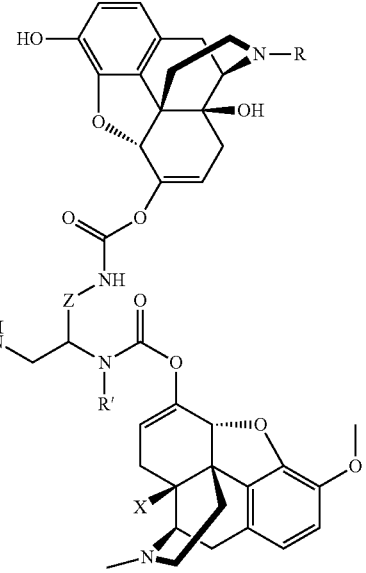

Wherein:
D is an opioid agonist, for example wherein D is a morphone, a codone, or morphine;
S$_1$ is a non-opioid releasing GI enzyme substrate or GI enzyme inhibitor subunit;
S$_3$ is an opioid antagonist releasing moiety;
each Z is independently a linking moiety;
X is OH or hydrogen;
R is cyclopropylmethyl or allyl; and
R' are each or independently hydrogen or methyl.
each A$_2$ is independently an amino acid side chain or an amino acid side-chain mimic that is capable of being recognized by a digestive enzyme.
In some embodiments A$_2$ can be:

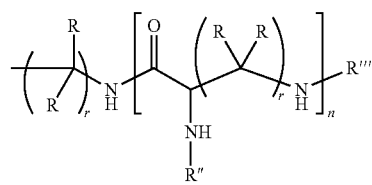

wherein:

R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$ wherein:
Z is a linker moiety as previously defined;
each x is independently 1 or 3 (thereby designating each $S_x$ as a $S_1$ or $S_3$ subunit);
n is an integer ranging from 1-10;
r is each or independently an integer from 1 to 6;
n is an integer from 0 to 10;
R'" is hydrogen, methyl, or
—C(=NR)—$NR_2$ wherein R is each or independently hydrogen or methyl; or

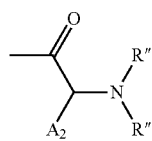

wherein $A_2$ is a natural or unnatural amino acid side chain, or an amino acid side-chain mimic that is capable of being recognized by a digestive enzyme that directs the regiospecific hydrolysis of the $S_2$ substrate prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof; R" is as defined above.

In some embodiments, $A_2$ directs the regiospecific hydrolysis of the $S_2$ substrate prior to the release of the appended opioid agonist from the $S_2$ subunit. In some embodiments, $A_2$ is the amino acid side chain of arginine, homoarginine, lysine, homolysine, ε-N-methyl lysine, ornithine, or structural/functional mimics thereof.

In some embodiments, compounds of the invention are represented by one of the following structures:

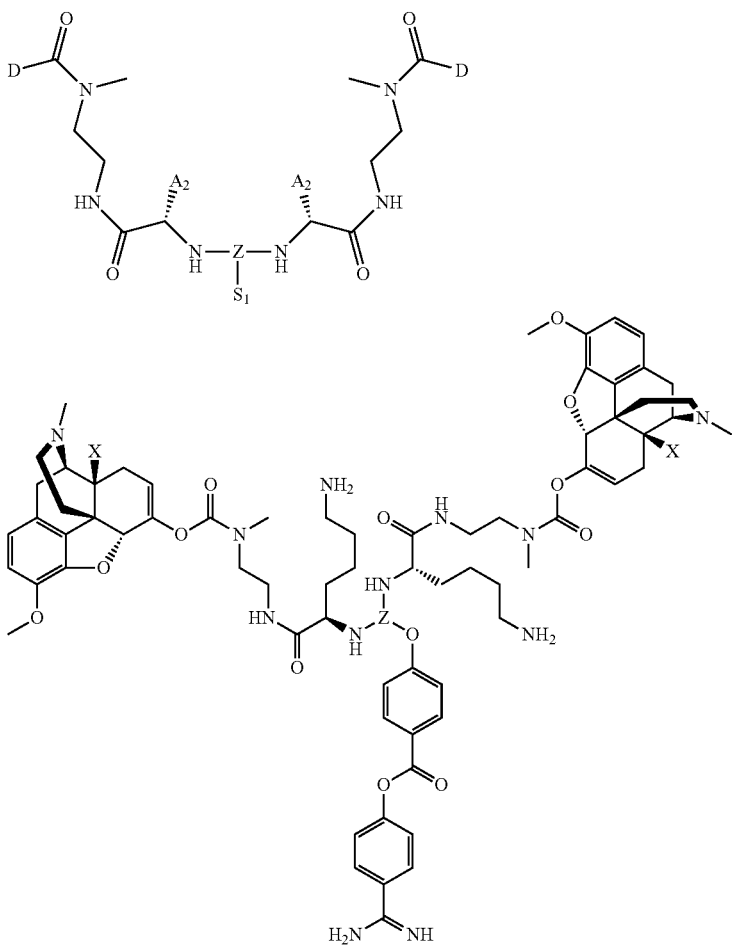

wherein:

D is an opioid agonist, for example wherein D is a morphone, a codone, or morphine;
X is OH or hydrogen;
$S_1$ is a non-opioid releasing GI enzyme substrate or GI enzyme inhibitor subunit;
Z is a linking moiety;

each $A_2$ is independently an amino acid side chain or an amino acid side-chain mimic that is capable of being recognized by a digestive enzyme.

In some embodiments $A_2$ can be:

[chemical structure]

wherein:
R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$
wherein:
Z is a linker moiety as previously defined;
each x is independently 1 or 3 (thereby designating each $S_x$ as a $S_1$ or $S_3$ subunit);
n is an integer ranging from 1-10;
r is each or independently an integer from 1 to 6;
n is an integer from 0 to 10;
R''' is hydrogen, methyl, or
—C(=NR)—$NR_2$ wherein R is each or independently hydrogen or methyl; or

[chemical structure]

limited to, the amino acid side chain of arginine, homoarginine, lysine, homolysine, ε-N-methyl lysine, ornithine, or structural/functional mimics thereof; R" is as defined above.

In some embodiments, $A_2$ directs the regiospecific hydrolysis of the $S_2$ substrate prior to the release of the appended opioid agonist from the $S_2$ subunit. In some embodiments, $A_2$ is the amino acid side chain of arginine, homoarginine, lysine, homolysine, ε-N-methyl lysine, ornithine, or structural/functional mimics thereof.

In another aspect, a composition of the invention is represented by the following formula:

$$[(S_2)_n\text{—}Z]_r\text{—}M\begin{Bmatrix}[Z\text{—}(S_1)_n]_m\\[Z\text{—}(S_3)_n]_p\end{Bmatrix}$$

wherein:
$S_1$ is a non-opioid releasing enzyme substrate or enzyme inhibitor;
$S_2$ is an opioid agonist releasing enzyme substrate;
$S_3$ is an optional opioid antagonist-releasing moiety;
M is a covalent scaffold;
Z is a linker moiety as previously described;
each r, m, n, is independently an integer ranging from 1 to 10, 1 to 100, 1 to 1,000, 1 to 100,000, 1 to 1,000,000, or 1 to 1,000,000,000;
p is an integer ranging from 0 to 10, 0 to 100, 0 to 1,000, 0 to 100,000, 0 to 1,000,000, or 0 to 1,000,000,000.

In some embodiments, M is a carboxymethylcellulose or a functionalized cellulose derivative, chitosan, or a poly[amino acid].

In some embodiments, a compound of the invention is represented by the structure:

[chemical structure]

wherein $A_2$ is a natural or unnatural amino acid side chain, or an amino acid side-chain mimic that is capable of being recognized by a digestive enzyme that directs the regiospecific hydrolysis of the $S_2$ substrate prior to the release of the appended opioid agonist from the $S_2$ subunit and can be, but is not wherein:
each $S_1$ is independently a non-opioid releasing GI enzyme substrate or GI enzyme inhibitor;
each $S_2$ is independently an opioid agonist releasing GI enzyme substrate;
each $S_3$ is an optional opioid antagonist releasing substrate;

each R is independently —H or —CH$_2$COOH;
each Z is independently a linking moiety as previously defined;
R' is —OR$_1$, or —NR$_1$R$_2$ where R$_1$ and R$_2$ are each or independently hydrogen, methyl, lower alkyl, or terminally functionalized polyethylene glycol;
n is an integer such that n/(m+n+r+x) is between 0.01 and 0.5;
m is an integer such that m/(m+n+r+x) is between 0.01 and 0.5;
r is an integer such that r/(m+n+r+x) is between 0 and 0.5;
x is an integer such that x/(m+n+r+x) is between 0 and 0.9.

In some embodiments, the carboxymethylcellulose polymer scaffold can have a molecular weight ranging from about 50-1000 kDa. In some embodiments, the scaffold comprises between 100 to 10,000, for example between 300 to 6,000 anhydroglucose subunits. In some embodiments, the scaffold has a degree of substitution of 0.65-0.85 carboxymethyl groups per anhydroglucose unit, for example resulting in a total of about 100 to 6,000 carboxymethyl substituted monomer units. The number of S$_1$ substituted monomer units, n, can be from about 1 to 10, 20, 30, 40, or 50% of the total number of carboxymethyl substituted monomer units. The number of S$_2$ substituted monomer units, m, can be from about 1 to 10, 20, 30, 40, or 50% of the total number of carboxymethyl substituted monomer units. The number of S$_3$ substituted monomer units, r, can be from about 0 to 10, 20, 30, 40, or 50% of the total number of carboxymethyl substituted monomer units. The number of R' substituted monomer units, x, can be from about 0 to 10, 20, 30, 40, 50, or 90% of the total number of carboxymethyl substituted monomer units. In preferred embodiments, covalent linkage of the S$_1$, S$_2$, S$_3$, and R' addends to the defined functional group contained in the monomer units of the polymeric scaffold occurs in a regiochemically random fashion, resulting in a random distribution of the S$_1$, S$_2$, S$_3$, and R' addends onto the polymer scaffold.

In some embodiments, a compound of the invention is represented by the structure:

wherein:
each S$_1$ is independently a non-opioid releasing GI enzyme substrate or GI enzyme inhibitor;
each S$_2$ is independently an opioid agonist releasing GI enzyme substrate;
each S$_1$ is a non-opioid releasing GI enzyme substrate or GI enzyme inhibitor subunit;
each Z is independently a linking moiety as previously defined;
R' is hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or one or more amino acids or structural mimics thereof;
n is an integer such that n/(m+n+r+x) is between 0.01 and 0.5;
m is an integer such that m/(m+n+r+x) is between 0.01 and 0.5;
r is an integer such that r/(m+n+r+x) is between 0 and 0.5;
x is an integer such that x/(m+n+r+x) is between 0 and 0.9.

In some embodiments, the scaffold can have a molecular weight ranging from about 30-300 kDa. In some embodiments, the scaffold comprises between about 100 and about 3,000 glucosamine subunits, for example about 150 to about 2,000 glucosamine subunits. The number of S$_1$ substituted monomer units, n, can be from about 1 to 50% of the total number of glucosamine monomer units. The number of S$_2$ substituted monomer units, m, can be from about 1 to 50% of the total number of glucosamine monomer units. The number of S$_3$ substituted monomer units, r, can be from about 0 to 50% of the total number of glucosamine monomer units. The number of R' substituted monomer units, x, can be from about 0 to 90% of the total number of glucosamine monomer units. In preferred embodiments, covalent linkage of the S$_1$, S$_2$, S$_3$, and R' addends to the defined functional group contained in the monomer units of the polymeric scaffold occurs in a regiochemically random fashion, resulting in a random distribution of the S$_1$, S$_2$, S$_3$, and R' addends onto the polymer scaffold.

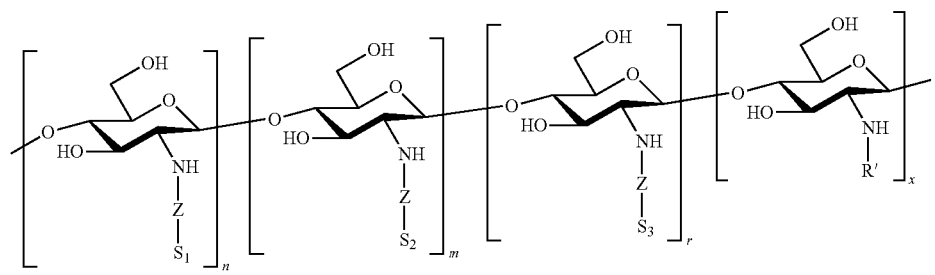

In some embodiments, a compound of the invention is represented by the structure:

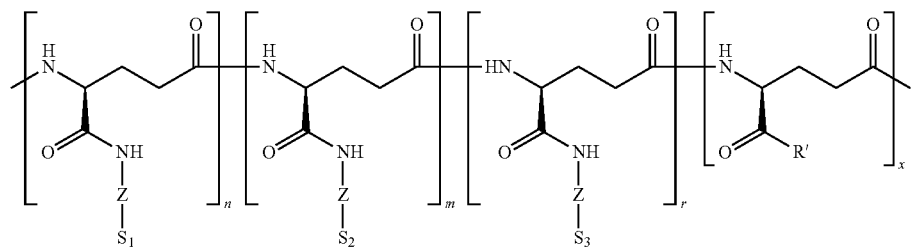

wherein:
each $S_1$ is independently a non-opioid releasing GI enzyme substrate or GI enzyme inhibitor;
each $S_2$ is independently an opioid agonist releasing GI enzyme substrate;
each $S_3$ is an opioid antagonist releasing substrate;
each Z is independently a linking moiety as previously defined;
R' is $-OR_1$, or $-NR_1R_2$ where $R_1$ and $R_2$ are each or independently hydrogen, methyl, lower alkyl, terminally functionalized polyethylene glycol;
n is an integer such that n/(m+n+r+x) is between 0.01 and 0.5;
m is an integer such that m/(m+n+r+x) is between 0.01 and 0.5;
r is an integer such that r/(m+n+r+x) is between 0 and 0.5;
x is an integer such that x/(m+n+r+x) is between 0 and 0.9.

In some embodiments, the scaffold can have a molecular weight ranging from about 200-1000 kDa. In some embodiments, the scaffold comprises a range of about 1,000 to 7,000 polyglutamic acid subunits. The number of $S_1$ substituted monomer units, n, can be from about 1 to 50% of the total number of polyglutamic acid monomer units. The number of $S_2$ substituted monomer units, m, can be from about 1 to 50% of the total number of polyglutamic acid monomer units. The number of $S_3$ substituted monomer units, r, can be from about 0 to 50% of the total number of polyglutamic acid monomer units. The number of R' substituted monomer units, x, can be from about 0 to 90% of the total number of polyglutamic acid monomer units. In preferred embodiments, covalent linkage of the $S_1$, $S_2$, $S_3$, and R' addends to the defined functional group contained in the monomer units of the polymeric scaffold occurs in a regiochemically random fashion, resulting in a random distribution of the $S_1$, $S_2$, $S_3$, and R' addends onto the polymer scaffold.

In some embodiments, a compound of the invention is represented by the structure:

wherein:
each $S_1$ is independently a non-opioid releasing GI enzyme substrate or GI enzyme inhibitor;
each $S_2$ is independently an opioid agonist releasing GI enzyme substrate;
each $S_3$ is an opioid antagonist releasing substrate;
each Z is independently a linking moiety as previously defined;
R' is hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or one or more amino acids or structural mimics thereof;
n is an integer such that n/(m+n+r+x) is between 0.01 and 0.5;
m is an integer such that m/(m+n+r+x) is between 0.01 and 0.5;
r is an integer such that r/(m+n+r+x) is between 0 and 0.5;
x is an integer such that x/(m+n+r+x) is between 0 and 0.9.

The starting polylysine polymer can have a molecular weight ranging from about 30-300 kDa that contains a range of 150 to 2,000 lysine subunits. The number of $S_1$ substituted lysine monomer units, n, can be from about 1 to 50% of the total number of lysine monomer units. The number of $S_2$ substituted monomer units, m, can be from about 1 to 50% of the total number of lysine monomer units. The number of $S_3$ substituted monomer units, r, can be from about 0 to 50% of the total number of lysine monomer units. The number of R' substituted monomer units, x, can be from about 0 to 90% of the total number of lysine monomer units. In preferred embodiments, covalent linkage of the $S_1$, $S_2$, $S_3$, and R' addends to the defined functional group contained in the monomer units of the polymeric scaffold occurs in a regiochemically random fashion, resulting in a random distribution of the $S_1$, $S_2$, $S_3$, and R' addends onto the polymer scaffold.

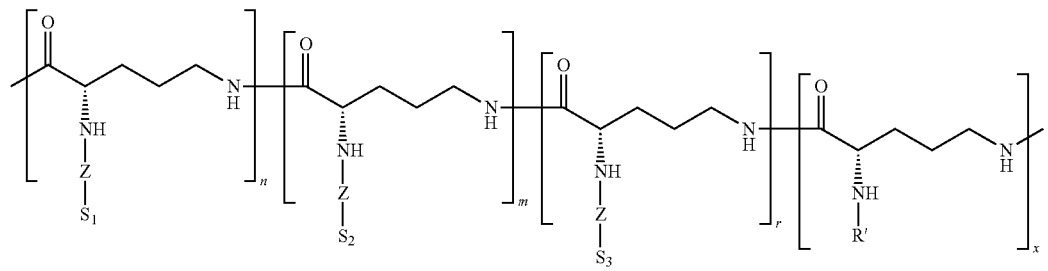

In some embodiments, a compound of the invention is represented by the structure:

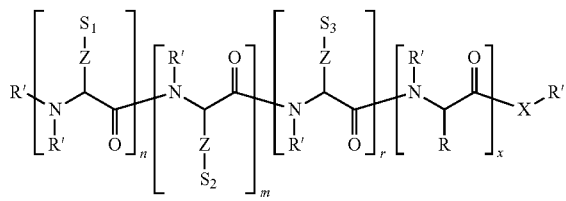

wherein:
each $S_1$ is independently a non-opioid releasing GI enzyme substrate or GI enzyme inhibitor;
each $S_2$ is independently an opioid agonist releasing GI enzyme substrate;
each $S_3$ is an opioid antagonist releasing substrate;
each Z is independently a linking moiety as previously defined;
R is hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, an amino acid side chain or an amino acid side-chain structural mimic;
X can be oxygen or nitrogen;
R' is hydrogen, alkyl, aryl, substituted alkyl, substituted aryl, heteroalkyl, substituted heteroalkyl, polyethylene glycol containing alkyl, or one or more amino acids;
n is an integer from 1 to 10;
m is an integer from 1 to 10;
r is an integer from 0 to 10;
x is an integer from 0 to 10.

In some embodiments, the polypeptide scaffold can be comprised of a range of 2 to 40 natural or non-natural amino acid monomer units. The number of $S_1$ substituted monomer units, n, can be from about 1 to 50% of the total number of monomer units. The number of $S_2$ substituted monomer units, m, can be from about 1 to 50% of the total number of monomer units. The number of $S_3$ substituted monomer units, r, can be from about 0 to 50% of the total number of monomer units. The number of R' substituted monomer units, x, can be from about 0 to 50% of the total number of monomer units. In preferred embodiments, the $S_1$, $S_2$, $S_3$, and R' substituted monomer units can be distributed in a regiochemically random fashion.

In some embodiments, a compound of the invention is represented by one of the structures:

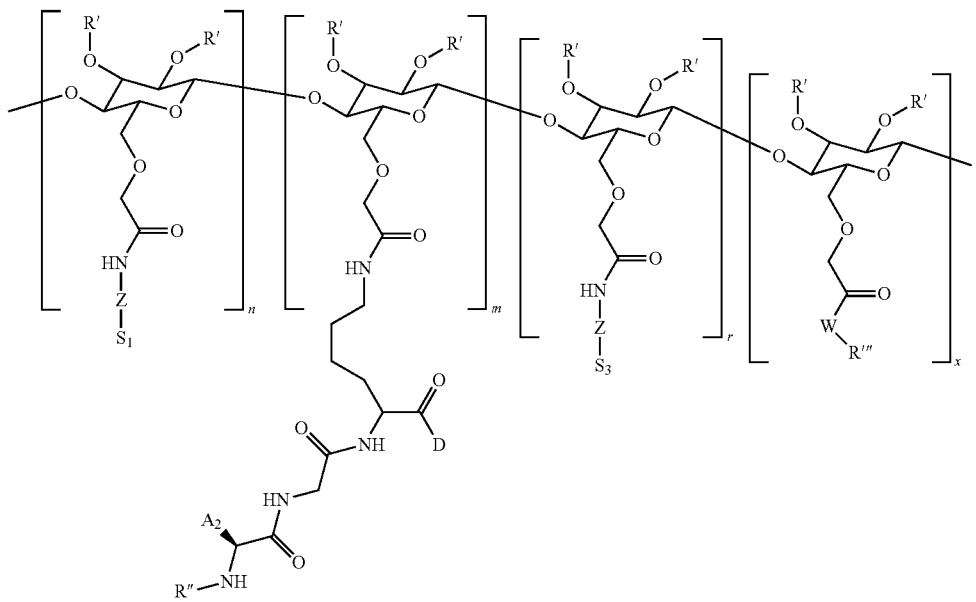

-continued

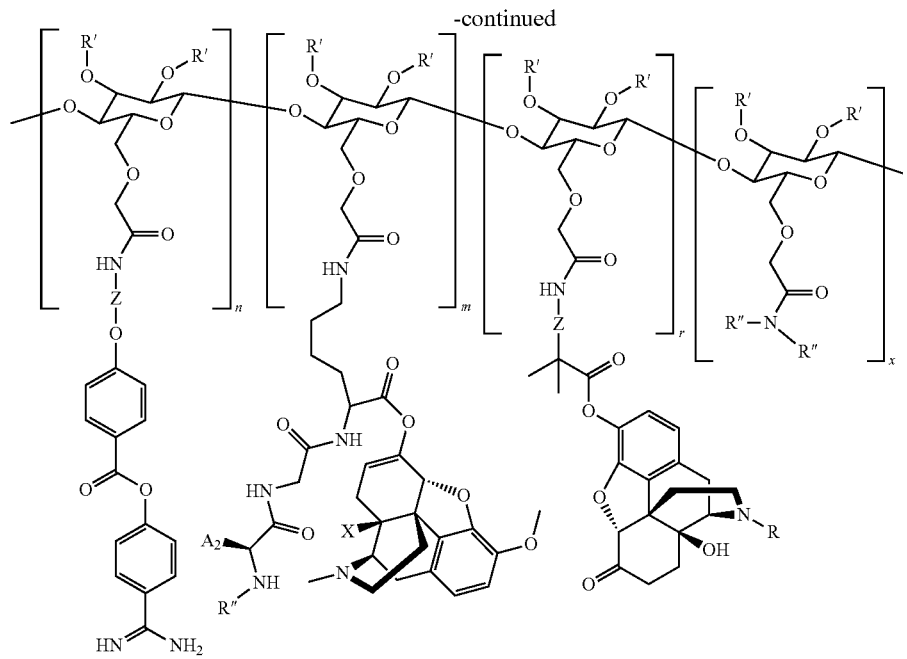

wherein:

D is an opioid agonist, for example wherein D is a morphone, a codone, or morphine;

X is OH or hydrogen;

each $S_1$ is a non-opioid releasing GI enzyme substrate subunit or GI enzyme inhibitor;

each $S_3$ is an opioid antagonist releasing moiety;

R is cyclopropylmethyl or allyl;

each Z is a linking moiety;

R" is hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or one or more amino acids or structural or functional mimics thereof R' is H or —CH$_2$COOH;

W can be oxygen or nitrogen;

R''' is hydrogen, alkyl, aryl, substituted alkyl, substituted aryl, heteroalkyl, substituted heteroalkyl, polyethylene glycol containing alkyl, or one or more amino acids;

$A_2$ is an amino acid side chain, or an amino acid side-chain mimic that is capable of being recognized by a digestive enzyme; for example, $A_2$ can be the amino acid side chain of arginine, homoarginine, lysine, homolysine, ε-N-methyl lysine, ornithine, or structural/functional mimics thereof;

n is an integer such that n/(m+n+r+x) is between 0.01 and 0.5;

m is an integer such that m/(m+n+r+x) is between 0.01 and 0.5;

r is an integer such that r/(m+n+r+x) is between 0 and 0.5;

x is an integer such that x/(m+n+r+x) is between 0 and 0.9.

In some embodiments, the carboxymethylcellulose scaffold can have a molecular weight ranging from about 50-1000 kDa. In some embodiments, the scaffold comprises a range of 300 to 6,000 anhydroglucose subunits. In some embodiments, the scaffold has a degree of substitution of 0.65-0.85 carboxymethyl groups per anhydroglucose unit, resulting in a total of about 100 to 6,000 carboxymethyl substituted monomer units. The number of substituted monomer units, n, can be from about 1 to 50% of the total number of carboxymethyl substituted monomer units. The number of substituted monomer units, m, can be from about 1 to 50% of the total number of carboxymethyl substituted monomer units. The number of substituted monomer units, r, can be from about 0 to 50% of the total number of carboxymethyl substituted monomer units. The number of substituted monomer units, x, can be from about 0 to 90% of the total number of carboxymethyl substituted monomer units. In preferred embodiments, covalent linkage of the defined addends to the monomer units of the polymeric scaffold occurs in a regiochemically random fashion, resulting in a random distribution of the addends onto the polymer scaffold.

In some embodiments, a compound of the invention is represented by the structure:

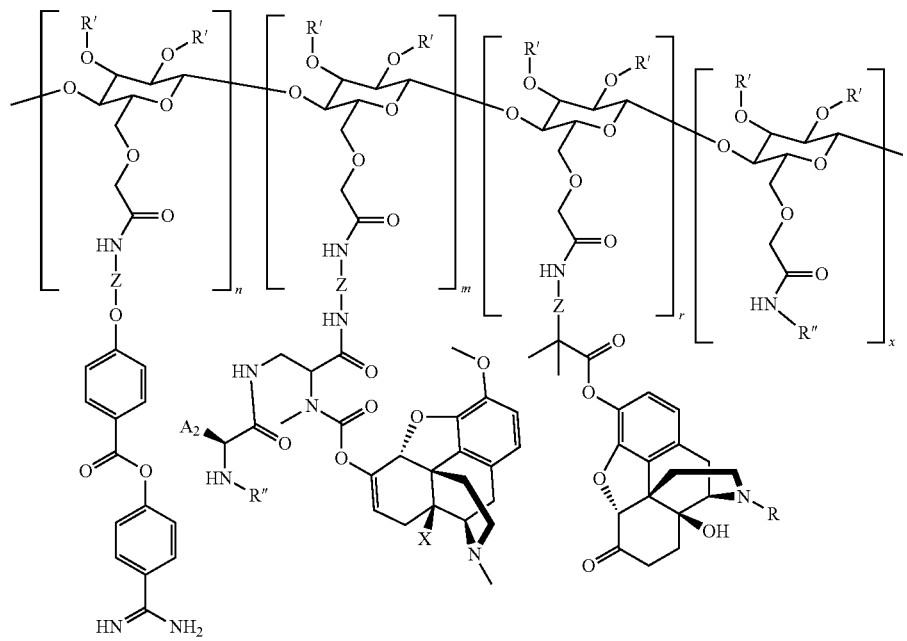

wherein:
R'=H or —CH$_2$COOH.
R is cyclopropylmethyl or allyl,
X is OH or hydrogen;
each Z is independently a linking moiety as previously defined;
each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—(S$_2$)$_n$, or —Z—(S$_x$)$_n$
  wherein:
  Z is a linker moiety as previously defined;
  each x is independently 1 or 3 (thereby designating each S$_x$ as a S$_1$ or S$_3$ subunit);
  n is an integer ranging from 1-10;
n is an integer such that n/(m+n+r+x) is between 0.01 and 0.5;
m is an integer such that m/(m+n+r+x) is between 0.01 and 0.5;
r is an integer such that r/(m+n+r+x) is between 0 and 0.5;
x is an integer such that x/(m+n+r+x) is between 0 and 0.9;
A$_2$ is independently an amino acid side chain or an amino acid side-chain mimic that is capable of being recognized by a digestive enzyme.
In some embodiments A$_2$ can be:

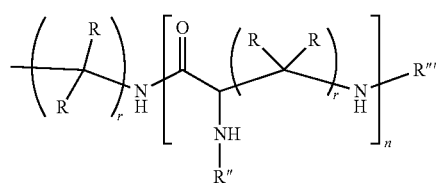

wherein:
R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—(S$_2$)$_n$, or —Z—(S$_x$)$_n$
  wherein:
  Z is a linker moiety as previously defined;
  each x is independently 1 or 3 (thereby designating each S$_x$ as a S$_1$ or S$_3$ subunit);
  n is an integer ranging from 1-10;
r is each or independently an integer from 1 to 6;
n is an integer from 0 to 10;
R'" is hydrogen, methyl, or
—C(=NR)—NR$_2$ wherein R is each or independently hydrogen or methyl; or

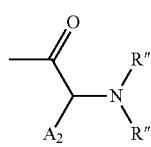

wherein A$_2$ is a natural or unnatural amino acid side chain, or an amino acid side-chain mimic that is capable of being recognized by a digestive enzyme that directs the regiospecific hydrolysis of the S$_2$ substrate prior to the release of the appended opioid agonist from the S$_2$ subunit and can be, but is not limited to, the amino acid side chain of arginine, homoarginine, lysine, homolysine, ε-N-methyl lysine, ornithine, or structural/functional mimics thereof; R" is as defined above.
In some embodiments, A$_2$ directs the regiospecific hydrolysis of the S$_2$ substrate prior to the release of the appended opioid agonist from the $S_2$ subunit. In some embodiments, $A_2$ is the amino acid side chain of arginine, homoarginine, lysine, homolysine, ε-N-methyl lysine, ornithine, or structural/functional mimics thereof.

The carboxymethylcellulose scaffold can have a molecular weight ranging from about 50-1000 kDa. In some embodiments, the scaffold comprises a range of 300 to 6,000 anhydroglucose subunits. In some embodiments, the scaffold has a degree of substitution of 0.65-0.85 carboxymethyl groups per anhydroglucose unit, resulting in a total of about 100 to 6,000 carboxymethyl substituted monomer units. The number of substituted monomer units, n, can be from about 1 to 50% of the total number of carboxymethyl substituted monomer units. The number of substituted monomer units, m, can be from about 1 to 50% of the total number of carboxymethyl substituted monomer units. The number of substituted monomer units, r, can be from about 0 to 50% of the total number of carboxymethyl substituted monomer units. The number of R" substituted monomer units, x, can be from about 0 to 90% of the total number of carboxymethyl substituted monomer units. In preferred embodiments, covalent linkage of the Z, and R" addends to the defined functional group contained in the monomer units of the polymeric scaffold occurs in a regiochemically random fashion, resulting in a random distribution of the addends onto the polymer scaffold.

In some embodiments, a compound of the invention is represented by one of the structures:

wherein:

D is an opioid agonist, for example wherein D is a morphone, a codone, or morphine;

X is OH or hydrogen;

each $S_1$ is independently a non-opioid releasing GI enzyme substrate or GI enzyme inhibitor;

contained in the monomer units of the polymeric scaffold occurs in a regiochemically random fashion, resulting in a random distribution of the addends onto the polymer scaffold.

In some embodiments, a compound of the invention is represented by one of the structures:

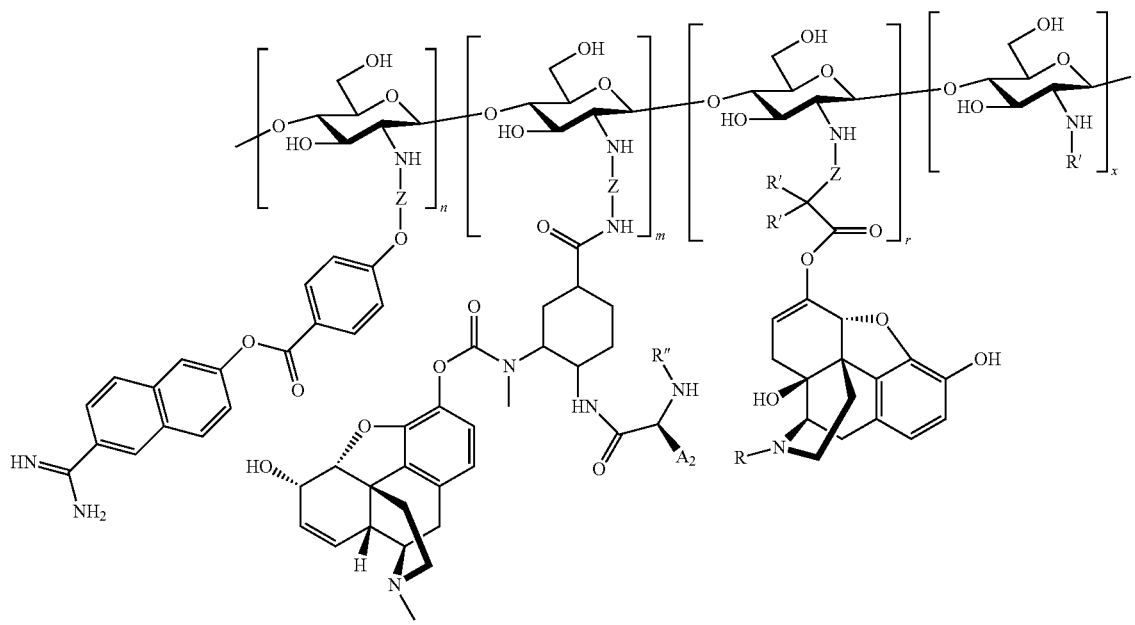

$S_3$ is an opioid antagonist-releasing moiety;

R is cyclopropylmethyl or allyl;

each Z is a linking moiety;

R" is hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or one or more amino acids or structural or functional mimics thereof R' is each or independently hydrogen or methyl;

$A_2$ is an amino acid side chain, or an amino acid side-chain mimic that is capable of being recognized by a digestive enzyme; for example, $A_2$ can be the amino acid side chain of arginine, homoarginine, lysine, homolysine, ε-N-methyl lysine, ornithine, or structural/functional mimics thereof;

n is an integer such that n/(m+n+r+x) is between 0.01 and 0.5;

m is an integer such that m/(m+n+r+x) is between 0.01 and 0.5;

r is an integer such that r/(m+n+r+x) is between 0 and 0.5;

x is an integer such that x/(m+n+r+x) is between 0 and 0.9.

The chitosan scaffold can have a molecular weight ranging from about 30-300 kDa that contains a range of 150 to 2,000 glucosamine subunits. The number of substituted monomer units, n, can be from about 1 to 50% of the total number of glucosamine monomer units. The number of substituted monomer units, m, can be from about 1 to 50% of the total number of glucosamine monomer units. The number of substituted monomer units, r, can be from about 0 to 50% of the total number of glucosamine monomer units. The number of R" substituted monomer units, x, can be from about 0 to 90% of the total number of glucosamine monomer units. In preferred embodiments, covalent linkage of the $S_1$, $S_2$, $S_3$, and R" addends to the defined functional group wherein:

R' are each of independently hydrogen or methyl,

R is cyclopropylmethyl or allyl;

each Z is independently a linking moiety as previously defined;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—($S_2$), or —Z—$(S_x)_n$ wherein:

Z is a linker moiety as previously defined;

each x is independently 1 or 3 (thereby designating each $S_x$ as a $S_1$ or $S_3$ subunit);

n is an integer ranging from 1-10;

n is an integer such that n/(m+n+r+x) is between 0.01 and 0.5;

m is an integer such that m/(m+n+r+x) is between 0.01 and 0.5;

r is an integer such that r/(m+n+r+x) is between 0 and 0.5;

x is an integer such that x/(m+n+r+x) is between 0 and 0.9;

$A_2$ is independently an amino acid side chain or an amino acid side-chain mimic that is capable of being recognized by a digestive enzyme.

In some embodiments $A_2$ can be:

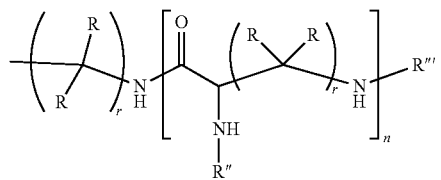

wherein:

R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$ wherein:

Z is a linker moiety as previously defined;
each x is independently 1 or 3 (thereby designating each $S_x$ as a $S_1$ or $S_3$ subunit);
n is an integer ranging from 1-10;
r is each or independently an integer from 1 to 6;
n is an integer from 0 to 10;
R''' is hydrogen, methyl, or

—C(═NR)—$NR_2$ wherein R is each or independently hydrogen or methyl; or

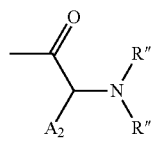

wherein $A_2$ is a natural or unnatural amino acid side chain, or an amino acid side-chain mimic that is capable of being recognized by a digestive enzyme that directs the regiospecific hydrolysis of the $S_2$ substrate prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof; and R" is as defined above.

In some embodiments, $A_2$ directs the regiospecific hydrolysis of the $S_2$ substrate prior to the release of the appended opioid agonist from the $S_2$ subunit. In some embodiments, $A_2$ is the amino acid side chain of arginine, homoarginine, lysine, homolysine, ε-N-methyl lysine, ornithine, or structural/functional mimics thereof.

The chitosan scaffold polymer can have a molecular weight ranging from about 30-300 kDa that contains a range of 150 to 2,000 glucosamine subunits. The number of substituted monomer units, n, can be from about 1 to 50% of the total number of glucosamine monomer units. The number of substituted monomer units, m, can be from about 1 to 50% of the total number of glucosamine monomer units. The number of substituted monomer units, r, can be from about 0 to 50% of the total number of glucosamine monomer units. The number of R" substituted monomer units, x, can be from about 0 to 90% of the total number of glucosamine monomer units. R' are each or independently hydrogen or methyl. In preferred embodiments, covalent linkage of the Z, and R" addends to the defined functional group contained in the monomer units of the polymeric scaffold occurs in a regiochemically random fashion, resulting in a random distribution of the addends onto the polymer scaffold.

In some embodiments, a compound of the invention is represented by one of the structures:

-continued

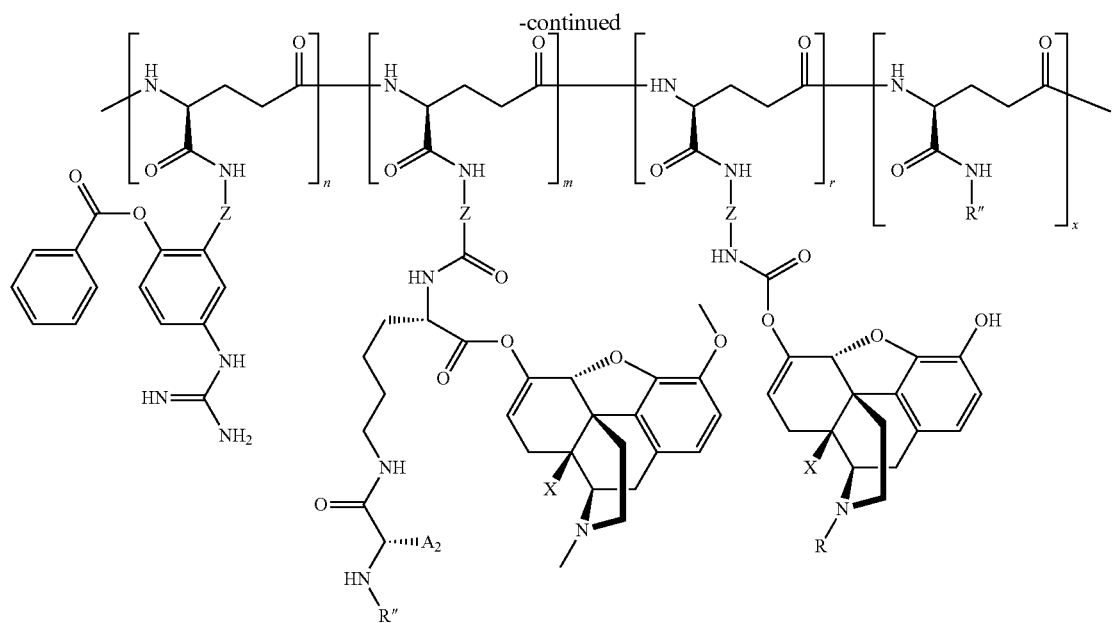

wherein:

D is an opioid agonist, for example wherein D is a morphone, a codone, or morphine;

X is OH or hydrogen;

each $S_1$ is independently a non-opioid releasing GI enzyme substrate or GI enzyme inhibitor;

$S_3$ is an opioid antagonist releasing moiety;

R is cyclopropylmethyl or allyl;

each Z is a linking moiety;

R" is hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or one or more amino acids or structural or functional mimics thereof;

$A_2$ is an amino acid side chain, or an amino acid side-chain mimic that is capable of being recognized by a digestive enzyme; for example, $A_2$ can be the amino acid side chain of arginine, homoarginine, lysine, homolysine, ε-N-methyl lysine, ornithine, or structural/functional mimics thereof;

n is an integer such that n/(m+n+r+x) is between 0.01 and 0.5;

m is an integer such that m/(m+n+r+x) is between 0.01 and 0.5;

r is an integer such that r/(m+n+r+x) is between 0 and 0.5;

x is an integer such that x/(m+n+r+x) is between 0 and 0.9.

The polyglutamic acid polymer can have a molecular weight ranging from about 200-1000 kDa that contains a range of about 1000 to 7,000 polyglutamic acid subunits. The number of substituted monomer units, n, can be from about 1 to 50% of the total number of polyglutamic acid monomer units. The number of substituted monomer units, m, can be from about 1 to 50% of the total number of polyglutamic acid monomer units. The number of substituted monomer units, r, can be from about 0 to 50% of the total number of polyglutamic acid monomer units. The number of R" substituted monomer units, x, can be from about 0 to 90% of the total number of polyglutamic acid monomer units. In preferred embodiments, covalent linkage of the Z and R" addends to the defined functional group contained in the monomer units of the polymeric scaffold occurs in a regiochemically random fashion, resulting in a random distribution of the addends onto the polymer scaffold.

In some embodiments, a compound of the invention is represented by one of the structures:

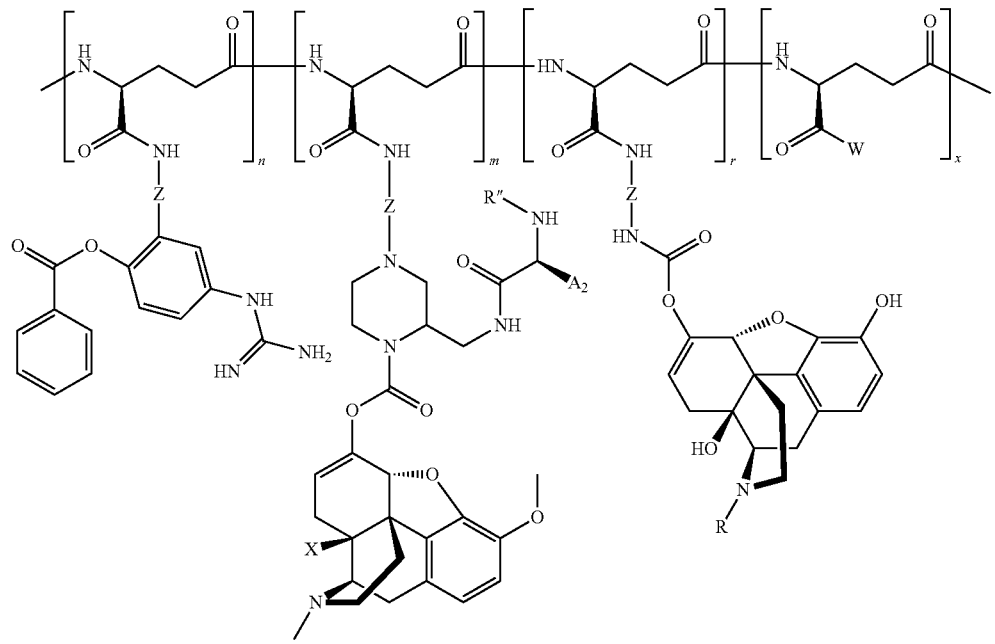

wherein:
X is OH or hydrogen;
each Z is independently a linking moiety as previously defined;
W is hydrogen or —OH; X' is —OH, —OR" or —NH$_2$, or —NHR", or —N(R")$_2$
R is cyclopropylmethyl or allyl;
R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—(S$_2$)—, or Z—(S$_x$)$_m$
  wherein:
  Z is a linker moiety as previously defined;
  each x is independently 1 or 3 (thereby designating each S$_x$ as a S$_1$ or S$_3$ subunit);
  n is an integer ranging from 1-10;
n is an integer such that n/(m+n+r+x) is between 0.01 and 0.5;
m is an integer such that m/(m+n+r+x) is between 0.01 and 0.5;
r is an integer such that r/(m+n+r+x) is between 0 and 0.5;
x is an integer such that x/(m+n+r+x) is between 0 and 0.9;
A$_2$ is independently an amino acid side chain or an amino acid side-chain mimic that is capable of being recognized by a digestive enzyme.
  In some embodiments A$_2$ can be:

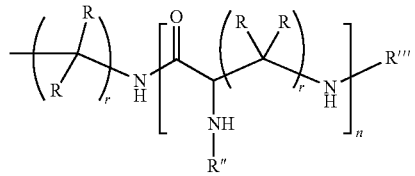

wherein:
R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—(S$_2$)$_n$, or —Z—(S$_x$)$_n$
  wherein:
  Z is a linker moiety as previously defined;
  each x is independently 1 or 3 (thereby designating each S$_x$ as a S$_1$ or S$_3$ subunit);
  n is an integer ranging from 1-10;
r is each or independently an integer from 1 to 6;
n is an integer from 0 to 10;
R'" is hydrogen, methyl, or
—C(=NR)—NR$_2$ wherein R is each or independently hydrogen or methyl; or

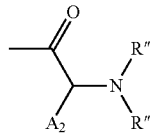

wherein A$_2$ is a natural or unnatural amino acid side chain, or an amino acid side-chain mimic that is capable of being recognized by a digestive enzyme that directs the regiospecific hydrolysis of the S$_2$ substrate prior to the release of the appended opioid agonist from the S$_2$ subunit and can be, but is not limited to, the amino acid side chain of arginine, homoarginine, lysine, homolysine, ε-N-methyl lysine, ornithine, or structural/functional mimics thereof; and
R" is as defined above.

In some embodiments, $A_2$ directs the regiospecific hydrolysis of the $S_2$ substrate prior to the release of the appended opioid agonist from the $S_2$ subunit. In some embodiments, $A_2$ is the amino acid side chain of arginine, homoarginine, lysine, homolysine, ε-N-methyl lysine, ornithine, or structural/functional mimics thereof.

The polyglutamic acid polymer can have a molecular weight ranging from about 200-1000 kDa that contains a range of about 1000 to 7,000 polyglutamic acid subunits. The number of substituted monomer units, n, can be from about 1 to 50% of the total number of polyglutamic acid monomer units. The number of substituted monomer units, m, can be from about 1 to 50% of the total number of polyglutamic acid monomer units. The number of substituted monomer units, r, can be from about 0 to 50% of the total number of polyglutamic acid monomer units. The number of R" substituted monomer units, x, can be from about 0 to 90% of the total number of polyglutamic acid monomer units. In preferred embodiments, covalent linkage of the Z and R" addends to the defined functional group contained in the monomer units of the polymeric scaffold occurs in a regiochemically random fashion, resulting in a random distribution of the addends onto the polymer scaffold.

In some embodiments, a compound of the invention is represented by one of the structures:

n is an integer such that n/(m+n+r+x) is between 0.01 and 0.5;

m is an integer such that m/(m+n+r+x) is between 0.01 and 0.5;

r is an integer such that r/(m+n+r+x) is between 0 and 0.5;

x is an integer such that x/(m+n+r+x) is between 0 and 0.9;

$A_2$ is independently an amino acid side chain or an amino acid side-chain mimic that is capable of being recognized by a digestive enzyme;

In some embodiments $A_2$ can be:

wherein:

R is each or independently hydrogen or methyl; R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$ wherein:

each Z is independently a linking moiety as previously defined;

R' are each or independently hydrogen or methyl;

X is hydrogen or —OH;

R is cyclopropylmethyl or allyl;

R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$ wherein:

Z is a linker moiety as previously defined;

each x is independently 1 or 3 (thereby designating each $S_x$ as a $S_1$ or $S_3$ subunit);

n is an integer ranging from 1-10;

wherein:

Z is a linker moiety as previously defined;

each x is independently 1 or 3 (thereby designating each $S_x$ as a $S_1$ or $S_3$ subunit);

n is an integer ranging from 1-10;

r is each or independently an integer from 1 to 6;

n is an integer from 0 to 10;

R''' is hydrogen, methyl, or

—C(═NR)—$NR_2$ wherein R is each or independently hydrogen or methyl; or wherein $A_2$ is a natural or unnatural amino acid side chain, or an amino acid side-chain mimic that is capable of being recognized by a digestive enzyme that directs the regiospecific hydrolysis of the $S_2$ substrate prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof; R" is as defined above.

In some embodiments, $A_2$ directs the regiospecific hydrolysis of the $S_2$ substrate prior to the release of the appended opioid agonist from the $S_2$ subunit. In some embodiments, $A_2$ is the amino acid side chain of arginine, homoarginine, lysine, homolysine, ε-N-methyl lysine, ornithine, or structural/functional mimics thereof.

The polylysine scaffold can have a molecular weight ranging from about 30-300 kDa that contains a range of 150 to 2,000 lysine subunits. The number of substituted lysine monomer units, n, can be from about 1 to 50% of the total number of lysine monomer units. The number of substituted monomer units, m, can be from about 1 to 50% of the total number of lysine monomer units. The number of substituted monomer units, r, can be from about 0 to 50% of the total number of lysine monomer units. The number of R" substituted monomer units, x, can be from about 0 to 90% of the total number of lysine monomer units. In preferred embodiments, covalent linkage of the Z and R" addends to the defined functional group contained in the monomer units of the polymeric scaffold occurs in a regiochemically random fashion, resulting in a random distribution of the addends onto the polymer scaffold.

In some embodiments, a compound of the invention is represented by one of the structures:

Wherein:

D is an opioid agonist, for example wherein D is a morphone, a codone, or morphine;

X is OH or hydrogen;

each $S_1$ is a non-opioid releasing GI enzyme substrate or GI enzyme inhibitor subunit;

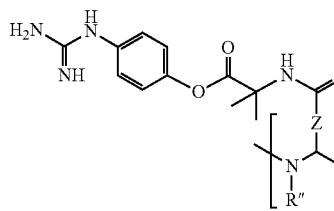

$S_3$ is an opioid antagonist releasing moiety;

R is cyclopropylmethyl or allyl;

each Z is a linking moiety;

R" is hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or one or more amino acids or structural or functional mimics thereof;

R' is hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, an amino acid side chain or an amino acid side-chain structural mimic;

W is OH, O-alkyl, $NH_2$, NHR", or $N(R")_2$;

$A_2$ is an amino acid side chain, or an amino acid side-chain mimic that is capable of being recognized by a digestive enzyme; for example, $A_2$ can be the amino acid side chain of arginine, homoarginine, lysine, homolysine, ε-N-methyl lysine, ornithine, or structural/functional mimics thereof;

n is an integer from 1 to 10;

m is an integer from 1 to 10;

r is an integer from 0 to 10;

x is an integer from 0 to 10.

In some embodiments, the polypeptide scaffold can be comprised of a range of 2 to 40 natural or unnatural amino acid monomer units. The number of substituted monomer units, n, can be from about 1 to 50% of the total number of monomer units. The number of substituted monomer units, m, can be from about 1 to 50% of the total number of monomer units. The number of substituted monomer units, r, can be from about 0 to 50% of the total number of monomer units. The number of R' substituted monomer units, x, can be from about 0 to 50% of the total number of monomer units. All possible regiochemical distributions of the Z and R' containing addends on the peptide backbone are covered within the scope of the invention.

In some embodiments, a compound of the invention is represented by one of the structures:

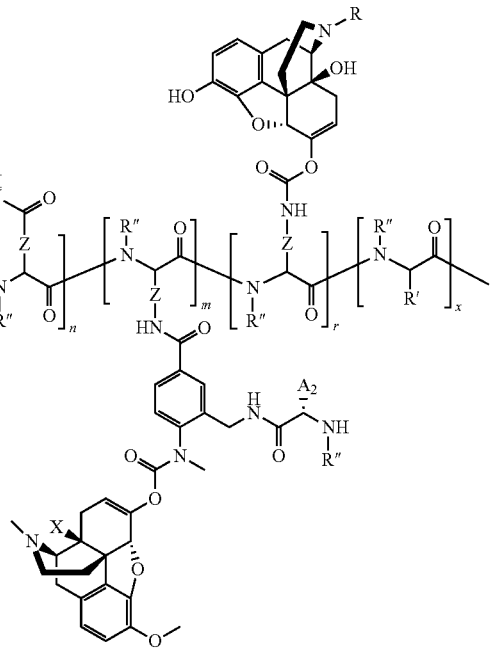

wherein:

each Z is independently a linking moiety as previously defined;

X is hydrogen or —OH;

R is cyclopropylmethyl or allyl;

R' is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or Z, a linker moiety as previously defined;

each R" is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$ wherein:

Z is a linker moiety as previously defined;

each x is independently 1 or 3 (thereby designating each $S_x$ as a $S_1$ or $S_3$ subunit);

n is an integer ranging from 1-10;

$A_2$ is independently an amino acid side chain or an amino acid side-chain mimic that is capable of being recognized by a digestive enzyme.

219

In some embodiments $A_2$ can be:

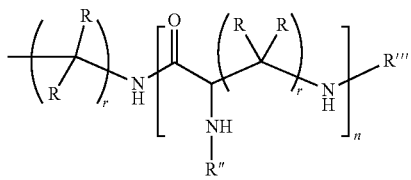

wherein:
R is each or independently hydrogen or methyl; R''' is independently hydrogen, alkyl, aryl, substituted alkyl, substituted aryl, heteroalkyl, substituted heteroalkyl, acyl, substituted acyl group, polyethylene glycol containing acyl, polyethylene glycol containing alkyl, or a natural or unnatural amino acid, an amino acid mimic, or —Z—$(S_2)_n$, or —Z—$(S_x)_n$
wherein:
Z is a linker moiety as previously defined;
each x is independently 1 or 3 (thereby designating each $S_x$ as a $S_1$ or $S_3$ subunit);
n is an integer ranging from 1-10;
r is each or independently an integer from 1 to 6;
n is an integer from 0 to 10;
R''' is hydrogen, methyl, or
—C(=NR)—$NR_2$ wherein R is each or independently hydrogen or methyl; or

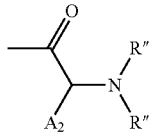

wherein $A_2$ is a natural or unnatural amino acid side chain, or an amino acid side-chain mimic that is capable of being recognized by a digestive enzyme that directs the regiospecific hydrolysis of the $S_2$ substrate prior to the release of the appended opioid agonist from the $S_2$ subunit and can be, but is not limited to, the amino acid side chain of arginine, homoarginine, lysine, homolysine, ε-N-methyl lysine, ornithine, or structural/functional mimics thereof; R'' is as defined above.

In some embodiments, $A_2$ directs the regiospecific hydrolysis of the $S_2$ substrate prior to the release of the appended opioid agonist from the $S_2$ subunit. In some embodiments, $A_2$ is the amino acid side chain of arginine, homoarginine, lysine, homolysine, s-N-methyl lysine, ornithine, or structural/functional mimics thereof.

In some embodiments, the polypeptide scaffold can be comprised of a range of 2 to 20 natural or unnatural amino acid monomer units. The number of substituted monomer units, n, can be from about 1 to 50% of the total number of monomer units. The number of substituted monomer units, m, can be from about 1 to 50% of the total number of monomer units. The number of substituted monomer units, r, can be from about 0 to 50% of the total number of monomer units. The number of R' substituted monomer units, x, can be from about 0 to 50% of the total number of monomer units. All possible regiochemical distributions of the Z and R' addends on the peptide backbone are covered within the scope of the invention.

220

In certain embodiments, the specification provides compounds wherein an opioid agonist is bound covalently to a GI enzyme inhibitor or substrate to attenuate the effects of the opioid agonist. The opioid agonist may be covalently bound to the GI enzyme inhibitor through a scaffold such as an optionally substituted alkyl or optionally substituted heteroalkyl scaffold. In certain embodiments, said scaffold includes from 1 to 100 atoms, such as from about 5 to 50 atoms. In certain embodiments, the scaffold is absent and the opioid agonist is bound directly to a GI enzyme inhibitor. In certain embodiments, a compound of the disclosure is represented by the structure of Formula (I):

$$[R^1\text{-}L^1\text{-}]_n Q\text{-}[L^2\text{-}R^2]_m \quad (I)$$

or a salt thereof, wherein:
Q is independently selected from optionally substituted heteroalkyl and optionally substituted alkyl;
$L^1$ is independently at each occurrence absent or a cleavable or non-cleavable linker;
$L^2$ is independently at each occurrence absent or a cleavable or non-cleavable linker;
$R^1$ is independently selected at each occurrence from a GI enzyme substrate, a GI enzyme inhibitor,
$R^2$ is an opioid agonist covalently bound to a GI enzyme substrate; and
m and n are independently selected at each occurrence from 1 to 1,000,000.

In some embodiments, for the compound or salt of Formula (I), Q is an optionally substituted heteroalkyl group.

In some embodiments, for the compound or salt of Formula (I), Q is an optionally substituted peptide.

In certain embodiments, for the compound or salt of Formula (I), Q is an optionally substituted heteroalkyl group. Heteroalkyl includes an alkyl chain that is interrupted by one or more heteroatoms, such as O, N, or S. Heteroalkyl chains can include form about 4 to about 100 atoms. A heteroalkyl chain may be optionally substituted by one or more substitutent. In certain embodiments, heteroalkyl is a peptide such as -ala-gly- or -arg-ala-.

In some embodiments, for the compound or salt of Formula (I), Q is an optionally substituted peptide with from 1 to 500 amino acids. In some embodiments, for the compound or salt of Formula (I), Q is an optionally substituted peptide with from 1 to 50 amino acids. In some embodiments, for the compound or salt of Formula (I), Q is an optionally substituted peptide with from 1 to 10 amino acids. In some embodiments, for the compound or salt of Formula (I), Q is an optionally substituted peptide with from 1 to 3 amino acids.

In some embodiments, a compound or salt of Formula (I) is represented by a structure of Formula (IA), (IB), or (IC):

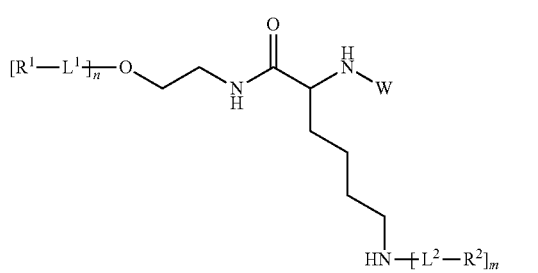

(IA)

(IB)
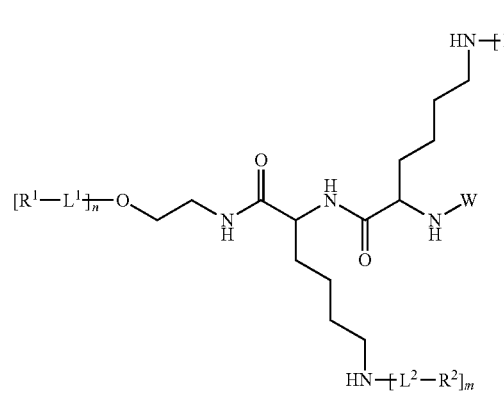
(IC)
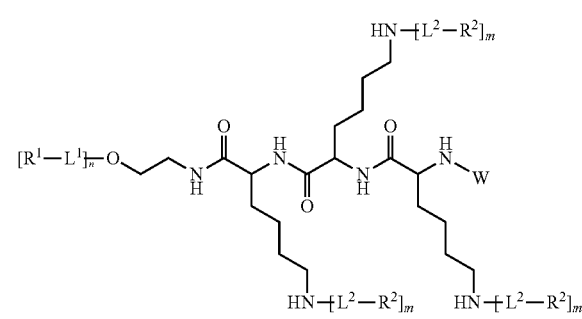
wherein W is selected from hydrogen, optionally substituted alkyl, optionally substituted acyl, and optionally substituted alkoxycarbonyl.
In some embodiments, a compound or salt of Formula (I) is represented by a structure of Formula (ID), (IE), or (IF):
(ID)
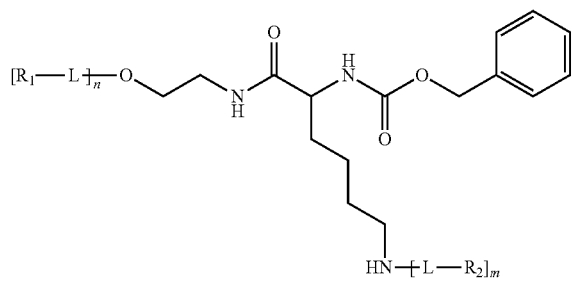
(IE)
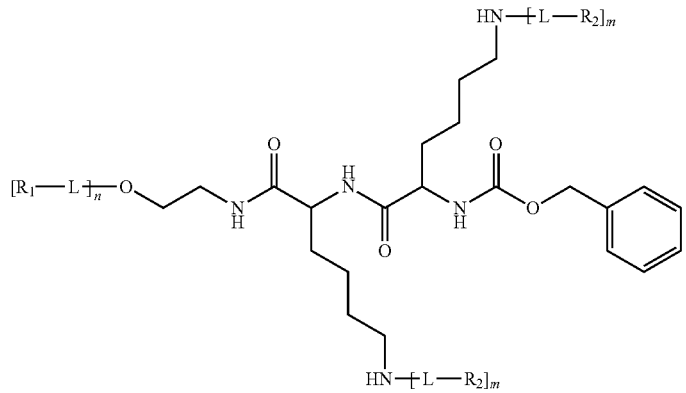
(IF)
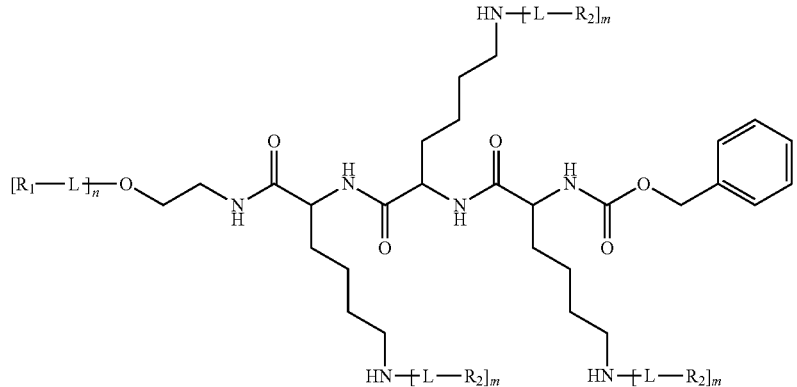

In some embodiments, the compound or salt, wherein $R^1$ is independently selected at each occurrence from a GI enzyme inhibitor. In some embodiments, for the compound or salt of Formula (I), $R^1$ at each occurrence is a serine protease inhibitor. In some embodiments, for the compound or salt of Formula (I), Q at each occurrence is a trypsin inhibitor.

In some embodiments, for the compound or salt of Formula (I), $R^1$-$L^1$ is independently selected at each occurrence from:

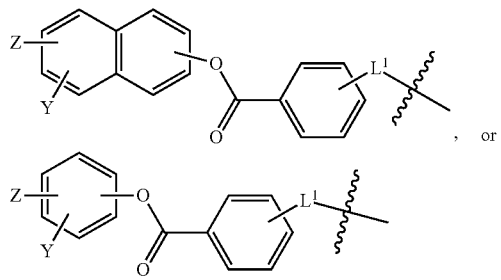

, or wherein:

Y is independently selected from an amidine, guanidine, benzylamine, alkyl substituted amidine, alkyl substituted guanidine, alkyl substituted benzylamine, benzylguanidine, alkyl substituted benzylamidine, or alkyl substituted benzyl; and Z is independently selected from hydrogen, cyano, nitro, halogen, alkyl and alkoxy.

In some embodiments, for the compound or salt of Formula (I), Y is amidine.

In some embodiments, for the compound or salt of Formula (I), $R^1$-$L^1$ is represented by the formula:

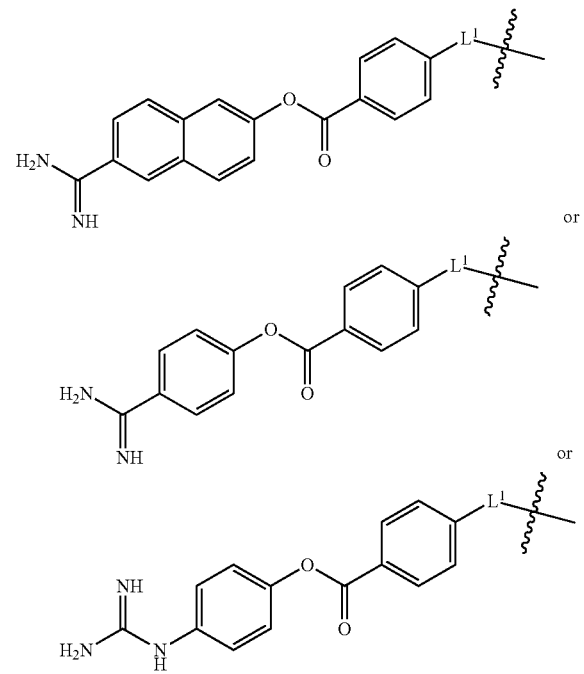

In some embodiments, for the compound or salt of Formula (I), $L^1$ at each occurrence is selected from a cleavable or non-cleavable linker including from 2 to 15 atoms.

In some embodiments, for the compound or salt of Formula (I), $L^1$ is —O—CH$_2$—CH$_2$—NH— or —O—CH$_2$—CH$_2$—O—.

In some embodiments, for the compound or salt of Formula (I), n is selected from 1 to 20. In some embodiments, for the compound or salt of Formula (I), n is selected from 1 to 10. In some embodiments, for the compound or salt of Formula (I), n is selected from 1 to 3.

In some embodiments, for the compound or salt of Formula (I), $R^2$-$L^2$ is independently selected at each occurrence from:

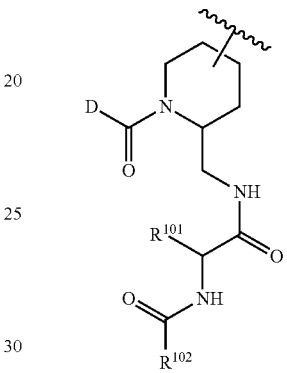

wherein:

D is an opioid agonist;

$R^{101}$ and $R^{102}$ are independently selected from optionally substituted alkyl, an amino acid side chain and an amino acid side-chain mimic.

The term "substituted" refers to moieties having substituents replacing a hydrogen on one or more carbons or substitutable heteroatoms, e.g., NH, of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—

NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

In certain embodiments, a linker L$^1$ or L$^2$ is selected from a linker that is cleavable in vitro or in vivo. Cleavable linkers may include chemically or enzymatically unstable or degradable linkages. Cleavable linkers described herein rely on gastrointestinal processes, such as exposure to acidic conditions and exposure to GI enzymes to cleave the linkers. Cleavable linkers generally incorporate one or more chemical bonds that are either chemically or enzymatically cleavable while the remainder of the linker is noncleavable.

In certain embodiments, a linker L$^1$ or L$^2$ is selected from non-cleavable linkers. In certain embodiments, noncleavable linkers are not cleaved by the gastrointestinal processes. Exemplary linkers of the disclosure include:

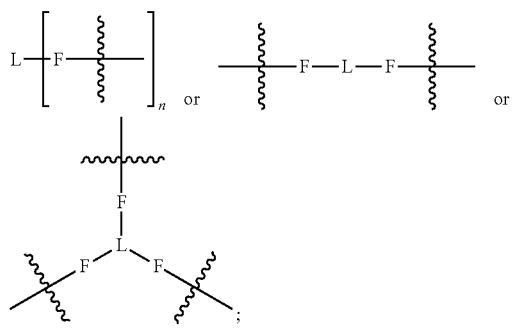

wherein:
each F is independently:

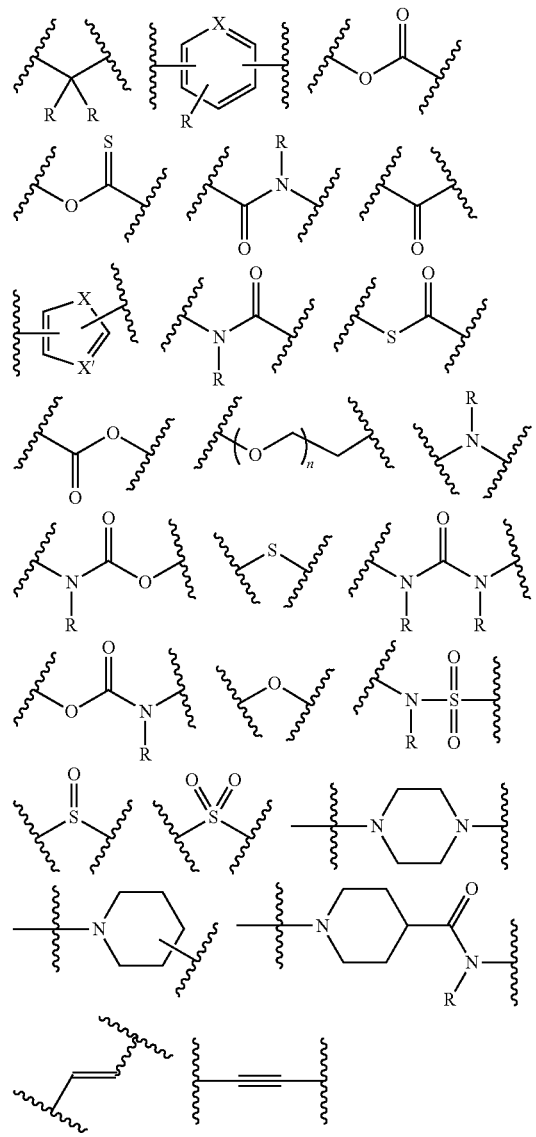

wherein:
each R is independently hydrogen, methyl, lower alkyl, aryl, or arylalkyl;
X can be carbon, oxygen, or nitrogen;
L can be linear, branched, or a multivalent scaffold comprised of alkyl, aryl, substituted alkyl, substituted aryl, heteroalkyl, substituted heteroalkyl, polyalkylene glycol, polypeptide, polyamide, polycarbamate, polyurea, polycarbonate, or a combination thereof.

Preparation of Compounds of the Invention

Compounds of the invention can be synthesized using techniques and materials known to those of skill in the art, such as described, for example, in Smith and March, MARCH'S ADVANCED ORGANIC CHEMISTRY: Reactions, Mechanisms, and Structure, Fifth Edition, (Wiley-Interscience, 2001), Vogel, A TEXTBOOK OF PRACTICAL ORGANIC CHEMISTRY, Including Qualitative Organic Analysis, Fourth Edition, New York, (Longman, 1978), Carey and Sundberg, ADVANCED ORGANIC CHEMISTRY 3rd Ed., Vols. A and B (Plenum 1992), and Green and Wuts, PROTECTIVE GROUPS IN ORGANIC SYNTHESIS 2nd Ed. (Wiley 1991). Starting materials for the compounds of the invention can be obtained using standard techniques and commercially available precursor materials, such as those available from Aldrich Chemical Co. (Milwaukee, Wis.), Sigma Chemical Co. (St. Louis, Mo.), Lancaster Synthesis (Ward Hill, Mass.), Apin Chemicals, Ltd. (New Brunswick, N.J.), Ryan Scientific (Columbia, S.C.), Maybridge (Cornwall, England) and Trans World Chemicals (Rockville, Md.).

The procedures described herein for synthesizing the compounds of the invention can include one or more steps of protection and deprotection (e.g., the formation and removal of suitable protecting groups). In addition, the synthetic procedures disclosed below can include various purifications, such as column chromatography, flash chromatography, thin-layer chromatography (TLC), recrystallization, distillation, high-pressure liquid chromatography (HPLC), dialysis, size-exclusion chromatography, and the like. Also, various techniques well known in the chemical arts for the identification and quantification of chemical reaction products, such as proton and carbon-13 nuclear magnetic resonance ($^1$H and $^{13}$C NMR), infrared and ultra-violet spectroscopy (IR and UV), X-ray crystallography, elemental analysis (EA), HPLC and mass spectroscopy (MS), and multi-angle light scattering (MALS) can be used as well. Methods of protection and deprotection, purification and identification and quantification are well known in the chemical arts.

In some embodiments, the synthetic methods use polymeric scaffolds having multiple repeating functional groups, where the functional groups can react with a complementary functional Z group on the $S_1$, $S_2$ or $S_3$ substrate subunits thereby providing a covalently-bonded unimolecular poly-substrate construct. The functional groups of the polymer scaffold can be, for example, a carboxylic acid, an ester, an aldehyde, an alcohol, an amine, an isocyanate, an epoxide, and the like.

Compounds of the invention can be collected and purified using methods known in the art. In general, compound of the invention as described herein can be purified by any of the means known in the art, including chromatographic means, such as high performance liquid chromatography (HPLC), preparative thin layer chromatography, flash column chromatography and ion exchange chromatography, size exclusion chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

Compound of the invention described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of compound of the invention including the stereoisomerically pure forms (e.g., geometrically pure, enantiomerically pure or diastereomerically pure) and enantiomeric or stereoisomeric mixtures are included in the description of compound of the invention described herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Representative synthetic routes useful for the preparation of exemplary compounds of the invention are depicted below in the following schemes.

Scheme A

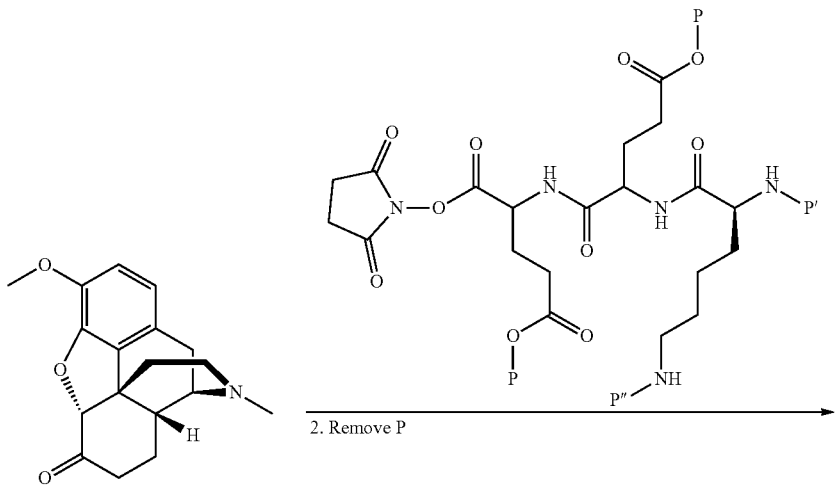

-continued
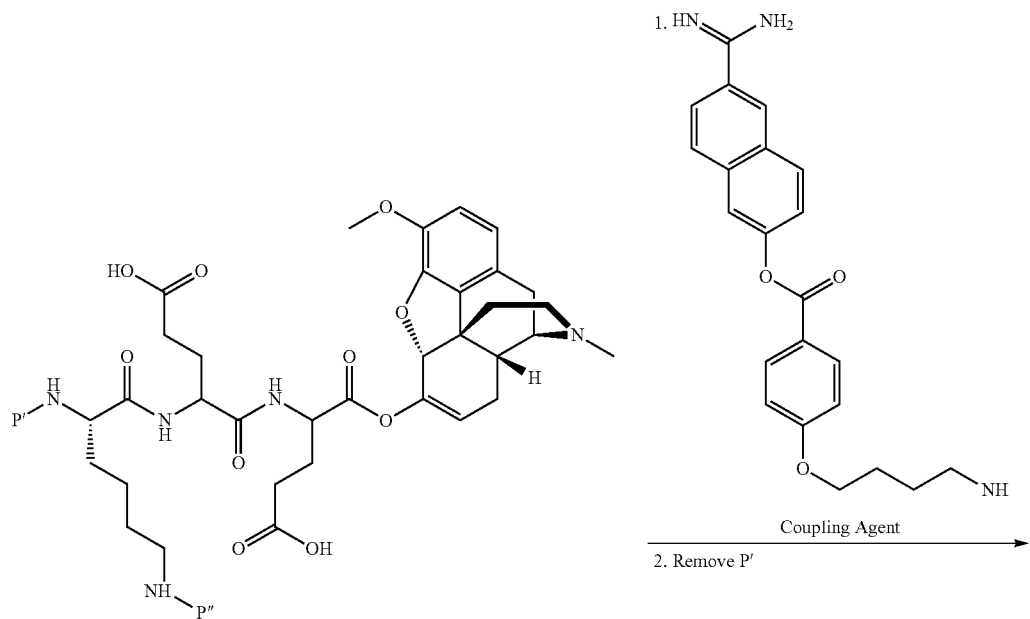
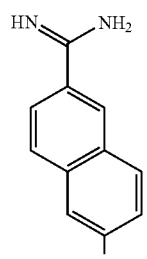
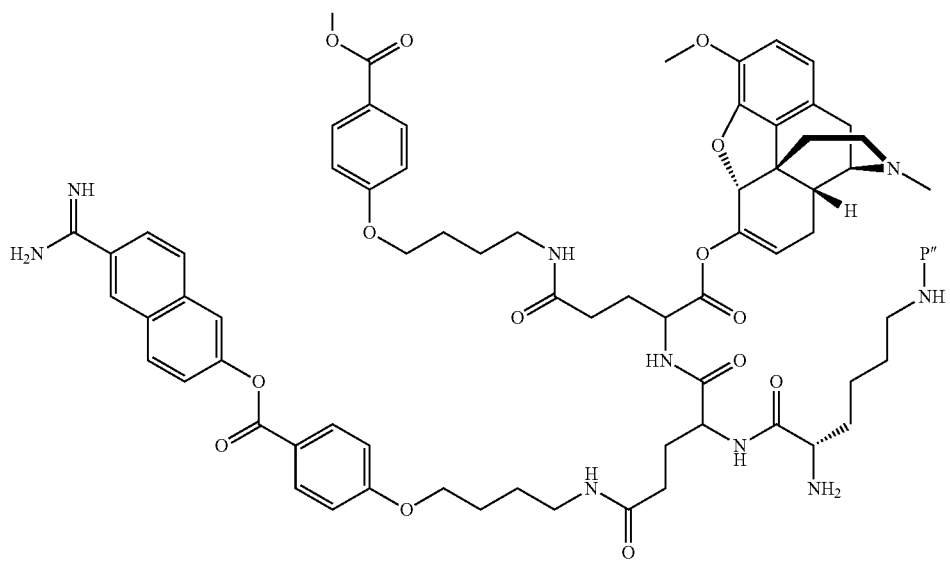
A

-continued
1. KHMDS
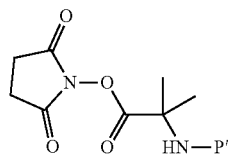
2. Remove P'
3.
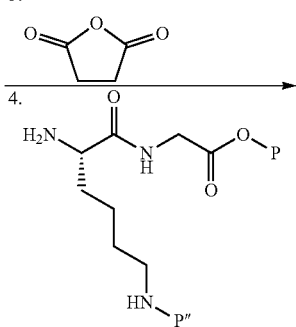
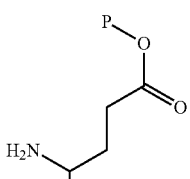
4.
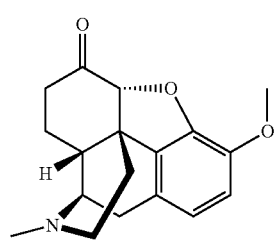
Coupling Agent
5. Remove P
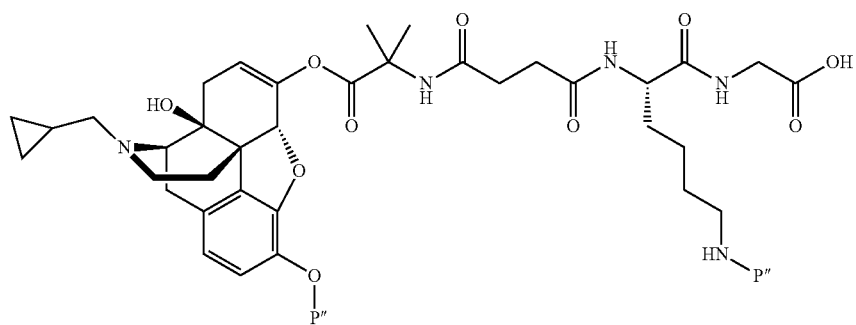
B
1. KHMDS
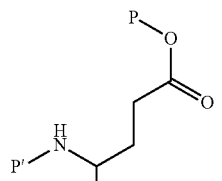
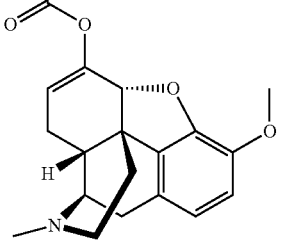
2. Remove P'
1. B
   Coupling Agent
2. Remove P
3. A
   Coupling Agent
4. Remove P''

233
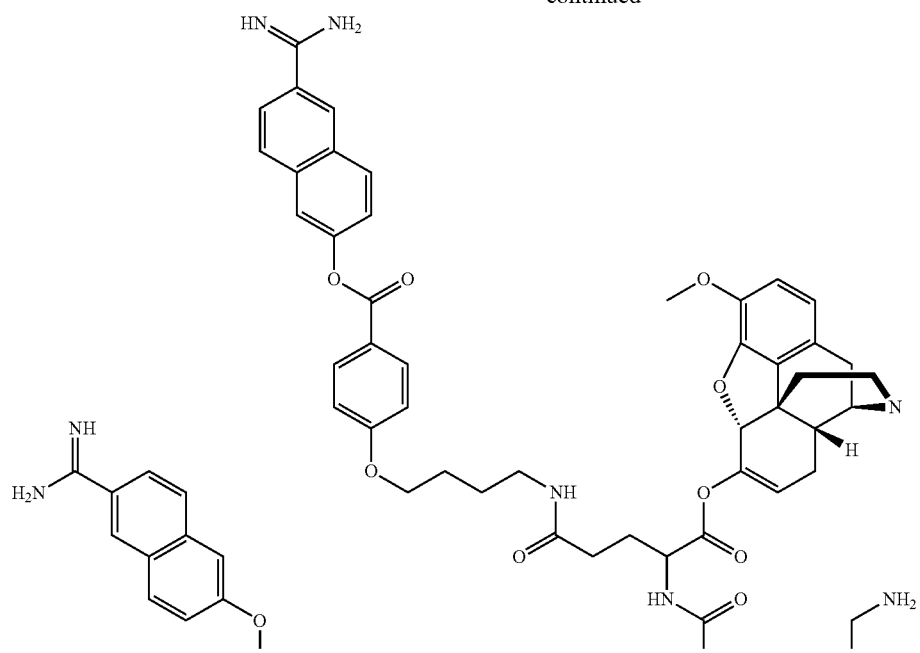
234
-continued
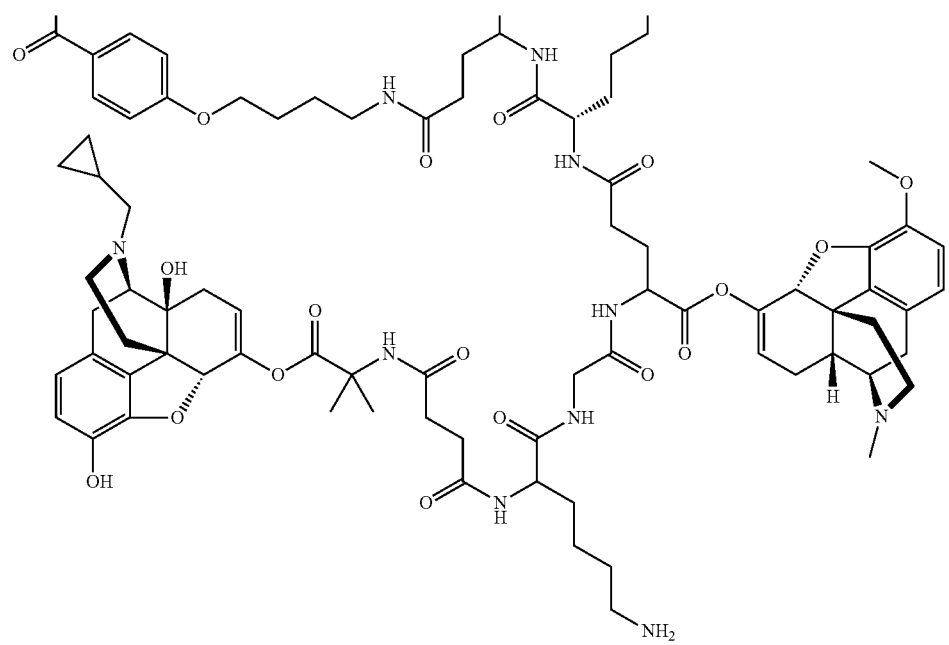

Scheme B
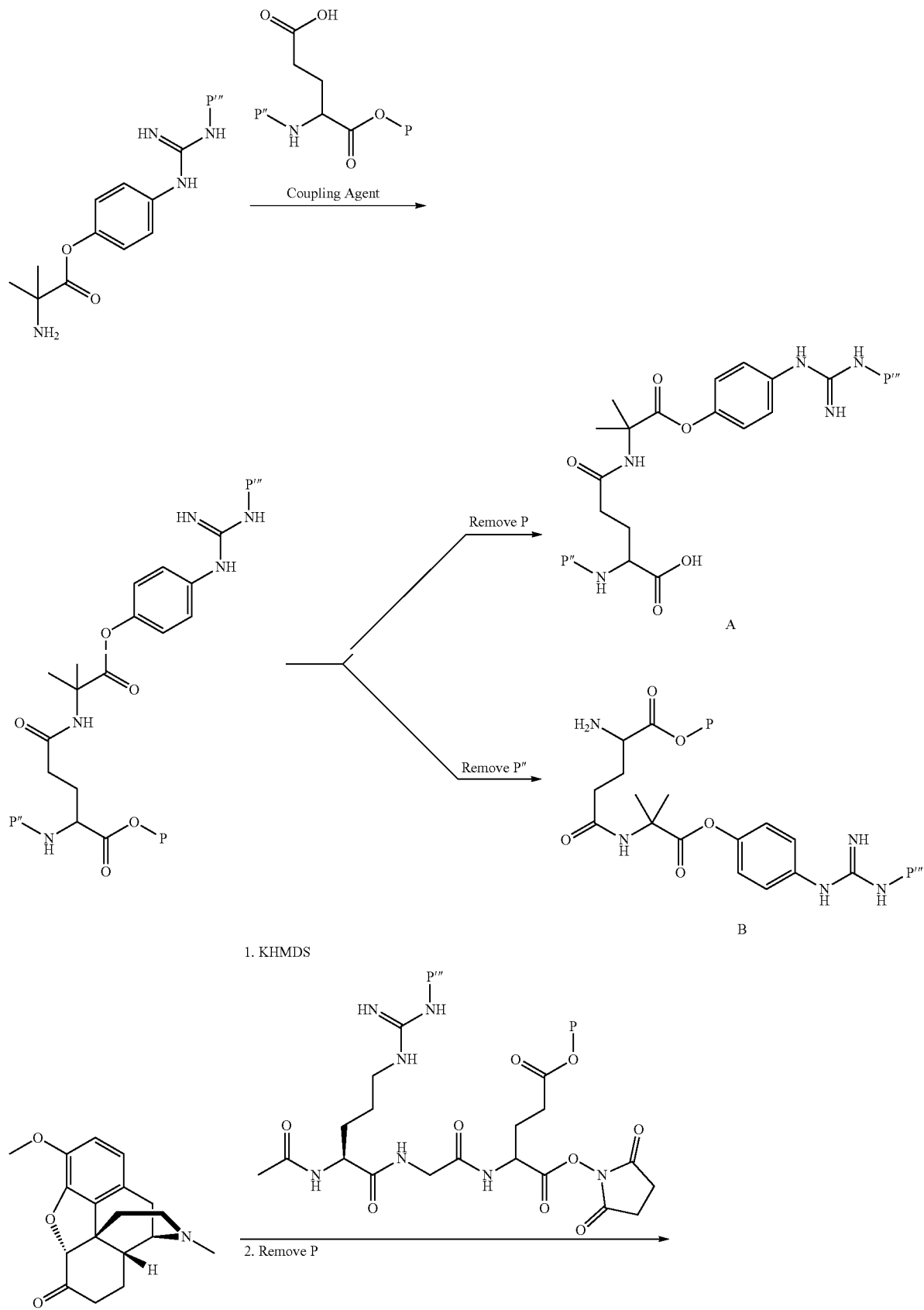

-continued
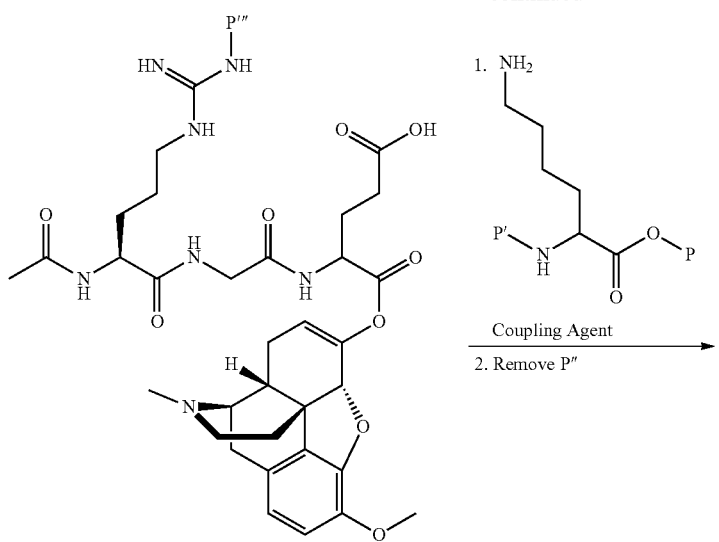
Coupling Agent
2. Remove P″
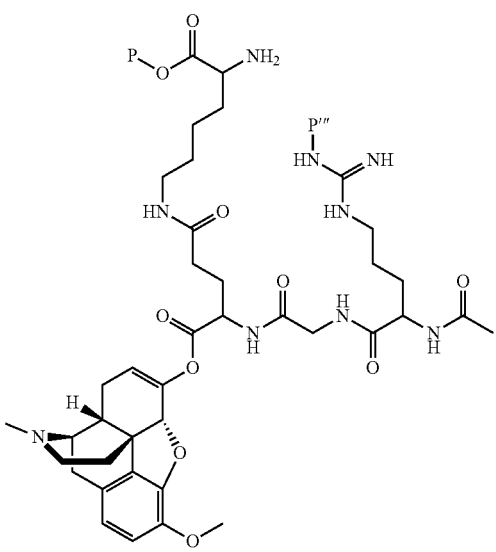
C
1. KHMDS
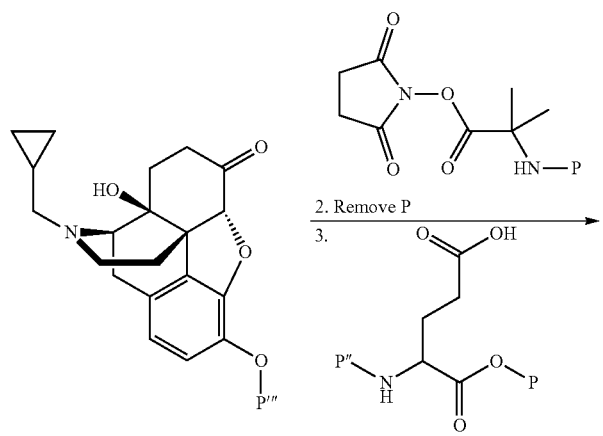
2. Remove P
3.
Coupling Agent
4. Remove P″

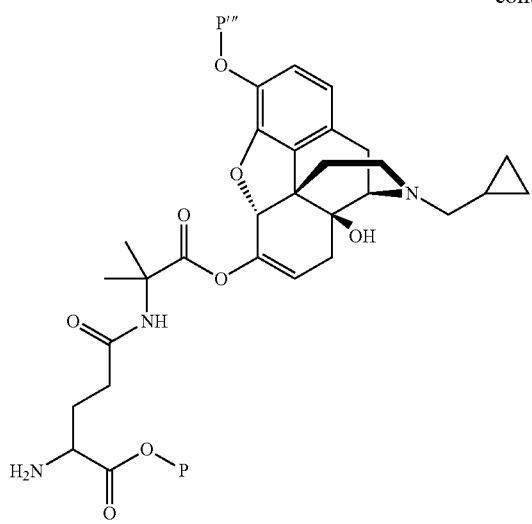
D
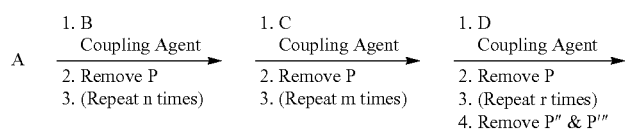
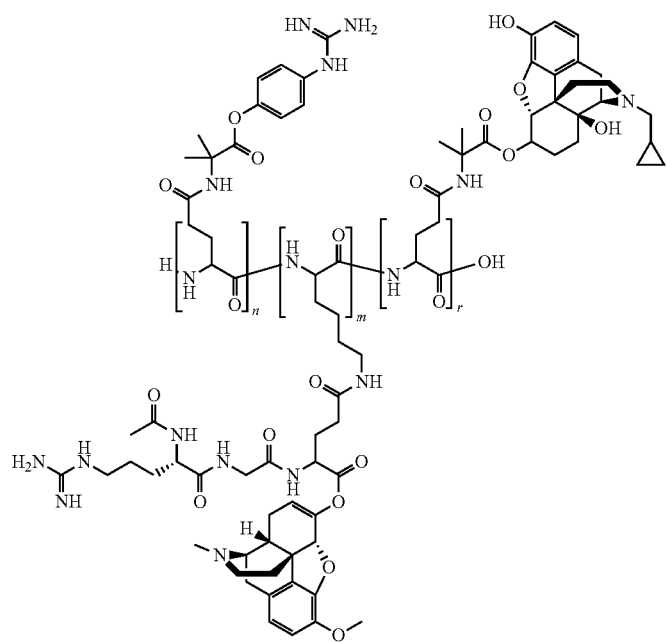

Scheme C
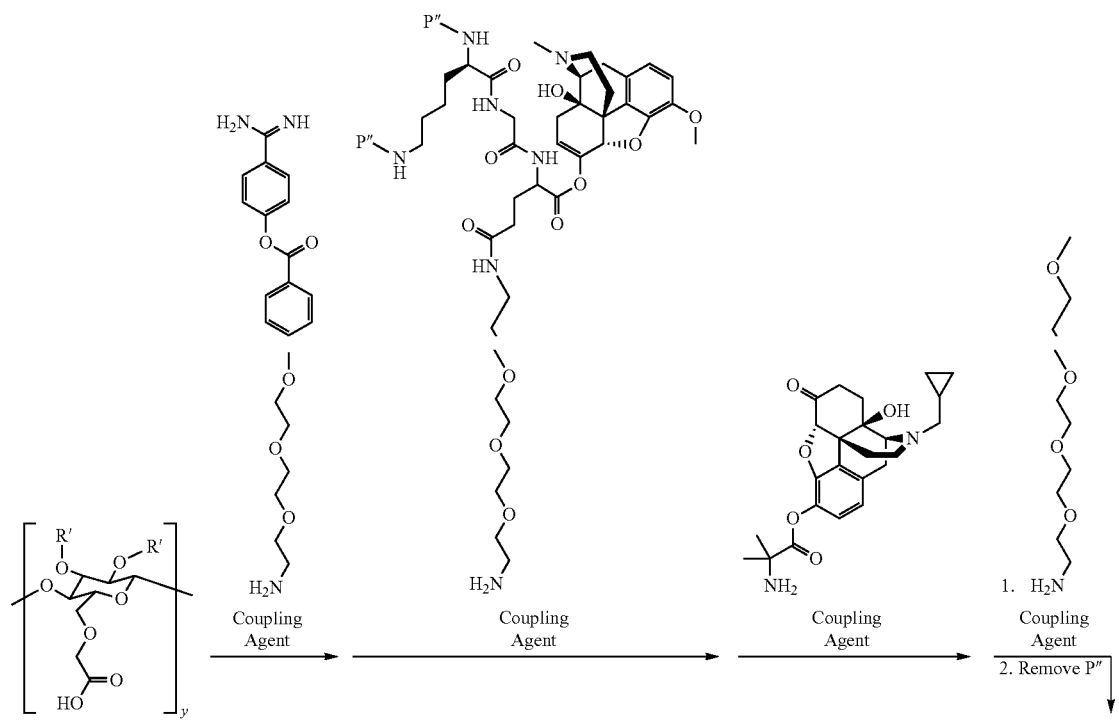
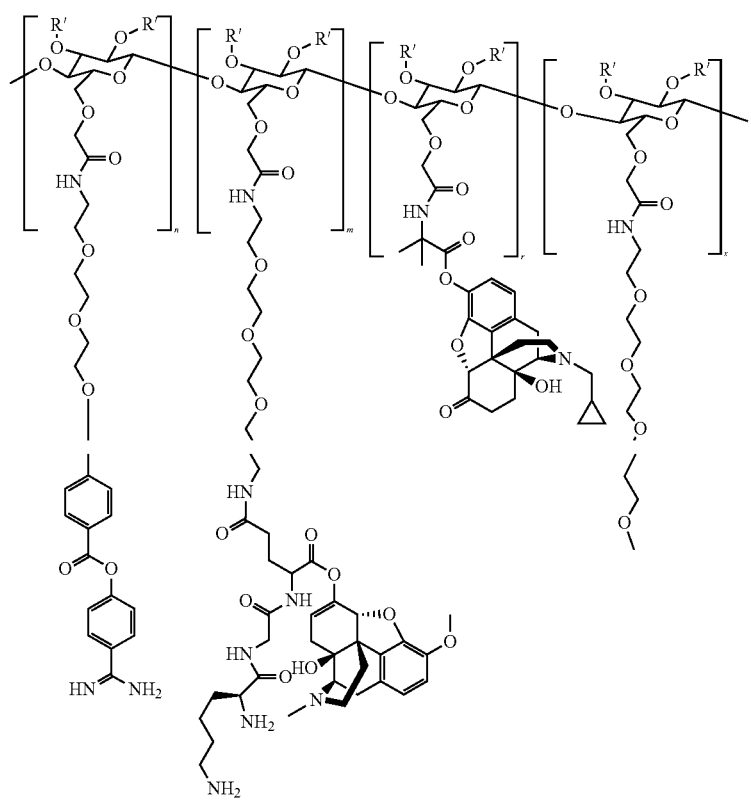

Scheme D
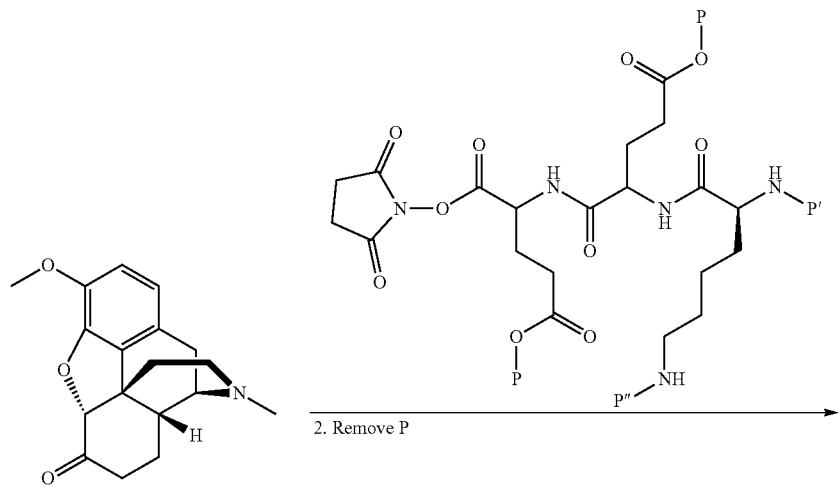
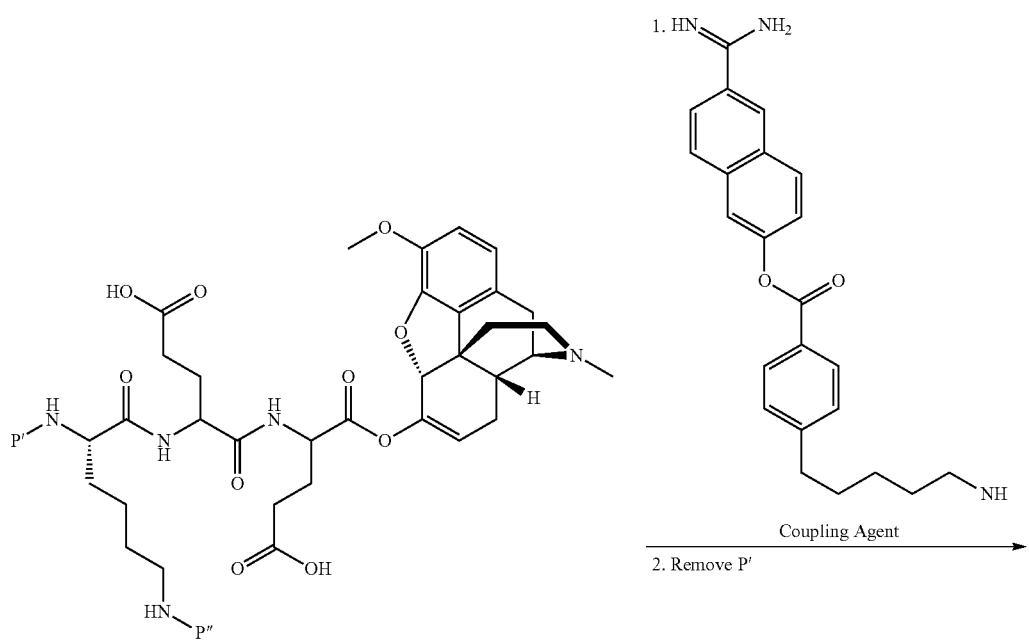
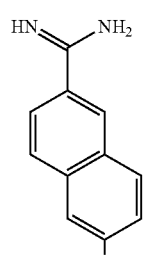

-continued
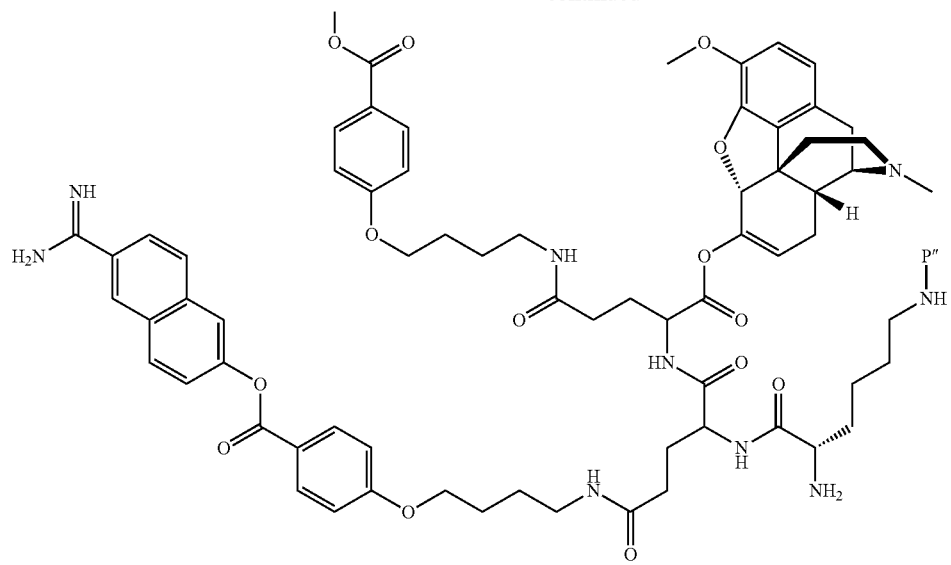
A
1. KHMDS
2. 
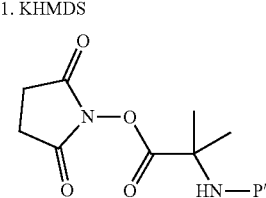
2. Remove P'
3. 
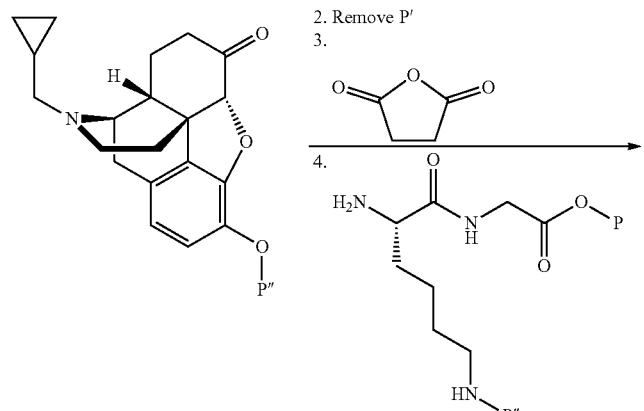
Coupling Agent
5. Remove P
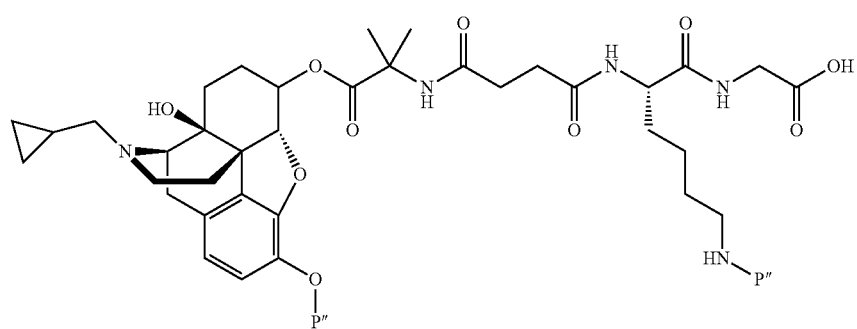
B -continued
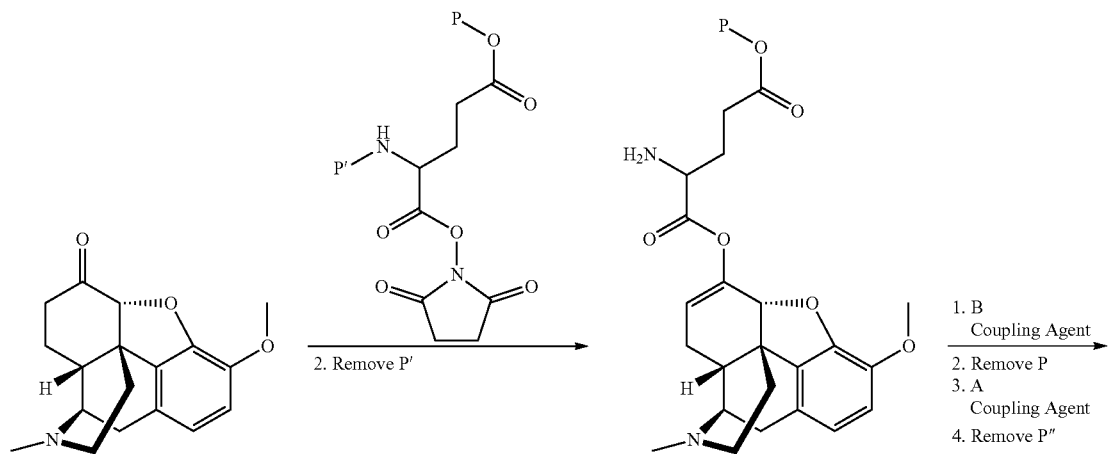
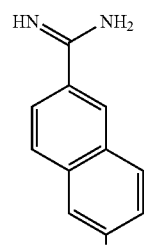
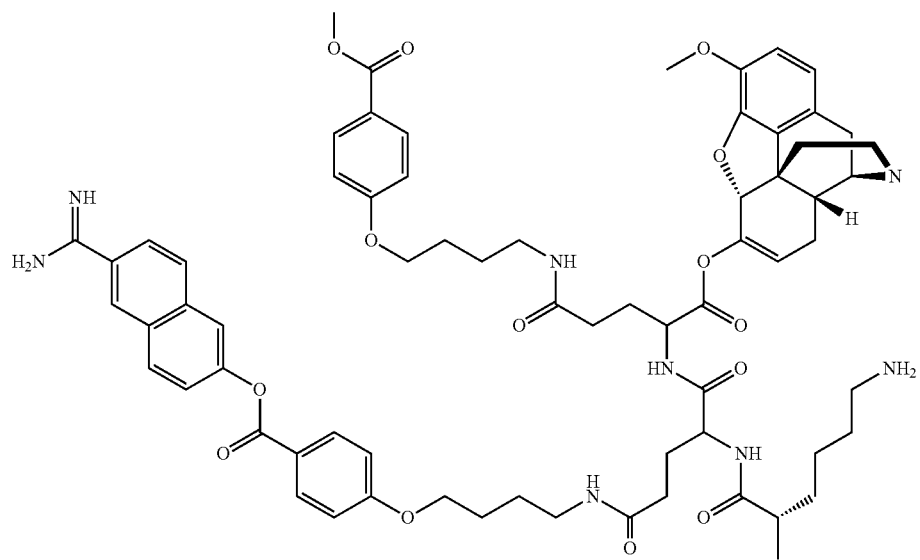

249
250
-continued
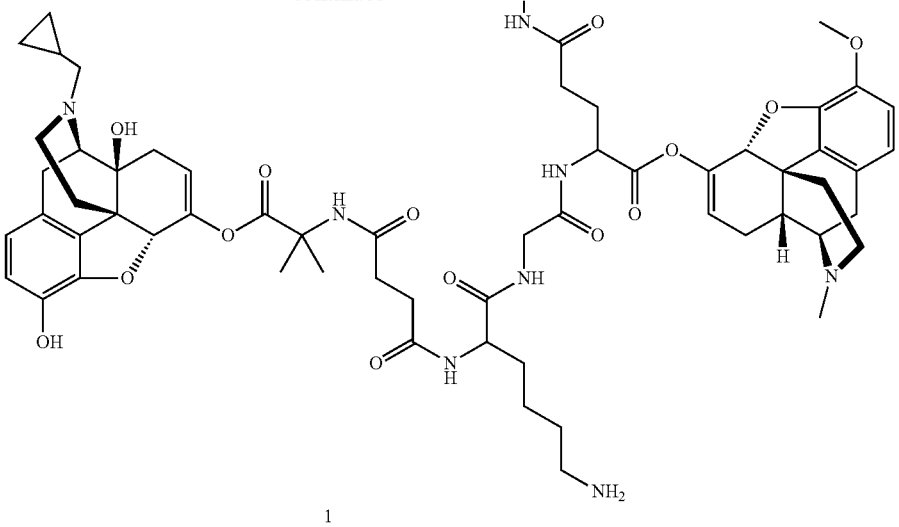
1
Scheme E
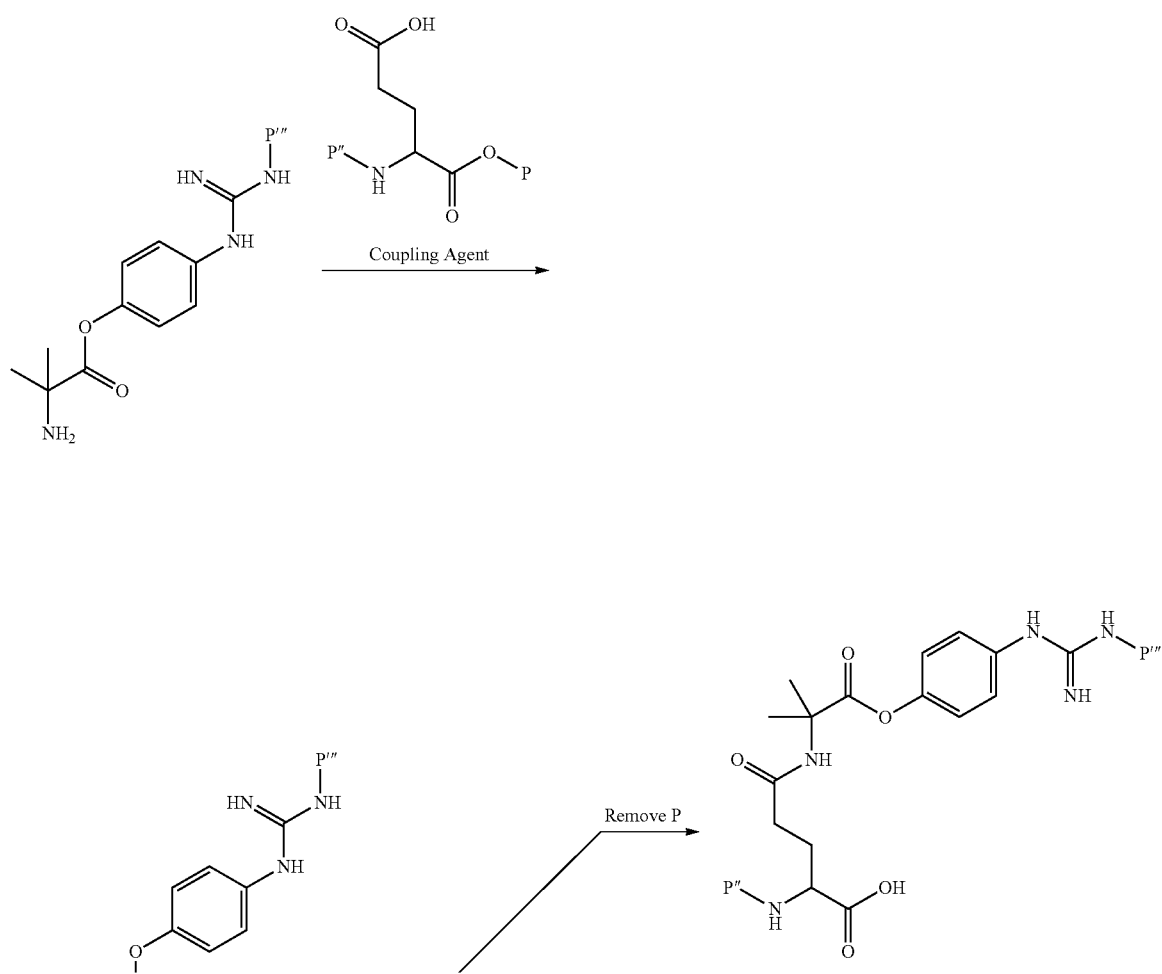

-continued
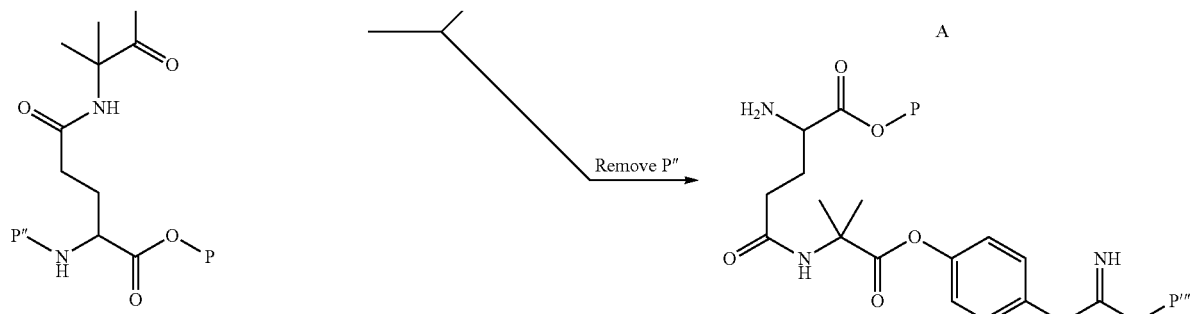
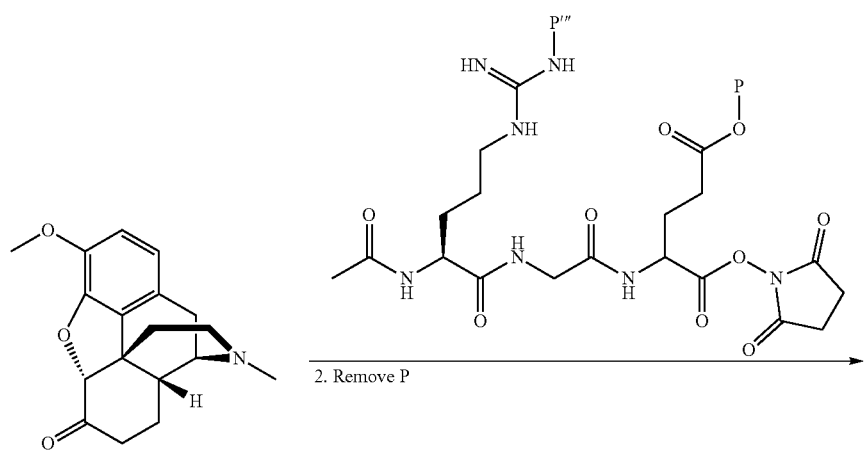
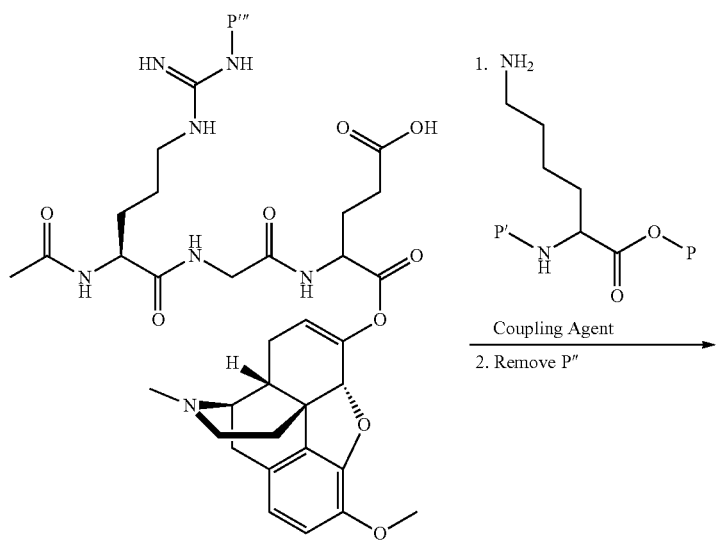

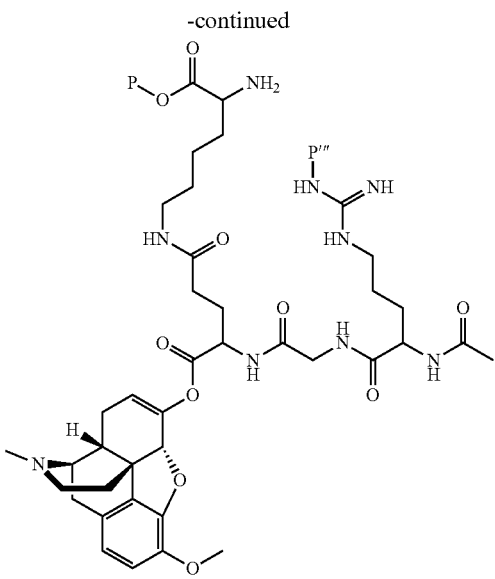
C
1. KHMDS
2. Remove P
3. 
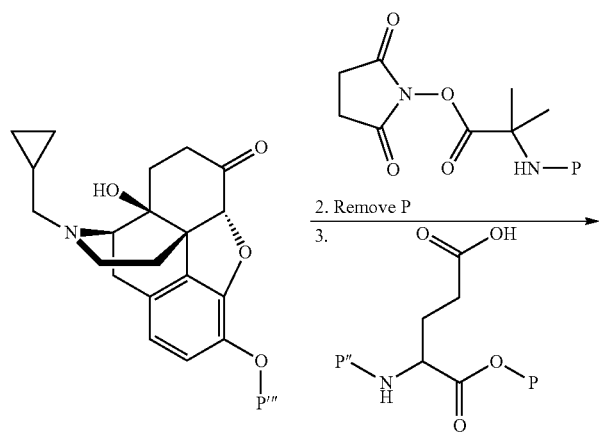
Coupling Agent
4. Remove P''
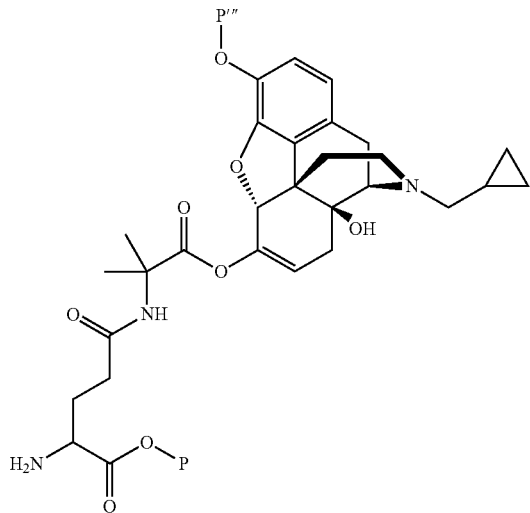
D

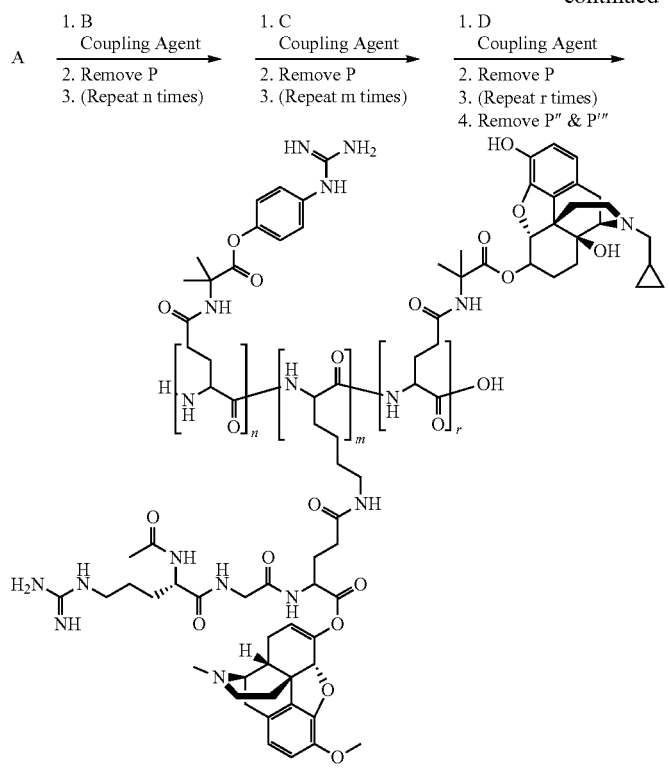
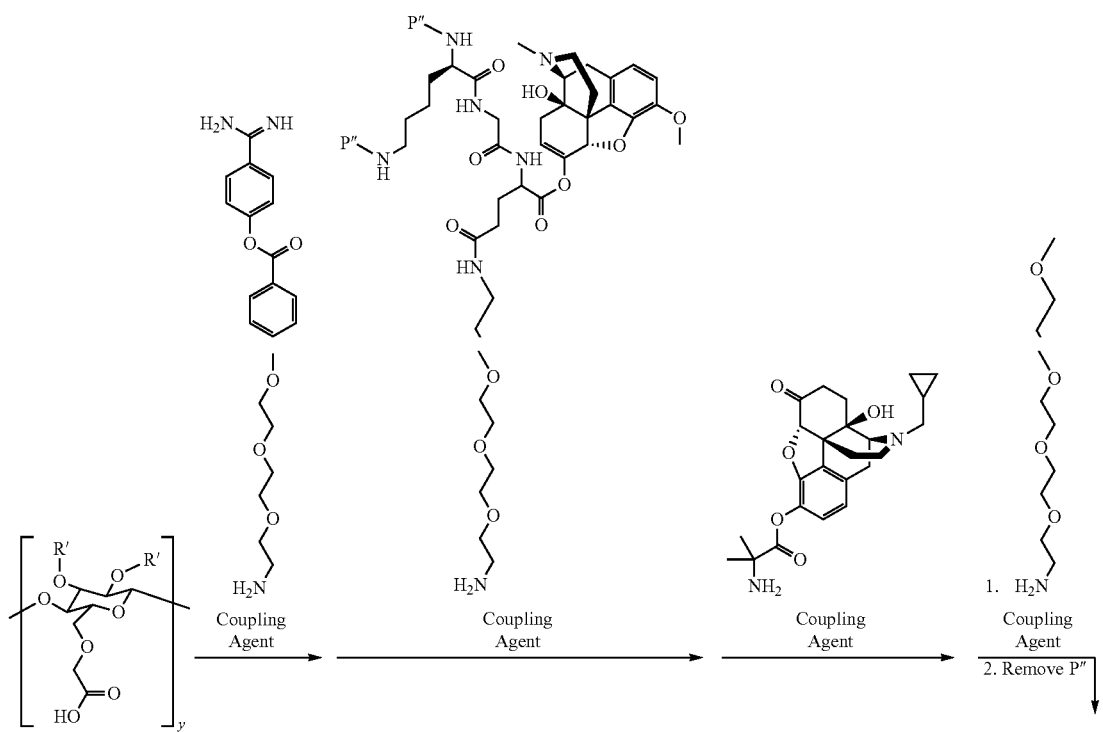
Scheme F

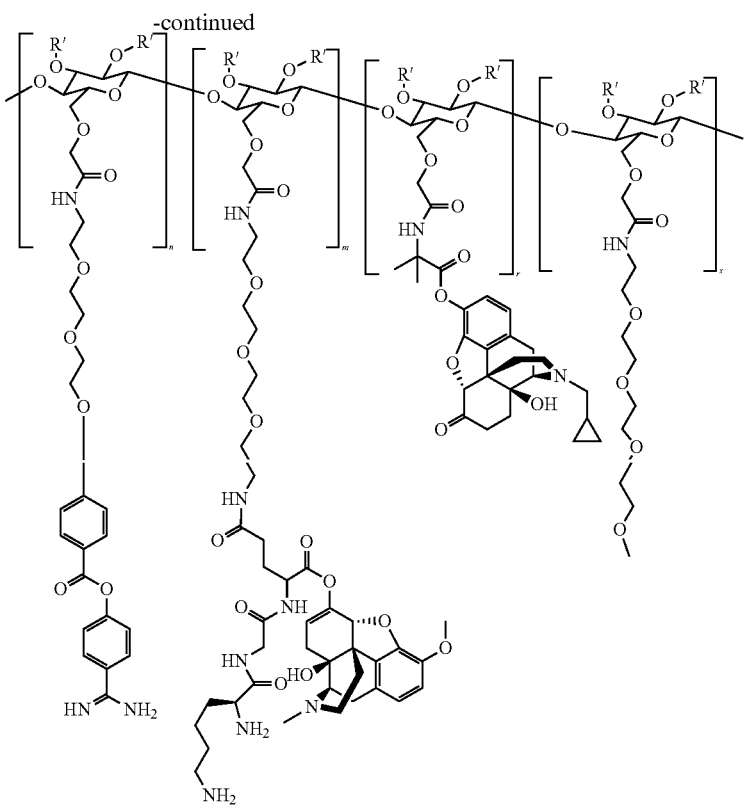
Specific synthetic routes used for the preparation of exemplary compounds of the invention are depicted below in the following schemes.

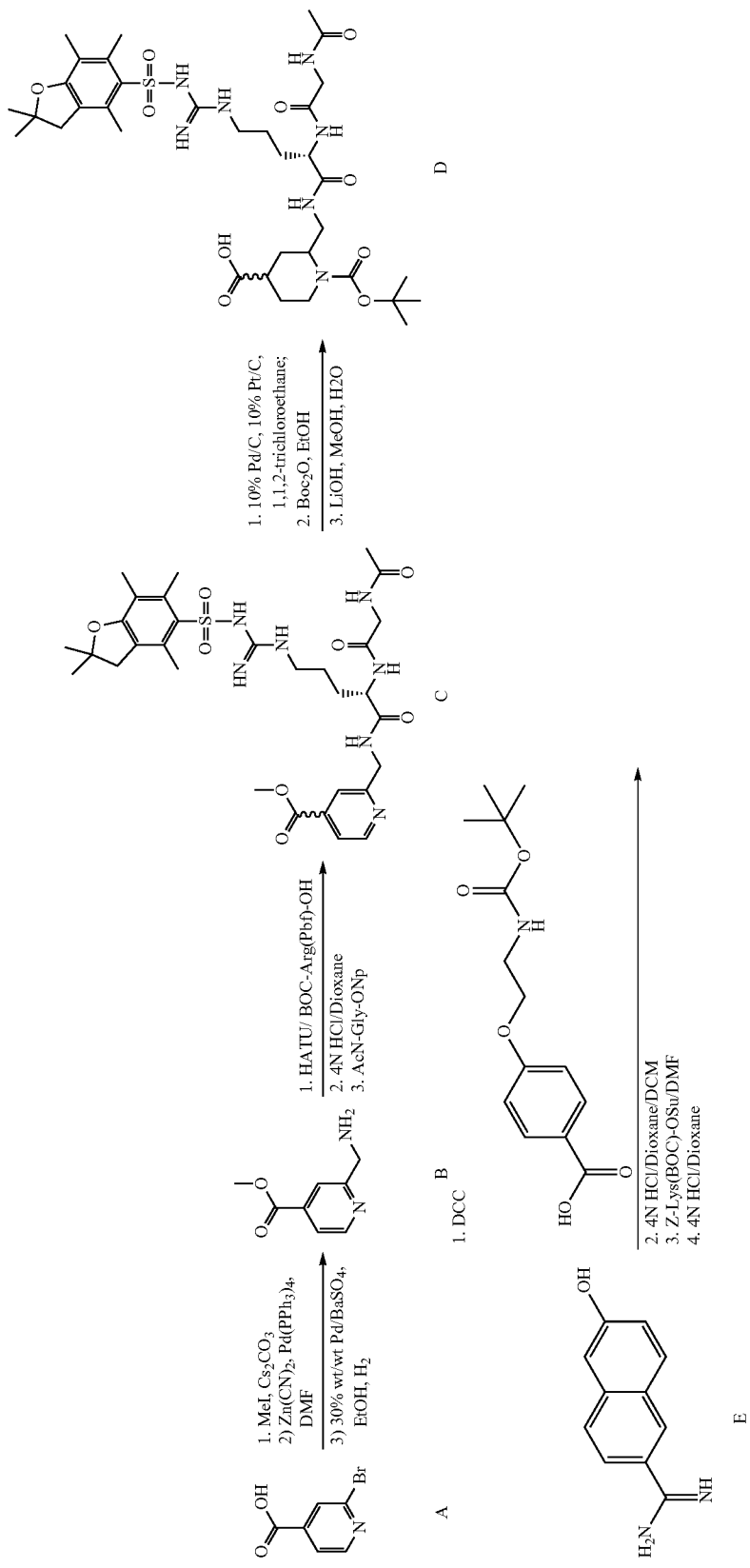

-continued
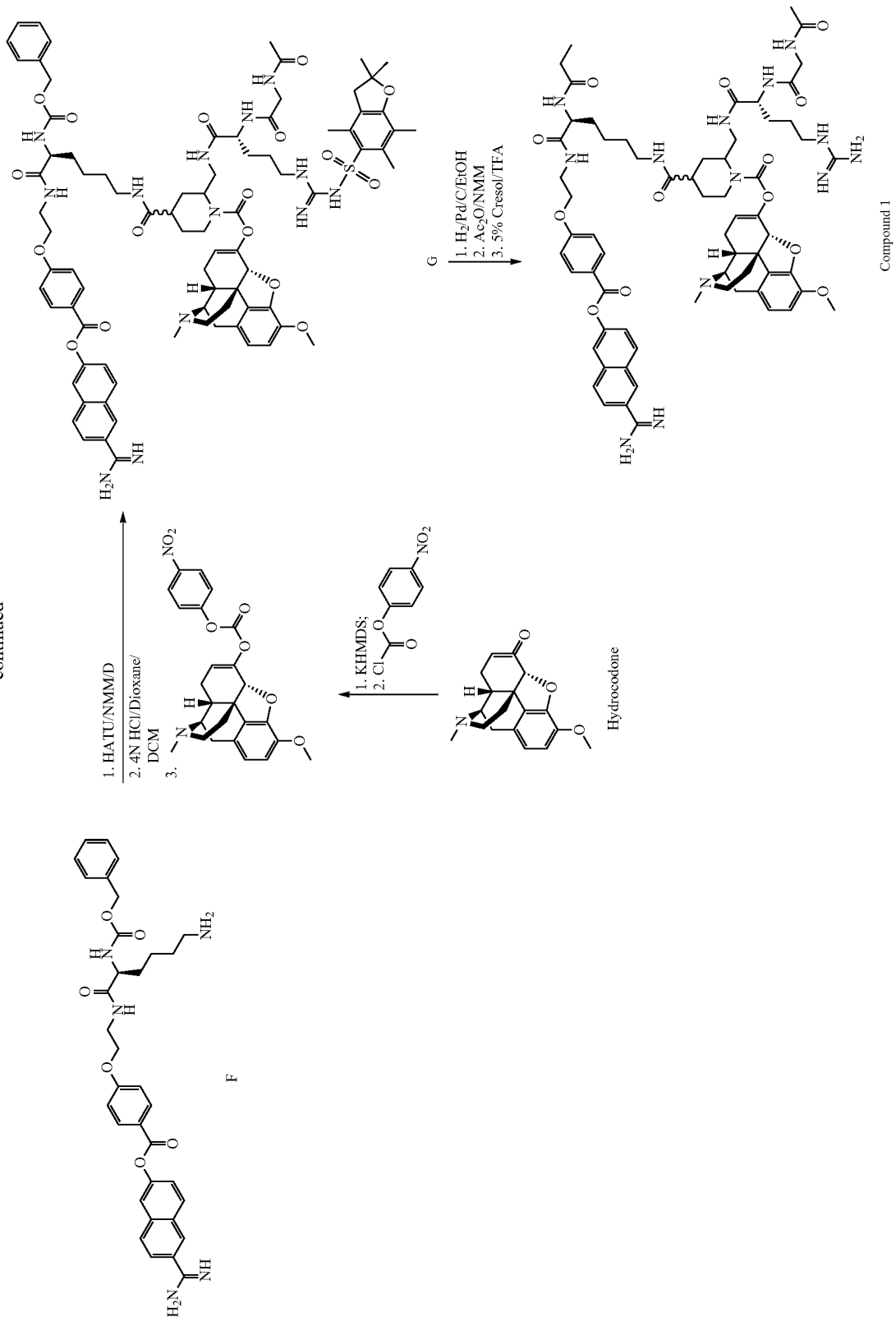

Preparation of Compound B

2-Bromo isonicotinic acid (20.2 g, 100 mmol) was dissolved in DMF (500 mL) at ambient temperature. $Cs_2CO_3$ (32.6 g, 100 mmol) was added in one portion, followed by MeI (6.3 mL, 100 mmol). The mixture was stirred at ambient temperature for 15 h, followed by the addition of water (500 mL). The mixture was extracted with EtOAc (500 mL). The organic layer was washed with water (500 mL), brine (500 mL) and then dried over $Na_2SO_4$. The organic layer was then filtered and concentrated to give a white solid (18.3 g, 84.7 mmol). LC-MS: [M+H] 217.1 ($C_6H_6BrNO_2$+H, calc: 216.1). The crude product was used directly without further purification.

The crude product of the previous reaction was dissolved in DMF (100 mL), followed by the addition of $Zn(CN)_2$ (3.42 g, 29.11 mmol) in one portion. The mixture was degassed using nitrogen and then $Pd(PPh_3)_4$ (2.82 g) was added. The mixture was degassed again and then heated in an oil bath (120° C.). After 2.5 h, the reaction was cooled to ambient temperature and water (120 mL) was added. The mixture was stirred for 30 min and then filtered through a frit. The solid collected was washed with water (2×60 mL) and then dried under vacuum to give an off-white solid (5.2 g, 32.6 mmol). LC-MS: [M+H] 163.3 ($C_8H_6N_2O_2$+H, calc: 163.1). The crude product was used directly without further purification.

The crude product of the previous reaction (8.0 g, 49.36 mmol) was dissolved in EtOH (200 mL). Pd/5% on barium sulfate (2.4 g) and 4N HCl (in 1,4-Dioxane; 20 mL) was added to the reaction mixture. The mixture was hydrogenated at 55 psi for 4 h on a Parr hydrogenator. The mixture was then filtered through a celite pad and then the celite pad was washed with MeOH (3×50 mL). The combined filtrate was then concentrated and the residue was partitioned between EtOAc (120 mL) and water (50 mL). The organic layer was washed with 10% citric acid (20 mL) and brine (20 mL), followed by drying over $Na_2SO_4$. Next the mixture was filtered and concentrated to afford compound B in 86% yield (10.5 g, 40.2 mmol). LC-MS: [M+H] 266.7 ($C_{13}H_{18}N_2O_4$+H, calc: 266.1). Compound B was used directly without further purification.

Preparation of Compound C

To a solution of Boc-Arg(Pbf)-OH (6.31 g, 12.0 mmol), Compound B (2.30 g, 11.4 mmol) and HATU (4.43 g, 12.56 mmol) in DMF (120 mL) at 5° C. was added DIPEA (8.0 mL, 45.66 mmol) dropwise over 5 min. The temperature of the reaction mixture was raised to ambient temperature and stirring was continued for an additional hour. Upon reaction completion, DMF was removed under vacuum and the reaction mixture was then diluted DCM. The organic layer was washed with 1N HCl, saturated $NaHCO_3$, brine and then dried over $MgSO_4$. The organic layer was then filtered and condensed to afford an off-white solid. (7.18 g, 10.6 mmol) LC-MS: [M+H] 675.9 ($C_{32}H_{46}N_6O_8S$+H, calc: 675.41). The crude product was used directly without further purification.

The crude product of the previous reaction (7.0 g, 10.36 mmol) was dissolved in DCM (50 mL) was treated with 4 M solution of hydrogen chloride in 1,4-dioxane (50 mL). After 1 h, solvent was removed under vacuum until about ~50 mL remained. Diethyl ether (~500 mL) was added to the reaction mixture, which produced a fine white precipitate. The precipitate was filtered off, washed with ether (3×150 mL) and dried under vacuum to give a fine white solid. (6.42 g, 9.9 mmol) LC-MS: [M+H] 575.7 ($C_{27}H_{38}N_6O_6S$+H, calc: 575.26). The crude product was used directly without further purification.

The crude product of the previous reaction (6.2 g, 9.6 mmol) was dissolved in DMF and to the solution was added SuO-Gly-NAc (2.05 g, 9.6 mmol) at 5° C. was added DIPEA (5.2 mL, 30 mmol) dropwise over 5 min. The temperature of the reaction mixture was raised to ambient temperature and stirring was continued for an additional hour. Upon reaction completion, DMF was removed in high vacuum, and the reaction mixture was diluted with DCM (200 mL), washed with 1 N HCl (300 mL), then with sat $NaHCO_3$ (300 mL) and brine (500 mL). The organic phase was dried over $Na_2SO_4$, filtered and the solvent was evaporated. The oily product was dried under high vacuum overnight to afford compound C in 92.1% yield (5.93 g, 8.8 mmol) as a yellow oil. LC-MS: [M+H] 674.7 ($C_{31}H_{43}N_7O_8S$+H, calc: 674.29).

Preparation of Compound D

To a solution of compound C (4.40 g, 6.53 mmol) in MeOH (50 mL) was added, under nitrogen, 10% Pd/C (250 mg), 10% Pt/C (200 mg) and 1,1,2-trichloroethane (729 mL, 7.8 mmol, 1.2 eq). The reaction mixture was stirred at 65 psi overnight. Upon completion, the reaction mixture was filtered through a Celite-padded glass frit and washed with MeOH (3×20 mL). The filtrate was concentrated under vacuum to the volume ~10 mL and diethyl ether (300 mL) was added. The resulting fine white precipitate was filtered, washed with ether (2×100 mL) and dried under high vacuum. This afforded an off-white solid (3.78 g, 81%). LC-MS: [M+H] 680.6 ($C_{31}H_{49}N_7O_8S$+H, calc: 680.3). The crude product was used directly without further purification.

The crude product of the previous reaction (3.5 g, 4.89 mmol) was dissolved in ethanol (100 mL) followed by the addition of a $Boc_2O$ (1.07 g, 4.89). The reaction mixture was stirred at ambient temperature for 1 h. Next, the reaction mixture evaporated under vacuum to provide a thick light yellow oil (3.8 g, 4.86 mmol, 99%). LC-MS [M+H] 780.7 ($C_{36}H_{57}N_7O_{10}S$+H, calc: 780.4). The crude product was used directly without further purification.

The crude product of the previous reaction (3.8 g, 4.86 mmol) in methanol (75 mL) at 5° C. was added aqueous solution of LiOH (0.29 g, 12 mmol) in water (20 mL). The temperature of the reaction mixture was raised to ambient temperature and stirring was continued for an additional 4 h. Upon the reaction completion, the reaction mixture was neutralized with 1N HCl to pH ~7.0. Next, the methanol was evaporated under vacuum to afford an oily liquid, which was dried under high vacuum to give compound D in 79.9% yield (2.98 g, 3.88 mmol). LC-MS, [M+H] 766.8 ($C_{35}H_{55}N_7O_{10}S$+H, calc: 766.4).

Preparation of Compound F

A solution of compound E (Mesylate salt, 10.0 g, 35.5 mmol), 4-(2-((tert-butoxycarbonyl)amine)ethoxy) benzoic acid (10.0 g, 35.5 mmol) and DCC (11.0 g, 53.3 mmol) in pyridine (100 mL) was stirred overnight. Solvent was evaporated in vacuo. The residue was then dissolved in 4N hydrogen chloride in 1,4-dioxane (100 mL). After 1 h, solvent was removed under vacuum until about ~50 mL remained. Diethyl ether (~500 mL) was added to the reaction mixture, which produced an off-white/light tan precipitate. The precipitate was filtered off, washed with ether (3×150 mL) and dried under vacuum to give an off-white solid. The crude product triturated in acetone, followed by trituration in MTBE, filtered and dried to afford an off-white/light tan precipitate (11.1 g, 74%). LC-MS, [M+H] 350.4 ($C_{20}H_{19}N_3O_3$+H, calc: 350.1). The crude product was used without additional purification.

The crude product of the previous reaction (10.0 g, 24.2 mmol) was dissolved in DMF and to the solution was added SuO-Lys(Boc)-NCBZ (11.6 g, 24.2 mmol) at 5° C. was added DIPEA (17.4 mL, 100 mmol) dropwise over 5 min. The temperature of the reaction mixture was raised to ambient temperature and stirring was continued for an additional hour. Upon reaction completion, DMF was removed under high vacuum, and the reaction mixture was diluted with DCM (300 mL), washed with 1N HCl (500 mL), then with sat. NaHCO$_3$ (500 mL) and brine (750 mL). The organic phase was dried over MgSO$_4$, filtered and the solvent was evaporated. The oily product was dissolved in 4N hydrogen chloride in 1,4-dioxane (50 mL). After 1 h, solvent was removed under vacuum until about ~10 mL remained. Diethyl ether (~500 mL) was added to the reaction mixture, which produced an off-white/light tan precipitate. The precipitate was filtered off, washed with ether (3×150 mL) and dried under vacuum to give compound F (15.04 g, 91%). LC-MS, [M+H] 611.7 ($C_{34}H_{37}N_5O_6$+H, calc: 611.3). The crude product was used without additional purification.

Preparation of Compound G

To a solution of Compound F (1.96 g, 2.86 mmol), Compound D (2.19 g, 2.86 mmol) and HATU (1.30 g, 3.43 mmol) in DMF (200 mL) at −20° C. was added NMM (0.94 mL, 9 mmol) dropwise over 5 min. The temperature of the reaction mixture was raised to ambient temperature and stirring was continued for an additional hour. Upon reaction completion, DMF was removed under vacuum and the reaction mixture was then diluted DCM. The organic layer was washed with 1N HCl, saturated NaHCO$_3$, brine and then dried over MgSO4. The organic layer was then filtered and condensed to afford an off-white solid. (4.11 g) LC-MS: [M+H] 1360.0 ($C_{69}H_{90}N_{12}O_{15}S$+H, calc: 1359.6). The crude product was dissolved in 4N hydrogen chloride in 1,4-dioxane (50 mL). After 1 h, solvent was removed under vacuum until about ~10 mL remained. Diethyl ether (~500 mL) was added to the reaction mixture, which produced an off-white/light tan precipitate. The precipitate was filtered off, washed with ether (3×150 mL) and dried under vacuum to give a solid (Compound F') (3.12 g, 82%). LC-MS, [M+H] 1259.9 ($C_{64}H_{82}N_{12}O_{13}S$+H, calc: 1259.6). The crude product (Compound F') was used directly without further purification.

Preparation of Activated Hydrocodone

A solution of hydrocodone-free base (7.6 g, 25.36 mmol) in THF (200 mL) was cooled to −78° C. and then 0.5 M toluene solution of KHMDS (50.7 mL, 25.36 mmol) was added dropwise over 5 min under nitrogen. The reaction mixture was stirred for 30 min, and then added to a solution of 4-nitrophenyl chloroformate (5.1 g, 25.4 mmol) in THF (100 mL) dropwise over 5 min under nitrogen and cooling with dry ice/acetone. Upon completion, 2 M HCl in diethyl ether (100 mL) and ether (400 mL) was added dropwise to the reaction mixture to produce a fine white precipitate. The precipitate was filtered on a glass frit and washed with ether (3×200 mL). The solid was dried under high vacuum overnight, then dissolved in 5% aq KH$_2$PO$_4$ solution (800 mL) and extracted with DCM (2×200 mL). The organic phase was dried over Na$_2$SO$_4$ (anh.), filtered, and the solvent was concentrated under vacuum to the volume ~10 mL. To the mixture was added 2 M solution of HCl in diethyl ether (80 mL) and ether (400 mL). The resulting fine white precipitate was filtered off, washed with ether (2×200 mL) and dried under high vacuum to afford Activated Hydrocodone in 67% yield (8.4 g, 16.8 mmol). LC-MS [M+H]: 465.3 ($C_{25}H_{24}N_2O_7$+H, calc: 464.2).

Compound F' (2.0 g, 1.5 mmol) and Activated Hydrocodone (750 mg, 1.5 mmol) were dissolved in DMF (40 mL) and DIPEA (0.780 mL, 4.5 mmol) was added. The reaction mixture was stirred at 40° C. overnight. Upon reaction completion, the DMF was evaporated and the resulting oily product was dissolved in DCM (700 mL). The mixture was then washed with 5% sodium phosphate (2×100 mL), 0.1 N aq. HCl (100 mL) and brine (150 mL). The organic phase was dried over Na$_2$SO$_4$, filtered and the solvent was evaporated. The oily product was dried in high vacuum overnight to afford crude compound G in 88.7% yield. (2.15 g, 1.33 mmol) LC-MS: [M+H] 1585.1 ($C_{83}H_{101}N_{13}O_{17}S$+H, calc: 1584.7). The crude reaction mixture was then purified by preparative HPLC to afford the desired product (compound G) in 61% yield (1.51 g, 0.91 mmol).

Preparation of Compound 1

To a solution of compound G (1.50 g, 0.91 mmol) in MeOH (25 mL) was added, under nitrogen, 10% Pd/C (150 mg), 4N hydrogen chloride (in 1,4-Dioxane, 2 mL). The reaction mixture was stirred at 40 psi for 3 h. Upon completion, the reaction mixture was filtered through a Celite-padded glass frit and washed with MeOH (3×20 mL). The filtrate was concentrated under vacuum to the volume ~10 mL and diethyl ether (200 mL) was added. The resulting fine white precipitate was filtered, washed with ether (2×50 mL) and the resulting solution was evaporated under vacuum and dried under high vacuum overnight to afford a light yellow solid (1.39 g). LC-MS: [M+H]1451.1 ($C_{75}H_{95}N_{13}O_{15}S$+H, calc: 1450.7). The crude solid was dissolved in DCM (30 mL) and to the mixture was added NMM (1.0 mL, 5.5 mmol), followed by acetic anhydride (0.18 mL, 0.91 mmol). The reaction was allowed to stir for 1 h at ambient temperature. Next, the reaction was condensed and to the crude reaction mixture was added 5% Cresol in TFA (15 ml). The reaction was allowed to stir at room temperature for 4 h. Upon completion, the reaction mixture was condensed, taken up in 20% ACN/H2O (20 mL) and purified via preparative HPLC to afford compound 1 (890 mg, 0.63 mmol, 69.7% yield over 3 steps) as a white solid. LC-MS: [M+H] 1331.9 ($C_{32}H_{43}N_3O_8$+H, calc: 1331.6).

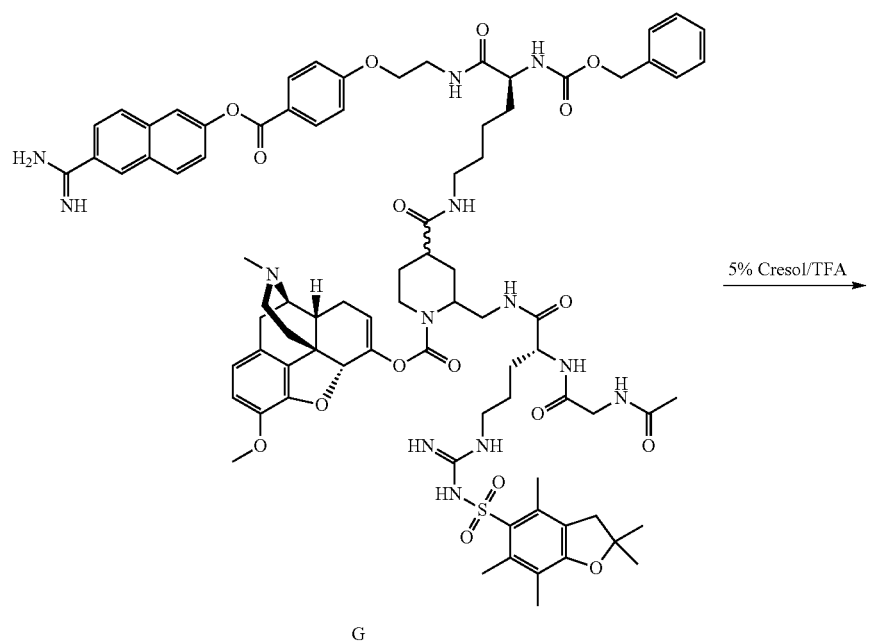
G
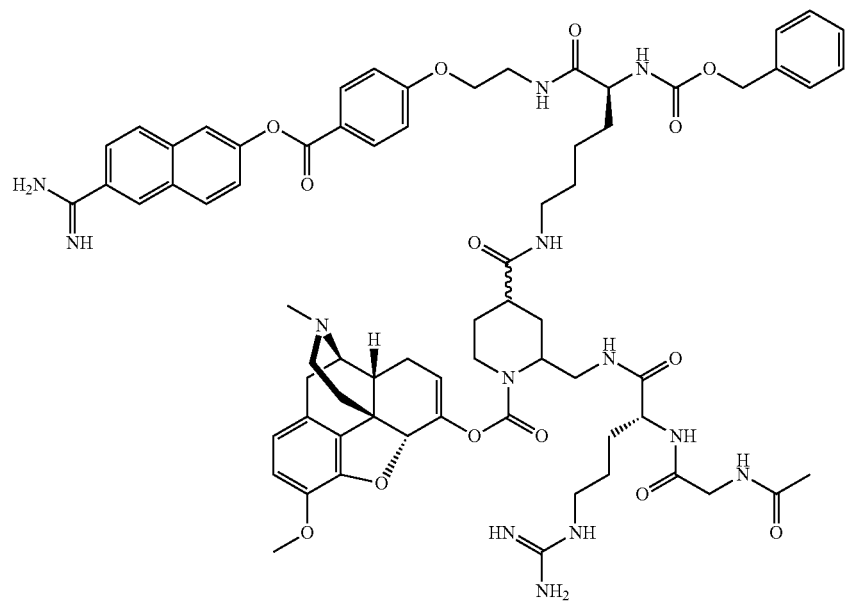
Compound 2
Preparation of Compound 2
To compound G (1.2 g, 0.741 mmol) was added 5% Cresol in TFA (10 ml). The reaction was allowed to stir at room temperature for 4 h. Upon completion, the reaction mixture was condensed, taken up in 20% ACN/H2O (20 mL) and purified via preparative HPLC to afford Compound 2 (0.73 g, 0.52 mmol, 70.2% yield) as an off-white solid. LC-MS: [M+H] 1332.9 ($C_{70}H_{85}N_{13}O_{14}$+H, calc: 1332.6).

269
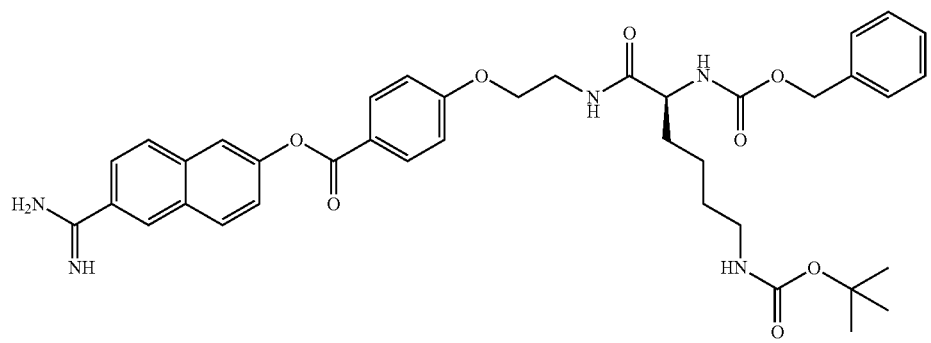
F'
1. Pd(OH)2/C, EtOH,H2
2. Z-Lys(BOC)-Osu/DMF
3. PD(OH)2/C, EtOH, H2
4. Z-Lys(BOC)-OSu/DMF
5. 4N HCl/Dioxane
270
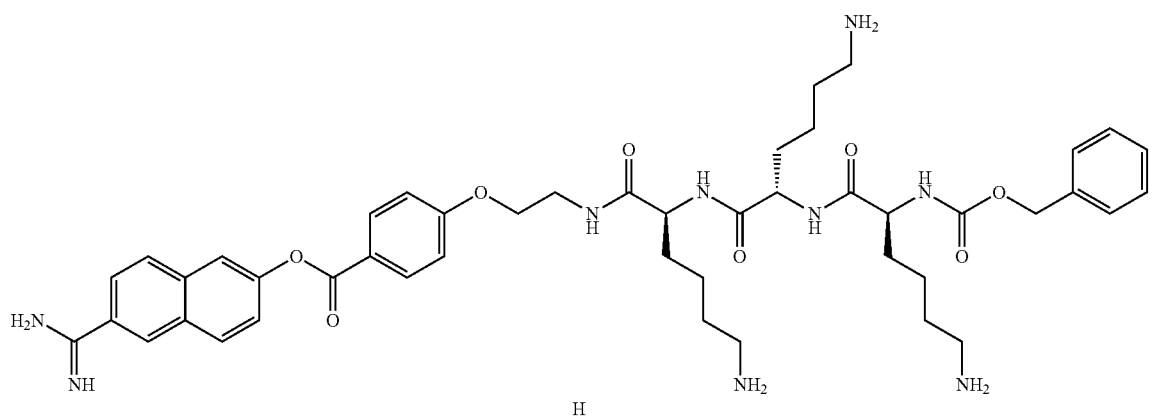
H
1. HATU/NMM/D
2. 4N HCl/Dioxane/DCM
3.
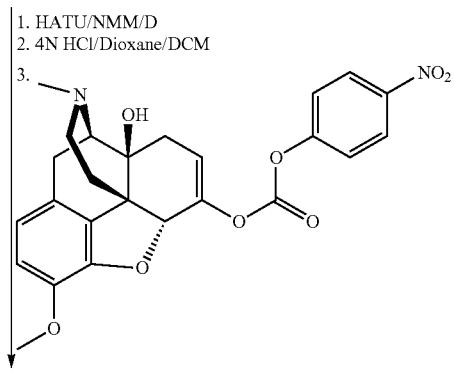

-continued
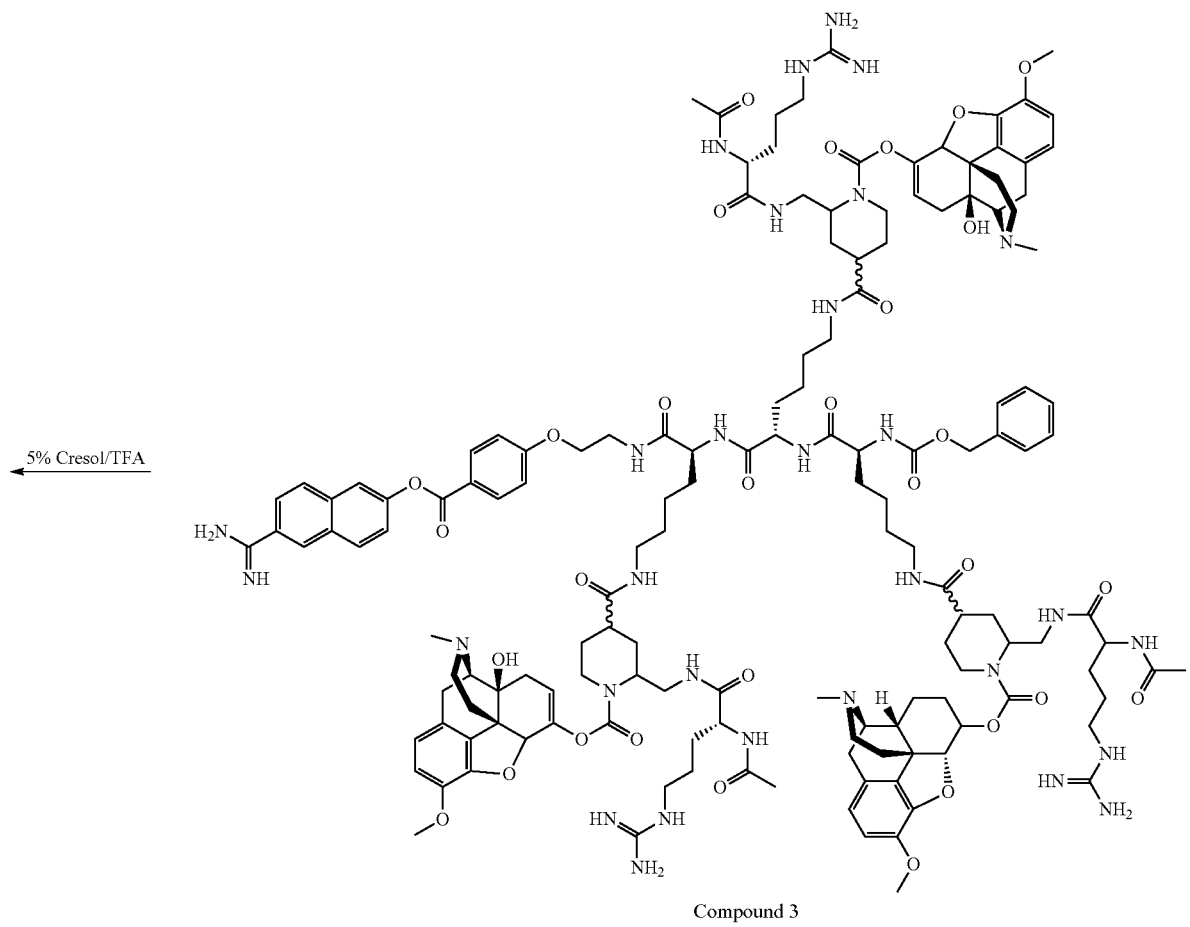
5% Cresol/TFA
Compound 3
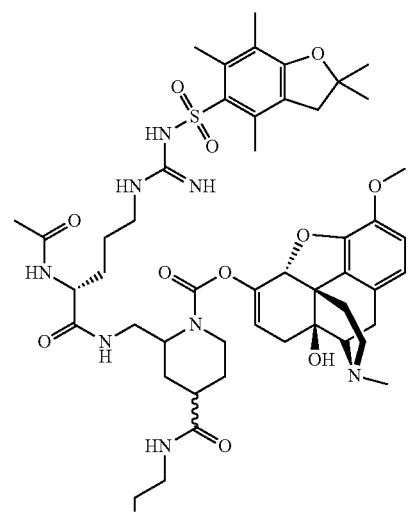

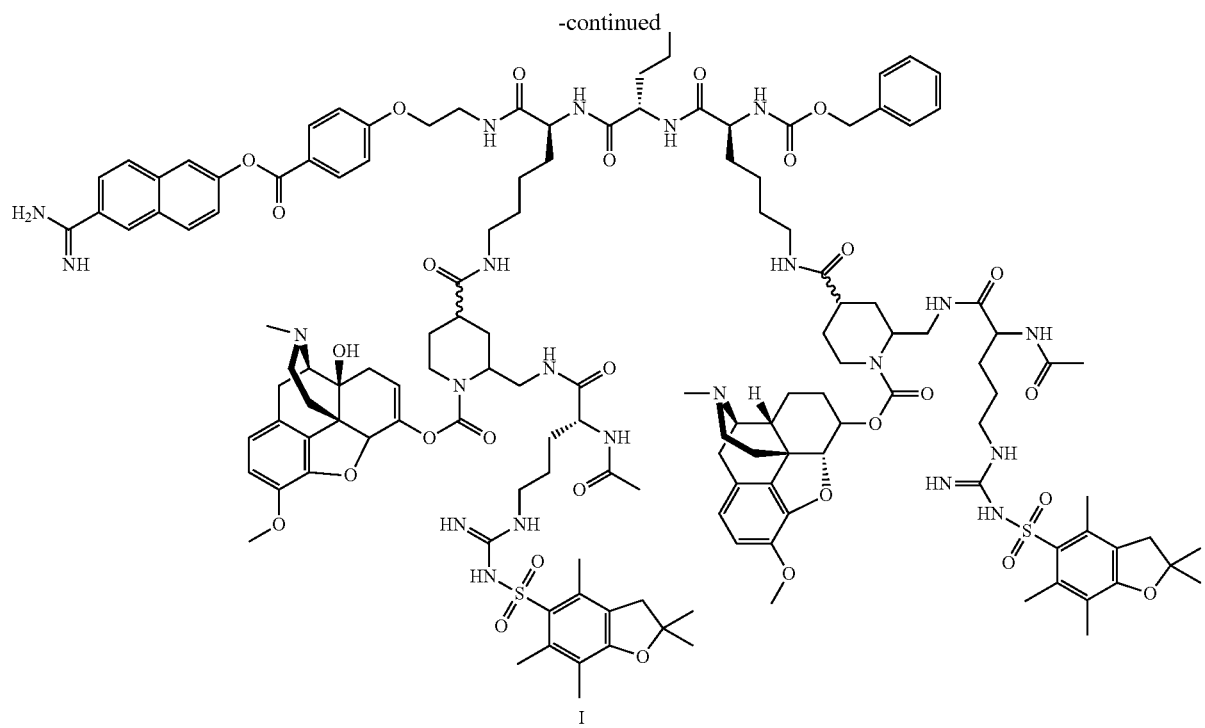

I

Preparation of Compound 3

Compound F' (3.0 g, 4.0 mmol) was dissolved in EtOH (40 mL). 10% Pd(OH)$_2$/C (0.3 g) and 4N HCl (in 1,4-Dioxane; 3 mL) was added to the reaction mixture. The mixture was hydrogenated at 40 psi for 4 h on a Parr hydrogenator. The mixture was then filtered through a celite pad and then the celite pad was washed with MeOH (3×10 mL). The reaction was condensed under vacuum. Next, the crude reaction mixture was dissolved in DMF (25 mL) and to the solution was added SuO-Lys(Boc)-NAc (1.91 g, 4.0 mmol) at 5° C., followed by DIPEA (2.08 mL, 12 mmol) dropwise over 5 min. The temperature of the reaction mixture was raised to ambient temperature and stirring was continued for an additional 1 h. Upon reaction completion, DMF was removed under high vacuum, and the reaction mixture was diluted with DCM (100 mL), washed with 1N HCl (100 mL), then with aqueous NaHCO$_3$ (100 mL) and brine (250 mL). The organic phase was dried over Na$_2$SO$_4$, filtered and the solvent was evaporated to afford an off-white solid. (3.10 g, 3.3 mmol) LC-MS: [M+H] 940.8 (C$_{50}$H$_{65}$N$_7$O$_{11}$+H, calc: 940.5). The crude product was used directly without further purification.

The crude product of the previous reaction (3.10 g, 3.3 mmol) was dissolved in EtOH (100 mL). 10% Pd(OH)$_2$/C (0.3 g) and 4N HCl (in 1,4-Dioxane; 4 mL) was added to the reaction mixture. The mixture was hydrogenated at 40 psi for 4 h on a Parr hydrogenator. The mixture was then filtered through a celite pad and then the celite pad was washed with MeOH (3×25 mL). The reaction was condensed under vacuum. Next, the crude reaction mixture was dissolved in DMF (25 mL) and to the solution was added SuO-Lys(Boc)-NAc (1.57 g, 3.3 mmol) at 5° C., followed by DIPEA (2.42 mL, 14 mmol) dropwise over 5 min. The temperature of the reaction mixture was raised to ambient temperature and stirring was continued for an additional 2 h. Upon reaction completion, DMF was removed under high vacuum, and the reaction mixture was diluted with DCM (300 mL), washed with 1N HCl (200 mL), then with aqueous NaHCO$_3$ (200 mL) and brine (250 mL). The organic phase was dried over Na$_2$SO$_4$, filtered and the solvent was evaporated to afford an off-white solid. (3.85 g, 3.3 mmol) LC-MS: [M+H] 1168.9 (C$_{61}$H$_{85}$N$_9$O$_{14}$+H, calc: 1168.6). The crude product was used directly without further purification.

The crude product of the previous reaction (3.85 g, 3.3 mmol) was dissolved in DCM (100 mL) was treated with 4 M solution of hydrogen chloride in 1,4-dioxane (15 mL). After 1 h, solvent was removed under vacuum until about ~50 mL remained. Diethyl ether (~300 mL) was added to the reaction mixture, which produced a fine white precipitate. The precipitate was filtered off, washed with ether (3×75 mL) and dried under vacuum to give compound H as a fine white solid. (3.3 g, 3.3 mmol) LC-MS: [M+H] 868.8 (C$_{46}$H$_{61}$N$_9$O$_8$+H, calc: 868.5). Crude compound H was used directly without further purification.

To a solution of Compound H (2.1 g, 2.0 mmol), Compound D (4.81 g, 6.3 mmol) and HATU (2.87 g, 7.56 mmol) in DMF (40 mL) at −20° C. was added DIPEA (3.95 mL, 22.7 mmol) dropwise over 5 min. The temperature of the reaction mixture was raised to ambient temperature and stirring was continued for an additional hour. Upon reaction completion, DMF was removed under vacuum and the reaction mixture was then diluted DCM. The organic layer was washed with 1N HCl, saturated NaHCO3, brine and then dried over MgSO4. The organic layer was then filtered and condensed to afford an off-white solid. (6.68 g) LC-MS: [M+H] 2939.9 (C$_{145}$H$_{211}$N$_{27}$O$_{32}$S$_3$+H, calc: 2939.5). The crude product was dissolved in 4N hydrogen chloride in 1,4-dioxane (50 mL). After 1 h, solvent was removed under vacuum until about ~10 mL remained. Diethyl ether (~500 mL) was added to the reaction mixture, which produced an off-white/light tan precipitate. The precipitate was filtered off, washed with ether (3×100 mL) and dried under vacuum to give a solid (Compound H') in 84% yield over 2 steps (4.67 g, 1.68 mmol). LC-MS: [M+H] 2639.7 ($C_{130}H_{187}N_{27}O_{26}S$+H, calc: 2639.3). The crude product (Compound H') was used directly without further purification.

Compound H' (3.0 g, 1.08 mmol) and Activated Hydrocodone (1.62 g, 3.23 mmol) were dissolved in DMF (40 mL) and DIPEA (1.68 mL, 9.7 mmol) was added. The reaction mixture was stirred at 40° C. overnight. Upon reaction completion, the DMF was evaporated and the resulting oily product was dissolved in DCM (200 mL). The mixture was then washed with 5% sodium phosphate (2×200 mL), 0.1 N aq. HCl (500 mL) and brine (250 mL). The organic phase was dried over $Na_2SO_4$, filtered and the solvent was evaporated. The oily product was dried in high vacuum overnight to afford crude compound I in 89.5% yield. (3.75 g, 0.967 mmol) LC-MS: [M+H] 3885.8 ($C_{187}H_{248}Cl_4IN_{30}O_{38}S_3$+H, calc: 3885.5). The crude reaction mixture was then purified by preparative HPLC to afford the desired product (compound I) in 62% yield (2.51 g, 0.67 mmol).

To compound I (1.50 g, 0.40 mmol) was added to 5% Cresol in TFA (10 ml). The reaction was allowed to stir at room temperature for 4 h. Upon completion, the reaction mixture was condensed, taken up in 20% ACN/H2O (20 mL) and purified via preparative HPLC to afford Compound 3 as an off-white solid in 83% yield (1.03 g, 0.33 mmol). LC-MS: [M+H] 578.6 ($C_{32}H_{43}N_3O_8$+H, calc: 578.7).

Pharmaceutical Compositions

Also embraced within this invention are pharmaceutical compositions comprising one or more compounds described above in association with one or more non-toxic, pharmaceutically acceptable carriers and/or diluents and/or adjuvants (collectively referred to herein as "carrier" materials) and, if desired, other active ingredients. The compounds and compositions of the present invention can be administered orally, preferably in the form of a pharmaceutical composition adapted to oral administration, and in a dose effective for the prevention or treatment of pain.

For oral administration, the pharmaceutical composition can be in the form of, for example, a tablet, capsule, a soft gelatin (softgel) capsule, a hard gelatin capsule, suspension or liquid.

The amount of each therapeutically active compound that is administered and the dosage regimen for treating or preventing of pain with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain compounds of the invention in the range of about 0.1 to 2000 mg, preferably in the range of about 0.5 to 1000 mg and most preferably between about 1 and 500 mg. A daily dose of about 0.01 to 100 mg/kg body weight, preferably between about 0.1 and about 50 mg/kg body weight and most preferably from about 0.5 to about 20 mg/kg body weight, may be appropriate. The daily dose can be administered in one to four to six to eight or more doses per day.

For therapeutic purposes, the compounds of this invention are ordinarily combined with one or more excipients appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

The pharmaceutical composition of this invention may be prepared by uniformly mixing predetermined amounts of the active ingredient, the absorption aid and optionally the base, etc. in a stirrer or a grinding mill, if required.

The pharmaceutical compositions disclosed herein comprise a compound of the invention disclosed herein with a suitable amount of a pharmaceutically acceptable vehicle, so as to provide a form for proper administration to a subject.

Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, gelling, lubricating and coloring, and/or agents designed to deter oral and non-oral abuse (e.g. gelling and or irritant agents) may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in a conventional manner using one or more physiologically acceptable carriers, diluents, excipients or auxiliaries, which facilitate processing of compositions and compounds disclosed herein into preparations that can be used pharmaceutically.

The present pharmaceutical compositions can take the form of solutions, suspensions, emulsion, tablets, pills, pellets, capsules, capsules containing liquids, powders, sustained-release formulations, emulsions, suspensions or any other form suitable for use known to the skilled artisan. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995).

Pharmaceutical compositions for oral delivery may be in the form of tablets, lozenges, aqueous or oily suspensions, granules, powders, emulsions, capsules, syrups, slurries, suspensions or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation.

Moreover, when in tablet or pill form, the compositions may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, sucrose, sorbitol, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), granulating agents, binding agents and disintegrating agents such as the cross-linked polyvinylpyrrolidone, agar, or alginic acid or a salt thereof such as sodium alginate etc.

The methods that involve oral administration of compounds disclosed herein of can also be practiced with a number of different dosage forms, which provide sustained release.

In some embodiments, the dosage form is comprised of beads that on dissolution or diffusion release compositions and/or compounds disclosed herein over an extended period of hours, preferably, over a period of at least 6 hours, more preferably, over a period of at least 8 hours and even more preferably, over a period of at least 12 hours and most preferably, over a period of at least 24 hours. The beads may have a central composition or core comprising compounds disclosed herein and pharmaceutically acceptable vehicles, including optional lubricants, antioxidants and buffers. The beads may be medical preparations with a diameter of about 1 to about 2 mm. Individual beads may comprise doses of the compounds disclosed herein. The beads, in some embodiments, are formed of non-cross-linked materials to enhance their discharge from the gastrointestinal tract. The beads may be coated with a release rate-controlling polymer that gives a timed-release profile.

The time-release beads may be manufactured into a tablet for therapeutically effective administration. The beads can be made into matrix tablets by direct compression of a plurality of beads coated with, for example, an acrylic resin and blended with excipients such as hydroxypropylmethyl cellulose. The manufacture of beads has been disclosed in the art (Lu, Int. J. Pharm. 1994, 112, 117-124; Pharmaceutical Sciences by Remington, 14$^{th}$ ed, pp 1626-1628 (1970); Fincher, J. Pharm. Sci. 1968, 57, 1825-1835; Benedikt, U.S. Pat. No. 4,083,949) as has the manufacture of tablets (Pharmaceutical Sciences, by Remington, 17$^{th}$ Ed, Ch. 90, pp 1603-1625 (1985).

In other embodiments, an oral sustained release pump may be used (Langer, supra; Sefton, 1987, CRC Crit Ref Biomed. Eng. 14:201; Saudek et al., 1989, N. Engl. J Med. 321:574).

In still other embodiments, polymeric materials can be used (See "Medical Applications of Controlled Release," Langer and Wise (eds.), CRC Press, Boca Raton, Fla. (1974); "Controlled Drug Bioavailability," Drug Product Design and Performance, Smolen and Ball (eds.), Wiley, New York (1984); Langer et al., 1983, J Macromol. Sci. Rev. Macromol Chem. 23:61; Levy et al., 1985, Science 228: 190; During et al., 1989, Ann. Neurol. 25:351; Howard et al., 1989, J. Neurosurg. 71:105). In some embodiments, polymeric materials are used for oral sustained release delivery. Such polymers include, for example, sodium carboxymethylcellulose, hydroxypropylcellulose, hydroxypropylmethylcellulose and hydroxyethylcellulose (most preferred, hydroxypropylmethylcellulose). Other cellulose ethers have been described (Alderman, Int. J. Pharm. Tech. & Prod. Mfr. 1984, 5(3) 1-9). Factors affecting drug release are well known to the skilled artisan and have been described in the art (Bamba et al., Int. J. Pharm. 1979, 2, 307).

In still other embodiments, enteric-coated preparations can be used for oral sustained release administration. Coating materials include, for example, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In yet other embodiments, drug-releasing lipid matrices can be used for oral sustained release administration. For example, solid microparticles of compositions and/or compounds disclosed herein may be coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles can optionally be compressed to form a tablet. Another controlled release lipid-based matrix material which is suitable for sustained release oral administration comprises polyglycolized glycerides as disclosed in Roussin et al., U.S. Pat. No. 6,171,615.

In yet other embodiments, waxes can be used for oral sustained release administration. Examples of suitable sustained releasing waxes are disclosed in Cain et al., U.S. Pat. No. 3,402,240 (carnauba wax, candedilla wax, esparto wax and ouricury wax); Shtohryn et al., U.S. Pat. No. 4,820,523 (hydrogenated vegetable oil, bees wax, caranuba wax, paraffin, candelillia, ozokerite and mixtures thereof); and Walters, U.S. Pat. No. 4,421,736 (mixture of paraffin and castor wax).

In still other embodiments, osmotic delivery systems are used for oral sustained release administration (Verma et al., Drug Dev. Ind. Pharm. 2000, 26:695-708). In some embodiments, OROS® systems made by Alza Corporation, Mountain View, Calif. are used for oral sustained release delivery devices (Theeuwes et al., U.S. Pat. No. 3,845,770; Theeuwes et al., U.S. Pat. No. 3,916,899).

In still other embodiments, the dosage form comprises compounds disclosed herein coated on a polymer substrate. The polymer can be an erodible or a nonerodible polymer. The coated substrate may be folded onto itself to provide a bilayer polymer drug dosage form. For example, compounds disclosed herein can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense the compounds over a sustained release period. Representative biodegradable polymers comprise a member selected from the group consisting of biodegradable poly(amides), poly (amino acids), poly(esters), poly(lactic acid), poly(glycolic acid), poly(carbohydrate), poly(orthoester), poly (orthocarbonate), poly(acetyl), poly(anhydrides), biodegradable poly(dihydropyrans), and poly(dioxinones) which are known in the art (Rosoff, Controlled Release of Drugs, Chap. 2, pp. 53-95 (1989); Heller et al., U.S. Pat. No. 3,811,444; Michaels, U.S. Pat. No. 3,962,414; Capozza, U.S. Pat. No. 4,066,747; Schmitt, U.S. Pat. No. 4,070,347; Choi et al., U.S. Pat. No. 4,079,038; Choi et al., U.S. Pat. No. 4,093,709).

In other embodiments, the dosage form comprises compounds disclosed herein loaded into a polymer that releases the drug(s) by diffusion through a polymer, or by flux through pores or by rupture of a polymer matrix. The drug delivery polymeric dosage form comprises a concentration of 10 mg to 2500 mg homogenously contained in or on a polymer. The dosage form comprises at least one exposed surface at the beginning of dose delivery. The non-exposed surface, when present, is coated with a pharmaceutically acceptable material impermeable to the passage of the drug(s). The dosage form may be manufactured by procedures known in the art. An example of providing a dosage form comprises blending a pharmaceutically acceptable carrier like polyethylene glycol, with a known dose of compositions and/or compounds disclosed herein at an elevated temperature, (e.g., 37° C.), and adding it to a silastic medical grade elastomer with a cross-linking agent, for example, octanoate, followed by casting in a mold. The step is repeated for each optional successive layer. The system is allowed to set for about 1 hour, to provide the dosage form. Representative polymers for manufacturing the dosage form comprise a member selected from the group consisting of olefin, and vinyl polymers, addition polymers, condensation polymers, carbohydrate polymers, and silicone polymers as represented by polyethylene, polypropylene, polyvinyl acetate, polymethylacrylate, polyisobutylmethacrylate, poly alginate, polyamide and polysilicone. The polymers and procedures for manufacturing them have been described in the art (Coleman et al., Polymers 1990, 31, 1187-1231; Roerdink et al., Drug Carrier Systems 1989, 9, 57-10; Leong et al., Adv. Drug Delivery Rev. 1987, 1, 199-233; Roff et al., Handbook of Common Polymers 1971, CRC Press; Chien et al., U.S. Pat. No. 3,992,518).

In other embodiments, the dosage form comprises a plurality of tiny pills. The tiny time-release pills provide a number of individual doses for providing various time doses for achieving a sustained-release drug delivery profile over an extended period of time up to 24 hours. The matrix comprises a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, gelatin, and a hydrophilic colloid. The hydrophilic matrix comprises a plurality of 4 to 50 tiny pills, each tiny pill comprises a dose population of from 10 ng, 0.5 mg, 1 mg, 1.2 mg, 1.4 mg, 1.6 mg, 5.0 mg, etc. The tiny pills comprise a release rate-controlling wall of 0.001 mm up to 10 mm thickness to provide for the timed release of drug(s). Representative wall forming materials include a triglyceryl ester selected from the group consisting of glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills are disclosed in Urquhart et al., U.S. Pat. No. 4,434,153; Urquhart et al., U.S. Pat. No. 4,721,613; Theeuwes, U.S. Pat. No. 4,853,229; Barry, U.S. Pat. No. 2,996,431; Neville, U.S. Pat. No. 3,139,383; Mehta, U.S. Pat. No. 4,752,470.

In other embodiments, the dosage form comprises an osmotic dosage form, which comprises a semipermeable wall that surrounds a therapeutic composition comprising compounds disclosed herein. In use within a subject, the osmotic dosage form comprising a homogenous composition, imbibes fluid through the semipermeable wall into the dosage form in response to the concentration gradient across the semipermeable wall. The therapeutic composition in the dosage form develops osmotic pressure differential that causes the therapeutic composition to be administered through an exit from the dosage form over a prolonged period of time up to 24 hours (or even in some cases up to 30 hours) to provide controlled and sustained release. These delivery platforms can provide an essentially zero order delivery profile as opposed to the spiked profiles of immediate release formulations.

In other embodiments, the dosage form comprises another osmotic dosage form comprising a wall surrounding a compartment, the wall comprising a semipermeable polymeric composition permeable to the passage of fluid and substantially impermeable to the passage of compounds disclosed herein present in the compartment, a drug-containing layer composition in the compartment, a hydrogel push layer composition in the compartment comprising an osmotic formulation for imbibing and absorbing fluid for expanding in size for pushing the drug composition layer from the dosage form, and at least one passageway in the wall for releasing the composition. The method delivers compounds disclosed herein by imbibing fluid through the semipermeable wall at a fluid imbibing rate determined by the permeability of the semipermeable wall and the osmotic pressure across the semipermeable wall causing the push layer to expand, thereby delivering the compounds disclosed herein from the dosage form through the exit passageway to a subject over a prolonged period of time (up to 24 or even 30 hours). The hydrogel layer composition may comprise 10 mg to 1000 mg of a hydrogel such as a member selected from the group consisting of a polyalkylene oxide of 1,000,000 to 8,000,000 weight-average molecular weight which are selected from the group consisting of a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer comprises 0.0 mg to 350 mg, in present manufacture; 0.1 mg to 250 mg of a hydroxyalkylcellulose of 7,500 to 4,500,000 weight-average molecular weight (e.g., hydroxymethylcellulose, hydroxyethylcellulose, hydroxypropylcellulose, hydroxybutylcellulose or hydroxypentylcellulose) in present manufacture; 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylated hydroxyquinone, butylhydroxyanisole, hydroxycoumarin, butylated hydroxytoluene, cephalm, ethyl gallate, propyl gallate, octyl gallate, lauryl gallate, propyl-hydroxybenzoate, trihydroxybutyrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laurate, salts of fatty acids, salts of alicyclic acids, salts of aromatic acids, stearic acid, oleic acid, palmitic acid, a mixture of a salt of a fatty, alicyclic or aromatic acid and a fatty, alicyclic or aromatic acid.

In the osmotic dosage forms, the semipermeable wall comprises a composition that is permeable to the passage of fluid and impermeable to the passage of compounds disclosed herein. The wall is non-toxic and comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from the group consisting of hydroxypropylcellulose or a hydroxypropylalkylcellulose such as hydroxypropylmethylcellulose. The total weight percent of all components comprising the wall is equal to 100 wt %. The internal compartment comprises the drug-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of compounds disclosed herein to a subject over time. The dosage form comprises a passageway in the wall that connects the exterior of the dosage form with the internal compartment. The osmotic powered dosage form can be made to deliver drug from the dosage form to the subject at a zero order rate of release over a period of up to about 24 hours.

The expression "passageway" as used herein comprises means and methods suitable for the metered release of the compounds disclosed herein from the compartment of the dosage form. The exit means comprises at least one passageway, including orifice, bore, aperture, pore, porous element, hollow fiber, capillary tube, channel, porous overlay, or porous element that provides for the osmotic controlled release of the compounds disclosed herein. The passageway includes a material that erodes or is leached from the wall in a fluid environment of use to produce at least one controlled-release dimensioned passageway. Representative materials suitable for forming a passageway, or a multiplicity of passageways comprise a leachable poly (glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of compositions and/or drugs from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in Theeuwes et al., U.S. Pat. No. 3,845,770; Theeuwes et al., U.S. Pat. No. 3,916,899; Saunders et al., U.S. Pat. No. 4,063,064; Theeuwes et al., U.S. Pat. No. 4,088,864 and Ayer et al., U.S. Pat. No. 4,816,263. Passageways formed by leaching are disclosed in Ayer et al., U.S. Pat. No. 4,200,098 and Ayer et al., U.S. Pat. No. 4,285,987.

In order to decrease dosing frequency and augment the convenience to the subject and increase subject compliance, the sustained release oral dosage form (regardless of the specific form of the sustained release dosage form) preferably, provides therapeutic concentrations of the compounds disclosed herein in the patient's blood over a period of at least about 6 hours, more preferably, over a period of at least about 8 hours, even preferably, over a period of at least about 12 hours and most preferably, over a period of at least 24 hours.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

When used to treat and/or prevent diseases the compounds disclosed herein and/or pharmaceutical compositions thereof may be administered alone or in combination with other pharmaceutical agents including compounds disclosed herein and/or pharmaceutical compositions thereof. The compounds disclosed herein may be administered or applied per se or as pharmaceutical compositions.

The amount of compounds disclosed herein and/or pharmaceutical compositions thereof that will be effective in the treatment or prevention of diseases in a patient will depend on the specific nature of the condition and can be determined by standard clinical techniques known in the art. The amount of compounds disclosed herein and/or pharmaceutical compositions thereof administered will, of course, be dependent on, among other factors, the subject being treated, the weight of the subject, the severity of the affliction, and the judgment of the prescribing physician.

In certain embodiments, compounds disclosed herein and/or pharmaceutical compositions thereof can be used in combination therapy with at least one other therapeutic agent. The compounds disclosed herein and/or pharmaceutical compositions thereof and the therapeutic agent can act additively or, more preferably, synergistically. In some embodiments, compounds disclosed herein and/or pharmaceutical compositions thereof are administered concurrently with the administration of another therapeutic agent. For example, compounds disclosed herein and/or pharmaceutical compositions thereof may be administered together with another therapeutic agent (e.g. including, but not limited to, peripheral opioid antagonists, laxatives, non-opioid analgesics and the like). In other embodiments, compounds disclosed herein and/or pharmaceutical compositions thereof are administered prior or subsequent to administration of other therapeutic agents.

Thus, in one aspect of the invention, the oral dosage form can contain one or more compounds of the invention and non-opioid drugs. Such non-opioid drugs would preferably provide additional analgesia and/or anti-inflammatory effects, and include, for example, aspirin, acetaminophen, non-steroidal anti-inflammatory drugs ("NSAIDS") such as, for example, naproxen, ibuprofen, ketoprofen, N-methyl-D-aspartate (NMDA) receptor antagonists, such as, for example, a morphinan such as dextromethorphan or dextrorphan, or ketamine, a cycooxygenase-II inhibitors ("COX-II inhibitors"); and/or glycine receptor antagonists.

All printed patents and publications referred to in this application are hereby incorporated herein in their entirety by this reference. While the preferred embodiment of the invention has been illustrated and described, it will be appreciated that various changes can be made therein without departing from the spirit and scope of the invention.

Pharmacokinetic and Pharmacodynamic Measurements

Pharmacokinetic and pharmacodynamic data can be obtained by various experimental techniques. Appropriate pharmacokinetic and pharmacodynamic profile components describing a particular composition can vary due to variations in drug metabolism in different subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined by calculating the average of all subject's measurements for each parameter measured.

A dose can be modulated to achieve a desired pharmacokinetic or pharmacodynamic profile, such as a desired or effective blood profile, as described herein. A compound of the invention can be present in a composition in a range of from about 1 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg. To better characterize the enzyme kinetics of a compound of the invention in vitro the $K_m$ and $V_{max}$ of a unimolecular entity can be described as illustrated in FIG. 2.

The outcome of treating a human subject with a combination therapy can be measured by calculating pharmacodynamic and pharmacokinetic parameters. Non-limiting examples of pharmacodynamic and pharmacokinetic parameters that can be used to determine the effect of treatment of a subject with a composition of the disclosure include: a) the amount of opioid agonist drug delivered, which can be represented as a dose D; b) the dosing interval, which can be represented as $\tau$; c) the apparent volume in which a drug is distributed, which can be represented as a volume of distribution $V_d$, where $V_d = D/C_0$; d) the amount of drug in a given volume of plasma, which can be represented as concentration $C_0$ or $C_{ss}$, where $C_0$ or $C_{ss} = D/Vd$; e) the half-life of a drug $t_{1/2}$, where $t_{1/2} = \ln(2)/k_e$; f) the rate at which a drug is removed from the body $k_e$, where $k_e = \ln(2)/t_{1/2} = CL/V_d$; g) the rate of infusion required to balance the equation $K_{in}$, where $K_{in} = C_{ss} \cdot CL$; h) the integral of the concentration-time curve after administration of a single dose, which can be represented as $AUC_{0-\infty}$, wherein $\int_0^\infty C\, dt$, or in steady-state, which can be represented as $AUC\tau_{,ss}$, wherein $\int_t^{t+\tau} C\, dt$; i) the volume of plasma cleared of the drug per unit time, which can be represented as CL (clearance), wherein $CL = V_d \cdot k_e = D/AUC$; j) the systemically available fraction of a drug, which can be represented as f, where $$f = \frac{AUCpo \cdot Div}{AUCiv \cdot Dpo};$$

k) the peak plasma concentration of a drug after administration $C_{max}$; l) the time taken by a drug to reach $C_{max}$, $T_{max}$; m) the lowest concentration that a drug reaches before the next dose is administered $C_{min}$; and n) the peak trough fluctuation within one dosing interval at steady state, which can be represented as % PTF=100.

$$\frac{(C\max, ss - C\min, ss)}{Cav, ss} \text{ where } C_{av,ss} = \frac{AUC\tau, ss}{\tau}.$$

The pharmacokinetics parameters can be any parameters suitable for describing the plasma profiles of the opioid agonist delivered by a compound of the invention. For example, the pharmacokinetic profile of an opioid agonist delivered by a compound of the invention can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

The pharmacokinetic parameters can be any parameters suitable for describing an opioid agonist, or agonists, delivered from compounds of the invention. The $C_{max}$ can be, for example, not less than about 1 ng/mL; not less than about 5 ng/mL; not less than about 10 ng/mL; not less than about 15 ng/mL; not less than about 20 ng/mL; not less than about 25 ng/mL; not less than about 50 ng/mL; not less than about 75 ng/mL; not less than about 100 ng/mL; not less than about 200 ng/mL; or any other $C_{max}$ appropriate for describing a pharmacokinetic profile of an opioid agonist described herein. The $C_{max}$ can be, for example, about 1 ng/mL to about 5 ng/mL; about 1 ng/mL to about 10 ng/mL; about 1 ng/mL to about 30 ng/mL; about 1 ng/mL to about 50 ng/mL; about 1 ng/mL to about 75 ng/mL; about 1 µg/mL to about 100 ng/mL; about 1 ng/mL to about 150 ng/mL; about 1 ng/mL to about 200 ng/mL; or about 1 ng/mL to about 300 ng/mL.

The $AUC_{(0-inf)}$ or $AUC_{(0-)}$ of a compound of the invention, or opioid agonist, or agonists, delivered therefrom as described herein can be, for example, not less than about 10 ng·hr/mL, not less than about 25 ng·hr/mL, not less than about 50 ng·hr/mL, not less than about 100 ng·hr/mL, not less than about 150 ng·hr/mL, not less than about 200 ng·hr/mL, not less than about 300 ng·hr/mL, not less than about 350 ng·hr/mL, not less than about 400 ng·hr/mL, not less than about 500 ng·hr/mL, not less than about 600 ng·hr/mL, not less than about 700 ng·hr/mL, not less than about 800 ng·hr/mL, not less than about 900 ng·hr/mL, not less than about 1000 ng·hr/mL, not less than about 2000 ng·hr/mL, not less than about 3000 ng·hr/mL, not less than about 4000 ng·hr/mL, or any other $AUC_{(0\text{-}inf)}$ appropriate for describing a pharmacokinetic profile of a unimolecular polysubstrate entity or opioid agonist, or agonists, delivered therefrom as described herein.

EXAMPLES

Example 1: In Vitro Characterization of an Overdose Protection Mechanism with Compounds of the Disclosure This example describes in vitro experiments with a compound of the disclosure to provide a mechanism of overdose protection. Specifically, this study was designed to assess the ability of increasing concentrations of compounds 2 and 3 to progressively inhibit trypsin activity.

The effect of increasing concentrations of compounds 2 and 3 on the rate and extent of the trypsin-catalyzed hydrolysis of a commercially available trypsin substrate $N_\alpha$-Benzoyl-L-arginine 4-nitroanilide hydrochloride was evaluated in the presence of trypsin (2,000 BAEE activity) in a pH 7.4 phosphate buffer at 37° C. in vitro. Both buffer alone (i.e. no trypsin) and trypsin (i.e. no compound 2 or 3) controls were run contemporaneously. The data are presented below in the Tables below, and clearly demonstrates the ability of compounds 2 and 3 to progressively inhibit trypsin in a concentration dependent manner with a steep concentration vs. inhibition relationship. Based on this data, it is reasonable to assume that compounds 2 and 3 are capable of rapidly auto-attenuating the trypsin-mediated release of their appended opioid agonists in vivo as multiple doses are co-ingested.

TABLE 1

Percent $N_\alpha$-Benzoyl-L-arginine 4-nitroanilide hydrochloride remaining vs. Time

| Compound | Concentration | Time (Minutes) Percent $N_\alpha$-Benzoyl-L-arginine 4-nitroanilide hydrochloride remaining | | | | | | |
|---|---|---|---|---|---|---|---|---|
| | | 2 | 13 | 24 | 80 | 102 | 119 | 234 |
| 2 | 1 mM | 100 | 100 | 99 | 100 | 100 | 100 | 100 |
| | 100 uM | 100 | 98 | 100 | 99 | 99 | 99 | 99 |
| | 10 uM | 100 | 98 | 96 | 94 | 93 | 94 | 87 |
| | 1 uM | 100 | 39 | 0 | 0 | 0 | 0 | 0 |
| Trypsin Control | | 100 | 0 | 0 | 0 | 0 | 0 | 0 |
| Buffer control (no Trypsin) | | 100 | 100 | 99 | 99 | 99 | 99 | 98 |

TABLE 2

Percent $N_\alpha$-Benzoyl-L-arginine 4-nitroanilide hydrochloride remaining vs. Time

| Compound | Concentration | Time (Minutes) Percent $N_\alpha$-Benzoyl-L-arginine 4-nitroanilide hydrochloride remaining | | | | | | | |
|---|---|---|---|---|---|---|---|---|---|
| | | 2 | 14 | 24 | 32 | 70 | 100 | 145 | 156 | 247 |
| 3 | 1 mM | 100 | 99 | 98 | 99 | 99 | 98 | 98 | 97 | 96 |
| | 100 uM | 100 | 99 | 100 | 100 | 100 | 100 | 100 | 100 | 100 |
| | 10 uM | 100 | 98 | 96 | 98 | 97 | 95 | 96 | 96 | 93 |
| | 1 uM | 100 | 20 | 11 | 0 | 0 | 0 | 0 | 0 | 0 |
| Trypsin Control | | 100 | 0 | 0 | 0 | 0 | 0 | 0 | 0 | 0 |
| Buffer control (no Trypsin) | | 100 | 100 | 100 | 100 | 100 | 99 | 99 | 98 | 98 |

Example 2: In Vivo Demonstration of Non-Linear Pharmacokinetics (i.e. Overdose Protection) with Compounds of the Disclosure This example describes in vivo experiments with a compound of the disclosure to demonstrate overdose protection (i.e. non-linear pharmacokinetics of delivered hydrocodone).

The effect of increasing oral doses of compounds 2 and 3 on the pharmacokinetics of delivered hydrocodone (i.e. measured plasma hydrocodone concentrations vs. time) was evaluated in dogs. Specific pharmacokinetics parameters of the delivered opioid were calculated (e.g. Cmax, Tmax, AUC) and are presented below in the Table below. This data clearly demonstrates the ability of increasing oral doses of compounds 2 and 3 of the invention to progressively attenuate the release of hydrocodone in vivo.

| Compound | Dose (umol/kg) | PK Parameter | | | | | |
|---|---|---|---|---|---|---|---|
| | | $AUC_{0-8\,h}$ of hydrocodone in dog plasma | | Maximum concentration (Cmax) of hydrocodone in dog plasma | | Time of maximum concentration (Tmax) of hydrocodone in dog plasma | |
| | | $AUC_{0-8\,h}$ (ng · h/mL) | SD | Cmax (ng/mL HC) | SD | Tmax (h) | SD |
| 1 | 5 | 7.51 | 1.39 | 2.58 | 0.57 | 0.96 | 0.39 |
| | 10 | 12.59 | 5.55 | 4 | 1.72 | 1.04 | 0.34 |
| | 35 | 27.8 | 1.76 | 6.76 | 0.88 | 2.25 | 0.96 |
| 2 | 1.66 | 7.79 | 1.12 | 2.87 | 0.16 | 0.96 | 0.39 |
| | 5 | 27 | 7.43 | 6.49 | 1.28 | 1.38 | 1.19 |
| | 10 | 37.68 | 9.25 | 8.37 | 1.94 | 2.08 | 1.69 |
| | 35 | 64.38 | 18.36 | 11.87 | 2.89 | 2.13 | 1.31 |

What is claimed is:

1. A composition comprising at least one compound comprising a GI enzyme-labile opioid agonist releasing subunit capable of releasing an opioid agonist upon the action of a GI enzyme, wherein the at least one GI enzyme-labile opioid agonist releasing subunit is covalently linked to at least one GI enzyme inhibitor subunit capable of inhibiting said GI enzyme.

2. The composition of claim 1, wherein the at least one GI enzyme-labile opioid releasing subunit and the at least one GI enzyme inhibitor subunit are covalently linked via a scaffold moiety.

3. The composition of claim 2, wherein the scaffold moiety comprises a polypeptide or polysaccharide.

4. The composition of claim 1, wherein the GI enzyme is trypsin.

5. The composition of claim 1, wherein the GI enzyme is chymotrypsin.

6. The composition of claim 1, wherein the GI enzyme-labile opioid releasing subunit releases the opioid agonist in the presence of the GI enzyme.

7. The composition of claim 1, wherein the opioid agonist is selected from the group consisting of morphine, hydromorphone, hydrocodone, oxycodone, codeine, levorphanol, meperidine, methadone, oxymorphone, dihydrocodeine, tramadol, tapentadol, buprenorphine, and pharmaceutically acceptable salts, and mixtures thereof.

8. The composition of claim 7, wherein the opioid agonist is oxycodone.

9. The composition of claim 7, wherein the opioid agonist is hydrocodone.

10. The composition of claim 7, wherein the opioid agonist is morphine.

11. The composition of claim 1, wherein the GI enzyme inhibitor subunit is capable of reducing a systemic exposure of delivered opioid agonist relative to a linear dose-proportional increase of systemic exposure of delivered opioid agonist when a dose of the GI enzyme-labile opioid agonist releasing subunit greater than a prescribed dose is ingested.

12. The composition of claim 1, wherein the compound is represented by a structure of formula (I):

or a salt thereof, wherein:
Q is alkyl or an optionally substituted peptide that, if substituted, is substituted on an N-terminus of the optionally substituted peptide by alkyl or —C(O)—R', wherein R' is selected from alkyl, aryl, substituted aryl, a natural amino acid, a non-natural amino acid, alkoxy, and aralkoxy;

$L^1$ is independently at each occurrence absent or a cleavable linker or a non-cleavable linker;

$L^2$ is independently at each occurrence absent or a cleavable linker or a non-cleavable linker;

$R^1$ is independently at each occurrence a GI enzyme inhibitor;

$R^2$ is independently at each occurrence an opioid agonist covalently bound to a GI enzyme substrate;

wherein the GI enzyme is a protease; and m and n are each independently integers from 1 to 1,000,000.

13. The composition of claim 12, wherein Q is an optionally substituted peptide.

14. The composition of claim 13, wherein Q is an optionally substituted peptide with from 1 to 500 amino acids.

15. The composition of claim 14, wherein Q is an optionally substituted peptide with from 1 to 50 amino acids.

16. The composition of claim 15, wherein Q is an optionally substituted peptide with from 1 to 10 amino acids.

17. The composition of claim 16, wherein Q is an optionally substituted peptide with from 1 to 3 amino acids.

18. The composition of claim 12, wherein $R^1$ is independently at each occurrence a serine protease inhibitor.

19. The composition of claim 12, wherein $R^1$ is independently at each occurrence a trypsin inhibitor.

20. The composition of claim 12, wherein $R^1$-$L^1$ is independently selected at each occurrence from:

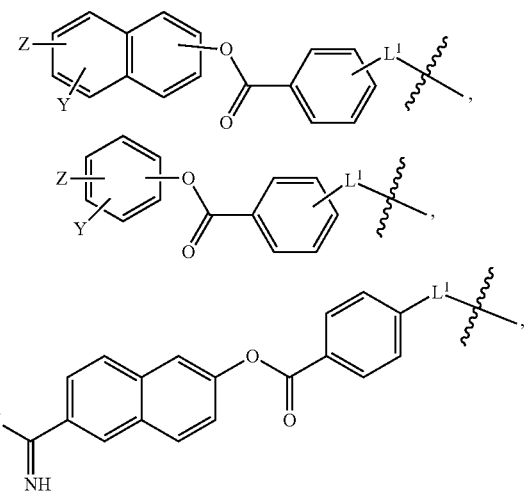

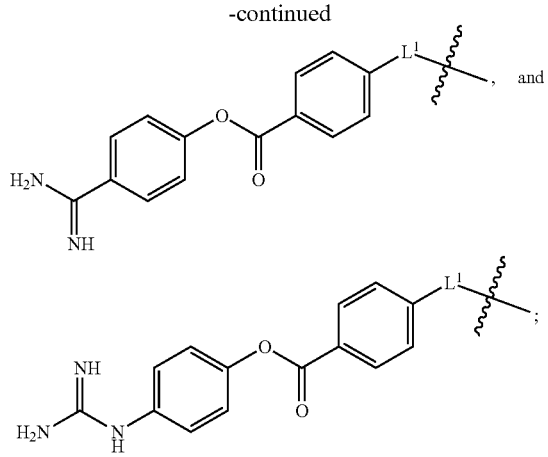

wherein:
  Y is independently selected at each occurrence from amidinyl, guanidinyl, aminomethyl, alkyl substituted amidinyl, alkyl substituted guanidinyl, alkyl substituted aminomethyl, amidinomethyl, and guanidinomethyl; and
  Z is independently selected at each occurrence from hydrogen, cyano, nitro, halogen, alkyl and alkoxy.

21. The composition of claim 20, wherein Y is independently selected at each occurrence from

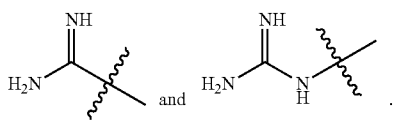

22. The composition of claim 21, wherein Y is

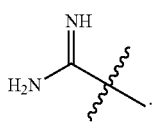

23. The composition of claim 21, wherein Y is

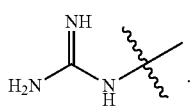

24. The composition of claim 12, wherein $L^1$ is selected independently at each occurrence from a cleavable linker and a non-cleavable linker, wherein the cleavable linker and the non-cleavable linker consist of from 2 to 15 atoms.

25. The composition of claim 20, wherein $L^1$ is O—CH$_2$—CH$_2$—NH— or —O—CH$_2$—CH$_2$—O—.

26. The composition of claim 12, wherein n is an integer from 1 to 20.

27. The composition of claim 26, wherein n is an integer from 1 to 10.

28. The composition of claim 27, wherein n is an integer from 1 to 3.

29. The composition of claim 12, wherein $R^2$-$L^2$ is independently at each occurrence:

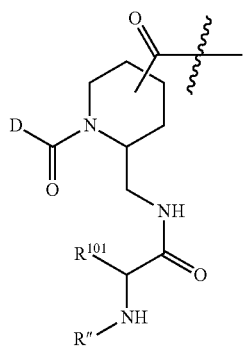

wherein:
  D is an opioid agonist;
  $R^{101}$ is selected from an amino acid side chain and an amino acid side-chain mimic; and
  R" is selected from acetyl, a natural amino acid, and a non-natural amino acid.

30. The composition of claim 29, wherein $R^{101}$ is an amino acid side chain, and R" is acetyl or a natural amino acid.

31. The composition of claim 29, wherein $R^{101}$ is an arginine side chain or a lysine side chain, and R" is acetyl, N-acetylglycine, or N-acetylalanine.

32. The composition of claim 31, wherein $R^{101}$ is an arginine side chain, and R" is N-acetylglycine.

33. The composition of claim 31, wherein $R^{101}$ is a lysine side chain, and R" is N-acetylglycine.

34. The composition of claim 29, wherein D is selected from phenol-linked morphine, alcohol-linked morphine, phenol-linked hydromorphone, enol-linked hydromorphone, enol-linked oxycodone, alcohol-linked oxycodone, alcohol-linked codeine, phenol-linked levorphanol, enol-linked methadone, phenol-linked oxymorphone, enol-linked oxymorphone, alcohol-linked oxymorphone, alcohol-linked dihydrocodeine, alcohol-linked tramadol, phenol-linked tapentadol, and phenol-linked buprenorphine.

35. The composition of claim 29, wherein D is represented by the formula:

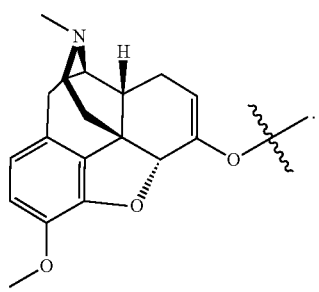 [SMILES: *OC1=CC[C@H]2[C@@H]3[N@@](C)[C@@]34Cc3ccc(OC)c5c3[C@@]2(C4)[C@H]1O5]

36. The composition of claim 12, wherein m is an integer from 1 to 20.

37. The composition of claim 36, wherein m is an integer from 1 to 10.

38. The composition of claim 37, wherein m is an integer from 1 to 3.

39. The composition of claim 12, wherein the compound is represented by the formula:

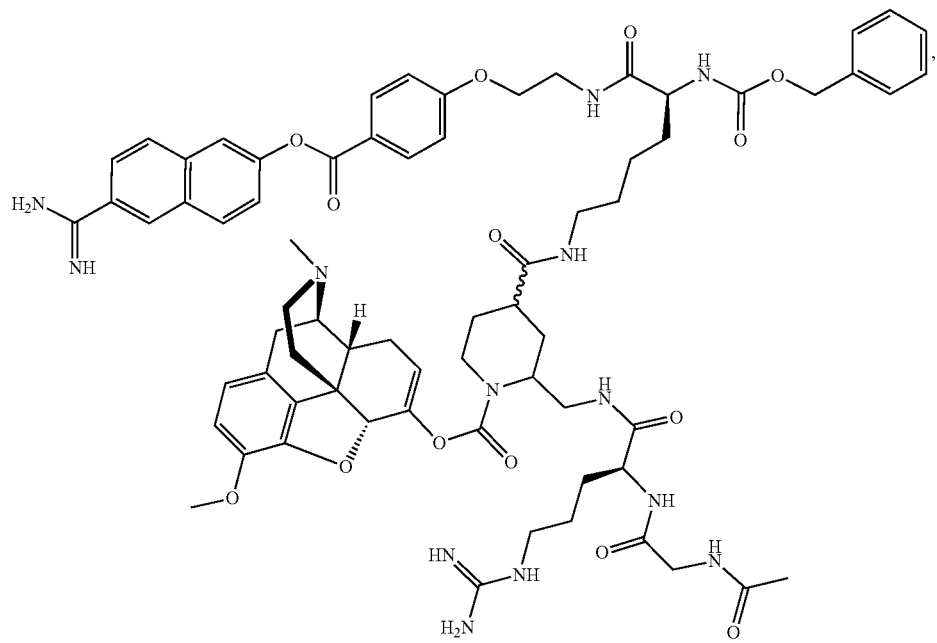

or a salt thereof; or by the formula:

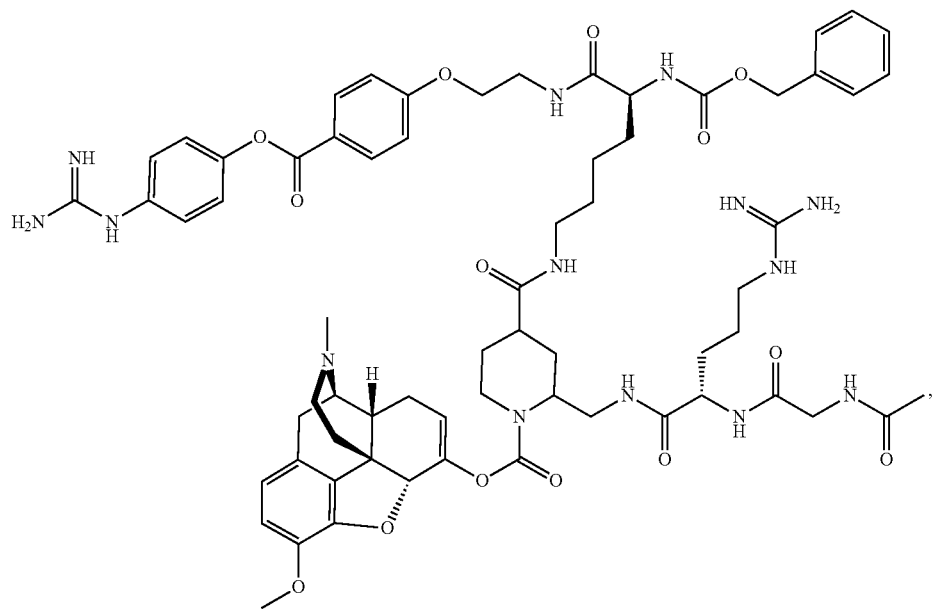

or a salt thereof.

40. The composition of claim 1, further comprising a pharmaceutically acceptable excipient.

41. The composition of claim 40, further formulated as an oral dose unit, wherein the compound is present in the dose unit in an amount effective to provide for a defined pharmacokinetic (PK) profile of the opioid agonist following ingestion of a prescribed dose.

42. The composition of claim 41, wherein the PK profile of the opioid agonist comprises at least one PK parameter value that demonstrates delay, or reduced dose-normalized exposures, of a released opioid agonist relative to a prescribed dose, when a dose in excess of the prescribed dose is ingested.

43. The composition of claim 42, wherein the PK parameter value is selected from a Cmax value, an AUC exposure value, and a Tmax value.

* * * * *